US006689607B2

(12) United States Patent
Ni et al.

(10) Patent No.: US 6,689,607 B2
(45) Date of Patent: Feb. 10, 2004

(54) HUMAN TUMOR, NECROSIS FACTOR RECEPTOR-LIKE PROTEINS TR11, TR11SV1 AND TR11SV2

(75) Inventors: Jian Ni, Germantown, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 5 days.

(21) Appl. No.: 09/915,593

(22) Filed: Jul. 27, 2001

(65) Prior Publication Data

US 2002/0098525 A1 Jul. 25, 2002

Related U.S. Application Data

(63) Continuation-in-part of application No. 09/512,363, filed on Feb. 23, 2000, and a continuation-in-part of application No. 09/176,200, filed on Oct. 21, 1998.
(60) Provisional application No. 60/221,577, filed on Jul. 28, 2000, provisional application No. 60/144,076, filed on Jul. 16, 1999, provisional application No. 60/134,172, filed on May 13, 1999, provisional application No. 60/121,648, filed on Feb. 24, 1999, and provisional application No. 60/063,212, filed on Oct. 21, 1997.

(51) Int. Cl.[7] ............................. C12N 5/16; C12N 5/22; C07K 16/28
(52) U.S. Cl. ................. 435/331; 530/387.1; 530/387.3; 530/387.7; 530/388.1; 530/388.15; 530/388.22; 530/388.75; 530/388.8; 530/388.85; 530/389.1; 530/389.7; 530/391.1; 530/391.3; 530/387.9; 435/7.1; 435/326; 435/328; 435/330; 435/334; 435/343.2; 435/344.1
(58) Field of Search ........................... 530/387.1, 387.3, 530/387.7, 388.1, 388.15, 388.22, 388.75, 388.8, 388.85, 389.1, 389.7, 391.1, 391.3, 387.9; 435/7.1, 326, 328, 330, 331, 334, 343.2, 344.1

(56) References Cited

U.S. PATENT DOCUMENTS

| | | |
|---|---|---|
| 5,116,964 A | 5/1992 | Capon et al. |
| 6,111,090 A | 8/2000 | Gorman et al. |

FOREIGN PATENT DOCUMENTS

| | | |
|---|---|---|
| WO | WO 96/09386 | 3/1996 |
| WO | WO 98/06842 | 2/1998 |
| WO | WO 98/07880 | 2/1998 |
| WO | WO 98/24895 A1 | 6/1998 |
| WO | WO 99/20758 A1 | 4/1999 |
| WO | WO 99/40196 A1 | 8/1999 |
| WO | WO 00/05374 A2 | 2/2000 |
| WO | WO 00/32221 A2 | 6/2000 |
| WO | WO 00/32778 A2 | 6/2000 |
| WO | WO 00/40716 A2 | 7/2000 |
| WO | WO 00/53753 A2 | 9/2000 |
| WO | WO 00/53757 A2 | 9/2000 |
| WO | WO 00/53758 A2 | 9/2000 |
| WO | WO 00/73445 A2 | 12/2000 |
| WO | WO 00/73452 A2 | 12/2000 |
| WO | WO 01/03720 A2 | 1/2001 |
| WO | WO 01/05972 A1 | 1/2001 |

OTHER PUBLICATIONS

Goding, James W. Monoclonal Antibodies: Principles and Practice, Second Edition, Academic Press, London, 1986, pp. 119–121.*
U.S. patent application Ser. No. 09/912,292, Rosen et al., filed Not Published, pp. 1–75 (pp. 1 & 2 partially redacted); portion of Table 2; and SEQ ID NOs: 6584, and 19302.
Baens, et al., Construction and Evaluation of a hncDNA Library of Human 12p Transcribed Sequences Derived from a Somatic Cell Hybrid, *Genomics,* 16:214–218 (1993).
Gurney, et al., GenBank Accession No. AF125304, Apr. 2, 1999.
Kwon, et al., Identification of a Novel Activation–Inducible Protein of the Tumor Necrosis Factor Receptor Superfamily and its Ligand, *J. Biol. Chem.,* 274:6056–6061 (1999).
International Search Report, mailed Jul. 31, 2000, in copending international application No. PCT/US00/04572.
Gurney, et al., Identification of a New Member of the Tumor Necrosis Factor Family and its Receptor, a Human Ortholog Of Mouse GITR, *Current Biology,* 9:215–218 (1999).
Beutler and Van Huffel, Unraveling Function in the TNF Ligand and Receptor Families, *Science,* 264:667–668 (1994).
Nocentini, et al., A New Member of the Tumor Necrosis Factor/Nerve Growth Factor Receptor Family Inhibits T Cell Receptor–Induced Apoptosis, Proc. Natl. Acad. Sci., 94:6216–6221 (1997).
Nocentini, et al., GenBank Accession No. AF241229, Apr. 12, 2000.

* cited by examiner

*Primary Examiner*—Anthony C. Caputa
*Assistant Examiner*—Anne L. Holleran
(74) *Attorney, Agent, or Firm*—Human Genome Sciences, Inc.

(57) ABSTRACT

The present invention relates to novel members of the Tumor Necrosis Factor family of receptors. The invention provides isolated nucleic acid molecules encoding human TR11, TR11SV1, and TR11SV2 receptors. TR11, TR11SV1, and TR11SV2 polypeptides are also provided, as are vectors, host cells and recombinant methods for producing the same. The invention further relates to screening methods for identifying agonists and antagonists of TR11, TR11SV1, and TR11SV2 receptor activity. The present invention further relates to antibodies that specifically bind TR11, TR11SV1, and/or TR11SV2. Also provided are diagnostic methods for detecting disease states related to the aberrant expression of TR11, TR11SV1, and TR11SV2 receptors. Further provided are therapeutic methods for treating disease states related to aberrant proliferation and differentiation of cells which express the TR11, TR11SV1, and TR11SV2 receptors.

60 Claims, 11 Drawing Sheets

```
  1 GCACTTCACCTGGGTCGGGATTCTCAGGTCATGAACGGTCCCAGCCACCTCCGGGCAGGG 60

61 CGGGTGAGGACGGGGACGGGGCGTGTCCAACTGGCTGTGGGCTCTTGAAACCCGAGCATG 120
  1                                                           M   1

121 GCACAGCACGGGGCGATGGGCGCGTTTCGGGCCCTGTGCCGGCCTGGCGCTGCTGTGCGCG 180
  2 A Q H G A M G A F R A L C G L A L L C A                      21

181 CTCAGCCTGGGTCAGCGCCCCACCGGGGGTCCCGGGTGCGGCCCTGGGCGCCTCCTGCTT 240
 22 L S L G Q R P T G G P G C G P G R L L          41

241 GGGACGGGAACGGACGCGCGCTGCTGCCGGGTTCACACGACGCGCTGCTGCCGCGATTAC 300
 42 G T G T D A R C C R V H T T R C C R D Y      61

301 CCGGGGCGAGGAGTGCTGTTCCGAGTGGGACTGCATGTGTGTCCAGCCTGAATTCCACTGC 360
 62 P G E E C C S E W D C M C V Q P E F H C       81
                        CD-II

361 GGAGACCCTTGCTGCACGACCTGCCGGCACCACCCCTTGTCCCCCAGGCCAGGGGGTACAG 420
 82 G D P C C T T C R H H P C P P P G Q G V Q    101
        CD-III

421 TCCCAGGGGAAATTCAGTTTTTGGCTTCCAGTGTATCGACTGTGCCTCGGGGACCTTCTCC 480
102 S Q G K F S F G F Q C I D C A S G T F S    121
                  CD-IV

481 GGGGGCCACGAAGGCCACTGCAAACCTTGGACAGACTGCACCCAGTTCGGGTTTCTCACT 540
122 G G H E G H C K P W T D C T Q F G F L T   141
              #         CD-V

541 GTGTTCCCTGGGAACAAGACCCACAACGCTGTGTGCGTCCCAGGGTCCCCGCCGGCAGAG 600
142 V F P G N K T H N A V C V P G S P P A E   161
                              CD-VI

601 CCGCTTGGGTGGCTGACCGTCGTCCTCCTGGCCGTGGCCGCCTGCGTCCTCCTCCTGACC 660
162 P L G W L T V V L L A V A A C V L L L T    181
                                CD-VII

661 TCGGCCCAGCTTGGACTGCACATCTGGCAGCTGAGGAAGACCCAGCTGCTGCTGGAGGTG 720
182 S A Q L G L H I W Q L R K T Q L L L E V    201
    CD-VII

721 CCGCCGTCGACCGAAGACGCCAGAAGCTGCCAGTTCCCCGAGGAAGAGCGGGGCGAGCGA 780
202 P P S T E D A R S C Q F P E E R G E R    221
          CD-IX

781 TCGGCAGAGGAGAAGGGGCGGCTGGGAGACCTGTGGGTGTGAGCCTGGCCGTCCTCCGGG 840
222 S A E E K G R L G D L W V                   234
          CD-X

841 GCCACCGACCGCAGCCAGCCCCTCCCCAGGAGCTCCCCAGGCCGCAGGGGCTCTGCGTTC 900
```

FIG. 1A

901 TGCTCTGGGCCCGGCCCTGCTCCCCTGGCAGCAGAAGTGGGTGCAGGAAGGTGGCAGTGA 960

961 CCAGCGCCCTGGACCATGCAGTT 983

FIG. 1B

```
  1 GTCGACCCACGCGTCCGGGGGGCCACCCCTGGGTCCTGCAGGGGCAGCTCCTGGTTGCAT  60

61 ATGGAGTTAGCACCTGGGCAGGGGCAGCTGTGGGGCGCAAAGGGGGAGTAGCCAGGCCAC 120

121 ATGGCCCCAGGAGAAAGAGACAGCTGGATAAACCCAGGTCCAGACTCCCAGCCAGGAGCC 180
  1 M  A  P  G  E  R  D  S  W  I  N  P  G  P  D  S  Q  P  G  A   20

181 CTCTGCTCCCTGGAGCCAACTGTGGGTGGAGAACGGACAACCTCACTCCCCTGGAGGGCC 240
 21 L  C  S  L  E  P  T  V  G  G  E  R  T  T  S  L  P  W  R  A   40

241 GAGGGGAGGCCTGGGGAGGAGGGGGCCTCAGCCCAGCTGCTGGGGGGCTGGCCTGTCTCC 300
 41 E  G  R  P  G  E  E  G  A  S  A  Q  L  L  G  G  W  P  V  S   60
                                    CD-I

301 TGCCCAGGCGAGGAGTGCTGTTCCGAGTGGGACTGCATGTGTGTCCAGCCTGAATTCCAC 360
 61 C  P  G  E  E  C  S  E  W  D  C  M  C  V  Q  P  E  F  H       80
                                    CD-II

361 TGCGGAGACCCTTGCTGCACGACCTGCCGGCACCACCCTTGTCCCCCAGGCCAGGGGGTA 420
 81 C  G  D  P  C  C  T  T  C  R  H  H  P  C  P  P  G  Q  G  V  100
    CD-II       CD-III

421 CAGTCCCAGGGGAAATTCAGTTTTGGCTTCCAGTGTATCGACTGTGCCTCGGGGACCTTC 480
101 Q  S  Q  G  K  F  S  F  G  F  Q  C  I  D  C  A  S  G  T  F  120
                        CD-IV

481 TCCGGGGGCCACGAAGGCCACTGCAAACCTTGGACAGACTGCACCCAGTTCGGGTTTCTC 540
121 S  G  G  H  E  G  H  C  K  P  W  T  D  C  T  Q  F  G  F  L  140
                   #     CD-V

541 ACTGTGTTCCCTGGGAACAAGACCCACAACGCTGTGTGCGTCCCAGGGTCCCCGCCGGCA 600
141 T  V  F  P  G  N  K  T  H  N  A  V  C  V  P  G  S  P  P  A  160
                                          CD-VI

601 GAGCCGCTTGGGTGGCTGACCGTCGTCCTCCTGGCCGTGGCCGCCTGCGTCCTCCTCCTG 660
161 E  P  L  G  W  L  T  V  V  L  L  A  V  A  A  C  V  L  L  L  180
                                              CD-VII

661 ACCTCGGCCCAGCTTGGACTGCACATCTGGCAGCTGAGGAGTCAGTGCATGTGGCCCCGA 720
181 T  S  A  Q  L  G  L  H  I  W  Q  L  R  S  Q  C  M  W  P  R  200
    CD-VII                             CD-VIII

721 GAGACCCAGCTGCTGCTGGAGGTGCCGCCGTCGACCGAAGACGCCAGAAGCTGCCAGTTC 780
201 E  T  Q  L  L  L  E  V  P  P  S  T  E  D  A  R  S  C  Q  F  220
    CD-VIII                    CD-IX

781 CCCGAGGAAGAGCGGGGCGAGCGATCGGCAGAGGAGAAGGGGCGGCTGGGAGACCTGTGG 840
221 P  E  E  R  G  E  R  S  A  E  E  K  G  R  L  G  D  K  W    240
                              CD-X

841 GTGTGAGCCTGGCCGTCCTCCGGGGCCACCGACCGCAGCCAGCCCCTCCCCAGGAGCTCC 900
241 V                                                            241
```

FIG. 2A

901 CCAGGCCGCAGGGGCTCTGCGTTCTGCTCTGGGCCGGGCCCTGCTCCCCTGGCAGCAGAA 960

961 GTGGGTGCAGGAAGGTGGCAGTGACCAGCGCCCTGGACCATGCAGTT 1007

FIG. 2B

```
  1 ATGGGCGCGTTTCGGGCCCTGTGCGGCCTGGCGCTGCTGTGCGCCCTCAGCCTGGGTCAG  60
  1 M G A F R A L C G L A L L C A L S L G Q                       20

61 CGCCCCACCGGGGGTCCCGGGTGCGGCCCTGGGCGCCTCCTGCTTGGGACGGGAACGGAC 120
 21 R P T G G P G C G P G R L L G T G T D                         40

121 GCGCGCTGCTGCCGGGTTCACACGACGCGCTGCTGCCGCGATTACCCGGCCCAGCTGCTG 180
 41 A R C C R V H T T R C C R D Y P A Q L L                       60
                                       CD-I

181 GGGGGCTGGCCTGTCTCCTGCCCAGGCGAGGAGTGCTGTTCCGAGTGGGACTGCATGTGT 240
 61 G G W P V S C P G E E C C S E W D C M C                       80
    CD-I                                 CD-II

241 GTCCAGCCTGAATTCCACTGCGGAGACCCTTGCTGCACGACCTGCCGGCACCACCCTTGT 300
 81 V Q P E F H C G D P C C T T C R H H P C                      100
    CD-II           CD-III

301 CCCCCAGGCCAGGGGGTACAGTCCCAGGGGAAATTCAGTTTTGGCTTCCAGTGTATCGAC 360
101 P P G Q G V Q S Q G K F S F G F Q C I D                      120
                                  CD-IV

361 TGTGCCTCGGGGACCTTCTCCGGGGGCCACGAAGGCCACTGCAAACCTTGGACAGACTGC 420
121 C A S G T F S G G H E G H C K P W T D C                      140
    CD-IV                        #       CD-V

421 ACCCAGTTCGGGTTTCTCACTGTGTTCCCTGGGAACAAGACCCACAACGCTGTGTGCGTC 480
141 T Q F G F L T V F P G N K T H N A V C V                      160
                                          CD-VI

481 CCAGGGTCCCCGCCGGCAGAGCCGCTTGGGTGGCTGACCGTCGTCCTCCTGGCCGTGGCC 540
161 P G S P P A E P L G W L T V V L L A V A                      180
    CD-VI

541 GCCTGCGTCCTCCTCCTGACCTCGGCCCAGCTTGGACTGCACATCTGGCAGCTGAGGAAG 600
181 A C V L L L T S A Q L G L H I W Q L R K                      200
       CD-VII

601 ACCCAGCTGCTGCTGGAGGTGCCGCCGTCGACCGAAGACGCCAGAAGCTGCCAGTTCCCC 660
201 T Q L L L E V P P S T E D A R S C Q F P                      220
                      CD-IX

661 GAGGAAGAGCGGGGCGAGCGATCGGCAGAGGAGAAGGGGCGGCTGGGAGACCTGTGGGTG 720
221 E E E R G E R S A E E K G R L G D L W V                      240
                      CD-X

721 TGAGCCTGGCCGTCCTCCGGGGCCACCGACCGCAGCCAGCCCCTCCCCAGGAGCTCCCCA 780

781 GGCCGCAGGGGCTCTGCGTTCTGCTCTGGGCCGGGCCCTGCTCCCCTGGCAGCAGAAGTG 840

841 GGTGCAGGAAGGTGGCAGTGACCAGCGCCCTGGACCATGCAGTTCGGCGGCCGCGGCTGG 900
```

FIG. 3A

```
901  GCCCTGCAGGAGGGAGAGAGAGACACAGTCATGGCCCCCTTCCTCCCTTGCTGGCCCTGA 960

961  TGGGGTGGGGTCTTAGGACGGGAGGCTGTGTCCGTGGGTGTGCAGTGCCCAGCACGGGAC 1020

1021 CCGGCTGCAGGGGACCTTCAATAAACACTTGTCCAGTAAAAAAAAAAAAAAAAA        1074
```

```
                                                                    mGITR.aa
                                                                    TR11.aa
                                                                    TR11SV1.aa
                                                                    TR11SV2.aa 210             220             230             240       250
176  HIWQLRRQHMCPRETQPFAEVQLSAEDACSFQFPEEERGEQT-EEKCHLG        mGITR.aa
188  HIWQLRK------TQLLLEVPPSTEDARSCQFPEEERGERSAEEKGRLG        TR11.aa
188  HIWQLRSQCMWPRETQLLLEVPPSTEDARSCQFPEEERGERSAEEKGRLG       TR11SV1.aa
194  HIWQLRK------TQLLLEVPPSTEDARSCQFPEEERGERSAEEKGRLG        TR11SV2.aa

225  GRWP
231  DLWV
238  DLWV
237  DLWV
```

HUMAN TUMOR, NECROSIS FACTOR RECEPTOR-LIKE PROTEINS TR11, TR11SV1 AND TR11SV2

RELATED APPLICATIONS

This application claims the benefit of priority under 35 U.S.C. §119(e) based on U.S. Provisional Application Ser. No. 60/221,577 filed Jul. 28, 2001. This application is also a continuation-in-part of U.S. Nonprovisional Application Ser. No. 09/512,363 filed Feb. 23, 2000 which claims the benefit of priority under 35 U.S.C. §119(e) based on U.S. Provisional Application Ser. No.: 60/144,076 filed Jul., 16, 1999; 60/134,172 filed May 13, 1999; and 60/121,648 filed Feb. 24, 1999. U.S. Nonprovisional Application Ser. No. 09/512,363 is also a continuation-in-part of 09/176,200 filed Oct. 21, 1998 which claims the benefit of priority under 35 U.S.C. §119(e) based on U.S. Provisional Application Ser. No. 60/063,212 filed Oct. 21, 1997. Each of the provisional and nonprovisional applications listed above is hereby incorporated by reference in its entirety.

FIELD OF THE INVENTION

The present invention relates to novel members of the Tumor Necrosis Factor (TNF) receptor family. More specifically, isolated nucleic acid molecules are provided encoding a human TNF receptor-related protein, referred to herein as the TR11 receptor of FIGS. 1A and 1B, and two splice variants thereof, referred to herein as the TR11SV1 and TR11SV2 receptors, of FIGS. 2A and 2B and 3A and 3B, respectively, each having considerable homology to murine glucocorticoid-induced tumor necrosis factor receptor family-related gene (GITR). TR11, TR11SV1, and TR11SV2 polypeptides are also provided. Further provided are vectors, host cells and recombinant methods for producing the same. The invention also relates to both the inhibition and enhancement of the activities of TR11, TR11SV1, and TR11SV2 receptor polypeptides and diagnostic methods for detecting TR11 receptor gene expression.

BACKGROUND OF THE INVENTION

Human tumor necrosis factors alpha (TNF-alpha) and beta (TNF-beta or lymphotoxin) are related members of a broad class of polypeptide mediators, which includes the interferons, interleukins and growth factors, collectively called cytokines (Beutler, B. and Cerami, A., Annu. Rev. Immunol., 7:625–655 (1989)).

Tumor necrosis factor (TNF-alpha and TNF-beta) was originally discovered as a result of its anti-tumor activity, however, now it is recognized as a pleiotropic cytokine playing important roles in a host of biological processes and pathologies. To date, there are ten known members of the TNF-related cytokine family, TNF-alpha, TNF-beta (lymphotoxin-alpha), LT-beta, TRAIL and ligands for the Fas receptor, CD30, CD27, CD40 (also known as CDw40), OX40 and 4-1BB receptors. These proteins have conserved C-terminal sequences and variable N-terminal sequences which are often used as membrane anchors, with the exception of TNF-beta. Both TNF-alpha and TNF-beta function as homotrimers when they bind to TNF receptors.

TNF is produced by a number of cell types, including monocytes, fibroblasts, T-cells, natural killer (NK) cells and predominately by activated macrophages. TNF-alpha has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata, et al., J. Immunol. 136:2483 (1987)), growth regulation, vascular endothelium effects and metabolic effects. TNF-alpha also triggers endothelial cells to secrete various factors, including PAI-1, IL-1, GM-CSF and IL-6 to promote cell proliferation. In addition, TNF-alpha up-regulates various cell adhesion molecules such as E-Selectin, ICAM-1 and VCAM-1. TNF-alpha and the Fas ligand have also been shown to induce programmed cell death.

TNF-beta has many activities, including induction of an antiviral state and tumor necrosis, activation of polymorphonuclear leukocytes, induction of class I major histocompatibility complex antigens on endothelial cells, induction of adhesion molecules on endothelium and growth hormone stimulation (Ruddle, N. and Homer, R., Prog. Allergy 40:162–182 (1988)).

Both TNF-alpha and TNF-beta are involved in growth regulation and interact with hematopoietic cells at several stages of differentiation, inhibiting proliferation of various types of precursor cells, and inducing proliferation of immature myelomonocytic cells (Porter, A., Tibtech 9:158–162 (1991)).

Recent studies with "knockout" mice have shown that mice deficient in TNF-beta production show abnormal development of the peripheral lymphoid organs and morphological changes in spleen architecture (reviewed by Aggarwal, et al., Eur Cytokine Netw, 7:93–124 (1996)). With respect to the lymphoid organs, the popliteal, inguinal, para-aortic, mesenteric, axillary and cervical lymph nodes failed to develop in TNF-beta –/–mice. In addition, peripheral blood from TNF-beta –/–mice contained a threefold reduction in white blood cells as compared to normal mice. Peripheral blood from TNF-beta –/–mice, however, contained four fold more B cells as compared to their normal counterparts. Further, TNF-beta, in contrast to TNF-alpha, has been shown to induce proliferation of EBV-infected B cells. These results indicate that TNF-beta is involved in lymphocyte development.

The first step in the induction of the various cellular responses mediated by TNF-alpha or TNF-beta is their binding to specific cell surface or soluble receptors. Two distinct TNF receptors of approximately 55-KDa (TNF-RI) and 75-KDa (TNF-RII) have been identified (Hohman, et al., J. Biol. Chem., 264:14927–14934 (1989)), and human and mouse cDNAs corresponding to both receptor types have been isolated and characterized (Loetscher, et al., Cell, 61:351 (1990)). Both TNF-Rs share the typical structure of cell surface receptors including extracellular, transmembrane and intracellular regions.

These molecules exist not only in cell bound forms, but also in soluble forms, consisting of the cleaved extra-cellular domains of the intact receptors (Nophar, et al., EMBO Journal, 9:3269–76 (1990)) and otherwise intact receptors wherein the transmembrane domain is lacking. The extracellular domains of TNF-RI and TNF-RII share 28% identity and are characterized by four repeated cysteine-rich motifs with significant intersubunit sequence homology. The majority of cell types and tissues appear to express both TNF receptors and both receptors are active in signal transduction, however, they are able to mediate distinct cellular responses. Further, TNF-RII was shown to exclusively mediate human T-cell proliferation by TNF as shown in PCT WO 94/09137.

TNF-RI dependent responses include accumulation of C-FOS, IL-6, and manganese superoxide dismutase mRNA, prostaglandin E2 synthesis, IL-2 receptor and MHC class I and II cell surface antigen expression, growth inhibition, and cytotoxicity. TNF-RI also triggers second messenger systems such as phospholipase A, protein kinase C, phosphatidylcholine-specific phospholipase C and sphingomyelinase (Pfefferk, et al., Cell, 73:457–467 (1993)).

Several interferons and other agents have been shown to regulate the expression of TNF receptors. Retinoic acid, for example, has been shown to induce the production of TNF receptors in some cells type while down regulating production in other cells. In addition, TNF-alpha has been shown to affect the localization of both types of receptor. TNF-alpha induces internalization of TNF-RI and secretion of TNF-RII (reviewed in Aggarwal, et al., supra). Thus, the production and localization of both TNF-Rs are regulated by a variety of agents.

Both the yeast two hybrid system and co-precipitation and purification have been used to identify ligands which associate with both types of the TNF-Rs (reviewed by Aggarwal, et al., supra; Vandenabeele, et al., Trends in Cell Biol. 5:392–399 (1995)). Several proteins have been identified which interact with the cytoplasmic domain of a murine TNF-R. Two of these proteins appear to be related to the baculovirus inhibitor of apoptosis, suggesting a direct role for TNF-R in the regulation of programmed cell death.

Thus, there is a need for polypeptides that function as receptors for cytokines and cytokine-like molecules which are involved in the regulation of cellular processes such as cell-growth and differentiation, since disturbances of such regulation may be involved in disorders relating to hemostasis, angiogenesis, tumor metastisis, cellular migration, and neurogenesis. Therefore, there is a need for identification and characterization of such human polypeptides which can play a role in detecting, preventing, ameliorating, regulating or correcting such disorders.

SUMMARY OF THE INVENTION

The present invention provides isolated nucleic acid molecules comprising or alternatively consisting of, polynucleotides encoding TR11, TR11SV1, and TR11SV2 receptors having the amino acid sequences shown in FIGS. 1A and 1B (SEQ ID NO:2), 2A and 2B (SEQ ID NO:4), and 3A and 3B (SEQ ID NO:6), respectively, or the amino acid sequences encoded by the cDNA clones encoding the TR11, TR11SV1, and TR11SV2 receptors, respectively, deposited as ATCC Deposit Numbers 209341, 209343 and 209342, respectively, on Oct. 7, 1997. The present invention also relates to recombinant vectors, which include the isolated nucleic acid molecules of the present invention, and to host cells containing the recombinant vectors, as well as to methods of making such vectors and host cells and for using them for production of TR11, TR11SV1, and TR11SV2 polypeptides or peptides by recombinant techniques.

The invention further provides isolated TR11, TR11SV1, and TR11SV2 polypeptides having amino acid sequences encoded by the polynucleotides described herein.

The invention further provides antibodies that specifically bind TR11, TR11SV1,and TR11SV2. In particular embodiments, the present invention encompasses antibodies that specifically bind one, two or all three polypeptides selected from the group consisting of TR11, TR11SV1, and TR11SV2. In other embodiments, the present invention encompasses antibodies that bind a polypeptide comprising, or alternatively consisting of amino acid, residues 1–62 of SEQ ID NO:4, 51–62 of SEQ ID NO:4 and 38–49 OF SEQ ID NO:6 (which correspond to amino acid residues 57–68 of as shown and numbered in FIGS. 3A–B). In still other embodiments, the present invention provides antibodies that bind an epitope of TR11SV1 wherein the epitope consists, in full or in part, of amino acid residues from the region consisting of amino acid residues 1–62 of SEQ ID NO:4. In still other embodiments, the present invention provides antibodies that bind an epitope of TR11SV1 wherein the epitope consists, in full or in part, of amino acid residues from the region consisting of amino acid residues 38–49 OF SEQ ID NO:6 (which correspond to amino acid residues 57–68 of as shown and numbered in FIGS. 3A–B).

In certain embodiments, TR11, TR11SV1, and/or TR11SV2 polypeptides of the invention, or agonists or antagonists thereof, are used, to treat, prevent, prognose and/or diagnose an immunodeficiency (e.g., severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency) or conditions associated with an immunodeficiency.

In certain embodiments, TR11, TR11SV1, and/or TR11SV2 polypeptides of the invention, or agonists or antagonists thereof, are used, to treat, prevent, prognose and/or diagnose a T cell related immunodeficiency. T cell related immunodeficiencies that may be treated, prevented, prognosed and/or diagnosed using the TR11, TR11SV1, TR11SV2 polypeptides (e.g., TR11-Fc or TR11-albumin fusion proteins containing the extracellular domain of TR11, and antagonistic anti-TR11 antibodies) or polynucleotides of the invention, or antagonists or agonists thereof include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are treated, prevented, prognosed and/or diagnosed using the TR11, TR11SV1, TR11SV2 polypeptides (e.g., TR11-Fc fusion proteins or TR11-albumin-fusion proteins containing the extracellular domain of TR11, and antagonistic anti-TR11 antibodies) or polynucleotides of the invention, or antagonists or agonists thereof.

In a specific embodiment, TR11, TR11SV1, and/or TR11SV2 polypeptides or polynucleotides of the invention, or agonists or antagonists thereof, are used to treat, prevent, prognose and/or diagnose common variable immunodeficiency.

In a specific embodiments, TR11, TR11SV1, and/or TR11SV2 polypeptides, antibodies, or polynucleotides of the invention, and/or agonists or antagonists thereof, are used to treat, prevent, prognose and/or diagnose X-linked agammaglobulinemia. In another specific embodiment, TR11, TR11SV1, and/or TR11SV2 polypeptides, antibodies, or polynucleotides of the invention, and/or agonists or antagonists thereof, is used to treat, prevent, prognose and/or diagnose severe combined immunodeficiency (SCID). In another specific embodiment, TR11, TR11SV1, and/or TR11SV2 polypeptides, antibodies, or polynucleotides of the invention, and/or agonists or antagonists thereof, is used to treat, prevent, prognose and/or diagnose X-linked Ig deficiency with hyper IgM.

In another embodiment, TR11, TR11SV1, and/or TR11SV2 polypeptides, antibodies, or polynucleotides of the invention, and/or agonists or antagonists (e.g., an anti-TR11, anti-TR11SV1, and/or anti-TR11SV2 antibody), is used to treat, prevent, prognose and/or diagnose an autoimmune disease (e.g., rheumatoid arthritis, systemic lupus erhythematosus, idiopathic thrombocytopenia purpura, autoimmune hemolytic anemia, autoimmune neonatal thrombocytopenia, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye, autoimmune thyroiditis, hypothyroidism (i.e., Hashimoto's thyroiditis, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mollitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders) or conditions associated with an autoimmune disease.

In a specific preferred embodiment, rheumatoid arthritis is treated, prevented, prognosed and/or diagnosed using TR11, TR11SV1, and/or TR11SV2 polypeptides, antibodies, or polynucleotides of the invention, and/or agonists or antagonists of the invention. In another specific preferred embodiment, systemic lupus erythemosus is treated, prevented, prognosed, and/or diagnosed using TR11, TR11SV1, and/or TR11SV2 polypeptides, antibodies, or polynucleotides of the invention, and/or agonists or antagonists of the invention. In another specific preferred embodiment, idiopathic thrombocytopenia purpura is treated, prevented, prognosed, and/or diagnosed using TR11, TR11SV1, and/or TR11SV2 polypeptides, antibodies, or polynucleotides of the invention, and/or agonists or antagonists of the invention. In another specific preferred embodiment IgA nephropathy is treated, prevented, prognosed and/or diagnosed using TR11, TR11SV1, and/or TR11SV2 polypeptides, antibodies, or polynucleotides of the invention, and/or agonists or antagonists of the invention. In a preferred embodiment, the autoimmune diseases and disorders and/or conditions associated with the diseases and disorders recited above are treated, prevented, prognosed and/or diagnosed using anti-TR11, anti-TR11SV1, and/or anti-TR11SV2 antibodies.

Similarly, allergic reactions and conditions, such as asthma (particularly allergic asthma) or other respiratory problems, may also be treated using TR11, TR11SV1, and/or TR11SV2 polypeptides, antibodies, or polynucleotides of the invention, and/or agonists or antagonists thereof. Moreover, these molecules can be used to treat anaphylaxis, hypersensitivity to an antigenic molecule, or blood group incompatibility.

In specific embodiments, TR11, TR11SV1, and/or TR11SV2 polypeptides, antibodies, or polynucleotides of the invention, and/or agonists or antagonists thereof, are useful to treat, diagnose, prevent, and/or prognose transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE).

Moreover, inflammatory conditions may also be treated, diagnosed, prevented and/or prognosed with TR11, TR11SV1, and/or TR11SV2 polypeptides, antibodies, or polynucleotides of the invention, and/or agonists or antagonists of TR11, TR11SV1, and/or TR11SV2 (e.g., anti-TR11 and/or anti-TR11SV11 antibodies) of the invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (13 and C), rheumatoid arthritis, gout, trauma, septic shock, pancreatitis, sarcoidosis, dermatitis, renal ischemia-reperfusion injury, Grave's disease, systemic lupus erythematosus, diabetes mellitus (i.e., type 1 diabetes), and allogenic transplant rejection).

TR11, TR11SV1, and/or TR11SV2 polypeptides, antibodies, or polynucleotides of the invention, and/or agonists or antagonists thereof, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of TR11, TR11SV1, and/or TR11SV2 polypeptides, antibodies, or polynucleotides of the invention, and/or agonists or antagonists of TR11, TR11SV1, or TR11SV2, that inhibits an immune response, particularly the activation, proliferation, differentiation, or chemotaxis of T--cells, may be an effective therapy in preventing organ rejection or GVHD.

Similarly TR11, TR11SV1, and/or TR11SV2 polypeptides, antibodies, or polynucleotides of the invention, and/or agonists or antagonists of the invention may also be used to modulate inflammation. For example, since TR11, TR11SV1, and/or TR11SV2 polypeptides, antibodies, or polynucleotides of the invention, and/or agonists or antagonists of the invention, inhibit the activation, proliferation and/or differentiation of cells involved in an inflammatory response, these molecules can be used to treat inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, and resulting from over production of cytokines (e.g., TNF or IL-1.).

Moreover, TR11, TR11SV1, and/or TR11SV2 polypeptides, antibodies, or polynucleotides of the invention, and/or agonists or antagonists of the invention can also be used to modulate hemostatic (the stopping of bleeding) or thrombolytic activity (clot formation). For example, by increasing hemostatic or thrombolytic activity, TR11, TR11SV1, and/or TR11SV2 polypeptides, antibodies, or polynucleotides of the invention, and/or agonists or antagonists of the invention could be used to treat blood coagulation disorders (e.g., afibrinogenemia, factor deficiencies), blood platelet disorders (e.g. thrombocytopeniza), or wounds resulting from trauma, surgery, or other causes. Alternatively, TR11, TR11SV1, and/or TR11SV2 polypeptides, antibodies, or polynucleotides of the invention, and/or agonists or antagonists of the invention, that can decrease hemostatic or thrombolytic activity could be used to inhibit or dissolve clotting, important in the treatment of heart attacks (infarction), strokes, or scarring.

The invention further provides compositions comprising a TR11, TR11SV1, and/or TR11SV2 polynucleotide, a TR11, TR11SV1, and/or TR11SV2 polypeptide, and/or an anti-TR11, anti-TR11SV1, and/or anti-TR11SV2 antibody, for administration to cells in vitro, to cells ex vivo, and to cells in vivo, or to a multicellular organism. In preferred embodiments, the compositions of the invention comprise a TR11, TR11SV1, and/or TR11SV2 polynucleotide for expression of a TR11, TR11SV1, and/or TR11SV2 polypeptide in a host organism for treatment of disease. In a most preferred embodiment, the compositions of the invention comprise a TR11, TR11SV1, and/or TR11SV2 polynucleotide for expression of a TR11, TR11SV1, and/or TR11SV2 polypeptide in a host organism for treatment of an immunodeficiency and/or conditions associated with an immunodeficiency. In another preferred embodiment, the compositions of the invention comprise a TR11, TR11SV1, and/or TR11SV2 polynucleotide for expression of a TR11, TR11SV1, and/or TR11SV2 polypeptide in a host organism for treatment of an autoimmune disease or disorder and/or conditions associated with an autoimmune disease or disorder. Particularly preferred embodiments of the invention relate to the expression in a human patient for treatment of a dysfunction associated with aberrant endogenous activity of a TR11 gene (e.g., expression to enhance or suppress the normal T-cell function by expanding or reducing T-cell numbers, increase or decrease T-cell activation, and/or or increase or decrease T-cell lifespan; or expression to enhance or suppress the normal B-cell function by expanding or reducing B-cell numbers, increase or decrease B-cell activation, and/or increase or decrease B-cell lifespan). Particularly preferred in this regard is expression in a human patient for treatment of a dysfunction associated with aberrant endogenous activity of a TR11 gene The present invention also provides a screening method for identifying compounds capable of enhancing or inhibiting a cellular response induced by TR11, TR11SV1, and TR11SV2 receptors, which involves contacting cells which express TR11, TR11SV1 or TR11SV2 receptors (e.g., activated T cells) with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on the binding of cellular ligands to TR11, TR11SV1, and TR11SV2 receptors (e.g., endokine-alpha (which is disclosed in International Publication WO98/07880) and APRIL (J. Exp. Med. 188(6):1185–1190 (1998)). In particular, the method involves contacting TR11, TR11SV1, and TR11SV2 receptors with a ligand polypeptide and a candidate compound and determining whether ligand binding to the TR11, TR11SV1, and/or TR11SV2 receptors is increased or decreased due to the presence of the candidate compound.

The invention further provides a diagnostic method useful during diagnosis or prognosis of one or more disease states resulting from aberrant cell proliferation or activation due to alterations in TR11, TR11SV1, and/or TR11SV2 receptor expression.

An additional aspect of the invention is related to a method for treating, detecting, and/or preventing an individual in need of an increased level of a TR11, TR11SV1 and/or TR11SV2 receptor activity in the body comprising, administering to such an individual a composition comprising a therapeutically effective amount of isolated TR11, TR11SV1 and/or TR11SV2 polypeptides of the invention or an agonist thereof.

A still further aspect of the invention is related to a method for treating, detecting, and/or preventing an individual in need of a decreased level of a TR11, TR11SV1 and/or TR11SV2 receptor activity in the body comprising, administering to such an individual a composition comprising a therapeutically effective amount of a TR11, TR11SV1 and/or TR11SV2 receptor antagonist (e.g., a soluble polypeptide comprising all or a portion of the extracellular domain of TR11 or an anti-TR11 antibody).

The invention additionally provides soluble forms of the polypeptides of the present invention. Soluble peptides are defined by amino acid sequences wherein the sequence comprises the polypeptide sequence lacking a transmembrane domain. Such soluble forms of the TR11, TR11SV1, and TR11SV2 receptors are useful as antagonists of the membrane bound forms of the receptors.

BRIEF DESCRIPTION OF THE FIGURES

FIGS. 1A and 1B show the nucleotide (SEQ ID NO:1) and deduced amino acid (SEQ ID NO:2) sequence of a TR11 receptor. A potential secretory leader sequence has been predicted for the complete polypeptide, of about 25 amino acid residues. The predicted secretory leader sequence is underlined in FIGS. 1A and 1B (amino acid residues −25 to −1 in SEQ ID NO:2). The deduced complete amino acid sequence includes 234 amino acid residues and has a deduced molecular weight of about 25,113 Da. It is further predicted that amino acid residues from about 26 to about 162 in FIGS. 1A and 1B (amino acid residues 1 to 137 in SEQ ID NO:2) constitute the extracellular domain; from about 163 to about 179 (amino acid residues 138 to 154 in SEQ ID NO:2) constitute the transmembrane domain; and from about 180 to about 234 (amino acid residues 155 to 209 in SEQ ID NO:2) constitute the intracellular domain.

Figure 5:
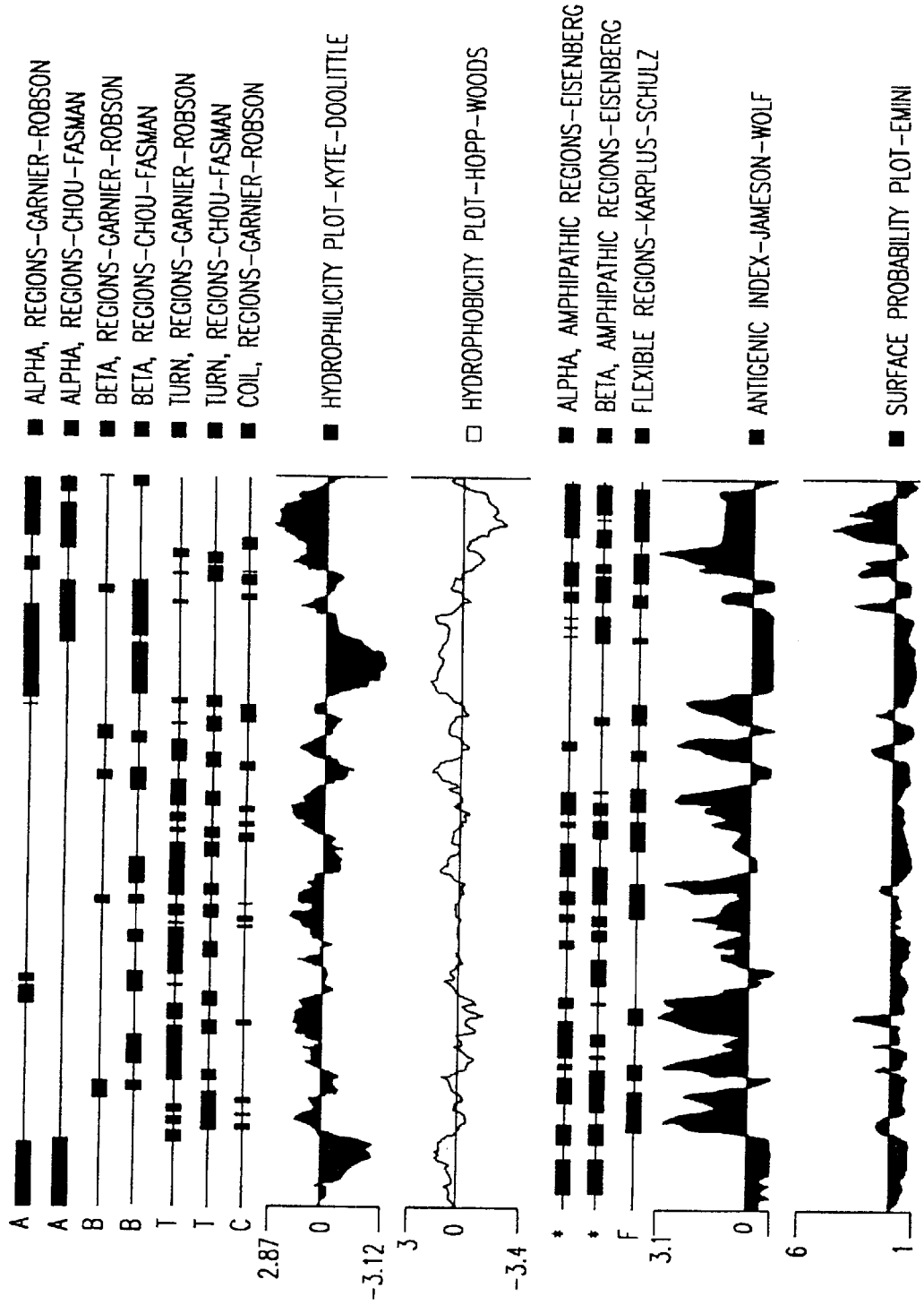

FIGS. 2A and 2B shows the nucleotide (SEQ ID NO:3) and deduced amino acid (SEQ ID NO:4) sequence of a TR11SV1 receptor. The deduced complete amino acid sequence includes 241 amino acid residues and has a deduced molecular weight of about 26,029 Da. It is further predicted that amino acid residues from about 1 to about 162 in FIGS. 2A and 2B (amino acid residues 1 to 162 in SEQ ID NO:4) constitute the extracellular domain; from about 163 to about 179 (amino acid residues 163 to 179 in SEQ ID NO:4) the transmembrane domain; and from about 180 to about 241 (amino acid residues 180 to 241 in SEQ ID NO:4) the intracellular domain.

FIGS. 3A and 3B shows the nucleotide (SEQ ID NO:5) and deduced amino acid (SEQ ID NO:6) sequence of a TR11SV2 receptor. A potential secretory leader sequence has been predicted for the complete polypeptide, of about 19 amino acid residues. The predicted secretory leader sequence is underlined in FIGS. 3A and 3B (amino acid residues −19 to −1 in SEQ ID NO:6). The deduced complete amino acid sequence includes 240 amino acid residues and has a deduced molecular weight of about 25,727 Da. It is further predicted that amino acid residues from about 20 to about 168 in FIGS. 3A and 3B (amino acid residues 1 to 149 in SEQ ID NO:6) constitute the extracellular domain; from about 169 to about 185 (amino acid residues 150 to 166 in SEQ ID NO:6) the transmembrane domain; and from about 186 to about 240 (amino acid residues 167 to 221 in SEQ ID NO:6) the intracellular domain.

A single potential asparagine-linked glycosylation site is marked in the amino acid sequence of TR11, TR11SV1, and TR11SV2. The potential site of glycosylation is at asparagine-146 in FIGS. 1A and 1B (asparagine-121 in SEQ ID NO:2), asparagine-146 in FIGS. 2A and 2B (asparagine-146 in SEQ ID NO:4), and asparagine-152 in FIGS. 3A and 3B (asparagine-133 in SEQ ID NO:6). The potential glycosylation sites are marked with a bold pound symbol (#) above the nucleotide sequence coupled with a bolded one letter abbreviation for the asparagine (N) in the amino acid sequence in FIGS. 1A and 1B, 2A and 2B, and 3A and 3B.

Figure 4A:
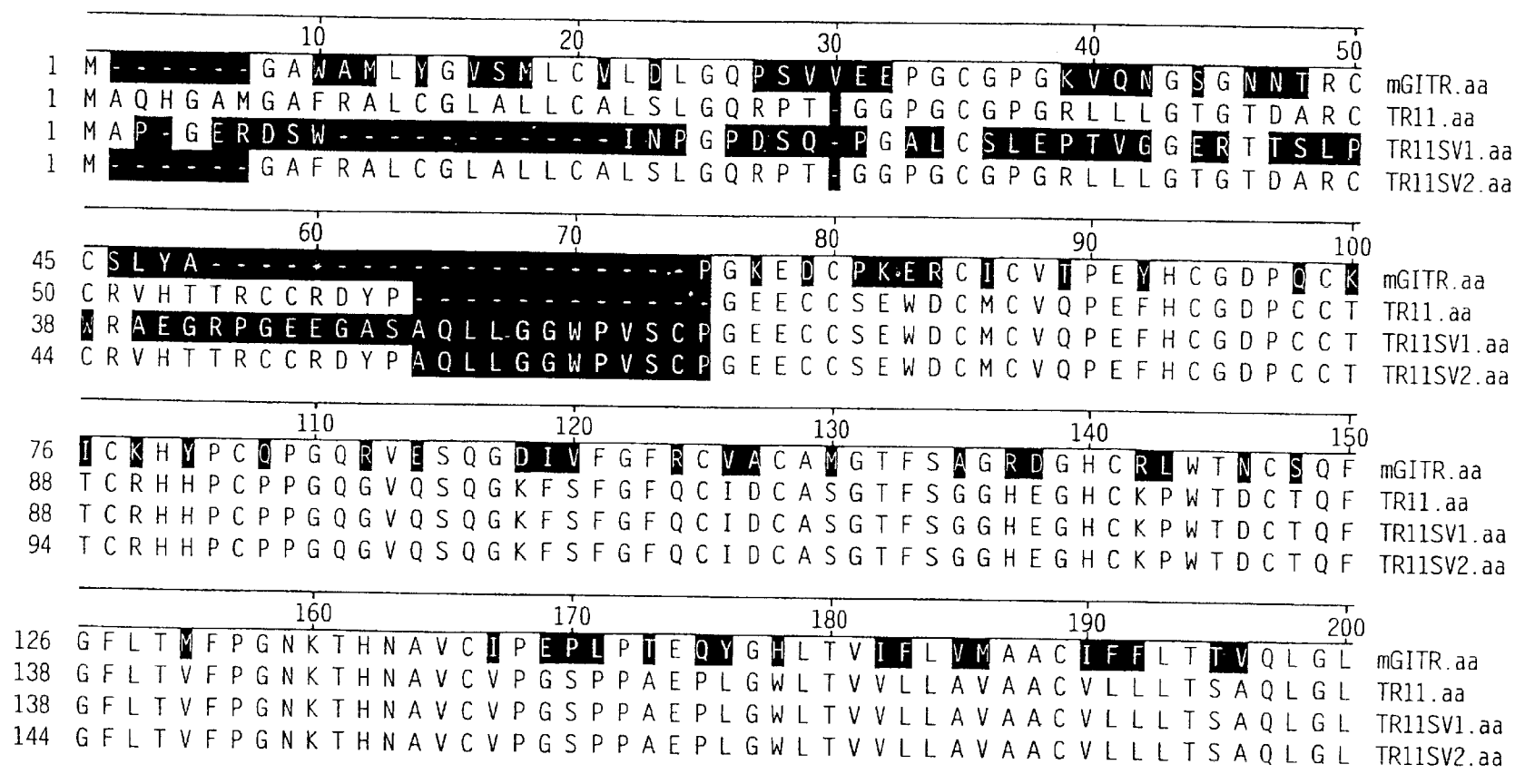

Regions of high identity between TR11, TR11SV1, and TR11SV2 and the closely related murine GITR (an alignment of these sequences is presented in FIGS. 4A and 4B) are delineated in FIGS. 1A and 1B, 2A and 2B, and 3A and 3B with a double underline. These regions are not limiting and are labeled as Conserved Domain (CD)-II, CD-III, CD-IV, CD-V, CD-VI, CD-VII, CD-IX, and CD-X in FIGS. 1A and 1B, 2A and 2B, and 3A and 3B. Conserved Domain (CD)-I is found only in TR11SV1 and TR11SV2 (i.e., FIGS. 2A and 2B and 3A and 3B) and CD-VIII is found only in TR11SV1 (i.e., FIGS. 2A and 2B).

FIGS. 4A and 4B show an alignment of the amino acid sequences of the murine glucocorticoid-induced tumor necrosis factor receptor family-related gene (GITR) receptor-like molecule, TR11, TR11SV1, and TR11SV2 (SEQ ID NO:7, SEQ ID NO:2, SEQ ID NO:4, and SEQ ID NO:6, respectively). The numbering of the TR11 amino acid sequences shown in this figure are relative to that presented in FIGS. 1A and 1B, 2A and 2B, and 3A and 3B, respectively. The alignment was generated using the "MegAlign" module of the DNA*Star Sequence Analysis computer program (DNASTAR, Inc.). Amino acid residues of mGITR, TR11SV1, and TR11SV2 which do not have identity with those of TR11 are highlighted in black in the alignment. The GenBank Accession No. for mGITR is U82534 (Nocentini, G., et al., Circ. Proc. Natl. Acad. Sci. USA 94:6216–6221 (1997)).

Figure 6:
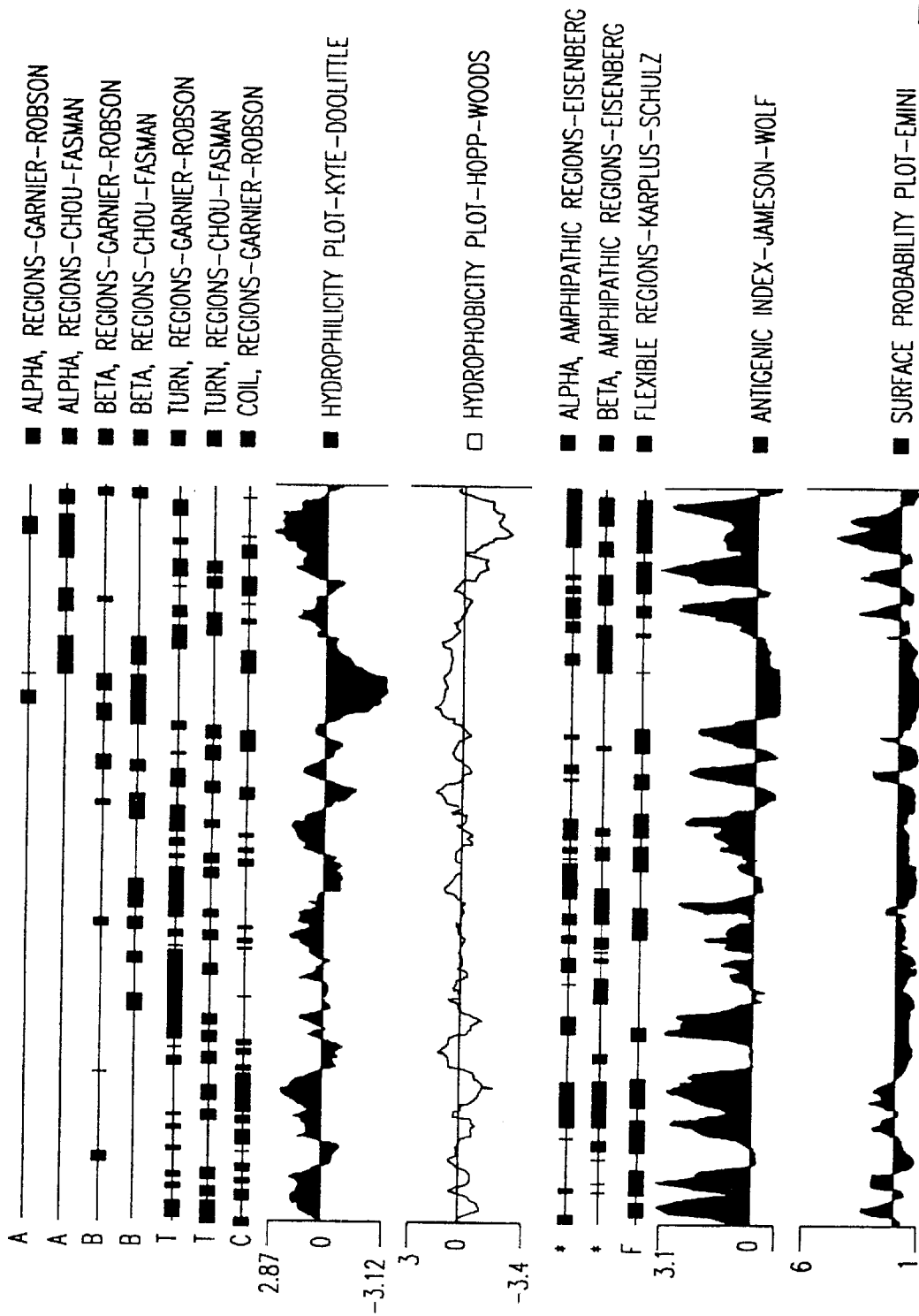
Figure 7:
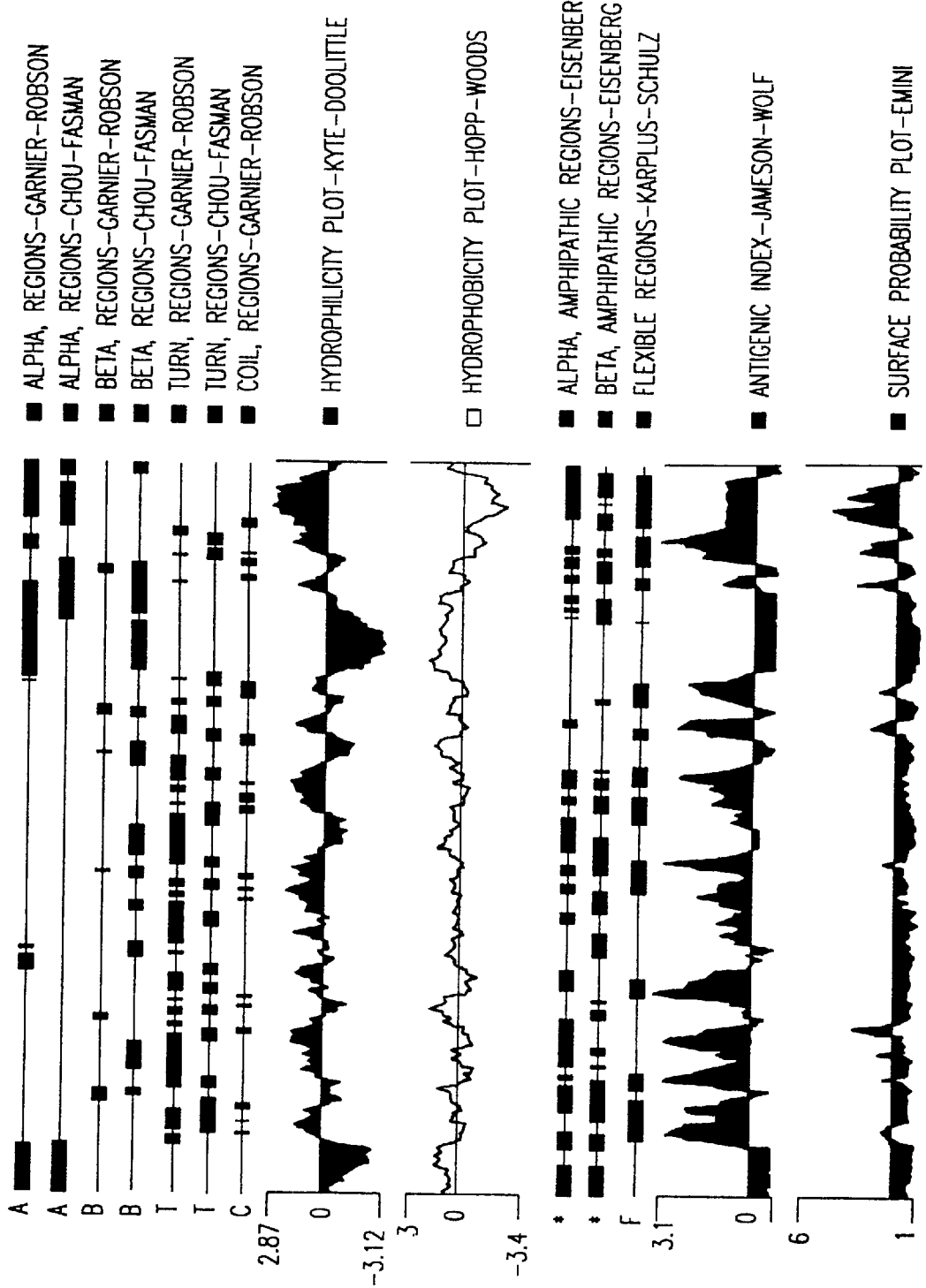

FIGS. 5, 6, and 7 show structural analyses of the TR11, TR11SV1, and TR11SV2 receptor amino acid sequences of FIGS. 1A and 1B, 2A and 2B, and 3A and 3B, respectively. Alpha, beta, turn and coil regions; hydrophilicity and hydrophobicity; amphipathic regions; flexible regions; antigenic index and surface probability are shown.

The DNA*STAR computer program will also represent the identical data presented in FIGS. 5, 6, and 7 in a tabular format. Such a tabular format may assist one practicing one or more aspects of the invention in which specific structural or other features of the invention are delineated according to the data presented in FIGS. 5, 6, and 7 herein. Such structural or other features of the polypeptides of the invention or of polynucleotides encoding such polypeptides which may be identified from the data presented in FIGS. 5, 6, and/or 7, or from tabular representations routinely generated from the identical data using the DNA*STAR computer program set on default settings, include, but are not limited to, Alpha, Regions-Garnier-Robson; Alpha, Regions-Chou-Fasman; Beta, Regions-Garnier-Robson; Beta, Regions-Chou-Fasman; Turn, Regions-Garnier-Robson; Turn, Regions-Chou-Fasman; Coil, Regions-Garnier-Robson; Hydrophilicity Plot-Kyte-Doolittle; Alpha, Amphipathic Regions-Eisenberg; Beta, Amphipathic Regions-Eisenberg; Flexible Regions-Karplus-Schulz; Antigenic Index-Jameson-Wolf; and Surface Probability Plot-Emini. Polynucleotides encoding these structural or other features are preferred embodiments of the present invention.

DETAILED DESCRIPTION OF THE PREFERRED EMBODIMENTS

The present invention provides isolated nucleic acid molecules comprising polynucleotides encoding TR11, TR11SV1, and TR11SV2 polypeptides (FIGS. 1A and 1B, 2A and 2B, and 3A and 3B (SEQ ID NO:2, SEQ ID NO:4, and SEQ ID NO:6, respectively), the amino acid sequences of which were determined by sequencing cloned cDNAs. The TR11, TR11SV1, and TR11SV2 proteins shown in FIGS. 1A and 1B, 2A and 2B, and 3A and 3B, respectively, share sequence homology with the human mGITR receptor-like protein (FIG. 2 (SEQ ID NO:7)). On Oct. 7, 1997, deposits of plasmid DNAs encoding TR11, TR11 SV1, and TR11SV2 were made at the American Type Culture Collection (ATCC), 10801 University Boulevard, Manassas, Virginia 20110-2209, and given accession numbers 209341, 209343 and 209342, respectively. The nucleotide sequences shown in FIGS. 1A and 1B, 2A and 2B, and 3A and 3B (SEQ ID NO:1, SEQ ID NO:3, and SEQ ID NO:5, respectively) were obtained by sequencing cDNA clones (Clone ID HHEAC71, HCFAZ22, and HT5EA78, respectively) containing the same amino acid coding sequences as the clones in ATCC Accession Nos. 209341, 209343 and 209342, respectively. The deposited clone encoding TR11 is contained in the pCMVSport3.0 plasmid (Life Technologies, Rockville, MD). The deposited clone encoding TR11SV1 is contained in the pBluescript SK(-) plasmid (Stratagene, La Jolla, CA). The deposited clone encoding TR11 SV2 is contained in the pSport1 plasmid (Life Technologies, Pockyille, MD).

As used herein, "TR11 protein", "TR11SV1 protein", "TR11SV2 protein", "TR11 receptor", "TR11SV1 receptor", "TR11SV2 receptor", "TR11 receptor protein", "TR11SV1 receptor protein", "TR11SV2 receptor protein", "TR11 polypeptide", "TR11SV1 polypeptide", and "TR11SV2 polypeptide" refer to all proteins resulting from the alternate splicing of the genomic DNA sequences encoding proteins having regions of amino acid sequence identity and receptor activity which correspond to the proteins shown in FIGS. 1A and 1B, 2A and 2B, and 3A and 3B (SEQ ID NO:2, SEQ ID NO:4, and SEQ ID NO:6, respectively). The TR11, TR11SV1, and TR11SV2 proteins shown in FIGS. 1A and 1B, 2A and 2B, and 3A and 3B are examples of such receptor proteins.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A and 1B, 2A and 2B, and 3A and 3B, nucleic acid molecules of the present invention encoding TR11, TR11SV1, and TR11SV2 polypeptides may be obtained using standard cloning and screening procedures, such as those used for cloning cDNAs using mRNA as starting material. Illustrative of the invention, the nucleic acid molecule described in FIGS. 1A and 1B (SEQ ID NO:1) was discovered in a cDNA library derived from T-helper cells. A cDNA clone encoding the TR11 polypeptide shown in FIG. 1A was not found in any other cDNA libraries examined. The nucleic acid molecule described in FIGS. 2A and 2B (SEQ ID NO:3) was discovered in a cDNA library derived from T-cells stimulated with PHA for 16 hours. A cDNA clone encoding the TR11SV1 polypeptide shown in FIGS. 2A and 2B was not found in any other cDNA libraries examined. Finally, the nucleic acid molecule described in FIGS. 3A and 3B (SEQ ID NO:5) was discovered in a cDNA library derived from activated T-cells. A cDNA clone encoding the TR11SV2 polypeptide shown in FIGS. 3A and 3B was not found in any other cDNA libraries examined.

The determined nucleotide sequence of the TR11 cDNA of FIGS. 1A and 1B (SEQ ID NO: 1) contains an open reading frame encoding a protein of about 241 amino acid residues, with a single potential predicted leader sequence of about 25 amino acid residues, and a deduced molecular weight of about 25,113 Da. The amino acid sequence of the potential predicted mature TR11 receptor is shown in FIGS. 1A and 1B, from amino acid residue about 26 to residue about 234 (amino acid residues 1 to 209 in SEQ ID NO:2). The TR11 protein shown in FIGS. 1A and 1B (SEQ ID NO:2) is about 58.6% identical and about 74.1% similar to the murine mGITR receptor protein shown in SEQ ID NO:7 (see FIGS. 4A and 4B) using the computer program "Bestfit".

The determined nucleotide sequence of the TR11SV1 cDNA of FIGS. 2A and 2B (SEQ ID NO:3) contains an open reading frame encoding a protein of about 241 amino acid residues, with a deduced molecular weight of about 26,029 Da. The TR11 protein shown in FIGS. 2A and 2B (SEQ ID NO:4) is about 53.1% identical and about 67.5% similar to the murine GITR receptor protein shown in SEQ ID NO:7 (see FIGS. 4A and 4B) using the computer program "Bestfit".

The determined nucleotide sequence of the TR11SV2 cDNA of FIGS. 3A and 3B (SEQ ID NO:5) contains an open reading frame encoding a protein of about 240 amino acid residues, with a single potential predicted leader sequence of about 19 amino acid residues, and a deduced molecular weight of about 25,727 Da. The amino acid sequence of the potential predicted mature TR11SV2 receptor is shown in FIGS. 3A and 3B, from amino acid residue about 20 to residue about 240 (amino acid residues 1 to 221 in SEQ ID NO:6). The TR11SV2 protein shown in FIGS. 3A and 3B (SEQ ID NO:6) is about 58.6% identical and about 74.1% similar to the murine GITR receptor protein shown in SEQ ID NO:7 (see FIGS. 4A and 4B) using the computer program "Bestfit".

GITR is a 228 amino acid type I transmembrane protein characterized by three cysteine pseudorepeats in the extracellular domain and is similar to CD27 and 4-1BB in the intracellular domain. GITR specifically protects T-cell receptor-induced apoptosis, although other apoptotic signals, including Fas triggering, dexamethasone treatment, or UV irradiation, do not. Thus, GITR is a new member of tumor necrosis factor/nerve growth factor receptor family and appears to be involved in the regulation of T-cell receptor-mediated cell death (Nocentini G, et al., *Proc. Natl. Acad. Sci. USA* 94:6216–6221 (1997)). Based on the high degree of conservation with murine GITR at the amino acid level, it is likely that TR11, TR11SV1, and TR11SV2 may also be involved in the regulation of cell-type specific receptor-mediated cell growth, differentiation, and, ultimately, cell death.

As indicated, the present invention also provides mature forms of the TR11 and TR11 SV2 receptors of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides nucleotide sequences encoding mature TR11 and TR11 SV2 polypeptides having the amino acid sequences encoded by the cDNA clones contained in ATCC Deposit Numbers 209341 and 209342 and as shown in FIGS. 1A and 1B and 3A and 3B, respectively (SEQ ID NO:2 and SEQ ID NO:6, respectively). By the mature TR11 and TR11 SV2 polypeptides having the amino acid sequences encoded by "the cDNA clones contained in ATCC Deposit Numbers 209341 and 209342" is meant the mature form(s) of the TR11 and TR11 SV2 receptors produced by expression in a mammalian cell (e.g., COS cells, as described below) of the complete open reading frame encoded by the human DNA sequence of the deposited clones.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80% (von Heinje, *supra*). However, the two methods do not always produce the same predicted cleavage point(s) for a given protein.

In the present case, the predicted amino acid sequences of the complete TR11, TR11SV1, and TR11SV2 polypeptides shown in FIGS. 1A and 1B, 2A and 2B, and 3A and 3B (SEQ ID NO:2, SEQ ID NO:4, and SEQ ID NO:6) were analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted a signal peptide cleavage site between amino acids 25 and 26 in FIGS. 1A and 1B (−1 and +1 in SEQ ID NO:2). Thus, the potential leader sequence for the TR11 protein shown in SEQ ID NO:2 is predicted to consist of amino acid residues −25 to −1 in SEQ ID NO:2, while the predicted mature TR11 protein consists of amino acid residues 1 to 209 for the TR11 protein shown in SEQ ID NO:2. Further, the analysis by the PSORT program predicted no signal peptide cleavage sites for the TR11SV1 protein shown in SEQ ID NO:4. Finally, the analysis by the PSORT program predicted a single signal peptide cleavage site between amino acids 19 and 20 in FIGS. 3A and 3B (−1 and +1 in SEQ ID NO:6). Thus, the potential leader sequence for the TR11SV2 protein shown in SEQ ID NO:6 is predicted to consist of amino acid residues −19 to −1 in SEQ ID NO:6, while the predicted mature TR11SV2 protein consists of amino acid residues 1 to 221 for the TR11SV2 protein shown in SEQ ID NO:6.

As one of ordinary skill would appreciate, however, due to the possibilities of sequencing errors, as well as the variability of cleavage sites for leaders in different known proteins, the TR11, TR11SV1, and TR11SV2 receptor polypeptides encoded by the cDNAs of ATCC Deposit Numbers 209341, 209343 and 209342, respectively, comprise about 241 amino acids (but may be anywhere in the range of 224 to 251 amino acids), about 241 amino acids (but may be anywhere in the range of 231 to 251 amino acids), and about 240 amino acids (but may be anywhere in the range of 230 to 250 amino acids). Further, the predicted leader sequences of these proteins are about 25, 0, and 19 amino acids, but the actual leaders may be anywhere in the range of about 15 to about 35, about 20 to about 40, and about 9 to about 29 amino acids, respectively.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread", as in a karyotype), is not "isolated" for the purposes of this invention. As discussed further herein, isolated nucleic acid molecules according to the present invention may be produced naturally, recombinantly, or synthetically.

Isolated nucleic acid molecules of the present invention include DNA molecules comprising an open reading frame (ORF) shown in FIGS. 1A and 1B (SEQ ID NO: 1); DNA molecules comprising the coding sequence for the mature TR11 receptor shown in FIGS. 1A and 1B (SEQ ID NO:2; about the last 209 amino acids; and DNA molecules which comprise a sequence substantially different from those described above but which, due to the degeneracy of the genetic code, still encode the TR11 receptor protein shown in FIG. 1A (SEQ ID NO:2). Isolated nucleic acid molecules of the present invention include DNA molecules comprising an open reading frame (ORF) shown in FIGS. 2A and 2B (SEQ ID NO:3); DNA molecules comprising the coding sequence for the mature TR11SV1 receptor shown in FIGS. 2A and 2B (SEQ ID NO:4; : about the last 241 amino acids); and DNA molecules which comprise a sequence substantially different from those described above but which, due to the degeneracy of the genetic code, still encode the TR11SV1 receptor protein shown in FIGS. 2A and 2B (SEQ ID NO:4). Isolated nucleic acid molecules of the present invention include DNA molecules comprising an open reading frame (ORF) shown in FIGS. 3A and 3B (SEQ ID NO:5); DNA molecules comprising the coding sequence for the mature TR11SV2 receptor shown in FIGS. 3A and 3B (SEQ ID NO:6; about the last 221 amino acids); and DNA molecules which comprise a sequence substantially different from those described above but which, due to the degeneracy of the genetic code, still encode the TR11SV2 receptor protein shown in FIGS. 3A and 3B (SEQ ID NO:6). Of course, the genetic code is well known in the art. Thus, it would be routine for one skilled in the art to generate such degenerate variants.

In another aspect, the invention provides isolated nucleic acid molecules encoding the TR11, TR11SV1, and TR11SV2 polypeptides having the amino acid sequence encoded by the cDNA clones contained in the plasmids deposited as ATCC Deposit Nos. 209341, 209343 and 209342, respectively, on Oct. 7, 1997. In a further embodiment, these nucleic acid molecules will encode a mature polypeptide or the full-length polypeptide lacking the N-terminal methionine. The invention further provides isolated nucleic acid molecules having the nucleotide sequences shown in FIGS. 1A and 1B (SEQ ID NO:1), 2A and 2B (SEQ ID NO:3), and 3A and 3B (SEQ ID NO:5), the nucleotide sequences of the cDNAs contained in the above-described deposited clones; or nucleic acid molecules having a sequence complementary to one of the above sequences. Such isolated molecules, particularly DNA molecules, are useful as probes for gene mapping, by in situ hybridization with chromosomes, and for detecting expression of the TR11, TR11SV1, and TR11SV2 receptor genes of the present invention in human tissue, for instance, by Northern blot analysis.

In addition, the invention provides nucleic acid molecules having nucleotide sequences related to extensive portions of SEQ ID NO: 1, SEQ ID NO:3, and SEQ ID NO:5 which have been determined from the following related cDNA clones: HEAC71RA (SEQ ID NO:8) and HCFAZ22R (SEQ ID NO:9).

The present invention is further directed to fragments of the isolated nucleic acid molecules described herein. By a fragment of an isolated nucleic acid molecule having the nucleotide sequence of the deposited cDNA or the nucleotide sequences shown in FIGS. 1A and 1B, 2A and 2B, and 3A and 3B (SEQ ID NO:1, SEQ ID NO:3, and SEQ ID NO:5, respectively) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–400 nt in length are also useful according to the present invention as are fragments corresponding to most, if not all, of the nucleotide sequences of the deposited cDNAs or as shown in FIGS. 1A and 1B, 2A and 2B, and 3A and 3B (SEQ ID NO:1, SEQ ID NO:3, and SEQ ID NO:5, respectively). By a fragment at least 20 nt in length, for example, is intended fragments which include 20 or more contiguous bases from the nucleotide sequences of the deposited cDNAs or the nucleotide sequence as shown in FIGS. 1A and 1B, 2A and 2B, and 3A and 3B (SEQ ID NO:1, SEQ ID NO:3, and SEQ ID NO:5, respectively). Further, the present invention is also directed to an isolated fragment of a nucleic acid molecule, comprising a polynucleotide having a sequence shown in FIGS. 1A and 1B, 2A and 2B, and 3A and 3B (SEQ ID NO:1, SEQ ID NO:3, and SEQ ID NO:5, respectively), or any sequence complementary to those shown in FIGS. 1A and 1B, 2A and 2B and 3A and 3B (SEQ ID NO: 1, SEQ ID NO:3, and SEQ ID NO:5, respectively), wherein said fragment comprises at least 30 to 50 contiguous nucleotides from SEQ ID NO:1, SEQ ID NO:3 or SEQ ID NO:5, provided that said isolated nucleic acid molecule is not SEQ ID NO:8, SEQ ID NO:9 or any subfragment thereof.

Preferred nucleic acid fragments of the present invention include nucleic acid molecules encoding: a polypeptide comprising the TR11 receptor protein of FIGS. 1A and 1B (SEQ ID NO:2) extracellular domain (predicted to constitute amino acid residues from about 26 to about 162 in FIGS. 1A and 1B (amino acid residues 1 to 137 in SEQ ID NO:2)); a polypeptide comprising the TR11SV1 receptor protein of FIGS. 2A and 2B (SEQ ID NO:4) extracellular domain (predicted to constitute amino acid residues from about 1 to about 162 in FIGS. 2A and 2B (amino acid residues 1 to 162 in SEQ ID NO:4)); a polypeptide comprising the TR11SV2 receptor protein of FIGS. 3A and 3B (SEQ ID NO:6) extracellular domain (predicted to constitute amino acid residues from about 20 to about 168 in FIGS. 3A and 3B (amino acid residues 1 to 149 in SEQ ID NO:6)); a polypeptide comprising the TR11 receptor transmembrane domain (amino acid residues 163 to 179 in FIGS. 1A and 1B (amino acid residues 138 to 154 in SEQ ID NO:2)); a polypeptide comprising the TR11SV1 receptor transmembrane domain (amino acid residues 163 to 179 in FIGS. 2A and 2B (amino acid residues 163 to 179 in SEQ ID NO:4)); a polypeptide comprising the TR11SV2 receptor transmembrane domain (amino acid residues 169 to 185 in FIGS. 3A and 3B (amino acid residues 150 to 166 in SEQ ID NO:6)); a polypeptide comprising the TR11 receptor intracellular domain (predicted to constitute amino acid residues from about 180 to about 234 in FIGS. 1A and 1B (amino acid residues 155 to 209 in SEQ ID NO:2)); a polypeptide comprising the TR11SV1 receptor intracellular domain (predicted to constitute amino acid residues from about 180 to about 241 in FIGS. 2A and 2B (amino acid residues 180 to 241 in SEQ ID NO:4)); a polypeptide comprising the TR11SV2 receptor intracellular domain (predicted to constitute amino acid residues from about 186 to about 240 in FIGS. 3A and 3B (amino acid residues 167 to 221 in SEQ ID NO:6)); a polypeptide comprising the TR11 receptor protein of FIGS. 1A and 1B (SEQ ID NO:2) extracellular and intracellular domains with all or part of the transmembrane domain deleted; a polypeptide comprising the TR11SV1 receptor protein of FIGS. 2A and 2B (SEQ ID NO:4) extracellular and intracellular domains with all or part of the transmembrane domain deleted; and a polypeptide comprising the TR11SV2 receptor protein of FIGS. 3A and 3B (SEQ ID NO:6) extracellular and intracellular domains with all or part of the transmembrane domain deleted.

As above with the leader sequence, the amino acid residues constituting the extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding epitope-bearing portions of the TR11 receptor proteins. In particular, such nucleic acid fragments of the present invention include nucleic acid molecules encoding: a polypeptide comprising amino acid residues from about Arg-2 to about Gly-11 in SEQ ID NO:2; a polypeptide comprising amino acid residues from about Thr-18 to about Arg-26 in SEQ ID NO:2; a polypeptide comprising amino acid residues from about Arg-34 to about Cys-42 in SEQ ID NO:2; a polypeptide comprising amino acid residues from about Arg-31 to about Glu-39 in SEQ ID NO:2; a polypeptide comprising amino acid residues from about Gly-38 to about Asp-46 in SEQ ID NO:2; a polypeptide comprising amino acid residues from about Gly-74 to about Ser-82 in SEQ ID NO:2; a polypeptide comprising amino acid residues from about Glu-100 to about Asp-108 in SEQ ID NO:2; a polypeptide comprising amino acid residues from about Phe-118 to about Ala-126 in SEQ ID NO:2; a polypeptide comprising amino acid residues from about Gly-131 to about Gly-139 in SEQ ID NO:2; a polypeptide comprising amino acid residues from about Pro-178 to about Cys-186 in SEQ ID NO:2; and a polypeptide comprising amino acid residues from about Ser-197 to about Gly-205 in SEQ ID NO:2. The inventors have determined that the above polypeptide fragments are antigenic regions of the TR11 receptors. Methods for determining other such epitope-bearing portions of the TR11 proteins are described in detail below.

Preferred nucleic acid fragments of the present invention further include nucleic acid molecules encoding epitope-bearing portions of the TR11SV1 receptor proteins. In particular, such nucleic acid fragments of the present invention include nucleic acid molecules encoding: a polypeptide comprising amino acid residues from about Ala-2 to about Ee-10 in SEQ ID NO:4; a polypeptide comprising amino acid residues from about Asn-11 to about Gly-19 in SEQ ID NO:4; a polypeptide comprising amino acid residues from about Thr-27 to about Ser-35 in SEQ ID NO:4; a polypeptide comprising amino acid residues from about Trp-38 to about Glu46 in SEQ ID NO:4; a polypeptide comprising amino acid residues from about Gly-42 to about Ser-50 in SEQ ID NO:4; a polypeptide comprising amino acid residues from about Glu-31 to about Glu-46 in SEQ ID NO:4; a polypeptide comprising amino acid residues from about Cys-61 to about Glu-69 in SEQ ID NO:4; a polypeptide comprising amino acid residues from about Gly-99 to about Ser-107 in SEQ ID NO:4; a polypeptide comprising amino acid residues from about Glu-125 to about Asp-133 in SEQ ID NO:4; a polypeptide comprising amino acid residues from about Phe-143 to about Ala-151 in SEQ ID NO:4; a polypeptide comprising amino acid residues from about Gly-156 to about Gly-164 in SEQ ID NO:4; a polypeptide comprising amino acid residues from about Cys-196 to about Leu-204 in SEQ ID NO:4; a polypeptide comprising amino acid residues from about Pro-209 to about Ser-217 in SEQ ID NO:4; and a polypeptide comprising amino acid residues from about Ser-229 to about Gly-237 in SEQ ID NO:4. The inventors have determined that the above polypeptide fragments are antigenic regions of the TR11SV1 receptors. Methods for determining other such epitope-bearing portions of the TR11SV1 proteins are described in detail below.

Preferred nucleic acid fragments of the present invention also include nucleic acid molecules encoding epitope-bearing portions of the TR11SV2 receptor proteins. In particular, such nucleic acid fragments of the present invention include nucleic acid molecules encoding: a polypeptide comprising amino acid residues from about Gln-1 to about Cys-9 in SEQ ID NO:6; a polypeptide comprising amino acid residues from about Gly-5 to about Arg-13 in SEQ ID NO:6; a polypeptide comprising amino acid residues from about Thr-18 to about Arg-26 in SEQ ID NO:6; a polypeptide comprising amino acid residues from about Thr-29 to about Pro-37 in SEQ ID NO:6; a polypeptide comprising amino acid residues from about Cys-48 to about Glu-56 in SEQ ID NO:6; a polypeptide comprising amino acid residues from about Val-87 to about Phe-95 in SEQ ID NO:6; a polypeptide comprising amino acid residues from about His-111 to about Thr-119 in SEQ ID NO:6; a polypeptide comprising amino acid residues from about Phe-130 to about Ala-138 in SEQ ID NO:6; a polypeptide comprising amino acid residues from about Gly-143 to about Gly-151 in SEQ ID NO:6; a polypeptide comprising amino acid residues from about Pro-190 to about Cys-198 in SEQ ID NO:6; and a polypeptide comprising amino acid residues from about Ser-209 to about Gly-217 in SEQ ID NO:6. The inventors have determined that the above polypeptide fragments are antigenic regions of the TR11SV2 receptors. Methods for determining other such epitope-bearing portions of the TR11SV2 proteins are described in detail below.

It is believed that the cysteine-rich motifs of TR11 are important for interactions between TR11 and its ligands. Accordingly, specific embodiments of the invention are directed to nucleic acid molecules comprising, or alternatively consisting of a polypeptide sequence encoding amino acids 9 to 47, 49 to 86, or 90 to 128 of SEQ ID NO:2. In a specific embodiment, the nucleic acid molecules of the invention comprise, or alternatively consist of, polynucleotide sequences encoding any combination of two, or all three of the above-recited TR11 cysteine-rich motifs. Polypeptides encoded by these polynucleotides are also encompassed by the invention.

In another embodiment, the invention provides isolated nucleic acid molecules comprising polynucleotides which hybridizes under stringent hybridization conditions to a portion of the polynucleotide of one of the nucleic acid molecules of the invention described above, for instance, the cDNA clones contained in ATCC Deposit Nos. 209341, 209343 and 209342, respectively. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequences as shown in FIGS. 1A and 1B, 2A and 2B, and 3A and 3B (SEQ ID NO:1, SEQ ID NO:3, and SEQ ID NO:5, respectively).

Of course, a polynucleotide which hybridizes only to a poly A sequence (such as the 3' terminal poly(A) tract of a cDNA sequence), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode TR11, TR11SV1 or TR11SV2 polypeptides may include, but are not limited to those encoding the amino acid sequences of the mature polypeptides, by themselves; the coding sequences for the mature polypeptides and additional sequences, such as those encoding the potential leader or signal peptide sequences, such as pre-, or pro- or prepro-protein sequences; the coding sequences of the mature polypeptides, with or without the aforementioned additional coding sequences, together with additional, non-coding sequences, including for example, but not limited to, introns and non-coding 5' and 3' sequences, such as the transcribed, non-translated sequences that play a role in transcription, mRNA processing, including splicing and polyadenylation signals, for example-ribosome binding and stability of mRNA; an additional coding sequence which codes for additional amino acids, such as those which provide additional functionalities. Thus, the sequences encoding the polypeptides may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described by Gentz and colleagues (*Proc. Natl. Acad. Sci. USA* 86:821–824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the TR11 receptors fused to IgG-Fc or human serum albumin at the N- or C-terminus.

The present invention further relates to variants of the nucleic acid molecules of the present invention, which encode portions, analogs or derivatives of the TR11, TR11SV1, and TR11SV2 receptors. Variants may occur naturally, such as a natural allelic variant. By an "allelic variant" is intended one of several alternate forms of a gene occupying a given locus on a chromosome of an organism. *Genes II,* Lewin, B., ed., John Wiley & Sons, New York (1985). Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., Nucl. Acids Res. 13:4331 (1986); and Zoller et al., Nucl. Acids Res. 10:6487 (1982)), cassette mutagenesis (see e.g., Wells et al., Gene 34:315 (1985)), restriction selection mutagenesis (see e.g., Wells et al., Philos. Trans. R. Soc. London SerA 317:415 (1986)).

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TR11, TR11SV1, and TR11SV2 receptors or portions thereof. Also especially preferred in this regard are conservative substitutions.

Further embodiments of the invention include isolated nucleic acid molecules comprising a polynucleotide having a nucleotide sequence at least 80%, 85%, or 90% identical, and more preferably at least 95%, 96%, 97%, 98% or 99% identical to: (a) a nucleotide sequence encoding the TR11 polypeptide having the complete amino acid sequence shown in FIGS. 1A and 1B (amino acid residues -25 to 209 in SEQ ID NO:2); (b) a nucleotide sequence encoding the TR11SV1 polypeptide having the complete amino acid sequence shown in FIGS. 2A and 2B (amino acid residues 1 to 241 in SEQ ID NO:4); (c) a nucleotide sequence encoding the TR11SV2 polypeptide having the complete amino acid sequence shown in FIGS. 3A and 3B (amino acid residues -19 to 221 in SEQ ID NO:6); (d) a nucleotide encoding the complete amino sequence shown in FIGS. 1A and 1B but lacking the N-terminal methionine (i.e., amino acids -24 to 209 in SEQ ID NO:2); (e) a nucleotide encoding the complete amino sequence shown in FIGS. 2A and 2B but lacking the N-terminal methionine (i.e., amino acids 2 to 241 in SEQ ID NO:4); (f) a nucleotide encoding the complete amino sequence shown in FIGS. 3A and 3B but lacking the N-terminal methionine (i.e., amino acids -18 to 221 in SEQ ID NO:6); (g) a nucleotide sequence encoding the predicted mature TR11 receptor comprising the amino acid sequence at positions from 26 to 234 in FIGS. 1A and 1B (amino acid residues 1 to 209 in SEQ ID NO:2); (h) a nucleotide sequence encoding the predicted mature TR11SV 1 receptor comprising the amino acid sequence at positions from 1 to 241 in FIGS. 2A and 2B (amino acid residues 1 to 241 in SEQ ID NO:4); (i) a nucleotide sequence encoding the predicted mature TR1SV2 receptor comprising the amino acid sequence at positions from 20 to 240 in FIGS. 3A and 3B (amino acid residues 1 to 221 in SEQ ID NO:6); 6) a nucleotide sequence encoding the TR11 polypeptide having the complete amino acid sequence including the leader encoded by the cDNA clone contained in ATCC Deposit Number 209341; (k) a nucleotide sequence encoding the TR11SV1 polypeptide having the complete amino acid sequence including the leader encoded by the cDNA clone contained in ATCC Deposit Number 209343; (l) a nucleotide sequence encoding the TR11SV2 polypeptide having the complete amino acid sequence including the leader encoded by the cDNA clone contained in ATCC Deposit Number 209342; (m) a nucleotide sequence encoding the mature TR11 receptor having the amino acid sequences encoded by the cDNA clone contained in ATCC Deposit Number 209341; (n) a nucleotide sequence encoding the mature TR11SV1 receptor having the amino acid sequences encoded by the cDNA clone contained in ATCC Deposit Number 209343; (o) a nucleotide sequence encoding the mature TR11SV2 receptor having the amino acid sequences encoded by the cDNA clone contained in ATCC Deposit Number 209342; (p) a nucleotide sequence encoding the TR11 receptor extracellular domain; (q) a nucleotide sequence encoding the TR11SV1 receptor extracellular domain; (r) a nucleotide sequence encoding the TR11SV2 receptor extracellular domain; (s) a nucleotide sequence encoding the TR11 receptor transmembrane domain; (t) a nucleotide sequence encoding the TR11SV1 receptor transmembrane domain; (u) a nucleotide sequence encoding the TR11SV2 receptor transmembrane domain; (v) a nucleotide sequence encoding the TR11 receptor intracellular domain; (w) a nucleotide sequence encoding the TR11SV1 receptor intracellular domain; (x) a nucleotide sequence encoding the TR11SV2 receptor intracellular domain; (y) a nucleotide sequence encoding the TR11 receptor extracellular and intracellular domains with all or part of the transmembrane domain deleted; (z) a nucleotide sequence encoding the TR11SV1 receptor extracellular and intracellular domains with all or part of the transmembrane domain deleted; (aa) a nucleotide sequence encoding the TR11SV2 receptor extracellular and intracellular domains with all or part of the transmembrane domain deleted; and (bb) a nucleotide sequence complementary to any of the nucleotide sequences in (a), (b), (c), (d), (e), (f), (g), (h), (i), (j), (k), (l), (in), (n), (o), (p), (q), (r), (s), (t), (u), (v), (w), (x), (y), (z) or (aa). Polypeptides encoded by In another embodiment, the invention provides an isolated nucleic acid molecule comprising a polynucleotide which hybridizes under stringent hybridization conditions to the complement of a polynucleotide sequence encoding one, two, or all three of the cysteine-rich motifs described above, or the complimentary strand thereto (e.g., the sequence of SEQ ID NO: 1). The meaning of the phrase "stringent conditions" as used herein is described infra. Polypeptides encoded by these polynucleotides are also encompassed by the invention.

A further nucleic acid embodiment of the invention relates to an isolated nucleic acid molecule comprising a polynucleotide which encodes the amino acid sequence of a TR11, TR11SV1 and/or TR11SV2 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a TR11, TR11SV1 or TR11SV2 polypeptide to have an amino acid sequence which contains not more than 7–10, 5–10, 3–7, 3–5, 2–5, 1–5, 1–3, 10, 9, 8, 7, 6, 5, 4, 3, 2 or 1 conservative amino acid substitutions. Polypeptides encoded by these polynucleotides are also encompassed by the invention.

The present invention also relates to recombinant vectors, which include the isolated nucleic acid molecules of the present invention, and to host cells containing the recombinant vectors, as well as to methods of making such vectors and host cells and for using them for production of TR11, TR11SV1 or TR11SV2 polypeptides or peptides by recombinant techniques.

By a polynucleotide having a nucleotide sequence at least, for example, 95% "identical" to a reference nucleotide sequence encoding a TR11, TR11SV1 or TR11SV2 polypeptide is intended that the nucleotide sequence of the polynucleotide is identical to the reference sequence except that the polynucleotide sequence may include up to five point mutations per each 100 nucleotides of the reference nucleotide sequence encoding the TR11, TR11SV1 or TR11SV2 receptors. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80%, 85%, 90%, 95%, 96%, 97%, 98% or 99% identical to, for instance, the nucleotide sequence shown in FIGS. 1A and 1B, 2A and 2B, and/or 3A and 3B, or to the nucleotides sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determining the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 80%, 85%, 90%, 95%, 96%, 97%, 98% or 99% identical to the nucleic acid sequences shown in FIGS. 1A and 1B, 2A and 2B, and 3A and 3B (SEQ ID NO:1, SEQ ID NO:3, and SEQ ID NO:5, respectively) or to the nucleic acid sequence of the deposited cDNAs, irrespective of whether they encode a polypeptide having TR11, TR11SV1 or TR11SV2 receptor activity. The present application is also directed to nucleic acid molecules at least 80%, 85%, 90%, 95%, 96%, 97%, 98% or 99% identical to the nucleic acid sequences encoding polypeptides set forth herein as $n^1$-$m^1$, $n^2$-$m^2$, $n^3$-$m^3$, $n^4$-$m^4$, $n^5$-$m^5$, $n^6$-$m^6$, and/or $n^7$-$m^7$, irrespective of whether they encode a polypeptide having TR11, TR11SV1 or TR11SV2 receptor activity. Polypeptides encoded by these polynucleotides are also encompassed by the invention.

In preferred embodiments, the application is directed to nucleic acid molecules at least 80%, 85%, 90%, 95%, 96%, 97%, 98% or 99% identical to the nucleic acid sequences encoding polypeptides having the amino acid sequence of the specific N- and C-terminal deletions recited herein, irrespective of whether they encode a polypeptide having TR11, TR11SV1 or TR11SV2 receptor activity. Polypeptides encoded by these polynucleotides are also encompassed by the invention.

The invention is directed to polynucleotides irrespective of whether they encode a polypeptide having TR11, TR11SV, or TR11SV2 receptor activity because, even where a particular nucleic acid molecule does not encode a polypeptide having TR11, TR11SV1 or TR11SV2 receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR11, TR11SV1 or TR11SV2 receptor activity include, inter alia, (1) isolating a TR11, TR11SV1 or TR11SV2 receptor gene or allelic or splice variants thereof in a cDNA library; (2) in situ hybridization (e.g., "FISH") to metaphase chromosomal spreads to provide precise chromosomal location of a TR11, TR11SV1 or TR11SV2 receptor gene, as described by Verma and colleagues (*Human Chromosomes: A Manual of Basic Techniques,* Pergamon Press, New York (1988)); and (3) Northern Blot analysis for detecting TR11, TR11SV1 or TR11SV2 receptor mRNA expression in specific tissues.

Preferred, however, are nucleic acid molecules having sequences at least 80%, 85%, 90%, 95%, 96%, 97%, 98% or 99% identical to the nucleic acid sequences shown in FIGS. 1A and 1B, 2A and 2B, and 3A and 3B (SEQ ID NO:1, SEQ ID NO:3, and SEQ ID NO:5, respectively) or to the nucleic acid sequence of the deposited cDNAs which do, in fact, encode a polypeptide having TR11, TR11SV1, and TR11SV2 receptor functional activity, respectively. Polypeptides encoded by these polynucleotides are also encompassed by the invention.

By "a polypeptide having TR11, TR11SV1, and TR11SV2 receptor activity" is intended polypeptides exhibiting activity similar, but not necessarily identical, to an activity of the TR11, TR11SV1, and TR11SV2 receptors of the present invention (either the full-length protein, the splice variants, or, preferably, the mature protein), as measured in a particular biological assay. For example, TR11, TR11SV1, and TR11SV2 receptor activities can be measured by determining the ability of a TR11, TR11SV1, or TR11SV2 polypeptide-Fc fusion protein to inhibit or stimulate lymphocyte (e.g., T cell) proliferation, differentiation or activation and/or to extend T cell survival. TR11, TR11SV1, and TR11SV2 receptor activities may also be measured by determining the ability of a polypeptide, such as cognate ligand (e.g., Endokine-alpha and APRIL) which is free or expressed on a cell surface, to confer, inhibit, or reduce, T cell proliferatory activity, differentiation, activation, and/or increase or decrease T cell survival, in intact cells expressing one or more of the receptors (e.g., activated T cells).

Of course, due to the degeneracy of the genetic code, one of ordinary skill in the art will immediately recognize that a large number of the nucleic acid molecules having a sequence at least 80%, 85%, 90%, 95%, 96%, 97%, 98%, or 99% identical to the nucleic acid sequences of the deposited cDNAs or the nucleic acid sequence shown in FIGS. 1A and 1B, 2A and 2B, and 3A and 3B (SEQ ID NO:1, SEQ ID NO:3, and SEQ ID NO:5, respectively) will encode polypeptides "having TR11, TR11SV1 or TR11SV2 receptor activity." In fact, since degenerate variants of any of these nucleotide sequences all encode the same polypeptide, this will be clear to the skilled artisan even without performing the above described comparison assays. It will be further recognized in the art that, for such nucleic acid molecules that are not degenerate variants, a reasonable number will also encode a polypeptide having TR11, TR11SV1 or TR11SV2 protein activities. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided by Bowie and colleagues ("Deciphering the Message in Protein Sequences: Tolerance to Amino Acid Substitutions," *Science* 247:1306–1310 (1990)), wherein the authors indicate that proteins are surprisingly tolerant of amino acid substitutions.

Production of TR11, TR11SV1, and TR11SV2 Polypeptides

The present invention also relates to vectors which include the isolated DNA molecules of the present invention, host cells which are genetically engineered with the recombinant vectors, and the production of TR11, TR11SV1, and TR11SV2 polypeptides or fragments thereof by recombinant or synthetic techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate heterologous hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pHE4 (ATCC Accession Number 209645), pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWL EO, pSV2CAT, pOG44, pXT1 and pSG available from Stratagene; and pSVK3, pBPV, pMSG and pSVL available from Pharmacia. Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, pPIC9K, and PA0815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

TR11, TR11SV1, and/or TR11SV2 polypeptides can be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

TR11, TR11SV1, and/or TR11SV2 polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eufkaryotic host, including, for example, bacterial, yeast, higher plant, insect, and mammalian cells.

In one embodiment, the yeast Pichia pastoris is used to express TR11, TR11SV1, and/or TR11SV2 protein in aeukaryotic system. Pichia pastoris is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111–21 (1985); Koutz, P. J, et al., Yeast 5:167–77 (1989); Tschopp, J. F., et al., Nudl. Acids Res. 15:3859–76 (1987). Thus, a heterologous coding sequence, such as, for example, a TR11, TR11SV1, and/or TR11SV2 polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a TR11, TR11SV1, and/or TR11SV2 polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a TR11, TR11SV1, and/or TR11SV2 protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PA0815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a TR11, TR11SV1, and/or TR11SV2 polynucleotide of the present invention, may be achieved by cloning the heterologous polynucleotide of the invention into an expression vector such as, for example, pGAPZ or pGAPZalpha, and growing the yeast culture in the absence of methanol.

Depending upon the host employed in a recombinant production procedure, the TR11, TR11SV1, and/or TR11SV2 polypeptides may be glycosylated or may be non-glycosylated. In addition, TR11, TR11SV1, and/or TR11SV2 polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TR11, TR11SV1 and/or TR11SV2 coding sequence), and/or to include genetic material (e.g., heterologous polynucleotide sequences) that is operably associated with TR11, TR11SV1 and/or TR11SV2 polynucleotides of the invention, and which activates, alters, and/or amplifies endogenous TR11, TR11SV1 and/or TR11SV2 polynucleotides. For example, techniques known in the art may be used to operably associate heterologous control regions (e.g., promoter and/or enhancer) and endogenous TR11, TR11SV1 and/or TR11SV2 polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

The polypeptides of the invention may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins.

For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor has been fused with Fc portions for the purpose of high-throughput screening assays to identify antagonists of hIL-5. See, D. Bennett et al., Journal of Molecular Recognition, Vol. 8:52–58 (1995) and K. Johanson et al., J. Biol. Chem., 270(16):9459–9471 (1995).

In certain preferred embodiments, TR11, TR11SV1 and/or TR11SV2 polypeptides of the invention comprise fusion proteins wherein the TR11, TR11SV1 and/or TR11SV2 polypeptides are those described as $n^1$-$m^1$, $n^2$-$m^2$, $n^3$-$n^3$, $n^4$-$m^4$, $n^5$-$m^5$, $n^6$-$m^6$, $n^7$-$m^7$ herein. In preferred embodiments, the invention is directed to nucleic acid molecules at least 80%, 85%, 90%, 95%, 96%, 97%, 98% or 99% identical to the nucleic acid sequences encoding polypeptides having the amino acid sequence of the specific N- and C-terminal deletions recited herein.

In addition, polypeptides of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310:105–111). For example, a peptide corresponding to a fragment of the TR11, TR11SV1 and/or TR11SV2 polypeptides of the invention can be synthesized by use of a peptide synthesizer. Furthermore, if desired, nonclassical amino acids or chemical amino acid analogs can be introduced as a substitution or addition into the TR11, TR11SV1 and/or TR11SV2 polynucleotide sequence. Nonclassical amino acids include, but are not limited to, to the D-isomers of the common amino acids, 2,4-diaminobutyric acid, alpha-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, alpha-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to, oligonucleotide mediated 1; mutagenesis, alanine scanning, PCR mutagenesis, site directed mutagenesis (see, e.g., Carter et al., Nucl. Acids Res. 13:4331 (1986); and Zoller et al., Nucl. Acids Res. 10:6487 (1982)), cassette mutagenesis (see, e.g., Wells et al., Gene 34:315 (1985)), restriction selection mutagenesis (see, e.g., Wells et al., Philos. Trans. R. Soc. London SerA 317:415 (1986)).

The invention encompasses TR11, TR11SV1 and/or TR11SV2 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, 1 including but not limited to, specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or 0-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of TR11, TR11SV1 and/or TR11SV2 which may provide additional advantages such as increased solubility, stability and circulating time of the polypeptide, or decreased immunogenicity (see U. S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59–72 (1996); Vorobjev et al., Nucleosides Nucleotides 18:2745–2750 (1999); and Caliceti et al., Bioconjug. Chem. 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249–304 (1992); Francis et al., Intern. J. of Hematol. 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached Lo amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., Crit. Rev. Thera. Drug Carrier Sys. 9:249–304 (1992).

TR11, TR11SV1 and TR11SV2 receptors can be recovered and purified from by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety. Further, the contents of each of the documents recited in this paragraph is herein incorporated by reference in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytocherically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of TR11, TR11SV1 and/or TR11SV2 polypeptides, studying conditions and/or disorders associated with aberrant TR11, TR11SV1 and/or TR11SV2 expression, and in screening for compounds effective in ameliorating such conditions and/or disorders.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible 1-cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

TR11, TR11SV1, and TR11SV2 Polypeptides and Fragments

The TR11 polypeptides of the invention may be in monomers or multimers (i.e., dimers, trimers, tetramers and higher multimers). Accordingly, the present invention relates to monomers and multimers of the TR11, TR11SV1 and/or TR11SV2 polypeptides of the invention, their preparation, and compositions (preferably, pharmaceutical lcompositions) containing them. Antibodies that bind to TR11, TR11SV1, and/or TR11SV2 monomers and/or multimers (e.g., TR11 homotrimers) of the invention are also encompassed by the invention. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only TR11, TR11SV1 and/or TR11SV2 polypeptides of the invention (including fragments, variants, and fusion proteins, as described herein, of TR11, TR11SV1 and/or TR11SV2). In specific embodiments, a TR11 homomer will contain only TR11 polypeptides of the invention (including fragments, variants, and fusion proteins, as described herein, of TR11), whereas a TR11SV1 homomer will contain only TR11SV1 polypeptides of the invention (including fragments, variants, and fusion proteins, as described herein, of TR11SV1), and a TR11SV2 homomer will contain only TR11SV2 polypeptides of the invention (including fragments, variants, and fusion proteins, as described herein, of TR11SV2). In other specific embodiments, homomers may contain TR11, TR11SV1 and/or TR11SV2 polypeptides having identical or different amino acid sequences. In a specific embodiment, a homomer of the invention is a multimer containing only TR11, TR11SV1 and/or TR11SV2 polypeptides having an identical amino acid sequence. In another specific embodiment, a homomer of the invention is a multimer containing TR11, TR11SV1 and/or TR11SV2 polypeptides having different amino acid sequences. In specific embodiments, the multimer of the invention is a homodimer (e.g., containing TR11, TR11SV1 and/or TR11SV2 polypeptides having identical or different amino acid sequences) or a homotrimer (e.g., containing TR11, TR11SV1 and/or TR11SV2 polypeptides having identical or different amino acid sequences). In additional embodiments, the homomeric multimer of the invention is at least a homodimer, at least a homotrimer, or at least a homotetramer.

As used herein, the term heteromer refers to a multimer containing heterologous polypeptides (i.e., polypeptides of a different protein) in addition to the TR11, TR11SV1 and/or TR11SV2 polypeptides of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the TR11, TR11SV1 and/or TR11SV2 polypeptides of the invention. Such covalent associations may involve one or more amino acid residues contained in the TR11, TR11SV1 and/or TR11SV2 polypeptide sequences (e.g., those recited in SEQ ID NO:2, SEQ ID NO:4 or SEQ ID NO:6, or contained in the respective TR11, TR11SV1 and TR11SV2 polypeptides encoded by the respective clones HBEAC71, HCFAZ22, and HT5EA78). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR11, TR11SV1 or TR11SV2 fusion protein. In one example, covalent associations are between the heterologous sequence contained in a fusion protein of the invention (see, e.g., U.S. Pat. No. 5,478,925). In a specific example, the covalent associations are between the heterologous sequence contained in a TR11-Fc, TR11SV1-Fc or TR11SV2-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more TR11, TR11SV1, TR11SV2 polypeptides of the invention are joined through synthetic linkers (e.g., peptide, carbohydrate or soluble polymer linkers). Examples include, but are not limited to, those peptide linkers described in U.S. Pat. No. 5,073,627 (hereby incorporated by reference). Proteins comprising multiple TR11, TR11SV1, TR11SV2 polypeptides separated by peptide linkers may be produced using conventional recombinant DNA technology.

Another method for preparing multimer TR11, TR11SV1, TR11SV2 polypeptides of the invention involves use of TR11, TR11SV1, TR11SV2 polypeptides fused to a leucine zipper or isoleucine zipper polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR11, TR11SV1, TR11SV2 proteins are those described in PCT application WO 94/10308, hereby incorporated by reference. Recombinant fusion proteins comprising a soluble TR11, TR11SV1, TR11SV2 polypeptide fused to a peptide that dimerizes or trimerizes in solution are expressed in suitable host cells, and the resulting soluble multimeric TR11, TR11SV1, TR11SV2 is recovered from the culture supernatant using techniques known in the art.

Certain members of the TNF family of proteins are believed to exist in trimeric form (Beutler and Huffel, *Science* 264:667, 1994; Banner et al., *Cell* 73:431, 1993). Thus, trimeric TR11, TR11SV1, TR11SV2 may offer the advantage of enhanced biological activity. Preferred leucine zipper moieties are those that preferentially form trimers (e.g., isoleucine zippers). One example is a leucine zipper derived from lung surfactant protein D (SPD), as described in Hoppe et al. (FEBS *Letters* 344:191, (1994)) and in U.S. patent application Ser. No. 08/446,922, hereby incorporated by reference. Other peptides derived from naturally occurring trimeric proteins may be employed in preparing trimeric TR11, TR11SV1, TR11SV2.

In another example, proteins of the invention are associated by interactions between Flag® polypeptide sequence contained in Flag®-TR11, TR11SV1, TR11SV2 or Flag®-TR11, TR11SV1, TR11SV2 fusion proteins of the invention. In a further embodiment, associations proteins of the invention are associated by interactions between heterologous polypeptide sequence contained in Flag®-TR11, TR11SV1, TR11SV2 or Flag®-TR11, TR11SV1, TR11SV2 fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, I-polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

Representative examples of TR11 polynucleotide fragments include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950 or 951 to the end of SEQ ID NO: 1 or the cDNA contained in the deposited clone. Polypeptides encoded by these polynucleotides are also encompassed by the invention. Representative examples of TR11SV1 polynucleotide fragments include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1007 or 951 to the end of SEQ ID NO:3 or the cDNA contained in the deposited clone. Polypeptides encoded by these polynucleotides are also encompassed by the invention. Representative examples of TR11SV2 polynucleotide fragments include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051 to the end of SEQ ID NO:5 or the cDNA contained in the deposited clone. Polypeptides encoded by these polynucleotides are also encompassed by the invention. In this context, "about" means the particularly recited ranges and ranges larger or smaller by several, a few, 5, 4, 3, 2 or 1 amino acid residues at either or both the amino- and carboxy-termini. Preferably, these fragments encode a polypeptide which has biological activity. More preferably, these polynucleotides can be used as probes or primers as discussed herein.

In the present invention, a "polypeptide fragment" refers to a amino acid sequence contained in SEQ ID NO:2, SEQ ID NO:4, SEQ ID NO:6 or encoded by the cDNA contained in the deposited clones. Protein fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, a sequence from about amino acid number 1–20, 21–40, 41–60, 61–80, 81–100, 102–120, 121–140, 141–160, 161–180, 181–200, 201–220, 221 to the end of the coding region of SEQ ID NO:2; 1–20, 21–40, 41–60, 61–80, 81–100, 102–120, 121–140, 141–160, 161–180, 181–200, 201–220, 221 to the end of the coding region of SEQ ID NO:4; or 1–20, 21–40, 41–60, 61–80, 81–100, 102–120, 121–140, 141–160, 161–180, 181–200, 201–220, and 221 to the end of the coding region of SEQ ID NO:6. Moreover, polypeptide fragments can be at least about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes. Polynucleotides encoding these polypeptide fragments of the invention are also encompassed by the invention.

In specific embodiments, polypeptides of the invention comprise, or alternatively consist of, amino acid residues Met-1 to Pro-62, Ala-2 to Pro-62, Met-1 to Ser-50, Ala-2 to Ser-50, Ser-50 to Pro-62, Met-1 to Trp-196, Met-1 to Gln-197, Met-1 to Leu-198, Met-1 to Arg-199, Met-1 to Lys-200, Met-1 to Thr-201, Met-1 to Gln-202, Met-1 to Leu-203, Met-1 to Leu-204, Met-1 to Leu-205, Ala-2 to Trp-196, Ala-2 to Gln-197, Ala-2 to Leu-198, Ala-2 to Arg-199, Ala-2 to Lys-200, Ala-2 to Thr-201, Ala-2 to Gln-202, Ala-2 to Leu-203, Ala-2 to Leu-204, Ala-2 to Leu-205, Ser-50 to Trp-196, Ser-50 to Gln-197, Ser-50 to Leu-198, Ser-50 to Arg-199, Ser-50 to Lys-200, Ser-50 to Thr-201, Ser-50 to Gln-202, Ser-50 to Leu-203, Ser-50 to Leu-204, Ser-50 to Leu-205, Pro-62 to Trp-196, Pro-62 to Gln-197, Pro-62 to Leu-198, Pro-62 to Arg-199, Pro-62 to Lys-200, Pro-62 to Thr-201, Pro-62 to Gln-202, Pro-62 to Leu-203, Pro-62 to Leu-204, Pro-62 to Leu-205, Trp-196 to Leu-205, Gln-197 to Leu-205, Leu-198 to Leu-205, Arg-199 to Leu-205, Lys-200 to Leu-205, Thr-201 to Leu-205, Gln-202 to Leu-205, Trp-196 to Leu-204, Gln-197 to Leu-204, Leu-198 to Leu-204, Arg-199 to Leu-204, Lys-200 to Leu-204, Thr-201 to Leu-204, Trp-196 to Leu-203, Gln-197 to Leu-203, Leu-198 to Leu-203, Arg-199 to Leu-203, Lys-200 to Leu-203, Trp-196 to Gln-202, Gln-197 to Gln-202, Leu-198 to Gln-202, Arg-199 to Gln-202, Trp-196 to Thr-201, Gln-197 to Thr-201, Leu-198 to Thr-201, Trp-196 to Lys-200, and Gln-197 to Lys-200 of SEQ ID NO:4. Polynucleotides encoding these polypeptide fragments are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

However, many polynucleotide sequences, such as EST sequences, are publicly available and accessible through sequence databases. Some of these sequences are related to SEQ ID NO: 1, SEQ ID NO:3 and/or SEQ ID NO:5 and may have been publicly available prior to conception of the present invention. Preferably, such related polynucleotides are specifically excluded from the scope of the present invention. To list every related sequence would be cumbersome. Similarly, preferably excluded from the present invention are one or more polynucleotides comprising a nucleotide sequence described by the general formula of $a^1-b^1$, where $a^1$ is any integer between 1 to 969 of SEQ ID NO:1, $b^1$ is an integer of 15 to 983, where both $a^1$ and $b^1$ correspond to the positions of nucleotide residues shown in SEQ ID NO: 1, and where the $b^1$ is greater than or equal to $a^1+14$. Similarly, preferably excluded from the present invention are one or more polynucleotides comprising a nucleotide sequence described by the general formula of $a^2-b^2$, where $a^2$ is any integer between 1 to 993 of SEQ ID NO:3, $b^2$ is an integer of 15 to 1007, where both $a^2$ and $b^2$ correspond to the positions of nucleotide residues shown in SEQ ID NO:3, and where the $b^2$ is greater than or equal to $a^2+14$. Accordingly, preferably excluded from the present invention are one or more polynucleotides comprising a nucleotide sequence described by the general formula of $a^3-b^3$, where $a^3$ is any integer between 1 to 1060 of SEQ ID NO:5, $b^3$ is an integer of 15 to 1074, where both $a^3$ and $b^3$ correspond to the positions of nucleotide residues shown in SEQ ID NO:5, and where the $b^3$ greater than or equal to $a^3+14$.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of TR11, TR11SV1, or TR11SV2 coding sequence, but do not comprise all or a portion of any TR11, TR11SV1, or TR11SV2 intron. In another embodiment, the nucleic acid comprising TR11, TR11SV1, or TR11SV2 coding sequence does not contain coding sequences of a genomic flanking gene (i.e., 5' or 3' to the TR11, TR11SV1, or TR11SV2 gene in the genome).

In specific embodiments, the polynucleotides of the invention are less than 100,000 kb, 50,000 kb, 10,000 kb, 1,000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of TR11, TR11SV1 or TR11SV2 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide sequences set forth in FIGS. 1A and 1B (SEQ ID NO:1), FIGS. 2A and 2B (SEQ ID NO:3), and FIGS. 3A and 3B (SEQ ID NO:5), respectively. In further embodiments, polynucleotides of the invention comprise at least 15, at least 30, at least 50, at least 100, or at least 250, at least 500, or at least 1000 contiguous nucleotides of TR11, TR11SV1 and/or TR11SV2 coding sequence, but do not comprise all or a portion of any TR11, TR11SV1 and/or TR11SV2 intron. In another embodiment, the nucleic acid comprising TR11, TR11SV1 and/or TR11SV2 coding sequence does not contain coding sequences of a genomic flanking gene (i.e., 5' or 3' to the TR11, TR11SV1 and/or TR11SV2 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

The invention further provides isolated TR11, TR11SV1, and TR11SV2 polypeptides having the amino acid sequence encoded by the deposited cDNAs, or the amino acid sequences in FIGS. 1A and 1B, 2A and 2B, and 3A and 3B (SEQ ID NO:2, SEQ ID NO:4, and SEQ ID NO:6, respectively) or a peptide or polypeptide comprising a portion of the above polypeptides.

To improve or alter the characteristics of TR11, TR11SV1, and/or TR11SV2 polypeptides, protein engineering may be employed. Recombinant DNA technology known to those skilled in the art can be used to create novel mutant proteins or muteins, including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.,* 268:2984–2988 (1993)) reported modified KGF proteins that had heparin binding activity even if 3, 8, or 27 N-terminal amino acid residues were missing. Similarly, many examples of biologically functional C-terminal deletion muteins are known. For instance, Interferon gamma shows up to ten times higher activities by deleting 8–10 amino acid residues from the carboxy terminus of the protein (Dobeli, et al., *J. Biotechnology* 7:199–216 (1988)).

Thus, even if deletion of one or more amino acids from the N-terinus of a protein results in modification of loss of one or more biological functions of the protein, other biological activities may still be retained. Thus, the ability of the shortened TR11, TR11SV1, and/or TR11SV2 mutein to induce and/or bind to antibodies which recognize the complete or mature form(s) of the protein generally will be retained when less than the majority of the residues of the complete or mature protein(s) are removed from the N-terminus. Whether a particular polypeptide lacking N-terminal residues of a complete protein retains such immunologic activities can readily be determined by routine methods described herein and otherwise known in the art. It is not unlikely that a TR11, TR11SV1, and/or TR11SV2 mutein with a large number of deleted N-terminal amino acid residues may retain some biological or immunogenic activities. In fact, peptides composed of as few as six TR11, TR11SV1 or TR11SV2 amino acid residues may often evoke an immune response.

Accordingly, the present invention further provides polypeptides having one or more residues deleted from the amino terminus of the TR11 amino acid sequence shown in FIGS. 1A and 1B (SEQ ID NO:2), up to the leucine residue at position number 229 and polynucleotides encoding such polypeptides. In particular, the present invention provides polypeptides comprising the amino acid sequence of residues $n^{1-234}$ of FIGS. 1A and 1B (SEQ ID NO:2), where $n^1$ is an integer in the range of 2 to 229, and 230 is the position of the first residue from the N-terminus of the complete TR11 polypeptide believed to be required for at least immunogenic activity of the TR11 protein.

More in particular, the invention provides polynucleotides encoding polypeptides comprising, or alternatively consisting of, the amino acid sequence of a member selected from the group consisting of residues of A-2 to V-234; Q-3 to V-234; H-4 to V-234; G-5 to V-234; A-6 to V-234; M-7 to V-234; G-8 to V-234; A-9 to V-234; [F-10 to V-234; R-11 to V-234; A-12 to V-234; L-13 to V-234; C-14 to V-234; G-15 to V-234; L-16 to V-234; A-17 to V-234; L-18 to V-234; L-19 to V-234; C-20 to V-234; A-21 to V-234; L-22 to V-234; S-23 to V-234; L-24 to V-234; G-25 to V-234; Q-26 to V-234; R-27 to V-234; P-28 to V-234; T-29 to V-234; G-30 to V-234; G-31 to V-234; P-32 to V-234; G-33 to V-234; C-34 to V-234; G-35 to V-234; P-36 to V-234; G-37 to V-234; R-38 to V-234; L-39 to V-234; L-40 to V-234; L-41 to V-234; G-42 to V-234; T-43 to V-234; G-44 to V-234; T-45 to V-234; D-46 to V-234; A-47 to V-234; R-48 to V-234; C-49 to V-234; C-50 to V-234; R-51 to V-234; V-52 to V-234; H-53 to V-234; T-54 to V-234; T-55 to V-234; R-56 to V-234; C-57 to V-234; C-58 to V-234; R-59 to V-234; D-60 to V-234; Y-61 to V-234; P-62 to V-234; G-63 to V-234; E-64 to V-234; E-65 to V-234; C-66 to V-234; C-67 to V-234; S-68 to V-234; E-69 to V-234; W-70 to V-234; D-71 to V-234; C-72 to V-234; M-73 to V-234; C-74 to V-234; V-75 to V-234; Q-76 to V-234; P-77 to V-234; E-78 to V-234; F-79 to V-234; H-80 to V-234; C-81 to V-234; G-82 to V-234; D-83 to V-234; P-84 to V-234; C-85 to V-234; C-86 to V-234; T-87 to V-234; T-88 to V-234; C-89 to V-234; R-90 to V-234; H-91 to V-234; H-92 to V-234; P-93 to V-234; C-94 to V-234; P-95 to V-234; P-96 to V-234; G-97 to V-234; Q-98 to V-234; G-99 to V-234; V-100 to V-234; Q-101 to V-234; S-102 to V-234; Q-103 to V-234; G-104 to V-234; K-105 to V-234; F-106 to V-234; S-107 to V-234; F-108 to V-234; G-109 to V-234; F-110 to V-234; Q-111 to V-234; C-112 to V-234; I-113 to V-234; D-114 to V-234; C-115 to V-234; A-116 to V-234; S-117 to V-234; G-118 to V-234; T-119 to V-234; F-120 to V-234; S-121 to V-234; G-122 to V-234; G-123 to V-234; H-124 to V-234; E-125 to V-234; G-126 to V-234; H-127 to V-234; C-128 to V-234; K-129 to V-234; P-130 to V-234; W-131 to V-234; T-132 to V-234; D-133 to V-234; C-134 to V-234; T-135 to V-234; Q-136 to V-234; F-137 to V-234; G-138 to V-234; F-139 to V-234; L-140 to V-234; T-141 to V-234; V-142 to V-234; F-143 to V-234; P-144 to V-234; G-145 to V-234; N-146 to V-234; K-147 to V-234; T-148 to V-234; H-149 to V-234; N-150 to V-234; A-151 to V-234; V-152 to V-234; C-153 to V-234; V-154 to V-234; P-155 to V-234; G-156 to V-234; S-157 to V-234; P-158 to V-234; P-159 to V-234; A-160 to V-234; E-161 to V-234; P-162 to V-234; L-163 to V-234; G-164 to V-234; W-165 to V-234; L-166 to V-234; T-167 to V-234; V-168 to V-234; V-169 to V-234; L-170 to V-234; L-171 to V-234; A-172 to V-234; V-173 to V-234; A-174 to V-234; A-175 to V-234; C-176 to V-234; V-177 to V-234; L-178 to V-234; L-179 to V-234; L-180 to V-234; T-181 to V-234; S-182 to V-234; A-183 to V-234; Q-184 to V-234; L-185 to V-234; G-186 to V-234; L-187 to V-234; H-188 to V-234; I-189 to V-234; W-190 to V-234; Q-191 to V-234; L-192 to V-234; R-193 to V-234; K-194 to V-234; T-195 to V-234; Q-196 to V-234; L-197 to V-234; L-198 to V-234; L-199 to V-234; E-200 to V-234; V-201 to V-234; P-202 to V-234; P-203 to V-234; S-204 to V-234; T-205 to V-234; E-206 to V-234; D-207 to V-234; A-208 to V-234; R-209 to V-234; S-210 to V-234; C-211 to V-234; Q-212 to V-234; F-213 to V-234; P-214 to V-234; E-215 to V-234; E-216 to V-234; E-217 to V-234; R-218 to V-234; G-219 to V-234; E-220 to V-234; R-221 to V-234; S-222 to V-234; A-223 to V-234; E-224 to V-234; E-225 to V-234; K-226 to V-234; G-227 to V-234; R-228 to V-234; and L-229 to V-234 of the TR11 amino acid sequence shown in FIGS. 1A and 1B (which is identical to the sequence shown as SEQ ID NO:2, with the exception that the amino acid residues in FIGS. 1A and 1B are numbered consecutively from 1 through 234 from the N-terminus to the C-terminus, while the amino acid residues in SEQ ID NO:2 are numbered consecutively from −25 through 209 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

Moreover, even if deletion of one or more amino acids from the C-terminus of a protein results in modification of loss of one or more biological functions of the protein, other biological activities may still be retained. Thus, the ability of the shortened TR11 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a TR11 mutein with a large number of deleted C-terminal amino acid residues may retain some biological or immunogenic activities. In fact, peptides composed of as few as six TR11 amino acid residues may often evoke an immune response.

Accordingly, the present invention further provides polypeptides having one or more residues deleted from the carboxy terminus of the amino acid sequence of the TR11 shown in FIGS. 1A and 1B (SEQ ID NO:2), up to the alanine residue at position number 6, and polynucleotides encoding such polypeptides. In particular, the present invention provides polypeptides comprising the amino acid sequence of residues 1–$m^1$ of FIGS. 1A and 1B (SEQ ID NO:2), where ml is an integer in the range of 6 to 234, and 6 is the position of the first residue from the C-terminus of the complete TR11 polypeptide believed to be required for at least immunogenic activity of the TR11 protein.

More in particular, the invention provides polynucleotides encoding polypeptides comprising, or alternatively consisting of, the amino acid sequence of a member selected from the group consisting of residues M-1 to W-233; M-1 to L-232; M-1 to D-231; M-1 to G-230; M-1 to L-229; M-1 to R-228; M-1 to G-227; M-1 to K-226; M-1 to E-225; M-1 to E-224; M-1 to A-223; M-1 to S-222; M-1 to R-221; M-1 to E-220; M-1 to G-219; M-1 to R-218; M-1 to E-217; M-1 to E-216; M-1 to E-215; M-1 to P-214; M-1 to F-213; M-1 to Q-212; M-1 to C-211; M-1 to S-210; M-1 to R-209; M-1 to A-208; M-1 to D-207; M-1 to E-206; M-1 to T-205; M-1 to S-204; M-1 to P-203; M-1 to P-202; M-1 to V-201; M-1 to E-200; M-1 to L-199; M-1 to L-198; M-1 to L-197; M-1 to Q-196; M-1 to T-195; M-1 to K-194; M-1 to R-193; M-1 to L-192; M-1 to Q-191; M-1 to W-190; M-1 to I-189; M-1 to H-188; M-1 to L-187; M-1 to G-186; M-1 to L-185; M-1 to Q-184; M-1 to A-183; M-1 to S-182; M-1 to T-181; M-1 to L-180; M-1 to L-179; M-1 to L-178; M-1 to V-177; M-1 to C-176; M-1 to A-175; M-1 to A-174; M-1 to V-173; M-1 to A-172; M-1 to L-171; M-1 to L-170; M-1 to V-169; M-1 to V-168; M-1 to T-167; M-1 to L-166; M-1 to W-165; M-1 to G-164; M-1 to L-163; M-1 to P-162; M-1 to E-161; M-1 to A-160; M-1 to P-159; M-1 to P-158; M-1 to S-157; M-1 to G-156; M-1 to P-155; M-1 to V-154; M-1 to C-153; M-1 to V-152; M-1 to A-151; M-1 to N-150; M-1 to H-149; M-1 to T-148; M-1 to K-147; M-1 to N-146; M-1 to G-145; M-1 to P-144; M-1 to F-143; M-1 to V-142; M-1 to T-141; M-1 to L-140; M-1 to F-139; M-1 to G-138; M-1 to F-137; M-1 to Q-136; M-1 to T-135; M-1 to C-134; M-1 to D-133; M-1 to T-132; M-1 to W-131; M-1 to P-130; M-1 to K-129; M-1 to C-128; M-1 to H-127; M-1 to G-126; M-1 to E-125; M-1 to H-124; M-1 to G-123; M-1 to G-122; M-1 to S-121; M-1 to F-120; M-1 to T-119; M-1 to G-118; M-1 to S-117; M-1 to A-116; M-1 to C-115; M-1 to D-114; M-1 to I-113; M-1 to C-112; M-1 to Q-111; M-1 to F-110; M-1 to G-109; M-1 to F-108; M-1 to S-107; M-1 to F-106; M-1 to K-105; M-1 to G-104; M-1 to Q-103; M-1 to S-102; M-1 to Q-101; M-1 to V-100; M-1 to G-99; M-1 to Q-98; M-1 to G-97; M-1 to P-96; M-1 to P-95; M-1 to C-94; M-1 to P-93; M-1 to H-92; M-1 to H-91; M-1 to R-90; M-1 to C-89; M-1 to T-88; M-1 to T-87; M-1 to C-86; M-1 to C-85; M-1 to P-84; M-1 to D-83; M-1 to G-82; M-1 to C-81; M-1 to H-80; M-1 to F-79; M-1 to E-78; M-1 to P-77; M-1 to Q-76; M-1 to V-75; M-1 to C-74; M-1 to M-73; M-1 to C-72; M-1 to D-71; M-1 to W-70; M-1 to E-69; M-1 to S-68; M-1 to C-67; M-1 to C-66; M-1 to E-65; M-1 to E-64; M-1 to G-63; M-1 to P-62; M-1 to Y-61; M-1 to D-60; M-1 to R-59; M-1 to C-58; M-1 to C-57; M-1 to R-56; M-1 to T-55; M-1 to T-54; M-1 to H-53; M-1 to V-52; M-1 to R-51; M-1 to C-50; M-1 to C-49; M-1 to R-48; M-1 to A-47; M-1 to D-46; M-1 to T-45; M-1 to G-44; M-1 to T-43; M-1 to G-42; M-1 to L41; M-1 to L-40; M-1 to L-39; M-1 to R-38; M-1 to G-37; M-1 to P-36; M-1 to G-35; M-1 to C-34; M-1 to G-33; M-1 to P-32; M-1 to G-31; M-1 to G-30; M-1 to T-29; M-1 to P-28; M-1 to R-27; M-1 to Q-26; M-1 to G-25; M-1 to L-24; M-1 to S-23; M-1 to L-22; M-1 to A-21; M-1 to C-20; M-1 to L-19; M-1 to L-18; M-1 to A-17; M-1 to L-16; M-1 to G-15; M-1 to C-14; M-1 to L-13; M-1 to A-12; M-1 to R-11; M-1 to F-10; M-1 to A-9; M-1 to G-8; M-1 to M-7; and M-1 to A-6 of the sequence of the TR11 sequence shown in FIGS. 1A and 1B (which is identical to the sequence shown as SEQ ID NO:2, with the exception that the amino acid residues in FIGS. 1A and 1B are numbered consecutively from 1 through 234 form the N-terminus to the C-terminus, while the amino acid residues in SEQ ID NO:2 are numbered consecutively from −25 through 209 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a soluble TR11 polypeptide, which may be described generally as having residues $n^1$-$m^1$ of FIGS. 1A and 1B (SEQ ID NO:2), where $n^1$ and $m^1$ are integers as described above.

The present invention further provides polypeptides having one or more residues deleted from the amino terminus of the TR11SV1 amino acid sequence shown in SEQ ID NO:4, up to the leucine residue at position number 236 and polynucleotides encoding such polypeptides. In particular, the present invention provides polypeptides comprising the amino acid sequence of residues $n^{2-241}$ of FIGS. 2A and 2B (SEQ ID NO:4), where $n^2$ is an integer in the range of 2 to 236, and 237 is the position of the first residue from the N-terminus of the complete TR11SV1 polypeptide believed to be required for at least immunogenic activity of the TR11SV1 protein.

More in particular, the invention provides polynucleotides encoding polypeptides comprising, or alternatively consisting of, the amino acid sequence of a member selected from the group consisting of residues of A-2 to V-241; P-3 to V-241; G-4 to V-241; E-5 to V-241; R-6 to V-241; D-7 to V-241; S-8 to V-241; W-9 to V-241; I-10 to V-241; N-11 to V-241; P-12 to V-241; G-13 to V-241; P-14 to V-241; D-15 to V-241; S-16 to V-241; Q-17 to V-241; P-18 to V-241; G-19 to V-241; A-20 to V-241; L-21 to V-241; C-22 to V-241; S-23 to V-241; L-24 to V-241; E-25 to V-241; P-26 to V-241; T-27 to V-241; V-28 to V-241; G-29 to V-241; G-30 to V-241; E-31 to V-241; R-32 to V-241; T-33 to V-241; T-34 to V-241; S-35 to V-241; L-36 to V-241; P-37 to V-241; W-38 to V-241; R-39 to V-241; A-40 to V-241; E-41 to V-241; G-42 to V-241; R-43 to V-241; P-44 to V-241; G-45 to V-241; E-46 to V-241; E-47 to V-241; G-48 to V-241; A-49 to V-241; S-50 to V-241; A-51 to V-241; Q-52 to V-241; L-53 to V-241; L-54 to V-241; G-55 to V-241; G-56 to V-241; W-57 to V-241; P-58 to V-241; V-59 to V-241; S-60 to V-241; C-61 to V-241; P-62 to V-241; G-63 to V-241; E-64 to V-241; E-65 to V-241; C-66 to V-241; C-67 to V-241; S-68 to V-241; E-69 to V-241; W-70 to V-241; D-71 to V-241; C-72 to V-241; M-73 to V-241;

C-74 to V-241; V-75 to V-241; Q-76 to V-241; P-77 to V-241; E-78 to V-241; F-79 to V-241; H-80 to V-241; C-81 to V-241; G-82 to V-241; D-83 to V-241; P-84 to V-241; C-85 to V-241; C-86 to V-241; T-87 to V-241; T-88 to V-241; C-89 to V-241; R-90 to V-241; H-91 to V-241; H-92 to V-241; P-93 to V-241; C-94 to V-241; P-95 to V-241; P-96 to V-241; G-97 to V-241; Q-98 to V-241; G-99 to V-241; V-100 to V-241; Q-101 to V-241; S-102 to V-241; Q-103 to V-241; G-104 to V-241; K-105 to V-241; F-106 to V-241; S-107 to V-241; F-108 to V-241; G-109 to V-241; F-110 to V-241; Q-111 to V-241; C-112 to V-241; I-113 to V-241; D-114 to V-241; C-115 to V-241; A-116 to V-241; S-117 to V-241; G-118 to V-241; T-119 to V-241; F-120 to V-241; S-121 to V-241; G-122 to V-241; G-123 to V-241; H-124 to V-241; E-125 to V-241; G-126 to V-241; H-127 to V-241; C-128 to V-241; K-129 to V-241; P-130 to V-241; W-131 to V-241; T-132 to V-241; D-133 to V-241; C-134 to V-241; T-135 to V-241; Q-136 to V-241; F-137 to V-241; G-138 to V-241; F-139 to V-241; L-140 to V-241; T-141 to V-241; V-142 to V-241; F-143 to V-241; P-144 to V-241; G-145 to V-241; N-146 to V-241; K-147 to V-241; T-148 to V-241; H-149 to V-241; N-150 to V-241; A-151 to V-241; V-152 to V-241; C-153 to V-241; V-154 to V-241; P-155 to V-241; G-156 to V-241; S-157 to V-241; P-158 to V-241; P-159 to V-241; A-160 to V-241; E-161 to V-241; P-162 to V-241; L-163 to V-241; G-164 to V-241; W-165 to V-241; L-166 to V-241; T-167 to V-241; V-168 to V-241; V-169 to V-241; L-170 to V-241; L-171 to V-241; A-172 to V-241; V-173 to V-241; A-174 to V-241; A-175 to V-241; C-176 to V-241; V-177 to V-241; L-178 to V-241; L-179 to V-241; L-180 to V-241; T-181 to V-241; S-182 to V-241; A-183 to V-241; Q-184 to V-241; L-185 to V-241; G-186 to V-241; L-187 to V-241; H-188 to V-241; I-189 to V-241; W-190 to V-241; Q-191 to V-241; L-192 to V-241; R-193 to V-241; S-194 to V-241; Q-195 to V-241; C-196 to V-241; M-197 to V-241; W-198 to V-241; P-199 to V-241; R-200 to V-241; E-201 to V-241; T-202 to V-241; Q-203 to V-241; L-204 to V-241; L-205 to V-241; L-206 to V-241; E-207 to V-241; V-208 to V-241; P-209 to V-241; P-210 to V-241; S-211 to V-241; T-212 to V-241; E-213 to V-241; D-214 to V-241; A-215 to V-241; R-216 to V-241; S-217 to V-241; C-218 to V-241; Q-219 to V-241; F-220 to V-241; P-221 to V-241; E-222 to V-241; E-223 to V-241; E-224 to V-241; R-225 to V-241; G-226 to V-241; E-227 to V-241; R-228 to V-241; S-229 to V-241; A-230 to V-241; E-231 to V-241; E-232 to V-241; K-233 to V-241; G-234 to V-241; R-235 to V-241; and L-236 to V-241 of the TR11SV1 amino acid sequence shown in FIGS. 2A and 2B (which is identical to the sequence shown as SEQ ID NO:4). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

As mentioned above, even if deletion of one or more amino acids from the C-terminus of a protein results in modification of loss of one or more biological functions of the protein, other biological activities may still be retained. Thus, the ability of the shortened TR11SV1 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a TR11SV1 mutein with a large number of deleted C-terminal amino acid residues may retain some biological or immunogenic activities. In fact, peptides composed of as few as six TR11SV1 amino acid residues may often evoke an immune response.

Accordingly, the present invention further provides polypeptides having one or more residues deleted from the carboxy terminus of the amino acid sequence of the TR11SV1 shown in SEQ ID NO:4, up to the arginine residue at position number 6, and polynucleotides encoding such polypeptides. In particular, the present invention provides polypeptides comprising the amino acid sequence of residues 1-m$^2$ of FIGS. 2A and 2B (SEQ ID NO:4), where m$^2$ is an integer in the range of 6 to 241, and 6 is the position of the first residue from the C-terminus of the complete TR11SV1 polypeptide believed to be required for at least immunogenic activity of the TR11SV1 protein.

More in particular, the invention provides polynucleotides encoding polypeptides comprising, or alternatively consisting of, the amino acid sequence of a member selected from the group consisting of residues M-1 to W-240; M-1 to L-239; M-1 to D-238; M-1 to G-237; M-1 to L-236; M-1 to R-235; M-1 to G-234; M-1 to K-233; M-1 to E-232; M-1 to E-231; M-1 to A-230; M-1 to S-229; M-1 to R-228; M-1 to E-227; M-1 to G-226; M-1 to R-225; M-1 to E-224; M-1 to E-223; M-1 to E-222; M-1 to P-221; M-1 to F-220; M-1 to Q-219; M-1 to C-218; M-1 to S-217; M-1 to R-216; M-1 to A-215; M-1 to D-214; M-1 to E-213; M-1 to T-212; M-1 to S-211; M-1 to P-210; M-1 to P-209; M-1 to V-208; M-1 to E-207; M-1 to L-206; M-1 to L-205; M-1 to L-204; M-1 to Q-203; M-1 to T-202; M-1 to E-201; M-1 to R-200; M-1 to P-199; M-1 to W-198; M-1 to M-197; M-1 to C-196; M-1 to Q-195; M-1 to S-194; M-1 to R-193; M-1 to L-192; M-1 to Q-191; M-1 to W-190; M-1 to I-189; M-1 to H-188; M-1 to L-187; M-1 to G-186; M-1 to L-185; M-1 to Q-184; M-1 to A-183; M-1 to S-182; M-1 to T-181; M-1 to L-180; M-1 to L-179; M-1 to L-178; M-1 to V-177; M-1 to C-176; M-1 to A-175; M-1 to A-174; M-1 to V-173; M-1 to A-172; M-1 to L-171; M-1 to L-170; M-1 to V-169; M-1 to V-168; M-1 to T-167; M-1 to L-166; M-1 to W-165; M-1 to G-164; M-1 to L-163; M-1 to P-162; M-1 to E-161; M-1 to A-160; M-1 to P-159; M-1 to P-158; M-1 to S-157; M-1 to G-156; M-1 to P-155; M-1 to V-154; M-1 to C-153; M-1 to V-152; M-1 to A-151; M-1 to N-150; M-1 to H-149; M-1 to T-148; M-1 to K-147; M-1 to N-146; M-1 to G-145; M-1 to P-144; M-1 to F-143; M-1 to V-142; M-1 to T-141; M-1 to L-140; M-1 to F-139; M-1 to G-138; M-1 to F-137; M-1 to Q-136; M-1 to T-135; M-1 to C-134; M-1 to D-133; M-1 to T-132; M-1 to W-131; M-1 to P-130; M-1 to K-129; M-1 to C-128; M-1 to H-127; M-1 to G-126; M-1 to E-125; M-1 to H-124; M-1 to G-123; M-1 to G-122; M-1 to S-121; M-1 to F-120; M-1 to T-119; M-1 to G-118; M-1 to S-117; M-1 to A-116; M-1 to C-115; M-1 to D-114; M-1 to I-113; M-1 to C-112; M-1 to Q-111; M-1 to F-110; M-1 to G-109; M-1 to F-108; M-1 to S-107; M-1 to F-106; M-1 to G-105; M-1 to Q-104; M-1 to E-103; M-1 to S-102; M-1 to Q-101; M-1 to V-100; M-1 to M-99; M-1 to Q-98; M-1 to G-97; M-1 to P-96; M- to P-95; M-1 to C-94; M-1 to P-93; M-1 to H-92; M-1 to H-91; M-1 to R-90; M-1 to C-89; M-1 to T-88; M-1 to T-87; M-1 to C-86; M-1 to C-85; M-1 to P-84; M-1 to D-83; M-1 to G-82; M-1 to C-81; M-1 to H-80; M-1 to F-79; M-1 to E-78; M-1 to P-77; M-1 to Q-76; M-1 to V-75; M-1 to C-74; M-1 to M-73; M-1 to C-72; M-1 to D-71; M-1 to W-70; M-1 to E-69; M-1 to S-68; M-1 to C-67; M-1 to C-66; M-1 to E-65; M-1 to E-64; M-1 to G-63; M-1 to P-62; M-1 to C-61; M-1 to S-60; M-1 to V-59; M-1 to P-58; M-1 to W-57; M-1 to G-56; M-1 to G-55; M-1 to L-54; M-1 to L-53; M-1 to Q-52; M-1 to A-51; M-1 to S-50; M-1 to A-49; M-1 to G-48; M-1 to E-47; M-1 to E-46; M-1 to G-45; M-1 to P-44; M-1 to R-43; M-1 to G-42; M-1 to E-41; M-1 to A-40; M-1 to R-39; M-1 to W-38; M-1 to P-37; M-1 to L-36; M-1 to S-35; M-1 to T-34; M-1 to T-33; M-1 to R-32; M-1 to E-31; M-1 to G-30; M-1 to G-29; M-1 to V-28; M-1 to T-27; M-1 to P-26; M-1 to E-25; M-1 to L-24; M-1 to S-23; M-1 to C-22; M-1 to L-21; M-1 to A-20; M-1 to G-19; M-1 to P-18; M-1 to Q-17; M-1 to S-16; M-1 to D-15; M-1 to P-14; M-1 to G-13; M-1 to P-12; M-1 to N-11; M-1 to I-10; M-1 to W-9; M-1 to S-8; M-1 to D-7; and M-1 to R-6 of the sequence of the TR11SV1 sequence shown in FIGS. 2A and 2B (which is identical to the sequence shown as SEQ ID NO:4). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a TR11SV1 polypeptide, which may be described generally as having residues $n^2$-$m^2$ of FIGS. 2A and 2B (SEQ ID NO:4), where $n^2$ and $m^2$ are integers as described above.

In addition, the present invention further provides polypeptides having one or more residues deleted from the amino terminus of the TR11SV2 amino acid sequence shown in FIGS. 3A and 3B (SEQ ID NO:6), up to the leucine residue at position number 235 and polynucleotides encoding such polypeptides. In particular, the present invention provides polypeptides comprising the amino acid sequence of residues $n^{3-240}$ of FIGS. 3A and 3B (SEQ ID NO:6), where $n^3$ is an integer in the range of 2 to 235, and 236 is the position of the first residue from the N-terminus of the complete TR11SV2 polypeptide believed to be required for at least immunogenic activity of the TR11SV2 protein.

More in particular, the invention provides polynucleotides encoding polypeptides comprising, or alternatively consisting of, the amino acid sequence of a member selected from the group consisting of residues of G-2 to V-240; A-3 to V-240; F-4 to V-240; R-5 to V-240; A-6 to V-240; L-7 to V-240; C-8 to V-240; G-9 to V-240; L-10 to V-240; A-11 to V-240; L-12 to V-240; L-13 to V-240; C-14 to V-240; A-15 to V-240; L-16 to V-240; S-17 to V-240; L-18 to V-240; G-19 to V-240; Q-20 to V-240; R-21 to V-240; P-22 to V-240; T-23 to V-240; G-24 to V-240; G-25 to V-240; P-26 to V-240; G-27 to V-240; C-28 to V-240; G-29 to V-240; P-30 to V-240; G-31 to V-240; R-32 to V-240; L-33 to V-240; L-34 to V-240; L-35 to V-240; G-36 to V-240; T-37 to V-240; G-38 to V-240; T-39 to V-240; D-40 to V-240; A-41 to V-240; R42 to V-240; C-43 to V-240; C-44 to V-240; R-45 to V-240; V-46 to V-240; H-47 to V-240; T-48 to V-240; T-49 to V-240; R-50 to V-240; C-51 to V-240; C-52 to V-240; R-53 to V-240; D-54 to V-240; Y-55 to V-240; P-56 to V-240; A-57 to V-240; Q-58 to V-240; L-59 to V-240; L-60 to V-240; G-61 to V-240; G-62 to V-240; W-63 to V-240; P-64 to V-240; V-65 to V-240; S-66 to V-240; C-67 to V-240; P-68 to V-240; G-69 to V-240; E-70 to V-240; E-71 to V-240; C-72 to V-240; C-73 to V-240; S-74 to V-240; E-75 to V-240; W-76 to V-240; ]D-77 to V-240; C-78 to V-240; M-79 to V-240; C-80 to V-240; V-81 to V-240; Q-82 to V-240; P-83 to V-240; E-84 to V-240; F-85 to V-240; H-86 to V-240; C-87 to V-240; G-88 to V-240; D-89 to V-240; P-90 to V-240; C-91 to V-240; C-92 to V-240; T-93 to V-240; T-94 to V-240; C-95 to V-240; R-96 to V-240; H-97 to V-240; H-98 to V-240; P-99 to V-240; C-100 to V-240; P-101 to V-240; P-102 to V-240; G-103 to V-240; Q-104 to V-240; G-105 to V-240; V-106 to V-240; Q-107 to V-240; S-108 to V-240; Q-109 to V-240; G-110 to V-240; K-111 to V-240; F-112 to V-240; S-113 to V-240; F-114 to V-240; G-115 to V-240; F-116 to V-240; Q-117 to V-240; C-118 to V-240; I-119 to V-240; D-120 to V-240; C-121 to V-240; A-122 to V-240; S-123 to V-240; G-124 to V-240; T-125 to V-240; F-126 to V-240; S-127 to V-240; G-128 to V-240; G-129 to V-240; H-130 to V-240; E-131 to V-240; G-132 to V-240; H-133 to V-240; C-134 to V-240; K-135 to V-240; P-136 to V-240; W-137 to V-240; T-138 to V-240; D-139 to V-240; C-140 to V-240; T-141 to V-240; Q-142 to V-240; F-143 to V-240; G-144 to V-240; F-145 to V-240; L-146 to V-240; T-147 to V-240; V-148 to V-240; F-149 to V-240; P-150 to V-240; G-151 to V-240; N-152 to V-240; K-153 to V-240; T-154 to V-240; H-155 to V-240; N-156 to V-240; A-157 to V-240; V-158 to V-240; C-159 to V-240; V-160 to V-240; P-161 to V-240; G-162 to V-240; S-163 to V-240; P-164 to V-240; P-165 to V-240; A-166 to V-240; E-167 to V-240; P-168 to V-240; L-169 to V-240; G-170 to V-240; W-171 to V-240; L-172 to V-240; T-173 to V-240; V-174 to V-240; V-175 to V-240; L-176 to V-240; L-177 to V-240; A-178 to V-240; V-179 to V-240; A-180 to V-240; A-181 to V-240; C-182 to V-240; V-183 to V-240; L-184 to V-240; L-185 to V-240; L-186 to V-240; T-187 to V-240; S-188 to V-240; A-189 to V-240; Q-190 to V-240; L-191 to V-240; G-192 to V-240; L-193 to V-240; H-194 to V-240; I-195 to V-240; W-196 to V-240; Q-197 to V-240; L-198 to V-240; R-199 to V-240; K-200 to V-240; T-201 to V-240; Q-202 to V-240; L-203 to V-240; L-204 to V-240; L-205 to V-240; E-206 to V-240; V-207 to V-240; P-208 to V-240; P-209 to V-240; S-210 to V-240; T-211 to V-240; E-212 to V-240; D-213 to V-240; A-214 to V-240; R-215 to V-240; S-216 to V-240; C-217 to V-240; Q-218 to V-240; F-219 to V-240; P-220 to V-240; E-221 to V-240; E-222 to V-240; E-223 to V-240; R-224 to V-240; G-225 to V-240; E-226 to V-240; R-227 to V-240; S-228 to V-240; A-229 to V-240; E-230 to V-240; E-231 to V-240; K-232 to V-240; G-233 to V-240; R-234 to V-240; and L-235 to V-240 of the TR11SV2 amino acid sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

Also as mentioned above, even if deletion of one or more amino acids from the C-terminus of a protein results in modification of loss of one or more biological functions of the protein, other biological activities may still be retained. Thus, the ability of the shortened TR11SV2 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a TR11SV2 mutein with a large number of deleted C-terminal amino acid residues may retain some biological or immunogenic activities. In fact, peptides composed of as few as six TR11SV2 amino acid residues may often evoke an immune response.

Accordingly, the present invention further provides polypeptides having one or more residues deleted from the carboxy terminus of the amino acid sequence of the TR11SV2 shown in FIGS. 3A and 3B (SEQ ID NO:6), up to the alanine residue at position number 6, and polynucleotides encoding such polypeptides. In particular, the present invention provides polypeptides comprising the amino acid sequence of residues 1-$m^3$ of FIGS. 3A and 3B (SEQ ID NO:6), where $m^3$ is an integer in the range of 6 to 240, and 6 is the position of the first residue from the C-terminus of the complete TR11SV2 polypeptide believed to be required for at least immunogenic activity of the TR11SV2 protein.

More in particular, the invention provides polynucleotides encoding polypeptides comprising, or alternatively consisting of, the amino acid sequence of a member selected from the group consisting of residues M-1 to W-239; M-1 to L-238; M-1 to D-237; M-1 to G-236; M-1 to L-235; M-1 to R-234; M-1 to G-233; M-1 to K-232; M-1 to E-231; M-1 to E-230; M-1 to A-229; M-1 to S-228; M-1 to R-227; M-1 to E-226; M-1 to G-225; M-1 to R-224; M-1 to E-223; M-1 to E-222; M-1 to E-221; M-1 to P-220; M-1 to F-219; M-1 to Q-218; M-1 to C-217; M-1 to S-216; M-1 to R-215; M-1 to A-214; M-1 to D-213; M-1 to E-212; M-1 to T-211; M-1 to S-210; M-1 to P-209; M-1 to P-208; M-1 to V-207; M-1 to E-206; M-1 to L-205; M-1 to L-204; M-1 to L-203; M-1 to Q-202; M-1 to T-201; M-1 to K-200; M-1 to R-199; M-1 to L-198; M-1 to Q-197; M-1 to W-196; M-1 to I-195; M-1 to H-194; M-1 to L-193; M-1 to G-192; M-1 to L-191; M-1 to Q-190; M-1 to A-189; M-1 to S-188; M-1 to T-187; M-1 to L-186; M-1 to L-185; M-1 to L-184; M-1 to V-183; M-1 to C-182; M-1 to A-181; M-1 to A-180; M-1 to V-179; M-1 to A-178; M-1 to L-177; M-1 to L-176; M-1 to V-175; M-1 to V-174; M-1 to T-173; M-1 to L-172; M-1 to W-171; M-1 to G-170; M-1 to L-169; M-1 to P-168; M-1 to E-167; M-1 to A-166; M-1 to P-165; M-1 to P-164; M-1 to S-163; M-1 to G-162; M-1 to P-161; M-1 to V-160; M-1 to C-159; M-1 to V-158; M-1 to A-157; M-1 to N-156; M-1 to H-155; M-1 to T-154; M-1 to K-153; M-1 to N-152; M-1 to G-151; M-1 to P-162; M-1 to F-149; M-1 to V-148; M-1 to T-147; M-1 to L-146; M-1 to F-145; M-1 to G-144; M-1 to F-143; M-1 to Q-142; M-1 to T-141; M-1 to C-140; M-1 to D-139; M-1 to T-138; M-1 to W-137; M-1 to P-136; M-1 to K-135; M-1 to C-134; M-1 to H-133; M-1 to G-132; M-1 to E-131; M-1 to H-130; M-1 to G-129; M-1 to G-128; M-1 to S-127; M-1 to F-126; M-1 to T-125; M-1 to G-124; M-1 to S-123; M-1 to A-122; M-1 to C-121; M-1 to D-120; M-1 to I-119; M-1 to C-118; M-1 to Q-117; M-1 to F-116; M-1 to G-115; M-1 to F-114; M-1 to S-113; M-1 to F-112; M-1 to K-111; M-1 to G-140; M-1 to Q-109; M-1 to T-108; M-1 to Q-107; M-1 to V-106; M-1 to G-105; M-1 to Q-104; M-1 to G-103; M-1 to P-102; M-1 to P-101; M-1 to C-100; M-1 to P-99; M-1 to H-98; M-1 to H-97; M-1 to R-96; M-1 to C-95; M-1 to T-94; M-1 to T-93; M-1 to C-92; M-1 to C-91; M-1 to P-90; M-1 to D-89; M-1 to G-88; M-1 to C-87; M-1 to H-86; M-1 to F-85; M-1 to E-84; M-1 to P-83; M-1 to Q-82; M-1 to V-81; M-1 to C-80; M-1 to M-79; M-1 to C-78; M-1 to D-77; M-1 to W-76; M-1 to E-75; M-1 to S-74; M-1 to C-73; M-1 to C-72; M-1 to E-71; M-1 to E-70; M-1 to G-69; M-1 to P-68; M-1 to C-67; M-1 to S-66; M-1 to V-65; M-1 to P-64; M-1 to W-63; M-1 to G-62; M-1 to G-61; M-1 to L-60; M-1 to L-59; M-1 to Q-58; M-1 to A-57; M-1 to P-56; M-1 to Y-55; M-1 to D-54; M-1 to R-53; M-1 to C-52; M-1 to C-51; M-1 to R-50; M-1 to T-49; M-1 to T-48; M-1 to H-47; M-1 to V-46; M-1 to R-45; M-1 to C-44; M-1 to C-43; M-1 to R-42; M-1 to A-41; M-1 to D-40; M-1 to T-39; M-1 to G-38; M-1 to T-37; M-1 to G-36; M-1 to L-35; M-1 to L-34; M-1 to L-33; M-1 to R-32; M-1 to G-31; M-1 to P-30; M-1 to G-29; M-1 to C-28; M-1 to G-27; M-1 to P-26; M-1 to G-25; M-1 to G-24; M-1 to T-23; M-1 to P-22; M-1 to R-21; M-1 to Q-20; M-1 to G-19; M-1 to L-18; M-1 to S-17; M-1 to L-16; M-1 to A-15; M-1 to C-14; M-1 to L-13; M-1 to L-12; M-1 to A-11; M-1 to L-10; M-1 to G-9; M-1 to C-8; M-1 to L-7; and M-1 to A-6 of the sequence of the TR11SV2 sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a TR11SV2 polypeptide, which may be described generally as having residues $n^3$-$m^3$ of FIGS. 3A and 3B (SEQ ID NO:6), where $n^3$ and $m^3$ are integers as described above.

In addition, the present invention further provides polypeptides having one or more residues deleted from the amino terminus of the predicted extracellular domain of the TR11 amino acid sequence shown in FIGS. 1A and 1B (SEQ ID NO:2), up to the glycine residue at position number 156 and polynucleotides encoding such polypeptides. In particular, the present invention provides polypeptides comprising the amino acid sequence of residues $n^{4-162}$ of FIGS. 1A and 1B (SEQ ID NO:2), where $n^4$ is an integer in the range of 25 to 156, and 157 is the position of the first residue from the N-terminus of the predicted extracellular domain of the TR11 polypeptide believed to be required for at least immunogenic activity of the predicted extracellular domain of the TR11 protein.

More in particular, the invention provides polynucleotides encoding polypeptides comprising, or alternatively consisting of, the amino acid sequence of a member selected from the group consisting of residues of G-25 to P-162; Q-26 to P-162; R-27 to P-162; P-28 to P-162; T-29 to P-162; G-30 to P-162; G-31 to P-162; P-32 to P-162; G-33 to P-162; C-34 to P-162; G-35 to P-162; P-36 to P-162; G-37 to P-162; R-38 to P-162; L-39 to P-162; L-40 to P-162; L-41 to P-162; G-42 to P-162; T-43 to P-162; G-44 to P-162; T-45 to P-162; D-46 to P-162; A-47 to P-162; R-48 to P-162; C-49 to P-162; C-50 to P-162; R-51 to P-162; V-52 to P-162; H-53 to P-162; T-54 to P-162; T-55 to P-162; R-56 to P-162; C-57 to P-162; C-58 to P-162; R-59 to P-162; D-60 to P-162; Y-61 to P-162; P-62 to P-162; G-63 to P-162; E-64 to P-162; E-65 to P-162; C-66 to P-162; C-67 to P-162; S-68 to P-162; E-69 to P-162; W-70 to P-162; D-71 to P-162; C-72 to P-162; M-73 to P-162; C-74 to P-162; V-75 to P-162; Q-76 to P-162; P-77 to P-162; E-78 to P-162; F-79 to P-162; H-80 to P-162; C-81 to P-162; G-82 to P-162; D-83 to P-162; P-84 to P-162; C-85 to P-162; C-86 to P-162; T-87 to P-162; T-88 to P-162; C-89 to P-162; R-90 to P-162; H-91 to P-162; H-92 to P-162; P-93 to P-162; C-94 to P-162; P-95 to P-162; P-96 to P-162; G-97 to P-162; Q-98 to P-162; G-99 to P-162; V-100 to P-162; Q-101 to P-162; S-102 to P-162; Q-103 to P-162; G-104 to P-162; K-105 to P-162; F-106 to P-162; S-107 to P-162; F-108 to P-162; G-109 to P-162; F-111 to P-162; Q-111 to P-162; C-112 to P-162; 1–113 to P-162; D-114 to P-162; C-115 to P-162; A-116 to P-162; S-117 to P-162; G-118 to P-162; T-119 to P-162; F-120 to P-162; S-121 to P-162; G-122 to P-162; G-123 to P-162; H-124 to P-162; E-125 to P-162; G-126 to P-162; H-127 to P-162; C-128 to P-162; K-129 to P-162; P-130 to P-162; W-131 to P-162; T-132 to P-162; D-133 to P-162; C-134 to P-162; T-135 to P-162; Q-136 to P-162; F-137 to P-162; G-138 to P-162; F-139 to P-162; L-140 to P-162; T-141 to P-162; V-142 to P-162; F-143 to P-162; P-144 to P-162; G-145 to P-162; N-146 to P-162; K-147 to P-162; T-148 to P-162; H-149 to P-162; N-150 to P-162; A-151 to P-162; V-152 to P-162; C-153 to P-162; V-154 to P-162; P-155 to P-162; and G-156 to P-162 of the TR11 amino acid sequence shown in FIGS. 1A and 1B (which is identical to the sequence shown as SEQ ID NO:2, with the exception that the amino acid residues in FIGS. 1A and 1B are numbered consecutively from 1 through 234 from the N-terminus to the C-terminus, while the amino acid residues in SEQ ID NO:2 are numbered consecutively from −25 through 209 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The present invention further provides polypeptides having one or more residues deleted from the carboxy terminus of the predicted extracellular domain of the amino acid sequence of the TR11 shown in FIGS. 1A and 1B (SEQ ID NO:2), up to the glycine residue at position number 31, and polynucleotides encoding such polypeptides. In particular, the present invention provides polypeptides comprising the amino acid sequence of residues 25-$m^4$ of FIGS. 1A and 1B (SEQ ID NO:2), where $m^4$ is an integer in the range of 31 to 162, and 30 is the position of the first residue from the C-terminus of the predicted extracellular domain of the TR11 polypeptide believed to be required for at least immunogenic activity of the TR11 protein.

More in particular, the invention provides polynucleotides encoding polypeptides comprising, or alternatively consisting of, the amino acid sequence of a member selected from the group consisting of residues G-25 to P-162; G-25 to E-161; G-25 to A-160; G-25 to P-159; G-25 to P-158; G-25 to S-157; G-25 to G-156; G-25 to P-155; G-25 to V-154; G-25 to C-153; G-25 to V-152; G-25 to A-151; G-25 to N-150; G-25 to H-149; G-25 to T-148; G-25 to K-147; G-25 to N-146; G-25 to G-145; G-25 to P-144; G-25 to F-143; G-25 to V-142; G-25 to T-141; G-25 to L-140; G-25 to F-139; G-25 to G-138; G-25 to F-137; G-25 to Q-136; G-25 to T-135; G-25 to C-134; G-25 to D-133; G-25 to T-132; G-25 to W-131; G-25 to P-130; G-25 to K-129; G-25 to C-128; G-25 to H-127; G-25 to G-126; G-25 to E-125; G-25 to H-124; G-25 to G-123; G-25 to G-122; G-25 to S-121; G-25 to F-120; G-25 to T-119; G-25 to G-118; G-25 to S-117; G-25 to A-116; G-25 to C-115; G-25 to D-114; G-25 to I-113; G-25 to C-112; G-25 to Q-111; G-25 to F-110; G-25 to G-109; G-25 to F-108; G-25 to S-107; G-25 to F-106; G-25 to K-105; G-25 to G-104; G-25 to Q-103; G-25 to S-102; G-25 to Q-101; G-25 to V-100; G-25 to G-99; G-25 to Q-98; G-25 to G-97; G-25 to P-96; G-25 to P-95; G-25 to C-94; G-25 to P-93; G-25 to H-92; G-25 to H-91; G-25 to R-90; G-25 to C-89; G-25 to T-88; G-25 to T-87; G-25 to C-86; G-25 to C-85; G-25 to P-84; G-25 to D-83; G-25 to G-82; G-25 to C-81; G-25 to H-80; G-25 to F-79; G-25 to E-78; G-25 to P-77; G-25 to Q-76; G-25 to V-75; G-25 to C-74; G-25 to M-73; G-25 to C-72; G-25 to D-71; G-25 to W-70; G-25 to E-69; G-25 to S-68; G-25 to C-67; G-25 to C-66; G-25 to E-65; G-25 to E-64; G-25 to G-63; G-25 to P-62; G-25 to Y-61; G-25 to D-60; G-25 to R-59; G-25 to C-58; G-25 to C-57; G-25 to R-56; G-25 to T-55; G-25 to T-54; G-25 to H-53; G-25 to V-52; G-25 to R-51; G-25 to C-50; G-25 to C-49; G-25 to R-48; G-25 to A-47; G-25 to D-46; G-25 to T-45; G-25 to G-44; G-25 to T-43; G-25 to G-42; G-25 to L-41; G-25 to L-40; G-25 to L-39; G-25 to R-38; G-25 to G-37; G-25 to P-36; G-25 to G-35; G-25 to C-34; G-25 to G-33; G-25 to P-32; and G-25 to G-31 of the sequence of the TR11 sequence shown in FIGS. 1A and 1B (which is identical to the sequence shown as SEQ ID NO:2, with the exception that the amino acid residues in FIGS. 1A and 1B are numbered consecutively from 1 through 234 from the N-terminus to the C-terminus, while the amino acid residues in SEQ ID NO:2 are numbered consecutively from −25 through 209 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a soluble TR 11 polypeptide, which may be described generally as having residues $n^4$-$m^4$ of FIGS. 1A and 1B (SEQ ID NO:2), where $n^4$ and $m^4$ are integers as described above.

In addition, the present invention further provides polypeptides having one or more residues deleted from the amino terminus of the predicted extracellular domain of the TR11SV1 amino acid sequence shown in FIGS. 2A and 2B (SEQ ID NO:4), up to the glycine residue at position number 156 and polynucleotides encoding such polypeptides. In particular, the present invention provides polypeptides comprising the amino acid sequence of residues $n^{5-162}$ of FIGS. 2A and 2B (SEQ ID NO:4), where $n^5$ is an integer in the range of 1 to 156, and 157 is the position of the first residue from the N-terminus of the predicted extracellular domain of the TR11SV1 polypeptide believed to be required for at least immunogenic activity of the predicted extracellular domain of the TR11SV1 protein.

More in particular, the invention provides polynucleotides encoding polypeptides comprising, or alternatively consisting of, the amino acid sequence of a member selected from the group consisting of residues of M-1 to P-162; A-2 to P-162; P-3 to P-162; G-4 to P-162; E-5 to P-162; R-6 to P-162; D-7 to P-162; S-8 to P-162; W-9 to P-162; I-10 to P-162; N-11 to P-162; P-12 to P-162; G-13 to P-162; P-14 to P-162; D-15 to P-162; S-16 to P-162; Q-17 to P-162; P-18 to P-162; G-19 to P-162; A-20 to P-162; L-21 to P-162; C-22 to P-162; S-23 to P-162; L-24 to P-162; E-25 to P-162; P-26 to P-162; T-27 to P-162; V-28 to P-162; G-29 to P-162; G-30 to P-162; E-31 to P-162; R-32 to P-162; T-33 to P-162; T-34 to P-162; S-35 to P-162; L-36 to P-162; P-37 to P-162; W-38 to P-162; R-39 to P-162; A-40 to P-162; E41 to P-162; G-42 to P-162; R-43 to P-162; P-44 to P-162; G-45 to P-162; E-46 to P-162; E-47 to P-162; G-48 to P-162; A-49 to P-162; S-50 to P-162; A-51 to P-162; Q-52 to P-162; L-53 to P-162; L-54 to P-162; G-55 to P-162; G-56 to P-162; W-57 to P-162; P-58 to P-162; V-59 to P-162; S-60 to P-162; C-61 to P-162; P-62 to P-162; G-63 to P-162; E-64 to P-162; E-65 to P-162; C-66 to P-162; C-67 to P-162; S-68 to P-162; E-69 to P-162; W-70 to P-162; D-71 to P-162; C-72 to P-162; M-73 to P-162; C-74 to P-162; V-75 to P-162; Q-76 to P-162; P-77 to P-162; E-78 to P-162; F-79 to P-162; H-80 to P-162; C-81 to P-162; G-82 to P-162; D-83 to P-162; P-84 to P-162; C-85 to P-162; C-86 to P-162; T-87 to P-162; T-88 to P-162; C-89 to P-162; R-90 to P-162; H-91 to P-162; H-92 to P-162; P-93 to P-162; C-94 to P-162; P-95 to P-162; P-96 to P-162; G-97 to P-162; Q-98 to P-162; G-99 to P-162; V-100 to P-162; Q-101 to P-162; S-102 to P-162; Q-103 to P-162; G-104 to P-162; K-105 to P-162; F-106 to P-162; S-107 to P-162; F-108 to P-162; G-109 to P-162; F-110 to P-162; Q-111 to P-162; C-112 to P-162; I-113 to P-162; D-114 to P-162; C-115 to P-162; A-116 to P-162; S-117 to P-162; G-118 to P-162; T-119 to P-162; F-120 to P-162; S-121 to P-162; G-122 to P-162; G-123 to P-162; H-124 to P-162; E-125 to P-162; G-126 to P-162; H-127 to P-162; C-128 to P-162; K-129 to P-162; P-130 to P-162; W-131 to P-162; T-132 to P-162; D-133 to P-162; C-134 to P-162; T-135 to P-162; Q-136 to P-162; F-137 to P-162; G-138 to P-162; F-139 to P-162; L-140 to P-162; T-141 to P-162; V-142 to P-162; F-143 to P-162; P-144 to P-162; G-145 to P-162; N-146 to P-162; K-147 to P-162; T-148 to P-162; H-149 to P-162; N-150 to P-162; A-151 to P-162; V-152 to P-162; C-153 to P-162; V-154 to P-162; P-155 to P-162; and G-156 to P-162 of the TR11SV1 amino acid sequence shown in FIGS. 2A and 2B (SEQ ID NO:4). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The present invention further provides polypeptides having one or more residues deleted from the carboxy terminus of the predicted extracellular domain of the amino acid sequence of the TR11SV1 shown in FIGS. 2A and 2B (SEQ ID NO:4), up to the arginine residue at position number 6, and polynucleotides encoding such polypeptides. In particular, the present invention provides polypeptides comprising the amino acid sequence of residues $1\text{-}m^5$ of FIGS. 2A and 2B (SEQ ID NO:4), where $m^5$ is an integer in the range of 6 to 162, and 6 is the position of the first residue from the C-terminus of the predicted extracellular domain of the TR11SV1 polypeptide believed to be required for at least immunogenic activity of the TR11SV1 protein.

More in particular, the invention provides polynucleotides encoding polypeptides comprising, or alternatively consisting of, the amino acid sequence of a member selected from the group consisting of residues M-1 to P-162; M-1 to E-161; M-1 to A-160; M-1 to P-159; M-1 to P-158; M-1 to S-157; M-1 to G-156; M-1 to P-155; M-1 to V-154; M-1 to C-153; M-1 to V-152; M-1 to A-151; M-1 to N-150; M-1 to H-149; M-1 to T-148; M-1 to K-147; M-1 to N-146; M-1 to G-145; M-1 to P-144; M-1 to F-143; M-1 to V-142; M-1 to T-141; M-1 to L-140; M-1 to F-139; M-1 to G-138; M-1 to F-137; M-1 to Q-136; M-1 to T-135; M-1 to C-134; M-1 to D-133; M-1 to T-132; M-1 to W-131; M-1 to P-130; M-1 to K-129; M-1 to C-128; M-1 to H-127; M-1 to G-126; M-1 to E-125; M-1 to H-124; M-1 to G-123; M-1 to G-122; M-1 to S-121; M-1 to F-120; M-1 to T-119; M-1 to G-118; M-1 to S-117; M-1 to A-116; M-1 to C-115; M-1 to D-114; M-1 to I-113; M-1 to C-112; M-1 to Q-111; M-1 to F-110; M-1 to G-109; M-1 to F-108; M-1 to S-107; M-1 to F-106; M-1 to K-105; M-1 to G-104; M-1 to Q-103; M-1 to S-102; M-1 to Q-101; M-1 to V-100; M-1 to G-99; M-1 to Q-98; M-1 to G-97; M-1 to P-96; M-1 to P-95; M-1 to C-94; M-1 to P-93; M-1 to H-92; M-1 to H-91; M-1 to R-90; M-1 to C-89; M-1 to T-88; M-1 to T-87; M-1 to C-86; M-1 to C-85; M-1 to P-84; M-1 to D-83; M-1 to G-82; M-1 to C-81; M-1 to H-80; M-1 to F-79; M-1 to E-78; M-1 to P-77; M-1 to Q-76; M-1 to V-75; M-1 to C-74; M-1 to M-73; M-1 to C-72; M-1 to D-71; M-1 to W-70; M-1 to E-69; M-1 to S-68; M-1 to C-67; M-1 to C-66; M-1 to E-65; M-1 to E-64; M-1 to G-63; M-1 to P-62; M-1 to C-61; M-1 to S-60; M-1 to V-59; M-1 to P-58; M-1 to W-57; M-1 to G-56; M-1 to G-55; M-1 to L-54; M-1 to L-53; M-1 to Q-52; M-1 to A-51; M-1 to S-50; M-1 to A-49; M-1 to G-48; M-1 to E-47; M-1 to E-46; M-1 to G-45; M-1 to P-44; M-1 to R-43; M-1 to G-42; M-1 to E-41; M-1 to A-40; M-1 to R-39; M-1 to W-38; M-1 to P-37; M-1 to L-36; M-1 to S-35; M-1 to T-34; M-1 to T-33; M-1 to R-32; M-1 to E-31; M-1 to G-30; M-1 to G-29; M-1 to V-28; M-1 to T-27; M-1 to P-26; M-1 to E-25; M-1 to L-24; M-1 to S-23; M-1 to C-22; M-1 to L-21; M-1 to A-20; M-1 to G-19; M-1 to P-18; M-1 to Q-17; M-1 to S-16; M-1 to D-15; M-1 to P-14; M-1 to G-13; M-1 to P-12; M-1 to N-11; M-1 to I-10; M-1 to W-9; M-1 to S-8; M-1 to D-7; and M-1 to R-6 of the sequence of the TR11SV1 sequence shown in FIGS. 2A and 2B (SEQ ID NO:4). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a soluble TR11SV1 polypeptide, which may be described generally as having residues $n^5\text{-}m^5$ of FIGS. 2A and 2B (SEQ ID NO:4), where $n^5$ and $m^5$ are integers as described above.

In addition, the present invention further provides polypeptides having one or more residues deleted from the amino terminus of the predicted extracellular domain of the TR11SV2 amino acid sequence shown in FIGS. 3A and 3B (SEQ ID NO:6), up to the glycine residue at position number 162 and polynucleotides encoding such polypeptides. In particular, the present invention provides polypeptides comprising the amino acid sequence of residues $n^{5-168}$ of FIGS. 3A and 3B (SEQ ID NO:6), where $n^6$ is an integer in the range of 20 to 162, and 163 is the position of the first residue from the N-terminus of the predicted extracellular domain of the TR11SV2 polypeptide believed to be required for at least immunogenic activity of the predicted extracellular domain of the TR11SV2 protein.

More in particular, the invention provides polynucleotides encoding polypeptides comprising, or alternatively consisting of, the amino acid sequence of a member selected from the group consisting of residues of Q-20 to P-168; R-21 to P-168; P-22 to P-168; T-23 to P-168; G-24 to P-168; G-25 to P-168; P-26 to P-168; G-27 to P-168; C-28 to P-168; G-29 to P-168; P-30 to P-168; G-31 to P-168; R-32 to P-168; L-33 to P-168; L-34 to P-168; L-35 to P-168; G-36 to P-168; T-37 to P-168; G-38 to P-168; T-39 to P-168; D-40 to P-168; A-41 to P-168; R-42 to P-168; C-43 to P-168; C-44 to P-168; R-45 to P-168; V-46 to P-168; H-47 to P-168; T-48 to P-168; T-49 to P-168; R-50 to P-168; C-51 to P-168; C-52 to P-168; R-53 to P-168; D-54 to P-168; Y-55 to P-168; P-56 to P-168; A-57 to P-168; Q-58 to P-168; L-59 to P-168; L-60 to P-168; G-61 to P-168; G-62 to P-168; W-63 to P-168; P-64 to P-168; V-65 to P-168; S-66 to P-168; C-67 to P-168; P-68 to P-168; G-69 to P-168; E-70 to P-168; E-71 to P-168; C-72 to P-168; C-73 to P-168; S-74 to P-168; E-75 to P-168; W-76 to P-168; D-77 to P-168; C-78 to P-168; M-79 to P-168; C-80 to P-168; V-81 to P-168; Q-82 to P-168; P-83 to P-168; E-84 to P-168; F-85 to P-168; H-86 to P-168; C-87 to P-168; G-88 to P-168; D-89 to P-168; P-90 to P-168; C-91 to P-168; C-92 to P-168; T-93 to P-168; T-94 to P-168; C-95 to P-168; R-96 to P-168; H-97 to P-168; H-98 to P-168; P-99 to P-168; C-100 to P-168; P-101 to P-168; P-102 to P-168; G-103 to P-168; Q-104 to P-168; G-105 to P-168; V-106 to P-168; Q-107 to P-168; S-108 to P-168; Q-109 to P-168; G-110 to P-168; K-111 to P-168; F-112 to P-168; S-113 to P-168; F-114 to P-168; G-115 to P-168; F-116 to P-168; Q-117 to P-168; C-118 to P-168; I-119 to P-168; D-120 to P-168; C-121 to P-168; A-122 to P-168; S-123 to P-168; G-124 to P-168; T-125 to P-168; F-126 to P-168; S-127 to P-168; G-128 to P-168; G-129 to P-168; H-130 to P-168; E-131 to P-168; G-132 to P-168; H-133 to P-168; C-134 to P-168; K-135 to P-168; P-136 to P-168; W-137 to P-168; T-138 to P-168; D-139 to P-168; C-140 to P-168; T-141 to P-168; Q-142 to P-168; F-143 to P-168; G-144 to P-168; F-145 to P-168; L-146 to P-168; T-147 to P-168; V-148 to P-168; F-149 to P-168; P-150 to P-168; G-151 to P-168; N-152 to P-168; K-153 to P-168; T-154 to P-168; H-155 Lo P-168; N-156 to P-168; A-157 to P-168; V-158 to P-168; C-159 to P-168; V-160 to P-168; P-161 to P-168; and G-162 to P-168 of the TR11SV2 amino acid sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The present invention further provides polypeptides having one or more residues deleted from the carboxy terminus of the predicted extracellular domain of the amino acid sequence of the TR11SV2 shown in FIGS. 3A and 3B (SEQ ID NO:6), up to the proline residue at position number 26, and polynucleotides encoding such polypeptides. In particular, the present invention provides polypeptides comprising the amino acid sequence of residues 20-$m^6$ of FIGS. 3A and 3B (SEQ ID NO:6), where $m^6$ is an integer in the range of 26 to 168, and 26 is the position of the first residue from the C-terminus of the predicted extracellular domain of the TR11SV2 polypeptide believed to be required for at least immunogenic activity of the TR11SV2 protein.

More in particular, the invention provides polynucleotides encoding polypeptides comprising, or alternatively consisting of, the amino acid sequence of a member selected from the group consisting of residues Q-20 to P-168; Q-20 to E-167; Q-20 to A-166; Q-20 to P-165; Q-20 to P-164; Q-20 to S-163; Q-20 to G-162; Q-20 to P-161; Q-20 to V-160; Q-20 to C-159; Q-20 to V-158; Q-20 to A-157; Q-20 to N-156; Q-20 to H-155; Q-20 to T-154; Q-20 to K-153; Q-20 to N-152; Q-20 to G-151; Q-20 to P-150; Q-20 to F-149; Q-20 to V-148; Q-20 to T-147; Q-20 to L-146; Q-20 to F-145; Q-20 to G-144; Q-20 to F-143; Q-20 to Q-142; Q-20 to T-141; Q-20 to C-140; Q-20 to D-139; Q-20 to T-138; Q-20 to W-137; Q-20 to P-136; Q-20 to K-135; Q-20 to C-134; Q-20 to H-133; Q-20 to G-132; Q-20 to E-131; Q-20 to H-130; Q-20 to G-129; Q-20 to G-128; Q-20 to S-127; Q-20 to F-126; Q-20 to T-125; Q-20 to G-124; Q-20 to S-123; Q-20 to A-122; Q-20 to C-121; Q-20 to D-120; Q-20 to I-119; Q-20 to C-118; Q-20 to Q-117; Q-20 to F-116; Q-20 to G-115; Q-20 to F-114; Q-20 to S-113; Q-20 to F-112; Q-20 to K-111; Q-20 to G-110; Q-20 to Q-109; Q-20 to S-108; Q-20 to Q-107; Q-20 to V-106; Q-20 to G-105; Q-20 to Q-104; Q-20 to G-103; Q-20 to P-102; Q-20 to P-101; Q-20 to C-100; Q-20 to P-99; Q-20 to H-98; Q-20 to H-97; Q-20 to R-96; Q-20 to C-95; Q-20 to T-94; Q-20 to T-93; Q-20 to C-92; Q-20 to C-91; Q-20 to P-90; Q-20 to D-89; Q-20 to G-88; Q-20 to C-87; Q-20 to H-86; Q-20 to F-85; Q-20 to E-84; Q-20 to P-83; Q-20 to Q-82; Q-20 to V-81; Q-20 to C-80; Q-20 to M-79; Q-20 to C-78; Q-20 to D-77; Q-20 to W-76; Q-20 to E-75; Q-20 to S-74; Q-20 to C-73; Q-20 to C-72; Q-20 to E-71; Q-20 to E-70; Q-20 to G-69; Q-20 to P-68; Q-20 to C-67; Q-20 to S-66; Q-20 to V-65; Q-20 to P-64; Q-20 to W-63; Q-20 to G-62; Q-20 to G-61; Q-20 to L-60; Q-20 to L-59; Q-20 to Q-58; Q-20 to A-57; Q-20 to P-56; Q-20 to Y-55; Q-20 to D-54; Q-20 to R-53; Q-20 to C-52; Q-20 to C-51; Q-20 to R-50; Q-20 to T-49; Q-20 to T-48; Q-20 to H-47; Q-20 to V-46; Q-20 to R-45; Q-20 to C-44; Q-20 to C-43; Q-20 to R-42; Q-20 to A-41; Q-20 to D-40; Q-20 to T-39; Q-20 to G-38; Q-20 to T-37; Q-20 to G-36; Q-20 to L-35; Q-20 to L-34; Q-20 to L-33; Q-20 to R-32; Q-20 to G-31; Q-20 to P-30; Q-20 to G-29; Q-20 to C-28; Q-20 to G-27; and Q-20 to P-26 of the sequence of the TR11SV2 sequence shown in FIGS. 3A and 3B (which is identical to the sequence shown as SEQ ID NO:6, with the exception that the amino acid residues in FIGS. 3A and 3B are numbered consecutively from 1 through 240 from the N-terminus to the C-terminus, while the amino acid residues in SEQ ID NO:6 are numbered consecutively from −19 through 221 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV 1, and/or TR11SV2 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a TR11SV2 polypeptide, which may be described generally as having residues $n^6$-$m^6$ of FIGS. 3A and 3B (SEQ ID NO:6), where $n^6$ and $m^6$ are integers as described above.

In certain preferred embodiments, the TR11 polynucleotide of the invention has the polynucleotide sequence shown in SEQ ID NO:28. In these preferred embodiments, the corresponding TR11 polypeptide has the polypeptide sequence shown in SEQ ID NO:28. As mentioned above, even if deletion of one or more amino acids from the N-terminus of a protein results in modification of loss of one or more biological functions of the protein, other biological activities may still be retained. Thus, the ability of shortened TR11 muteins in these preferred embodiments to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TR11 mutein with a large number of deleted N-terminal amino acid residues may retain some biological or immunogenic activities. In fact, peptides composed of as few as six TR11 amino acid residues may often evoke an immune response.

Accordingly, the present invention further provides polypeptides having one or more residues deleted from the amino terminus of the TR11 amino acid sequence shown as SEQ ID NO:28, up to the leucine residue at position number 236 and polynucleotides encoding such polypeptides. In particular, the present invention provides polypeptides comprising the amino acid sequence of residues $n^{7-241}$ of SEQ ID NO:28, where $n^7$ is an integer in the range of 2 to 236, and 237 is the position of the first residue from the N-terminus of the complete TR11 polypeptide believed to be required for at least immunogenic activity of the TR11 polypeptide.

More in particular, the invention provides polynucleotides encoding polypeptides comprising, or alternatively consisting of, the amino acid sequence of a member selected from the group consisting of A-2 to V-241; Q-3 to V-241; H-4 to V-241; G-5 to V-241; A-6 to V-241; M-7 to V-241; G-8 to V-241; A-9 to V-241; F-10 to V-241; R-11 to V-241; A-12 to V-241; L-13 to V-241; C-14 to V-241; G-15 to V-241; L-16 to V-241; A-17 to V-241; L-18 to V-241; L-19 to V-241; C-20 to V-241; A-21 to V-241; L-22 to V-241; S-23 to V-241; L-24 to V-241; G-25 to V-241; Q-26 to V-241; R-27 to V-241; P-28 to V-241; T-29 to V-241; G-30 to V-241; G-31 to V-241; P-32 to V-241; G-33 to V-241; C-34 to V-241; G-35 to V-241; P-36 to V-241; G-37 to V-241; R-38 to V-241; L-39 to V-241; L-40 to V-241; L-41 to V-241; G-42 to V-241; T-43 to V-241; G-44 to V-241; T-45 to V-241; D-46 to V-241; A-47 to V-241; R-48 to V-241; C-49 to V-241; C-50 to V-241; R-51 to V-241; V-52 to V-241; H-53 to V-241; T-54 to V-241; T-55 to V-241; R-56 to V-241; C-57 to V-241; C-58 to V-241; R-59 to V-241; D-60 to V-241; Y-61 to V-241; P-62 to V-241; G-63 to V-241; E-64 to V-241; E-65 to V-241; C-66 to V-241; C-67 to V-241; S-68 to V-241; E-69 to V-241; W-70 to V-241; D-71 to V-241; C-72 to V-241; M-73 to V-241; C-74 to V-241; V-75 to V-241; Q-76 to V-241; P-77 to V-241; E-78 to V-241; F-79 to V-241; H-80 to V-241; C-81 to V-241; G-82 to V-241; D-83 to V-241; P-84 to V-241; C-85 to V-241; C-86 to V-241; T-87 to V-241; T-88 to V-241; C-89 to V-241; R-90 to V-241; H-91 to V-241; H-92 to V-241; P-93 to V-241; C-94 to V-241; P-95 to V-241; P-96 to V-241; G-97 to V-241; Q-98 to V-241; G-99 to V-241; V-100 to V-241; Q-101 to V-241; S-102 to V-241; Q-103 to V-241; G-104 to V-241; K-105 to V-241; F-106 to V-241; S-107 to V-241; F-108 to V-241; G-109 to V-241; F-110 to V-241; Q-111 to V-241; C-112 to V-241; I-113 to V-241; D-114 to V-241; C-115 to V-241; A-116 to V-241; S-117 to V-241; G-118 to V-241; T-119 to V-241; F-120 to V-241; S-121 to V-241; G-122 to V-241; G-123 to V-241; H-124 to V-241; E-125 to V-241; G-126 to V-241; H-127 to V-241; C-128 to V-241; K-129 to V-241; P-130 to V-241; W-131 to V-241; T-132 to V-241; D-133 to V-241; C-134 to V-241; T-135 to V-241; Q-136 to V-241; F-137 to V-241; G-138 to V-241; F-139 to V-241; L-140 to V-241; T-141 to V-241; V-142 to V-241; F-143 to V-241; P-144 to V-241; G-145 to V-241; N-146 to V-241; K-147 to V-241; T-148 to V-241; H-149 to V-241; N-150 to V-241; A-151 to V-241; V-152 to V-241; C-153 to V-241; V-154 to V-241; P-155 to V-241; G-156 to V-241; S-157 to V-241; P-158 to V-241; P-159 to V-241; A-160 to V-241; E-161 to V-241; P-162 to V-241; L-163 to V-241; G-164 to V-241; W-165 to V-241; L-166 to V-241; T-167 to V-241; V-168 to V-241; V-169 to V-241; L-170 to V-241; L-171 to V-241; A-172 to V-241; V-173 to V-241; A-174 to V-241; A-175 to V-241; C-176 to V-241; V-177 to V-241; L-178 to V-241; L-179 to V-241; L-180 to V-241; T-181 to V-241; S-182 to V-241; A-183 to V-241; Q-184 to V-241; L-185 to V-241; G-186 to V-241; L-187 to V-241; H-188 to V-241; I-189 to V-241; W-190 to V-241; Q-191 to V-241; L-192 to V-241; R-193 to V-241; S-194 to V-241; Q-195 to V-241; C-196 to V-241; M-197 to V-241; W-198 to V-241; P-199 to V-241; R-200 to V-241; E-201 to V-241; T-202 to V-241; Q-203 to V-241; L-204 to V-241; L-205 to V-241; L-206 to V-241; E-207 to V-241; V-208 to V-241; P-209 to V-241; P-210 to V-241; S-211 to V-241; T-212 to V-241; E-213 to V-241; D-214 to V-241; A-215 to V-241; R-216 to V-241; S-217 to V-241; C-218 to V-241; Q-219 to V-241; F-220 to V-241; P-221 to V-241; E-222 to V-241; E-223 to V-241; E-224 to V-241; R-225 to V-241; G-226 to V-241; E-227 to V-241; R-228 to V-241; S-229 to V-241; A-230 to V-241; E-231 to V-241; E-232 to V-241; K-233 to V-241; G-234 to V-241; R-235 to V-241; and L-236 to V-241 of the TR11 sequence shown in SEQ ID NO:28. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

Also as mentioned above, even if deletion of one or more amino acids from the C-terminus of a protein results in modification of loss of one or more biological functions of the protein, other biological activities may still be retained. Thus, the ability of the shortened TR11 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TR11 mutein with a large number of deleted C-terminal amino acid residues may retain some biological or immunogenic activities. In fact, peptides composed of as few as six TR11 amino acid residues may often evoke an immune response.

Accordingly, the present invention further provides polypeptides having one or more residues deleted from the carboxy terminus of the amino acid sequence of the TR11 polypeptide shown as SEQ ID NO:28, up to the alanine residue at position number 6, and polynucleotides encoding such polypeptides. In particular, the present invention provides polypeptides comprising the amino acid sequence of residues 1-m$^7$ of SEQ ID NO:28, where m$^7$ is an integer in the range of 6 to 240, and 6 is the position of the first residue from the C-terminus of the complete TR11 polypeptide believed to be required for at least immunogenic activity of the TR11 polypeptide.

More in particular, the invention provides polynucleotides encoding polypeptides comprising, or alternatively consisting of, the amino acid sequence of a member selected from the group consisting of residues M-1 to W-240; M-1 to L-239; M-1 to D-238; M-1 to -237; M-1 to L-236; M-1 to R-235; M-1 to G-234; M-1 to K-233; M-1 to E-232; M-1 to E-231; M-1 to A-230; M-1 to S-229; M-1 to R-228; M-1 to E-227; M-1 to G-226; M-1 to R-225; M-1 to E-224; M-1 to E-223; M-1 to E-222; M-1 to P-221; M-1 to F-220; M-1 to Q-219; M-1 to C-218; M-1 to S-217; M-1 to R-216; M-1 to A-215; M-1 to D-214; M-1 to E-213; M-1 to T-212; M-1 to S-211; M-1 to P-210; M-1 to P-209; M-1 to V-208; M-1 to E-207; M-1 to L-206; M-1 to L-205; M-1 to L-204; M-1 to Q-203; M-1 to T-202; M-1 to E-201; M-1 to R-200; M-1 to P-199; M-1 to W-198; M-1 to M-197; M-1 to C-196; M-1 to Q-195; M-1 to S-194; M-1 to R-193; M-1 to L-192; M-1 to Q-191; M-1 to W-190; M-1 to I-189; M-1 to H-188; M-1 to L-187; M-1 to G-186; M-1 to L-185; M-1 to Q-184; M-1 to A-183; M-1 to S-182; M-1 to T-181; M-1 to L-180; M-1 to L-179; M-1 to L-178; M-1 to V-177; M-1 to C-176; M-1 to A-175; M-1 to A-174; M-1 to V-173; M-1 to A-172; M-1 to L-171; M-1 to L-170; M-1 to V-169; M-1 to V-168; M-1 to T-167; M-1 to L-166; M-1 to W-165; M-1 to G-164; M-1 to L-163; M-1 to P-162; M-1 to E-161; M-1 to A-160; M-1 to P-159; M-1 to P-158; M-1 to S-157; M-1 to G-156; M-1 to P-155; M-1 to V-154; M-1 to C-153; M-1 to V-152; M-1 to A-151; M-1 to N-150; M-1 to H-149; M-1 to T-148; M-1 to K-147; M-1 to N-146; M-1 to G-145; M-1 to P-144; M-1 to F-143; M-1 to V-142; M-1 to T-141; M-1 to L-140; M-1 to F-139; M-1 to G-138; M-1 to F-137; M-1 to Q-136; M-1 to T-135; M-1 to C-134; M-1 to D-133; M-1 to T-132; M-1 to W-131; M-1 to P-130; M-1 to K-129; M-1 to C-128; M-1 to H-127; M-1 to G-126; M-1 to E-125; M-1 to H-124; M-1 to G-123; M-1 to G-122; M-1 to S-121; M-1 to F-120; M-1 to T-119; M-1 to G-118; M-1 to S-117; M-1 to A-116; M-1 to C-115; M-1 to D-114; M-1 to I-113; M-1 to C-112; M-1 to Q-111; M-1 to F-110; M-1 to G-109; M-1 to F-108; M-1 to S-107; M-1 to F-106; M-1 to K-105; M-1 to G-104; M-1 to Q-103; M-1 to S-102; M-1 to Q-101; M-1 to V-100; M-1 to G-99; M-1 to Q-98; M-1 to G-97; M-1 to P-96; M-1 to P-95; M-1 to C-94; M-1 to P-93; M-1 to H-92; M-1 to H-91; M-1 to R-90; M-1 to C-89; M-1 to T-88; M-1 to T-87; M-1 to C-86; M-1 to C-85; M-1 to P-84; M-1 to D-83; M-1 to G-82; M-1 to C-81; M-1 to H-80; M-1 to F-79; M-1 to E-78; M-1 to P-77; M-1 to Q-76; M-1 to V-75; M-1 to C-74; M-1 to M-73; M-1 to C-72; M-1 to D-71; M-1 to W-70; M-1 to E-69; M-1 to S-68; M-1 to C-67; M-1 to C-66; M-1 to E-65; M-1 to E-64; M-1 to G-63; M-1 to P-62; M-1 to Y-61; M-1 to D-60; M-1 to R-59; M-1 to C-58; M-1 to C-57; M-1 to R-56; M-1 to T-55; M-1 to T-54; M-1 to H-53; M-1 to V-52; M-1 to R-51; M-1 to C-50; M-1 to C-49; M-1 to R-48; M-1 to A-47; M-1 to D-46; M-1 to T-45; M-1 to G-44; M-1 to T-43; M-1 to G-42; M-1 to L-41; M-1 to L-40; M-1 to L-39; M-1 to R-38; M-1 to G-37; M-1 to P-36; M-1 to G-35; M-1 to C-34; M-1 to G-33; M-1 to P-32; M-1 to G-31; M-1 to G-30; M-1 to T-29; M-1 to P-28; M-1 to R-27; M-1 to Q-26; M-1 to G-25; M-1 to L-24; M-1 to S-23; M-1 to L-22; M-1 to A-21; M-1 to C-20; M-1 to L-19; M-1 to L-18; M-1 to A-17; M-1 to L-16; M-1 to G-1 L-15; M-1 to C-14; M-1 to L-13; M-1 to A-12; M-1 to R-11; M-1 to F-10; M-1 to A-9; M-1 to G-8; M-1 to M-7; and M-1 to A-6 of the sequence of the TR11 sequence shown as SEQ ID NO:28. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR11, TR11SV1, and/or TR11SV2 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a TR11 polypeptide, which may be described generally as having residues $n^7$-$m^7$ of SEQ ID NO:28, where n and m are integers as described above.

The polypeptides of this invention may be membrane bound or may be in a soluble circulating form. Soluble peptides are defined by amino acid sequence wherein the sequence comprises the polypeptide sequence lacking the transmembrane domain.

The polypeptides of the present invention may exist as a membrane bound receptor having a transmembrane region and an intra- and extracellular region or they may exist in soluble form wherein the transmembrane domain is lacking. One example of such a form of the TR11, TR11SV1, and TR11SV2 receptors is the TR11, TR11SV1, and TR11SV2 receptors shown in FIGS. 1A and 1B, 2A and 2B, and 3A and 3B (SEQ ID NO:2, SEQ ID NO:4, and SEQ ID NO:6, respectively) which contain transmembrane, intracellular and extracellular domains. Thus, these forms of the TR11, TR11SV1, and TR11SV2 receptors appear to be localized in the cytoplasmic membrane of cells which express these proteins.

It will be recognized in the art that some amino acid sequences of the TR11, TR11SV1, and TR11SV2 receptors can be varied without significant effect to the structure or function of the protein. If such differences in sequence are contemplated, it should be remembered that there will be critical areas on the protein which determine activity. Thus, the invention further includes variations of the TR11, TR11SV1, and TR11SV2 receptors which show substantial TR11, TR11SV1 or TR11SV2 receptor activities or which include regions of TR11, TR11SV1, and TR11SV2 proteins such as the protein portions discussed below. Such mutants include deletions, insertions, repeats, and type substitutions. As indicated above, guidance concerning which amino acid changes are likely to be phenotypically silent can be found in the publication authored by Bowie and coworkers ("Deciphering the Message in Protein Sequences: Tolerance to Amino Acid Substitutions," Science 247:1306–1310 (1990)).

Thus, the fragments, derivatives or analogs of the polypeptides of FIGS. 1A and 1B, 2A and 2B, and 3A and 3B (SEQ ID NO:2, SEQ ID NO:4, and SEQ ID NO:6, respectively), or those encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR11, TR11SV1 or TR11SV2 proteins. The prevention of aggregation is highly desirable. Aggregation of proteins not only results in a loss of activity but can also be problematic when preparing pharmaceutical formulations, because they can be immunogenic (Pinckard, et al., Clin Exp. Immunol. 2:331–340 (1967); Robbins, et al., Diabetes 36:838–845 (1987); Cleland, et al. Crit. Rev. Therapeutic Drug Carrier Systems 10:307–377 (1993)).

The replacement of amino acids can also change the selectivity of binding to cell surface receptors. Ostade and colleagues (Nature 361:266–268 (1993)) describe certain mutations resulting in selective binding of TNF-alpha to only one of the two previously described types of TNF receptors. Thus, the TR11, TR11SV1, and TR11SV2 receptors of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table I).

TABLE I

| Conservative Amino Acid Substitutions. | |
|---|---|
| Aromatic | Phenylalanine |
|  | Tryptophan |
|  | Tyrosine |

TABLE I-continued

| Conservative Amino Acid Substitutions. | |
|---|---|
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

Embodiments of the invention are directed to polypeptides which comprise the amino acid sequence of a TR11, TR11SV1, and/or TR11SV2 polypeptide described herein, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, when compared with the TR11, TR11SV1, and/or TR11SV2 polynucleotide sequence described herein. Of course, in order of ever-increasing preference, it is highly preferable for a peptide or polypeptide to have an amino acid sequence which comprises the amino acid sequence of a TR11, TR11SV1, and/or TR11SV2 polypeptide, which contains at least one, but not more than 10, 9, 8, 7, 6, 5, 4, 3, 2 or 1 conservative amino acid substitutions.

Amino acids in the TR11, TR11SV1 and TR11SV2 proteins of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al. Science 255:306–312 (1992)).

To improve or alter the characteristics of TR11, TR11SV1 and/or TR11SV2 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., Nucl. Acids Res. 13:4331 (1986); and Zoller et al., Nucl. Acids Res. 10:6487 (1982)), cassette mutagenesis (see e.g., Wells et al., Gene 34:315 (1985)), restriction selection mutagenesis (see e.g., Wells et al., Philos. Trans. R. Soc. London SerA 317:415 (1986)).

Thus, the invention also encompasses TR11, TR11SV1 and/or TR11SV2 derivatives and analogs that have one or more amino acid residues deleted, added, or substituted to generate TR11, TR11SV1 and/or TR11SV2 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the TR11, TR11SV1 and/or TR11SV2 polypeptides of the invention, and/or an amino acid deletion at the second position of any one or more such recognition sequences will prevent glycosylation of TR11, TR11SV1 and/or TR11SV2 at the modified tripeptide sequence (see, e.g., Miyajimo et al., EMBO J 5(6): 1193–1197). Additionally, one or more of the amino acid residues of the polypeptides of the invention (e.g., arginine and lysine residues) may be deleted or substituted with another residue to eliminate undesired processing by proteases such as, for example, furins or kexins.

Additionally, the techniques of gene-shuffling, motif-shuffling, exon-shuffling, and/or codon-shuffling (collectively referred to as "DNA shuffling") may be employed to modulate the activities of TR11, TR11SV1 and/or TR11SV2 thereby effectively generating agonists and antagonists of TR11, TR11SV1 and/or TR11SV2. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of TR11, TR11SV1 and/or TR11SV2 polynucleotides and corresponding polypeptides may be achieved by DNA shuffling. DNA shuffling involves the assembly of two or more DNA segments into a desired TR11, TR11SV1 and/or TR11SV2 molecule by homologous, or site-specific, recombination. In another embodiment, TR11, TR11SV1 and/or TR11SV2 polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TR11, TR11SV1 and/or TR11SV2 may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185–1190(1998)), endokine-alpha (International Publication No. WO 98/07880), Neutrokine-alpha (International Publication No. WO 98/18921), OPG, OX40, and nerve growth factor (NGF), and soluble forms of Fas, CD30, CD27, CD40 and 4-1BB, DR3 (International Publication No. WO 97/33904), DR4 (International Publication No. WO 98/32856), TR5 (International Publication No. WO 98/30693), TR6 (International Publication No. WO 98/30694),TR7 (International Publication No. WO 98/41629), TRANK, TR9 (International Publication No. WO 98/56892),TR10 (International Publication No. WO 98/54202),312C2 (International Publication No. WO 98/06842), TR12, and TNF-R1, TRAMP/DR3/APO-3JWSULARD, TRAIL-R1/DR4/APO-2, TRAIL-R2/DR5, DcRI/TRAIL-R3/TRID/LIT, DcR2/TRAIL-R4, CAD, TRAIL, TRAMP, v-FLIP.

In further preferred embodiments, the heterologous molecules are any member of the TNF family.

Preferably, the polynucleotides of the invention (including TR11, TR11SV1 and/or TR11SV2 fragments, variants, derivatives and analogs) encode a polypeptide which demonstrates a TR11, TR11SV1 and/or TR11SV2 functional activity. By a polypeptide demonstrating a "functional activity" is meant, a polypeptide capable of displaying one or more known functional activities associated with a full-length and/or secreted TR11, TR11SV1 and/or TR11SV2 polypeptide. Such functional activities include, but are not limited to, biological activity (e.g., ability to regulate (i.e., stimulate or inhibit) B cell and/or T cell proliferation (e.g., see Example 31), differentiation, activation or stimulation (e.g., see Example 32), and/or survival), antigenicity [ability to bind (or compete with a TR11, TR11SV1 and/or TR11SV2 polypeptide for binding) to an anti-TR11 antibody, anti-TR11SV1 antibody and/or anti-TR11SV2 antibody], immunogenicity (ability to generate antibody which binds to a TR11, TR11SV1 and/or TR11SV2 polypeptide), ability to form multimers with TR11, TR11SV11 and/or TR11SV2 polypeptides of the invention, and ability to bind to a receptor or ligand for a TR11, TR11SV1 and/or TR11SV2 (e.g., Endokine-alpha (See, International Publication No. WO 98/07880 and Example 28) and APRIL (J. Exp. Med. 188(6):1185–1190 (1998)).

The functional activity of TR11, TR11SV1 and/or TR11SV2 polypeptides, and fragments, variants, derivatives, and analogs thereof, can be assayed by various methods.

For example, in one embodiment where one is assaying for the ability to bind or compete with full-length TR11, TR11SV1 and/or TR11SV2 polypeptide for binding to anti-TR11 antibody, anti-TR11SV1 antibody and/or anti-TR11SV2 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a TR11, TR11SV1 and/or TR11SV2 ligand is identified (e.g., Endokine-alpha (See, International Publication No. WO 98/07880 and Example 28) and APRIL (J. Exp. Med. 188(6):1185–1190 (1998)), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., Microbiol. Rev. 59:94–123 (1995). In another embodiment, physiological correlates of TR11, TR11SV1 and/or TR11SV2 binding to its substrates (signal transduction) can be assayed.

In addition, assays described herein (see, e.g., Example 28 and Example 32) and otherwise known in the art may routinely be applied to measure the ability of TR11, TR11SV1 and/or TR11SV2 polypeptides and fragments, variants derivatives and analogs thereof to elicit TR11, TR11SV1 and/or TR11SV2 related biological activity (e.g., to stimulate, or alternatively to inhibit or reduce B cell and/or T cell proliferation, differentiation, activation, and/or survival, in vitro or in vivo).

Other methods for assessing functional activity of TR11, TR11SV1 and/or TR11SV2 polypeptides of the invention will be known to the skilled artisan and are within the scope of the invention.

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of the TR11, TR11SV1, and TR11SV2 receptors can be substantially purified by the one-step method described in Smith and Johnson, Gene 67:31–40 (1988).

The polypeptides of the present invention also include: (a) the TR11 polypeptide encoded by the deposited cDNA including the leader; (b) the TR11SV1 polypeptide encoded by the deposited cDNA including the leader; (c) the TR11SV2 polypeptide encoded by the deposited cDNA including the leader; (d) the TR11 polypeptide encoded by the deposited the cDNA minus the leader (i.e., the mature protein); (e) the TR11SV1 polypeptide encoded by the deposited the cDNA minus the leader (i.e., the mature protein); (f) the TR11SV2 polypeptide encoded by the deposited the cDNA minus the leader (i.e., the mature protein); (g) the TR11 polypeptide of FIGS. 1A and 1B (SEQ ID NO:2) including the leader; (h) the TR11SV1 polypeptide of FIGS. 2A and 2B (SEQ ID NO:4) including the leader; (i) the TR11SV2 polypeptide of FIGS. 3A and 3B (SEQ ID NO:6) including the leader; (j) the TR11 polypeptide of FIGS. 1A and 1B (SEQ ID NO:2) including the leader but minus the N-terminal methionine; (k) the TR11SV1 polypeptide of FIGS. 2A and 2B (SEQ ID NO:4) including the leader but minus the N-terminal methionine; (I) the TR11SV2 polypeptide of FIGS. 3A and 3B (SEQ ID NO:6) including the leader but minus the N-terminal methionine; (m) the polypeptide of FIGS. 1A and 1B (SEQ ID NO:2) minus the leader; (n) the polypeptide of FIGS. 2A and 2B (SEQ ID NO:4) minus the leader; (o) the polypeptide of FIGS. 3A and 3B (SEQ ID NO:6) minus the leader; (p) the extracellular domain, the transmembrane domain, and the intracellular domain of the TR11 receptor shown in FIGS. 1A and 1B (SEQ ID NO:2); (q) the extracellular domain, the transmembrane domain, and the intracellular domain of the TR11SV1 receptor shown in FIGS. 2A and 2B (SEQ ID NO:4); (r) the extracellular domain, the transmembrane domain, and the intracellular domain of the TR11SV2 receptor shown in FIGS. 3A and 3B (SEQ ID NO:6); and polypeptides which are at least 80% identical, more preferably 85%, even more preferably at least 90% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TR11, TR11SV1 or TR11SV2 polypeptide is intended that the amino acid sequence of the polypeptide is identical to the reference sequence except that the polypeptide sequence may include up to five amino acid alterations per each 100 amino acids of the reference amino acid of a TR11, TR11SV1 or TR11SV2 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence shown in FIGS. 1A and 1B (SEQ ID NO:2), FIGS. 2A and 2B (SEQ ID NO:4), and/or FIGS. 3A and 3B (SEQ ID NO:6), the amino acid sequence encoded by deposited cDNA clones HBEAC71, HT5EA78, and HCFAZ22, respectively, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag and colleagues (Comp. App. Biosci. 6:237–245 (1990)). Preferred parameters used in a FASTDB amino acid alignment are: Matrix= PAM 0, k-tuple=2, Mismatch Penalty=1, Joining Penalty= 20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is 1 what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., Cell 37:767–778 (1984) at 777. Antigenic epitope-bearing peptides and polypeptides of the invention preferably contain a sequence of at least seven, more preferably at least nine, at least eleven, at least fifteen, at least twenty, at least thirty, at least forty, at least fifty, and most preferably between at least about 15 to about 30 amino acids contained within the amino acid sequence of a polypeptide of the invention.

Non-limiting examples of antigenic polypeptides or peptides that can be used to generate TR11 receptor-specific antibodies include: a polypeptide comprising, or alternatively consisting of, amino acid residues from about Arg-2 to about Pro-11 in SEQ ID NO:2; a polypeptide comprising, or alternatively consisting of, amino acid residues from about Thr-18 to about Arg-26 in SEQ ID NO:2; a polypeptide comprising, or alternatively consisting of, amino acid residues from about Arg-34 to about Cys-42 in SEQ ID NO:2; a polypeptide comprising, or alternatively consisting of, amino acid residues from about Arg-31 to about Glu-39 in SEQ ID NO:2; a polypeptide comprising, or alternatively consisting of, amino acid residues from about Gly-38 to about Asp-46 in SEQ ID NO:2; a polypeptide comprising, or alternatively consisting of, amino acid residues from about Gly-74 to about Ser-82 in SEQ ID NO:2; a polypeptide comprising, or alternatively consisting of, amino acid residues from about Glu-100 to about Asp-108 in SEQ ID NO:2; a polypeptide comprising, or alternatively consisting of, amino acid residues from about Phe-118 to about Ala-126 in SEQ ID NO:2; a polypeptide comprising, or alternatively consisting of, amino acid residues from about Gly-131 to about Gly-139 in SEQ ID NO:2; a polypeptide comprising, or alternatively consisting of, amino acid residues from about Pro-178 to about Cys-186 in SEQ ID NO:2; and a polypeptide comprising, or alternatively consisting of, amino acid residues from about Ser-197 to about Gly-205 in SEQ ID NO:2. As indicated above, the inventors have determined that the above polypeptide fragments are antigenic regions of the TR11 receptor proteins.

Non-limiting examples of antigenic polypeptides or peptides that can be used to generate TR11SV1 receptor-specific antibodies include: a polypeptide comprising, or alternatively consisting of, amino acid residues from about Ala-2 to about Ile-10 in SEQ ID NO:4; a polypeptide comprising, or alternatively consisting of, amino acid residues from about Asn-11 to about Gly-19 in SEQ ID NO:4; a polypeptide comprising, or alternatively consisting of, amino acid residues from about Thr-27 to about Ser-35 in SEQ ID NO:4; a polypeptide comprising, or alternatively consisting of, amino acid residues from about Trp-38 to about Glu-46 in SEQ ID NO:4; a polypeptide comprising, or alternatively consisting of, amino acid residues from about Gly-42 to about Ser-50 in SEQ ID NO:4; a polypeptide comprising, or alternatively consisting of, amino acid residues from about Glu-31 to about Glu-46 in SEQ ID NO:4; a polypeptide comprising, or alternatively consisting of, amino acid residues from about Cys-61 to about Glu-69 in SEQ ID NO:4; a polypeptide comprising, or alternatively consisting of, amino acid residues from about Gly-99 to about Ser-107 in SEQ I) NO:4; a polypeptide comprising, or alternatively consisting of, amino acid residues from about Glu-125 to about Asp-133 in SEQ If) NO:4; a polypeptide comprising, or alternatively consisting of, amino acid residues from about Phe-143 to about Ala-151 in SEQ ID NO:4; a polypeptide comprising, or alternatively consisting of, amino acid residues from about Gly-156 to about Gly-164 in SEQ ID NO:4; a polypeptide comprising, or alternatively consisting of, amino acid residues from about Cys-196 to about Leu-204 in SEQ ID NO:4; a polypeptide comprising, or alternatively consisting of, amino acid residues from about Pro-209 to about Ser-217 in SEQ ID NO:4; and a polypeptide comprising, or alternatively consisting of, amino acid residues from about Ser-229 to about Gly-237 in SEQ ID NO:4. As indicated above, the inventors have determined that the above polypeptide fragments are antigenic regions of the TR11SV1 receptor proteins.

Non-limiting examples of antigenic polypeptides or peptides that can be used to generate TR11SV2 receptor-specific antibodies include: a polypeptide comprising, or alternatively consisting of, amino acid residues from about Gln-1 to about Cys-9 in SEQ ID NO:6; a polypeptide comprising, or alternatively consisting of, amino acid residues from about Gly-5 to about Arg-13 in SEQ ID NO:6; a polypeptide comprising, or alternatively consisting of, amino acid residues from about Thr-18 to about Arg-26 in SEQ ID NO:6; a polypeptide comprising, or alternatively consisting of, amino acid residues from about Thr-29 to about Pro-37 in SEQ ID NO:6; a polypeptide comprising, or alternatively consisting of, amino acid residues from about Cys-48 to about Glu-56 in SEQ ID NO:6; a polypeptide comprising, or alternatively consisting of, amino acid residues from about Val-87 to about Phe-95 in SEQ ID NO:6; a polypeptide comprising, or alternatively consisting of, amino acid residues from about His-111 to about Thr-119 in SEQ ID NO:6; a polypeptide comprising, or alternatively consisting of, amino acid residues from about Phe-130 to about Ala-138 in SEQ ID NO:6; a polypeptide comprising, or alternatively consisting of, amino acid residues from about Gly-143 to about Gly-151 in SEQ ID NO:6; a polypeptide comprising, or alternatively consisting of, amino acid residues from about Pro-190 to about Cys-198 in SEQ ID NO:6; and a polypeptide comprising, or alternatively consisting of, amino acid residues from about Ser-209 to about Gly-217 in SEQ ID NO:6. As indicated above, the inventors have determined that the above polypeptide fragments are antigenic regions of the TR11SV2 receptor proteins.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986).

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric if polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

In specific embodiments, TR11-immunoglobulin fusion polypeptides of the invention comprise, or alternatively, consist of, amino acids −25 to 139, 1 to 139, 5 to 139, 1 to 130, 1 to 120, or 1 to 110, of SEQ ID NO:2 fused to an Fc domain.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC deposit No. 209341 or encoded by a polynucleotide that hybridizes to the complement of the sequence of SEQ ID NO:1 or contained in ATCC deposit No. 209341 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The present invention encompasses polypeptides comprising, or alternatively consisting of, an epitope of the polypeptide having an amino acid sequence of SEQ ID NO:4, or an epitope of the polypeptide sequence encoded by a polynucleotide sequence contained in ATCC deposit No. 209343 or encoded by a polynucleotide that hybridizes to the complement of the sequence of SEQ ID NO:3 or contained in ATCC deposit No. 209343 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The present invention encompasses polypeptides comprising, or alternatively consisting of, an epitope of the polypeptide having an amino acid sequence of SEQ ID NO:6, or an epitope of the polypeptide sequence encoded by a polynucleotide sequence contained in ATCC deposit No. 209342 or encoded by a polynucleotide that hybridizes to the complement of the sequence of SEQ ID NO:5 or contained in ATCC deposit No. 209342 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:5), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemocyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention (e.g., those comprising an immunogenic or antigenic epitope) can be fused to heterologous polypeptide sequences. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-x of human serum albumin, where x is an integer from 1 to 585 and the albumin fragment has human serum albumin activity. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

In another embodiment, the TR11, TR11SV1, and/or TR11SV2 polypeptides of the present invention and the epitope-bearing fragments thereof are fused with a heterologous antigen (e.g., polypeptide, carbohydrate, phospholipid, or nucleic acid). In specific embodiments, the heterologous antigen is an immunogen.

In a more specific embodiment, the heterologous antigen is the gp120 protein of HIV, or a fragment thereof. Polynucleotides encoding these polypeptides are also encompassed by the invention.

In another embodiment, the TR11, TR11SV1, and/or TR11SV2 polypeptides of the present invention and the epitope-bearing fragments thereof are fused with polypeptide sequences of another TNF family member (or biologically active fragments or variants thereof). In a specific embodiment, the TR11, TR11SV1, and/or TR11SV2 polypeptides of the present invention are fused with a CD40L polypeptide sequence. In a preferred embodiment, the CD40L polypeptide sequence is soluble.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO: 1, SEQ ID NO:3, and/or SEQ ID NO:5, and the polypeptides encoded by these polynucleotides, may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodimnent, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

In a preferred embodiments, TR11, TR11SV1, and/or TR11SV2 polypeptides of the invention (inlcuding biologically active fragments or variants thereof), are fused with soluble CD40L polypeptides, or biologically active fragments or variants thereof.

The polypeptides of the present invention have uses, which include, but are not limited to, as molecular weight marker on SDS-PAGE gels or on molecular sieve gel filtration columns using methods well known to those of skill in the art.

Antibodies

Further polypeptides of the invention relate to antibodies and T-cell antigen receptors (TCR) which immunospecifically bind a polypeptide (e.g., a TR11 homodimer or homotrimer), polypeptide fragment, or variant of SEQ ID NO:2, SEQ ID NO:4 and/or SEQ ID NO:6, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In specific embodiments, the immunoglobulin molecules of the invention are IgG1. In other specific embodiments, the immunoglobulin molecules of the invention are IgG4. Immunoglobulins may have both a heavy and light chain. An array of IgG, IgE, IgM, IgD, IgA, and IgY heavy chains may be paired with a light chain of the kappa or lambda forms.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdfv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

In one embodiment, the antibodies of the invention preferentially and specifically bind TR11 (SEQ ID NO:2), or fragments, variants, or fusion proteins thereof (e.g., the extracellular region of TR11 fused to an Fc domain or to human serum albumin) relative to their ability to bind TR11SV1 or TR11SV2 (SEQ ID NOS:4 and 6) or fragments, variants, or fusion proteins thereof.

In another preferred embodiment, antibodies of the invention preferentially and specifically bind TR11SV1 (SEQ ID NO:4), fragments, variants, or fusion proteins thereof (e.g., the extracellular region of TR11SV1 fused to an Fc domain or to human serum albumin) relative to their ability to bind TR11, TR11SV2 (SEQ ID NOS:2 and 6) or fragments, variants, or fusion proteins thereof.

In another preferred embodiment, antibodies of the invention preferentially and specifically bind TR11SV2 (SEQ ID NO:6), fragments, variants, or fusion proteins thereof (e.g., the extracellular region of TR11SV2 fused to an Fc domain or to human serum albumin) relative to their ability to bind TR11 and TR11SV1 (SEQ ID NOS:2 and 4) or fragments, variants, or fusion proteins thereof.

In other preferred embodiments, the antibodies of the invention preferentially and specifically bind to TR11 and TR11SV1 (SEQ ID NOS:2 and 4), or fragments and variants thereof relative to their ability to bind TR11SV2 (SEQ ID NO:6) or fragments, variants, or fusion proteins thereof.

In other preferred embodiments, the antibodies of the invention preferentially and specifically bind to TR11 and TR11SV2 (SEQ ID NOS:2 and 6), or fragments and variants thereof relative to their ability to bind TR11SV1 (SEQ ID NO:4) or fragments, variants, or fusion proteins thereof.

In other preferred embodiments, the antibodies of the invention preferentially and specifically bind to TR11SV1 and TR11SV2 (SEQ ID NOS:4 and 6), or fragments and variants thereof relative to their ability to bind TR11 (SEQ ID NO:2) or fragments, variants, or fusion proteins thereof.

In particular embodiments, antibodies of the invention recognize epitopes in TR11SV1 and TR11SV2 that are formed, in full or in part, by amino acid residues that are distinct in TR11SV1 and TR11SV2 compared to TR11. For example, the antibodies of the invention may bind epitopes that are formed, in full or in part, by amino acid residues 1–62 of TR11SV1 (SEQ ID NO:4 and FIGS. 2A and B) or by the N-terminal 62 amino acids of the polypeptide encoded by the cDNA contained in ATCC Deposit No. 209343. As another example, the antibodies of the invention may bind epitopes that are formed, in full or in part, by amino acid residues 51–62 of TR11SV1 (SEQ ID NO:4 and FIGS. 2A and B), by amino acid residues 38–49 of TR11SV2 (SEQ ID NO:6) (which correspond to amino acid residues 57–68 as shown and numbered in FIGS. 3A–B), or by the stretch of contiguous amino acid residues of the extracellular domain of the polypeptide encoded by the cDNA in ATCC Deposit No. 209342 which are distinct from the amino acid amino acid residues of the extracellular domain of the polypeptide encoded by the cDNA in ATCC Deposit No. 209343.

In particular embodiments, antibodies of the invention recognize epitopes in TR11SV1 and TR11SV2 that are formed in full or in part by amino acid residues that are distinct in TR11SV1 and TR11SV2 compared to TR11. For example, the antibodies of the invention may bind epitopes that are formed, in full or in part, by amino acid residues in the first 62 amino acid residues of TR11SV1 (as shown and numbered in FIGS. 2A and B) or by the N-terminal 62 amino acids of the polypeptide encoded by the cDNA contained in ATCC Deposit No. 209343. As another example, the antibodies of the invention may bind epitopes that are formed, in full or in part, by amino acid residues from the region comprising amino acid residues 51–62 of TR11SV1 (SEQ ID NO:4 and FIGS. 2A and B); from the region comprising amino acid residues 38–49 of TR11SV2 (SEQ ID NO:6) (which correspond to amino acid residues 57–68 of as shown and numbered in FIGS. 3A–B), or from the amino acid residues of the extracellular domain of the polypeptide encoded by the cDNA in ATCC Deposit No. 209342 which are distinct from the amino acid amino acid residues of the extracellular domain of the polypeptide encoded by the cDNA in ATCC Deposit No. 209343.

Antibodies that can preferentially and specifically bind one or two polypeptides selected from the group consisting of TR11, TR11SV1 and TR11SV2 may be used, for example, to distinguish the each of these splice variants from one another. The ability of an antibody to preferentially and specifically bind one antigen compared to another antigen may be determined using any method known in the art.

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. In specific embodiments, antibodies of the invention disrupt the receptor/ligand interactions between the polypeptides of the invention and endokine-alpha either partially or fully. In other specific embodiments, antibodies of the invention disrupt the receptor/ligand interactions between the polypeptides of the invention and APRIL either partially or fully. In other specific embodiments, antibodies of the invention disrupt the receptoriligand interactions between the polypeptides of the invention and both endokine-alpha and APRIL either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization or trimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6): 1981–1988 (1998); Chen et al., Cancer Res. 58(16): 3668–3678 (1998); Harrop et al., J. Immunol. 161(4): 1786–1794 (1998); Zhu et al., Cancer Res. 58(15): 3209–3214 (1998); Yoon et al., J. Immunol. 160(7): 3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

A "monoclonal antibody" may comprise, or alternatively consist of, two proteins, i.e., a heavy and a light chain.

Methods for producing and screening for specific antibodies using hybridoma technology are routine and well known in the art and are discussed in detail in the Examples (e.g., Example 9). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCTJGB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Patent Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment, detection, and/or prevention in human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immnunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize or alternatively function as an agonist of the polypeptide and/or its ligand. Such neutralizing anti-idiotypes or Fab fragments of such anti-idiotypes can be used in therapeutic regimens to neutralize polypeptide ligand. Such agonistic anti-idiotypes or Fab fragments of such anti-idiotypes can be used in therapeutic regimens to enhance activity of the polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2, and/or the amino acid sequence of SEQ ID NO:4, and/or the amino acid sequence of SEQ ID NO:6.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, NSO, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the E. coli expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5):155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2, a polypeptide, polypeptide fragment, or a variant of SEQ ID NO:4, and/or a polypeptide, polypeptide fragment, or a variant of SEQ ID NO:6, may be fused or conjugated to the above antibody portions to increase the in vivo half-life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fe portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof, or other polypeptides of the invention as described herein, conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidinfbiotin and avidinjbiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof, or other polypeptide of the invention as described herein, may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical Ichemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. lnmunol., 6:1567–1574 (1994)), VEGI (See, International Publication No. WO 99/23105), CD40 Ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. For example, TR11 polypeptides of the invention appear to be primarily expressed on the surface of activated T cells. Accordingly, in non limiting applications, antibodies of the invention may be utilized to identify and/or purify activated T cells expressing TR11, TR11SV1 and/or TR11SV2 polypeptides of the invention. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding EILSAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioirnmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating, detecting, and/or preventing one or more of the disclosed diseases, disorders, or conditions. Therapeutic compounds of the invention include, but are not limited to, antibodies of the invention (including fragments, variants and analogs and derivatives thereof as described herein) and nucleic acids encoding antibodies of the invention (including fragments, variants and analogs and derivatives thereof and anti-idiotypic antibodies as described herein). The agonistic and antagonistic antibodies of the invention can be used to treat, diagnose, inhibit or prevent diseases, disorders or conditions associated with aberrant expression and/or activity of a polypeptide of the invention, including, but not limited to, any one or more of the diseases, disorders, or conditions described herein (e.g., autoimmune diseases, disorders, or conditions associated with such diseases or disorders, including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, glaucomatous, degenerative, and atrophic disorders). The treatment, detection, and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

In a specific embodiment, agonistic or antagonistic antibodies of the invention are be used to treat, inhibit, prognose, diagnose or prevent diseases, disorders, or conditions associated with an autoimmune disease (e.g., an autoimmune disease described herein).

In a specific embodiment, antibodies of the invention are be used to treat, inhibit, prognose, diagnose or prevent rheumatoid arthritis.

In another specific embodiment, antibodies of the invention are used to treat, inhibit, prognose, diagnose or prevent systemic lupus erythematosus.

In a specific embodiment, agonistic or antagonistic antibodies of the invention are be used to treat, inhibit, prognose, diagnose or prevent diseases, disorders, or conditions associated with an immunodeficiency.

T cell related deficiencies that may be ameliorated treated, diagnosed, or prognosed using the antibodies of the invention (e.g., agonistic or antagonistic anti-TR11 antibodies), include, but are not limited to, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are ameliorated treated, diagnosed, or prognosed using the antibodies of the invention.

Other immunodeficiencies that may be ameliorated treated, diagnosed, or prognosed using the antibodies of the invention (e.g., agonistic or antagonistic anti-TR11 antibodies), include, but are not limited to, severe combined immunodeficiency (SCID; e.g., X-linked SCID, autosomal SCID, and adenosine deaminase deficiency), ataxia-telangiectasia, Wiskott-Aldrich syndrome, short-limber dwarfism, X-linked lymphoproliferative syndrome (XLP), Nezelof syndrome (e.g., punine nucleoside phosphorylase deficiency), and MHC Class II deficiency. In specific embodiments, ataxia-telangiectasia or conditions associated with ataxia-telangiectasia are ameliorated treated, diagnosed, or prognosed using the antibodies of the invention.

Additional immunodeficiencies that may be ameliorated treated, diagnosed, or prognosed using the antibodies of the invention (e.g., agonistic or antagonistic anti-TR11 antibodies), include, but are not limited to, X-linked agammaglobulinemia, Ig deficiency with hyper IgM, selective IgA deficiency, IgG subclass deficiency, antibody deficiency with normal or elevated levels of Igs, immunodeficiency with thymoma, common variable immunodeficiency (CVI), hypogammaglobulinemia, B cell lymphoproliferative disorder, kappa chain deficiency, Ig heavy chain deficiency, myeloperoxidase deficiency, C2 deficiency, chronic glaucomatous disease (CGD), and X-linked immunodeficiency with hyper IgM.

Similarly, allergic reactions and conditions, such as asthma (particularly allergic asthma) or other respiratory problems, may also be treated using TR11, TR11SV1, and/or TR11SV2 polypeptides, antibodies, or polynucleotides of the invention, and/or agonists or antagonists thereof. Moreover, these molecules can be used to treat anaphylaxis, hypersensitivity to an antigenic molecule, or blood group incompatibility.

In specific embodiments, TR11, TR11SV1, and/or TR11SV2 polypeptides, antibodies, or polynucleotides of the invention, and/or agonists or antagonists thereof, are useful to treat, diagnose, prevent, and/or prognose transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). In a preferred specific embodiment, antibodies of the invention are used to treat, inhibit, prognose, diagnose or prevent inflammation.

Moreover, inflammatory conditions may also be treated, diagnosed, prevented and/or prognosed with TR11, TR11SV1, and/or TR11SV2 polypeptides, antibodies, or polynucleotides of the invention, and/or agonists or antagonists of TR11, TR11SV1, and/or TR11SV2 (e.g., anti-TR11 and/or anti-TR11SV1 antibodies) of the invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosus, diabetes mellitus (i.e., type 1 diabetes), and allogenic transplant rejection).

TR11, TR11SV1, and/or TR11SV2 polypeptides, antibodies, or polynucleotides of the invention, and/or agonists or antagonists thereof, may also be used to treat and/or prevent organ rejection or graft-versus-host disease (GVHD). Organ rejection occurs by host immune cell destruction of the transplanted tissue through an immune response. Similarly, an immune response is also involved in GVID, but, in this case, the foreign transplanted immune cells destroy the host tissues. The administration of TR11, TR11SV1, and/or TR11SV2 polypeptides, antibodies, or polynucleotides of the invention, and/or agonists or antagonists of TR11, TR11SV1, or TR11SV2, that inhibits an immune response, particularly the activation, proliferation, differentiation, or chemotaxis of T-cells, may be an effective therapy in preventing organ rejection or GVHD. In a specific embodiment, antibodies of the invention are be used treat, inhibit, prognoses diagnose or prevent graft rejection.

Similarly TR11, TR11SV1, and/or TR11SV2 polypeptides, antibodies, or polynucleotides of the invention, and/or agonists or antagonists of the invention may also be used to modulate inflammation. For example, since TR11, TR11SV1, and/or TR11SV2 polypeptides, antibodies, or polynucleotides of the invention, and/or agonists or antagonists of the invention, inhibit the activation, proliferation and/or differentiation of cells involved in an inflammatory response, these molecules can be used to treat inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, and resulting from over production of cytokines (e.g., TNF or IL-1.)

Moreover, TR11, TR11SV1, and/or TR11SV2 polypeptides, antibodies, or polynucleotides of the invention, and/or agonists or antagonists of the invention can also be used to modulate hemostatic (the stopping of bleeding) or thrombolytic activity (clot formation). For example, by increasing hemostatic or thrombolytic activity, TR11, TR11SV1, and/or TR11SV2 polypeptides, antibodies, or polynucleotides of the invention, and/or agonists or antagonists of the invention could be used to treat blood coagulation disorders (e.g., afibiinogenemia, factor deficiencies), blood platelet disorders (e.g. thrombocytopenia), or wounds resulting from trauma, surgery, or other causes. Alternatively, TR11, TR11SV1, and/or TR11SV2 polypeptides, antibodies, or polynucleotides of the invention, and/or agonists or antagonists of the invention, that can decrease hemostatic or thrombolytic activity could be used to inhibit or dissolve clotting, important in the treatment of heart attacks (infarction), strokes, or scarring.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In another embodiment, the invention provides a method of delivering compositions containing the polypeptides of the invention (e.g., compositions containing anti-TR11, anti-TR11SV1 and/or anti-TR11SV2 antibodies associated with heterologous polypeptides, heterologous nucleic acids, toxins, or prodrugs) to targeted cells, such as, for example, activated T cells or other cells expressing TR11, TR11SV1 and/or TR11SV2. Antibodies of the invention may be associated with heterologous polypeptides, heterologous nucleic acids, toxins, or prodrugs via hydrophobic, hydrophilic, ionic and/or covalent interactions.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents, antibiotics, and immunoglobulin). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, and fragments or regions thereof, for both immunoassays directed to and therapy of disorders related to polynucleotides or polypeptides (including fragments), of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $>10^{-3}$M, $10^{-3}$M, $5\times10^{-4}$ M, $10^{-4}$M, $5\times10^{-5}$ M, $10^{-5}$ M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO 93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)).

These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO 94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried (3, out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92 m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help lidentify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112m}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, 166Ho, $^{90}$Y, $^{47}$Sc, 186Re, 188Re, $^{142}$Pr, 105Rh, 97Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

As described herein, specific embodiments of the invention are directed to the use of the antibodies of the invention to quantitate or qualitate concentrations of cells of T cell lineage. In further embodiments, antibodies of the invention are used to quantitate or 1 qualitate concentrations of activated T cells.

As described herein, specific embodiments of the invention are directed to the use of the antibodies of the invention to quantitate or qualitate concentrations of cells of B IF cell lineage or cells of monocytic lineage.

Also as described herein, antibodies of the invention may be used to ameliorate, treat, diagnose, or prognose an individual having an immunodeficiency, such as, for example, an immunodeficiency or associated condition described herein or otherwise known in the art. In specific embodiments, antibodies of the invention are used to ameliorate, treat, diagnose, or prognose an individual having a T-cell related immunodeficiency, such as, for example, a T-cell related immunodeficiency or associated condition described herein or otherwise known in the art.

Also as described herein, antibodies of the invention may be used to ameliorate, treat, diagnose, or prognose an individual having an autoimmune disease, such as, for example, an autoimmune disease or associated condition described herein or otherwise known in the art.

In a specific embodiment, antibodies of the invention are used to treat, diagnose, and/or prognose an individual having systemic lupus erythematosus, or a subset of the disease. In another specific embodiment, antibodies of the invention are used to treat, diagnose and/or prognose an individual having rheumatoid arthritis, or a subset of this disease.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain the specific protein. In vivo tumor imaging is described in S. W. Burchiel et al., "Irmunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention comprise two or more antibodies (monoclonal and/or polyclonal) that recognize the same and/or different sequences or regions of the polypeptide of the invention. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodarmine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies that do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. Further included are antibodies that bind to TR11, TR11SV1, and/or TR11SV2 irrespective of whether TR11, TR11SV1, and/or TR11SV2 is bound to a TR11, TR11SV1, and/or TR11SV2 ligand (e.g., endokine-alpha and APRIL). These antibodies act as TR11, TR11SV1, and/or TR11SV2 agonists as reflected in an increase or decrease in cellular proliferation and/or activation in response to binding of TR11, TR11SV1, and/or TR11SV2 to a TR11, TR11SV1, and/or TR11SV2 ligand in the presence of these antibodies. The above antibody agonists can be made using methods known in the art. See e.g., WO 96/40281; U.S. Pat. No. 5,811,097; Deng, B. et al., Blood 92(6):1981–1988 (1998); Chen, Z. et al., Cancer Res. 58(16) :3668–3678 (1998); Harrop, J. A. et al., J. Immunol. 161(4) :1786–1794 (1998); Zhu, Z. et al., Cancer Res. 58(15) :3209–3214 (1998); Yoon, D. Y. et al., J. Immunol. 160(7) :3170–3179 (1998); Prat, M. et al., J. Cell. Sci. 111(Pt2) :237–247 (1998); Pitard, V. et al., J. Immunol. Methods 205(2):177–190 (1997); Liautard, J. et al., Cytokine 9(4) :233–241 (1997); Carlson, N. G. et al., J. Biol. Chem. 272(17):11295–11301 (1997); Taryman, R. E. et al., Neuron 14(4):755–762 (1995); Muller, Y. A. et al., Structure 6(9) :1153–1167 (1998); Bartunek, P. et al., Cytokine 8(1):14–20 (1996) (said references incorporated by reference in their entireties).

The invention encompasses antibodies that inhibit or reduce the ability of TR11, TR11SV1, and/or TR11SV2 to bind TR11, TR11SV1, and/or TR11SV2 ligand in vitro and/or in vivo. In a specific embodiment, antibodies of the invention inhibit or reduce the ability of TR11, TR11SV1, and/or TR11SV2 to bind TR11, TR11SV1, and/or TR11SV2 ligand (e.g., endokine-alpha and APRIL) in vitro. In another nonexclusive specific embodiment, antibodies of the invention inhibit or reduce the ability of TR11, TR11SV1, and/or TR11SV2 to bind TR11, TR11SV1, and/or TR11SV2 ligand in vivo. Such inhibition can be assayed using techniques described herein or otherwise known in the art.

The invention also encompasses, antibodies that bind specifically to TR11, TR11SV1, and/or TR11SV2, but do not inhibit the ability of TR11, TR11SV1, and/or TR11SV2 to bind TR11, TR11SV1, and/or TR11SV2 ligand (e.g., endokine-alpha and APRIL) in vitro and/or in vivo. In a specific embodiment, antibodies of the invention do not inhibit or reduce the ability of TR11, TR11SV1, and/or TR11SV2 to bind TR11, TR11SV1, and/or TR11SV2 ligand in vitro. In another nonexclusive specific embodiment, antibodies of the invention do not inhibit or reduce the ability of TR11, TR11SV1, and/or TR11SV2 to bind TR11, TR11SV1, and/or TR11SV2 ligand in vivo.

As described above, the invention encompasses antibodies that activate, inhibit or reduce a TR11-, TR11SV1-, and/or TR11SV2-mediated biological activity in vitro and/or in vivo. In a specific embodiment, antibodies of the invention inhibit or reduce TR11, TR11SV 1, and/or TR11SV2-mediated B or T cell proliferation and/or activation in vitro. Such inhibition can be assayed by routinely modifying B or T cell proliferation assays described herein or otherwise known in the art. In another nonexclusive specific embodiment, antibodies of the invention inhibit or reduce TR11-, TR11SV1-, and/or TR11SV2-mediated B or T cell proliferation and/or activation in vivo.

Alternatively, the invention also encompasses, antibodies that bind specifically to a TR11, TR11SV1, and/or TR11SV2, but do not inhibit or reduce a TR11-, TR11SV1-, and/or TR11SV2-mediated biological activity in vitro and/or in vivo (e.g., stimulation or inhibition B or T cell activation and/or proliferation). In a specific embodiment, antibodies of the invention do not inhibit or reduce a TR11-, TR11SV1-, and/or TR11SV2-mediated biological activity in vitro. In another non-exclusive embodiment, antibodies of the invention do not inhibit or reduce a TR11-, TR11SV1-, and/or TR11SV2-mediated biological activity in vivo.

As described above, the invention encompasses antibodies that specifically bind to the same epitope as at least one of the antibodies specifically referred to herein, in vitro and/or in vivo.

In a specific embodiment, the specific antibodies described above are humanized using techniques described herein or otherwise known in the art and then used as therapeutics as described herein.

In another specific embodiment, any of the antibodies listed above are used in a soluble form.

In another specific embodiment, any of the antibodies listed above are conjugated to a toxin or a label (as described infra). Such conjugated antibodies are used to kill a particular population of cells or to quantitate a particular population of cells. In a preferred embodiment, such conjugated antibodies are used to kill B cells expressing TR11, TR11SV1, and/or TR11SV2 on their surface. In another preferred embodiment, such conjugated antibodies are used to quantitate B cells expressing TR11, TR11SV1, and/or TR11SV2 on their surface. In a preferred embodiment, such conjugated antibodies are used to kill T cells expressing TR11, TR11SV1, and/or TR11SV2 on their surface (e.g., activated T cells). In another preferred embodiment, such conjugated antibodies are used to quantitate T cells expressing TR11, TR11SV1, and/or TR11SV2 on their surface (e.g., activated T cells).

In another specific embodiment, any of the antibodies listed above are conjugated to a toxin or a label (as described infra). Such conjugated antibodies are used to kill a particular population of cells or to quantitate a particular population of cells (e.g., hematopoietic cells expressing TR11, TR11SV1, and/or TR11SV2 on their surface, preferably T cells, more preferably, activated T cells).

In one embodiment, the invention provides a method for the specific delivery of compositions of the invention to cells by administering polypeptides of the invention (e.g., antibodies of the invention) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., antibodies of the invention) in association with toxins or cytotoxic prodrugs.

In a specific embodiment, the invention provides a method for the specific destruction of activated T cells or other cells expressing TR11, TR11SV1 and/or TR11SV2 on their cell surface by administering antibodies of the invention in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, 85Sr, $^{32}$P, 35S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{17}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its I entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

The antibodies of the invention also have uses as therapeutics and/or prophylactics which include, but are not limited to, inactivating lymphocytes or blocking lymphocyte activation and/or killing lymphocyte lineages that express TR11, TR11SV1, and/or TR11SV2 on their cell surfaces (e.g., to treat, prevent, and/or diagnose myeloid leukemias, lymphocyte based leukemias (e.g., leukemias having T-cell lineage), and lymphomas, lymphocytosis, lymphocytopenia, rheumatoid arthritis, and other diseases or conditions associated with activated lymphocytes). In a specific embodiment, the antibodies of the invention fix complement. In other specific embodiments, as further described herein, the antibodies of the invention (or fragments thereof) are associated with heterologous polypeptides or nucleic acids (e.g. toxins, such as, compounds that bind and activate endogenous cytotoxic effecter systems, and radioisotopes; and cytotoxic prodrugs).

In another embodiment, one or more monoclonal antibodies are produced wherein they recognize or bind TR11, TR11SV1, and/or TR11SV2 and/or a mutein thereof, but do not recognize or bind TR11, TR11SV1, and/or TR11SV2 and/or a mutein thereof.

As discussed above, antibodies to the TR11, TR11SV1, and/or TR11SV2 polypeptides of the invention can, in turn, be utilized to generate anti-idiotype antibodies that "mimic" the TR11, TR11SV1, and/or TR11SV2, using techniques well known to those skilled in the art. (See, e.g., Greenspan & Bona, FASEB J. 7(5):437–444 (1989), and Nissinoff, J. Immunol. 147(8):2429–2438 (1991)). For example, antibodies which bind to TR11, TR11SV1, and/or TR11SV2 and competitively inhibit TR11, TR11SV1, and/or TR11SV2 multimerization and/or binding to ligand can be used to generate anti-idiotypes that "mimic" the TR11, TR11SV1, and/or TR11SV2 TNF mutimerization and/or binding domain and, as a consequence, bind to and neutralize TR11, TR11SV1, and/or TR11SV2 and/or its ligand. Such neutralizing anti-idiotypes or Fab fragments of such anti-idiotypes can be used in therapeutic regimens to neutralize TR11, TR11SV1, and/or TR11SV2 ligand. For example, such anti-idiotypic antibodies can be used to bind TR11, TR11SV1, and/or TR11SV2 on the surface of cells of B or T cell lineage, and thereby block or enhance TR11-, TR11SV1-, and/or TR11SV2-mediated regulation of B or T cell activation, proliferation, and/or differentiation. In a specific embodiment, anti-idiotypic antibodies of the invention are used to bind TR11, TR11SV, and/or TR11SV2 on the surface of cells of T cell lineage, and thereby block or enhance TR11 mediated T cell activation, proliferation, and/or differentiation.

Detection of Disease States

The TNF-family ligands induce various cellular responses by binding to TNF-family receptors, including the TR11, TR11SV1, and TR11SV2 receptors of the present invention. TNF-beta, a potent ligand of the TNF receptor proteins, is known to be involved in a number of biological processes including lymphocyte development, tumor necrosis, induction of an antiviral state, activation of polymorphonuclear leukocytes, induction of class I major histocompatibility complex antigens on endothelial cells, induction of adhesion molecules on endothelium and growth hormone stimulation (Ruddle and Homer, Prog. Allergy, 40:162–182 (1988)). TNF-alpha, also a ligand of the TNF receptor proteins, has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al, J. Immunol. 136 (7):2483 (1987); Porter, Tibtech 9:158–162 (1991)), growth regulation, vascular endothelium effects and metabolic effects. TNF-alpha also triggers endothelial cells to secrete various factors, including PAI-1, IL-1, GM-CSF and IL-6 to promote cell proliferation. In addition, TNF-alpha up-regulates various cell adhesion molecules such as E-Selectin, ICAM-1 and VCAM-1. TNF-alpha and the Fas ligand have also been shown to induce programmed cell death. TRAIL (also known as Apo-2L) is a member of the tumor necrosis factor (TNF) ligand family that rapidly induces apoptosis in a variety of transformed cell lines. One human receptor for TRAIL was found to be an undescribed member of the TNF receptor family designated death receptor (DR)-4 (Pan, G., et al., Science 276:111–113 (1997)).

Cells which express the TR11, TR11SV1 or TR11SV2 polypeptides and are believed to have a potent cellular response to TR11, TR11SV1 or TR11SV2 receptor ligands include activated T-cells. By "a cellular response to a TNF-family ligand" is intended any genotypic, phenotypic, and/or morphologic change to a cell, cell line, tissue, tissue culture or patient that is induced by a TNF-family ligand (e.g., endokine-alpha and APRIL). As indicated, such cellular responses include not only normal physiological responses to TNF-family ligands, but also diseases associated with increased cell proliferation or the inhibition of increased cell proliferation, such as by the inhibition of apoptosis. Apoptosis-programmed cell death-is a physiological mechanism involved in the deletion of peripheral T-lymphocytes of the immune system, and its dysregulation can lead to a number of different pathogenic processes (Ameisen, J. C., AIDS 8:1197–1213 (1994); Krammer, P. H. et al., Curr. Opin. Immunol. 6:279–289 (1994)).

It is believed that certain tissues in mammals with specific disease states associated with aberrant cell survival express significantly altered levels of the TR11, TR11SV1, and TR11SV2 receptor proteins and mRNAs encoding the TR11, TR11SV1, and TR11SV2 receptor proteins when compared to a corresponding "standard" mammal, i.e., a mammal of the same species not having the disease state. Further, since some forms of these proteins are secreted, it is believed that enhanced levels of the TR11, TR11SV1 or TR11SV2 receptor proteins can be detected in certain body fluids (e.g., sera, plasma, urine, and spinal fluid) from mammals with the disease state when compared to sera from mammals of the same species not having the disease state. Thus, the invention provides a diagnostic method useful during diagnosis of disease states, which involves assaying the expression level of the gene encoding the TR11, TR11SV1, and TR11SV2 receptor proteins in mammalian cells or body fluid and comparing the gene expression level with a standard TR11, TR11 SV1, and TR11SV2 receptor gene expression levels, whereby an increase or decrease in the gene expression level over the standard is indicative of certain disease states associated with aberrant cell survival.

Where diagnosis of a disease state involving the TR11, TR11SV1 or TR11SV2 receptors of the present invention has already been made according to conventional methods, the present invention is useful as a prognostic indicator, whereby patients exhibiting significantly aberrant TR11, TR11SV1 or TR11SV2 receptor gene expression will experience a worse clinical outcome relative to patients expressing the gene at a lower level.

By "assaying the expression level of the gene encoding the TR11, TR11SV1 or TR11SV2 receptor protein" is intended qualitatively or quantitatively measuring or estimating the level of the TR11, TR11SV1 or TR11SV2 receptor protein or the level of the mRNA encoding the TR11, TR11SV1 or TR11SV2 receptor protein in a first biological sample either directly (e.g., by determining or estimating absolute protein level or mRNA level) or relatively (e.g., by comparing to the TR11, TR11SV1 or TR11SV2 receptor protein level or mRNA level in a second biological sample).

Preferably, the TR11, TR11SV1 or TR11SV2 receptor protein levels or mRNA levels in the first biological sample is measured or estimated and compared to a standard TR11, TR11SV1 or TR11SV2 receptor protein level or mRNA level, the standard being taken from a second biological sample obtained from an individual not having the disease state. As will be appreciated in the art, once a standard TR11, TR11SV1 or TR11SV2 receptor protein level or mRNA level is known, it can be used repeatedly as a standard for comparison.

By "biological sample" is intended any biological sample obtained from an individual, cell line, tissue culture, or other source which contains TR11, TR11SV1 or TR11SV2 receptor protein or mRNA. Biological samples include mammalian body fluids (such as sera, plasma, urine, synovial fluid and spinal fluid) which contain secreted mature TR11, TR11SV1 or TR11SV2 receptor protein, and thymus, prostate, heart, placenta, muscle, liver, spleen, lung, kidney and other tissues. Methods for obtaining tissue biopsies and body fluids from mammals are well known in the art. Where the biological sample is to include mRNA, a tissue biopsy is the preferred source.

It is believed that TR11, TR11SV1 or TR11SV2 receptor polynucleotides and/or polypeptides of the invention regulate cell survival and/or proliferation. Diseases associated with increased cell survival, or the inhibition of apoptosis, that may be treated, detected or prevented with the polypeptides or polynucleotides of the invention, or agonists or antagonists thereof include, but are not limited to, cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. In preferred embodiments, TR11, TR11SV1 or TR11SV2 polynucleotides, polypeptides, agonists, or antagonists of the invention are used to diagnose and/or prevent graft vs. host disease (acute and chronic). In preferred embodiments, TR11, TR11SV1 or TR11SV2 polynucleotides, polypeptides, agonists, or antagonists of the invention are used to diagnose and/or prevent acute graft rejection. In preferred embodiments, TR11, TR11SV1 or TR11SV2 polynucleotides, polypeptides, agonists, or antagonists of the invention are used to diagnose and/or prevent chronic graft rejection. In preferred embodiments, TR11, TR11SV1 or TR11SV2 polynucleotides, polypeptides, agonists, or antagonists of the invention are used to diagnose and/or prevent growth, progression, and/or metastasis of cancers, in particular those listed above or in the paragraph that follows.

Additional diseases or conditions associated with increased cell survival that may be treated, detected or prevented with the polypeptides or polynucleotides of the invention, or agonists or antagonists thereof include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic if lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Thus, in preferred embodiments TR11, TR11SV1, TR11SV2 polynucleotides or polypeptides of the invention are used to treat, detect or prevent autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment TR11, TR11SV1, TR11SV2 polynucleotides or polypeptides of the invention are used to activate, differentiate or proliferate cancerous cells or tissue (e.g., T cell and/or B cell lineage related cancers (e.g., CLL and MLL), lymphocytic leukemia, or lymphoma) and thereby render the cells more vulnerable to cancer therapy (e.g., chemotherapy or radiation therapy).

Diseases associated with increased apoptosis that may be treated, detected or prevented with the polypeptides or polynucleotides of the invention, or agonists or antagonists thereof, include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Grave's disease Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis) myelodysplastic syndromes (such as aplastic anemia), graft vs. host disease (acute and/or chronic), ischemnic injury (such as that caused by myocardial infarction, stroke and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia and anorexia In preferred embodiments, TR11, TR11SV1 or TR11SV2 polynucleotides, polypeptides, agonists, or antagonists of the invention are used to diagnose, prevent, and/or treat the diseases and disorders listed above.

As discussed above, TR11 polypeptides are primarily expressed on the surface of activated T-cells. T cells are involved primarily in cell-mediated immune reactions and in the control of B-cell development. Accordingly, it is believed that certain tissues in mammals with specific disease states or disorder of the immune system express significantly altered levels of the TR11, TR11SV1, and TR11SV2 receptor proteins and mRNAs encoding the TR11, TR11SV1, and TR11SV2 receptor proteins when compared to a corresponding "standard" mammal, i.e., a mammal of the same species not having the disease state or disorder. Further, since some forms of these proteins are secreted, it is believed that enhanced levels of the TR11, TR11SV1 or TR11SV2 receptor proteins can be detected in certain body fluids (e.g., sera, plasma, urine, and spinal fluid) from mammals with the disease state when compared to sera from mammals of the same species not having the disease state. Thus, the invention provides a diagnostic method useful during diagnosis of disease states or conditions of the immune system, which involves assaying the expression level of the gene encoding the TR11, TR11SV1, and TR11SV2 receptor proteins in mammalian cells or body fluid and comparing the gene expression level with a standard TR11, TR11SV1, and TR11SV2 receptor gene expression levels, whereby an increase or decrease in the gene expression level over the standard is indicative of certain disease states or conditions associated with the immune system.

Where diagnosis of a disease state involving the TR11, TR11SV1 or TR11SV2 receptors of the present invention has already been made according to conventional methods, the present invention is useful as a prognostic indicator, whereby patients exhibiting significantly aberrant TR11, TR11SV1 or TR11SV2 receptor gene expression will experience a worse clinical outcome relative to patients expressing the gene at a lower level. Disease states or conditions of the immune system that may be diagnosed or prognosed according to the present invention, include, but are not limited to autoimmune diseases, immunodeficiencies, and inflammation.

Immunodeficiencies that may be treated, prevented, diagnosed, and/or prognosed with TR11, TR11SV1, and/or TR11SV2 polynucleotides or polypeptides or TR11, TR11SV1, and/or TR11SV2 agonists or antagonists (e.g., anti-TR11, anti-TR11SV1, and/or anti-TR11SV2 antibodies) of the invention, include, but are not limited to one or more immunodeficiencies selected from: severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In certain embodiments, TR11, TR11SV1, and/or TR11SV2 polypeptides of the invention, or agonists or antagonists thereof, are used, to treat, prevent, prognose and/or diagnose a T cell related immunodeficiency. T cell related immunodeficiencies that may be treated, prevented, prognosed and/or diagnosed using the TR11, TR11SV1, TR11SV2 polypeptides (e.g., TR11-Fc fusion proteins containing the extracellular domain of TR11, and antagonistic anti-TR11 antibodies) or polynucleotides of the invention, or antagonists or agonists thereof include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are treated, prevented, prognosed and/or diagnosed using the TR11, TR11SV1, TR11SV2 polypeptides (e.g., TR11-Fc fusion proteins containing the extracellular domain of TR11, and antagonistic anti-TR11 antibodies) or polynucleotides of the invention, or antagonists or agonists thereof.

In a specific embodiment, TR11, TR11SV1, and/or TR11SV2 polypeptides or polynucleotides of the invention, or agonists or antagonists thereof, are used to treat, prevent, prognose and/or diagnose common variable immunodeficiency.

In a specific embodiment, TR11, TR11SV1, and/or TR11SV2 polypeptides, antibodies, or polynucleotides of the invention, and/or agonists or antagonists thereof, are used to treat, prevent, prognose and/or diagnose X-linked agammaglobulinemia. In another specific embodiment, TR11, TR11SV1, and/or TR11SV2 polypeptides, antibodies, or polynucleotides of the invention, and/or agonists or antagonists thereof, is used to treat, prevent, prognose and/or diagnose severe combined immunodeficiency (SCID). In another specific embodiment, TR11, TR11SV1, and/or TR11SV2 polypeptides, antibodies, or polynucleotides of the invention, and/or agonists or antagonists thereof, is used to treat, prevent, prognose and/or diagnose X-linked Ig deficiency with hyper IgM.

TR11, TR11SV1, and/or TR11SV2 polynucleotides or polypeptides of the invention (e.g., agonistic anti-TR11 antibodies) and agonists or antagonists thereof, may also be useful in be treating, preventing, diagnosing, and/or prognosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, diagnosed, or prognosed using TR11, TR11SV1, and/or TR11SV2 polynucleotides or polypeptides or TR11, TR11SV1, and/or TR11SV2 agonists or antagonists (e.g., agonistic anti-TR11, anti-TR11SV1, and/or anti-TR11SV2 antibodies) of the invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Siogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, glaucomatous, degenerative, and atrophic disorders.

In a specific preferred embodiment, rheumatoid arthritis is treated, prevented, prognosed and/or diagnosed using TR11, TR11SV1, and/or TR11SV2 polypeptides, antibodies, or polynucleotides of the invention, and/or agonists or antagonists of the invention. In another specific preferred embodiment, systemic lupus erythematosus is treated, prevented, prognosed, and/or diagnosed using TR11, TR11SV1, and/or TR11SV2 polypeptides, antibodies, or polynucleotides of the invention, and/or agonists or antagonists of the invention. In another specific preferred embodiment, idiopathic thrombocytopenia purpura is treated, prevented, prognosed, and/or diagnosed using TR11, TR11SV1, and/or TR11SV2 polypeptides, antibodies, or polynucleotides of the invention, and/or agonists or antagonists of the invention. In another specific preferred embodiment IgA nephropathy is treated, prevented, prognosed and/or diagnosed using TR11, TR11SV1, and/or TR11SV2 polypeptides, antibodies, or polynucleotides of the invention, and/or agonists or antagonists of the invention. In a preferred embodiment, the autoimmune diseases and disorders and/or conditions associated with the diseases and disorders recited above are treated, prevented, prognosed and/or diagnosed using anti-TR11, anti-TR11SV1, and/or anti-TR11SV2 antibodies.

Similarly, allergic reactions and conditions, such as asthma (particularly allergic asthma) or other respiratory problems, may also be treated, prevented, prognosed and/or diagnosed using TR11, TR11SV1, and/or TR11SV2 polypeptides, antibodies, or polynucleotides of the invention, and/or agonists or antagonists thereof. Moreover, these molecules can be used to treat, prevent, prognose and/or diagnose anaphylaxis, hypersensitivity to an antigenic molecule, or blood group incompatibility.

In specific embodiments, TR11, TR11SV1, and/or TR11SV2 polypeptides, antibodies, or polynucleotides of the invention, and/or agonists or antagonists thereof, are useful to treat, diagnose, prevent, and/or prognose transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE).

Moreover, inflammatory conditions may also be treated, diagnosed, prevented and/or prognosed with TR11, TR11SV1, and/or TR11SV2 polypeptides, antibodies, or polynucleotides of the invention, and/or agonists or antagonists of TR11, TR11SV1, and/or TR11SV2 (e.g., anti-TR11, anti-TR11SV1, and/or anti-TR11SV2 antibodies) of the invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosus, diabetes mellitus (i.e., type 1 diabetes), and allogenic transplant rejection).

TR11, TR11SV1, and/or TR11SV2 polypeptides, antibodies, or polynucleotides of the invention, and/or agonists or antagonists thereof, may also be used to treat, prevent diagnose, or prognose, organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. TR11, TR11SV1, and/or TR11SV2 polypeptides, antibodies, or polynucleotides of the invention, and/or agonists or antagonists of TR11, TR11SV1, or TR11SV2, that inhibits an immune response, particularly the activation (e.g., stimulation), proliferation, differentiation, or chemotaxis of T-cells, may be an effective therapy in preventing organ rejection or GVHD.

Similarly TR11, TR11SV1, and/or TR11SV2 polypeptides, antibodies, or polynucleotides of the invention, and/or agonists or antagonists of the invention may also be used to modulate, diagnose, or prognose inflammation. For example, since TR11, TR11 SV1, and/or TR11SV2 polypeptides, antibodies, or polynucleotides of the invention, and/or agonists or antagonists of the invention, inhibit the activation, proliferation and/or differentiation of cells involved in an inflammatory response, these molecules can be used to treat, diagnose, or prognose, inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, and resulting from over production of cytokines (e.g., TNF or IL-1.)

Moreover, TR11, TR11SV1, and/or TR11SV2 polypeptides, antibodies, or polynucleotides of the invention, and/or agonists or antagonists of the invention can also be used to modulate, diagnose, or prognose hemostatic (the stopping of bleeding) or thrombolytic activity (clot formation). For example, TR11, TR11SV1, and/or TR11SV2 polypeptides, antibodies, or polynucleotides of the invention, and/or agonists or antagonists of the invention could be used to treat, prevent, diagnose, or prognose blood coagulation disorders (e.g., afibrinogenemia, factor deficiencies), blood platelet disorders (e.g. thrombocytopenia).

In additional embodiments, TR11, TR11SV1, and/or TR11SV2 polynucleotides or polypeptides of the invention, or agonists or antagonists thereof, may be used to diagnose, prognoses treat or prevent one or more of the following diseases or disorders, or conditions associated therewith: primary immunodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

In additional embodiments, TR11, TR11SV1, and/or TR11SV2 polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable multiple myeloma who are at high risk for infection (e.g., recurrent infection), autoimmune hemolytic anemia (e.g., warm-type autoimmune hemolytic anemia), thrombocytopenia (e.g, neonatal thrombocytopenia), and immune-mediated neutropenia), transplantation (e.g, cytomegalovirus (CMV)-negative recipients of CMV-positive organs), hypogammaglobulinemia (e.g., hypogammaglobulinemic neonates with risk factor for infection or morbidity), hypergammaglobulinemia, epilepsy (e.g. intractable epilepsy), systemic vasculitic syndromes, myasthenia gravis (e.g, decompensation in myasthenia gravis), dermatomyositis, and polymyositis.

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response. In a specific nonexclusive embodiment, TR11, TR11SV1, and/or TR11SV2, polypeptides, antibodies, polynucleotides, and/or agonists or antagonists of the invention, are administered to boost the immune system to produce increased quantities of IgG. In another specific nonexclusive embodiment, TR11, TR11SV1, and/or TR11SV2, polypeptides, anti bodies, polynucleotides, and/or agonists oantagonists of the invention, are administered to boost the immune system to produce increased quantities of IgA. In another specific nonexclusive embodiment, TR11, TR11SV1, and/or TR11SV2, polypeptides, antibodies, polynucleotides, and/or agonists or antagonists of the invention, are administered to boost the immune system to produce increased quantities of IgM.

Assays available to detect levels of soluble receptors are well known to those of skill in the art, for example, radioimmunoassays, competitive-binding assays, Western blot analysis, and preferably an ELISA assay may be employed polymyositis.

Agonists and Antagonists of TR11, TR11SV1, and TR11SV2 Receptor Function

In one embodiment, the present invention is directed to a method for inhibiting an activity of TR11, TR11SV1 or TR11SV2 induced by a TNF-family ligand (e.g., cell proliferation, hematopoietic development), which involves administering to a cell which expresses a TR11, TR11SV1 or TR11SV2 polypeptide an effective amount of a TR11, TR11SV1 or TR11SV2 receptor ligand, analog or an antagonist capable of decreasing TR11, TR11SV1 or TR11SV2, receptor mediated signaling. Preferably, TR11, TR11SV1 or TR11SV2 receptor mediated signaling is increased to treat, detect, and/or prevent a disease wherein increased cell proliferation is exhibited. An antagonist can include soluble forms of the TR11, TR11SV1 or TR11SV2 receptors and antibodies directed against the TR11, TR11SV1 or TR11SV2 polypeptides which block TR11, TR11SV1 or TR11SV2 receptor mediated signaling. Preferably, TR11, TR11SV1 or TR11SV2 receptor mediated signaling is decreased to treat, detect, and/or prevent a disease.

In a further embodiment, the present invention is directed to a method for increasing cell proliferation induced by a TNF-family ligand, which involves administering to a cell which expresses a TR11, TR11SV1 or TR11SV2 polypeptide an effective amount of an agonist capable of increasing TR11, TR11SV1 or TR11SV2 receptor mediated signaling. Preferably, TR11, TR11SV1 or TR11SV2 receptor mediated signaling is increased to treat, detect, and/or prevent a disease wherein decreased cell proliferation is exhibited. Agonists of the present invention include monoclonal antibodies directed against the TR11, TR11SV1 or TR11SV2 polypeptides which stimulate TR11, TR11SV1 or TR11SV2 receptor mediated signaling. Preferably, TR11, TR11SV1 or TR11V2 receptor mediated signaling is increased to treat, detect, and/or prevent a disease.

By "agonist" is intended naturally occurring and synthetic compounds capable of enhancing cell proliferation and differentiation mediated by TR11, TR11SV1 or TR11SV2 polypeptides. Such agonists include agents which increase expression of TR11, TR11SV1 or TR11SV2 receptors or increase the sensitivity of the expressed receptor. By "antagonist" is intended naturally occurring and synthetic compounds capable of inhibiting TR11, TR11SV1 or TR11SV2 mediated cell proliferation and differentiation. Such antagonists include agents which decrease expression of TR11, TR11SV1 or TR11SV2 receptors or decrease the sensitivity of the expressed receptor. Whether any candidate "agonist" or "antagonist" of the present invention can enhance or inhibit cell proliferation and differentiation can be determined using art-known TNF-family ligand/receptor cellular response assays, including those described in more detail below.

One such screening technique involves the use of cells which express the receptor (for example, transfected CHO cells) in a system which measures extracellular pH changes caused by receptor activation, for example, as described in Science 246:181–296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Soluble forms of the polypeptides of the present invention may be utilized in the ligand binding assay described above. These forms of the TR11, TR11SV1, and TR11SV2 receptors are contacted with ligands in the extracellular medium after they are secreted. A determination is then made as to whether the secreted protein will bind to TR11, TR11SV1 or TR11SV2 receptor ligands.

Further screening assays for agonist and antagonist of the present invention are described in Tartaglia, L. A., and Goeddel, D. V., J. Biol. Chem. 267(7):4304–4307(1992).

Thus, in a further embodiment, a screening method is provided for determining whether a candidate agonist or antagonist is capable of enhancing or inhibiting a cellular response to a TNF-family ligand. The method involves contacting cells which express TR11, TR11SV1 or TR11SV2 polypeptides with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing a TR11, TR11SV1 or TR11SV2 polypeptide can be contacted with either an endogenous or exogenously administered TNF-family ligand.

In an additional aspect, a thymocyte proliferation assay may be employed to identify both ligands and potential drug candidates. For example, thymus cells are disaggregated from tissue and grown in culture medium. Incorporation of DNA precursors such as [3H]-thymidine or 5-bromo-2'-deoxyuridine (BrdU) is monitored as a parameter for DNA synthesis and cellular proliferation. Cells which have incorporated BrdU into DNA can be detected using a monoclonal antibody against BrdU and measured by an enzyme or fluorochrome-conjugated second antibody. The reaction is quantitated by fluorimetry or by spectrophotometry. Two control wells and an experimental well are set up as above and TNF-beta or cognate ligand is added to all wells while soluble receptor polypeptides of the present invention are added individually to the second control wells, with the experimental well containing a compound to be screened. The ability of the compound to be screened to stimulate or inhibit the above interaction may then be quantified.

Agonists according to the present invention include compounds such as, for example, TNF-family ligand peptide fragments, transforming growth factors, and neurotransmitters (such as glutamate, dopamine, N-methyl-D-aspartate). Preferred agonists include polyclonal and monoclonal antibodies raised against TR11, TR11SV1 or TR11SV2 polypeptides, or a fragments thereof. Such agonist antibodies raised against a TNF-family receptor are disclosed in Tartaglia, L. A., et al., Proc. Natl. Acad. Sci. USA 88:9292–9296 (1991); and Tartaglia, L. A., and Goeddel, D. V., J. Biol. Chem. 267 (7):4304–4307 (1992). See, also, PCT Application WO 94/09137. Further preferred agonists include chemotherapeutic drugs such as, for example, cisplatin, doxorubicin, bleomycin, cytosine arabinoside, nitrogen mustard, methotrexate and vincristine. Others include ethanol and amyloid peptide. (Science 267:1457–1458 (1995)).

In specific embodiments, antagonists according to the present invention are nucleic acids corresponding to the sequences contained in TR11, TR11SV 1 and/or TR11SV2, or the complementary strand thereof, and/or to nucleotide sequences contained in the deposited clones HHEAC71, HCFAZ22, and ITF5EA78, respectively. In one embodiment, antisense sequence is generated internally by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the TR11, TR11SV1 and/or TR11SV2 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR11, TR11SV1 and/or TR11SV2 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TR11, TR11SV1 and/or TR11SV2, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a TR11, TR11SV1 and/or TR11SV2 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR11, TR11SV1 and/or TR11SV2 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR11, TR11SV1 and/or TR11SV2 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of the TR11, TR11SV1 and/or TR11SV2 shown in FIGS. 1A–B, 2A–B, and 3A–B, respectively, could be used in an antisense approach to inhibit translation of endogenous TR11, TR11SV1 and/or TR11SV2 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of TR11, TR11SV1 and/or TR11SV2 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published December 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiarnidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the TR11, TR11SV1 and/or TR11SV2 coding region sequences could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy TR11, TR11SV1 and/or TR11SV2 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of TR11, TR11SV1 and/or TR11SV2 (see FIGS. 1A–B, 2A–B, and 3A–B, respectively). Preferably, the ribozyme is engineered so that the cleavage recognition site is located near the 5' end of the TR11, TR11SV1 and/or TR11SV2 mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express TR11, TR11SV1 and/or TR11SV2 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TR11, TR11SV1 and/or TR11SV2 messages and inhibit translation. Since ribozymes unlike antisense molecules, are catalytic, a lower intracellular concentration is required for efficiency.

Endogenous gene expression can also be reduced by inactivating or "knocking out" the TR11, TR11SV1 and/or TR11SV2 gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

Antagonists according to the present invention include soluble forms of the TR11, TR11SV1, and TR11SV2 receptors (e.g., fragments of the TR11, TR11SV1, and TR11SV2 receptors shown in FIGS. 1A and 1B, 2A and 2B, and 3A and 3B, respectively, that include the ligand binding domain from the extracellular region of the full length receptor). Such soluble forms of the receptor, which may be naturally occurring or synthetic, antagonize TR11, TR11SV1, and TR11SV2 mediated signaling by competing with the cell surface bound forms of the receptor for binding to TNF-family ligands. For example, a TR11-Fc fusion protein, containing the extracellular domain of TR11 has been found by the inventors to inhibit B cell proliferation (data not shown). Antagonists of the present invention also include TR11-, TR11SV1-, and TR11SV2-Fc fusion proteins, TR11-, TR11SV1-, and TR11SV2-albumin fusion proteins antibodies specific for TNF-family ligands and.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, TNF-alpha, lymphotoxin-alpha (LT-alpha, also known as TNF-beta), LT-beta (found in complex heterotrimer LT-alpha2-beta), OPGL, FasL, 1CD27L, CD30L, CD40L, 4–1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185–1190 (1998)), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-1BB, DR3 (International Publication No. WO 97/33904), DR4 (International Publication No. WO 98/32856), TR5 (International Publication No. WO 98/30693), TR6 (International Publication No. WO 98/30694),TR7 (International Publication No. WO 98/41629), TRANK, TR9 (International Publication No. WO 98/56892),TR10 (International Publication No. WO 98/54202),312C2 (International Publication No. WO 98/06842), and TR12, and soluble forms CD154, CD70, and CD153.). In specific embodiments, the TNF-family ligand is APRIL. In other specific embodiments, the TNF-family ligand is Endokine-alpha.

TNF-alpha has been shown to protect mice from infection with herpes simplex virus type 1 (HSV-1). Rossol-Voth, R. et al., J Gen. Virol. 72:143–147 (1991). The mechanism of the protective effect of TNF-alpha is unknown but appears to involve neither interferons not NK cell killing. One member of the TNFR family has been shown to mediate HSV-1 entry into cells. Montgomery, R. et al., Eur. Cytokine Newt. 7:159 (1996). Further, antibodies specific for the extracellular domain of this TNFR block HSV-1 entry into cells. Thus, TR11, TR11SV1, and TR11SV2 antagonists of the present invention include both TR11, TR11SV1, and TR11SV2 amino acid sequences and antibodies capable of preventing TNFR mediated viral entry into cells. Such sequences and antibodies can function by either competing with cell surface localized TNFR for binding to virus or by directly blocking binding of virus to cell surface receptors.

Antibodies according to the present invention may be prepared by any of a variety of methods using TR11, TR11SV1, and TR11SV2 receptor immunogens of the present invention. Such TR11, TR11SV1, and TR11SV2 receptor immunogens include the TR11, TR11SV1, and TR11SV2 receptor proteins shown in FIGS. 1A and 1B, 2A and 2B, and 3A and 3B (SEQ ID NO:2, SEQ ID NO:4, and SEQ ID NO:6, respectively; which may or may not include a leader sequence) and polypeptide fragments of the receptor comprising the ligand binding, extracellular, transmembrane, the intracellular domains of the TR11, TR11SV1, and TR11SV2 receptors, or any combination thereof.

Polyclonal and monoclonal antibody agonists or antagonists according to the present invention can be raised according to the methods disclosed in Tartaglia and Goeddel, J. Biol. Chem. 267(7):4304–4307(1992)); Tartaglia et al., Cell 73:213–216 (1993)), and PCT Application WO 94/09137. The term "antibody" (Ab) or "monoclonal antibody" (mAb) as used herein is meant to include intact molecules as well as fragments thereof (such as, for example, Fab and F(ab') fragments) which are capable of binding an antigen. Fab and F(ab') fragments lack the Fc fragment of intact antibody, clear more rapidly from the circulation, and may have less non-specific tissue binding of an intact antibody (Wahl et al., J. Nucl. Med. 24:316–325 (1983)).

In a preferred method, antibodies according to the present invention are mAbs. Such mAbs can be prepared using hybridoma technology (Kohler and Milstein, Nature 256:495–497 (1975) and U.S. Pat. No. 4,376,110; Harlow et al., Antibodies: A Laboratory Manual, Cold Spring Harbor Laboratory Press, Cold Spring Harbor, N.Y., 1988; Monoclonal Antibodies and Hybridomas: A New Dimension in Biological Analyses, Plenum Press, New York, N.Y., 1980; Campbell, "Monoclonal Antibody Technology," In: Laboratory Techniques in Biochemistry and Molecular Biology, Volume 13 (Burdon et al., eds.), Elsevier, Amsterdam (1984)).

Proteins and other compounds which bind the TR11, TR11SV1, and TR11SV2 receptor domains are also candidate agonist and antagonist according to the present invention. Such binding compounds can be "captured" using the yeast two-hybrid system (Fields and Song, Nature 340:245–246 (1989)). A modified version of the yeast two-hybrid system has been described by Roger Brent and his colleagues (Gyuris, J. et al., Cell 75:791–803 (1993); Zervos, A. S. et al., Cell 72:223–232 (1993)). Preferably, the yeast two-hybrid system is used according to the present invention to capture compounds which bind to the ligand binding, extracellular, intracellular, and transmembrane domains of the TR11, TR11SV1, and TR11SV2 receptors. Such compounds are good candidate agonist and antagonist of the present invention.

Using the two-hybrid assay described above, the intracellular domain of the TR11, TR11SV1, and TR11SV2 receptors, or portions thereof, may be used to identify cellular proteins which interact with the receptor in vivo. Such an assay may also be used to identify ligands with potential agonistic or antagonistic activity of TR11, TR11SV1, and TR11SV2 receptor function. This screening assay has previously been used to identify protein which interact with the cytoplasmic domain of the murine TNF-RII and led to the identification of two receptor associated proteins (Rothe, M. et al., Cell 78:681 (1994)). Such proteins and amino acid sequences which bind to the cytoplasmic domain of the TR11, TR11SV1, and TR11SV2 receptors are good candidate agonists and antagonists of the present invention.

Other screening techniques include the use of cells which express the polypeptide of the present invention (for example, transfected CHO cells) in a system which measures extracellular pH changes caused by receptor activation, for example, as described in Science, 246:181–296 (1989). In another example, potential agonists or antagonists may be contacted with a cell which expresses the polypeptide of the present invention and a second messenger response, e.g., signal transduction may be measured to determine whether the potential antagonist or agonist is effective.

Diagnostics and Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," Symp. Quant. Biol. 51:597–609 (1986), Cold Spring Harbor; Beutler, B., and Cerami, A., Annu. Rev. Biochem. 57:505–518 (1988); Old, L. J., Sci. Am. 258:59–75 (1988); Fiers, W., FEBS Lett. 285:199–224 (1991)). The TNF-family ligands induce such various cellular responses by binding to TNF-family receptors.

TR11,TR11SV1, and TR11SV2 agonists or antagonists of the invention (including TR11, TR11SV1, and TR11SV2 polynucleotides, polypeptides, or antibodies) may be used in developing treatments for any disorder mediated (directly or indirectly) by defective, or insufficient amounts of TR11, TR11SV1, and/or TR11SV2. TR11, TR11SV1, and TR11SV2 polypeptides, agonists or antagonists may be administered to a patient (e.g., mammal, preferably human) afflicted with such a disorder. Alternatively, a gene therapy approach may be applied to treat and/or prevent such disorders. Disclosure herein of TR11, TR11SV1, and TR11SV2 nucleotide sequences permits the detection of defective TR11, TR11SV1, and TR11SV2 genes, and the replacement thereof with normal TR11, TR11SV1, and TR11SV2 encoding genes. Defective genes may be detected in in vitro diagnostic assays, and by comparison of the TR11, TR11SV1, and TR11SV2 nucleotide sequence disclosed herein with that of a TR11, TR11SV1, and TR11SV2 gene derived from a patient suspected of harboring a defect in this gene.

In another embodiment, a purified TR11, TR11SV1, and/or TR11SV2 antagonist (including soluble TR11, TR11SV1, and/or TR11SV2 polypeptides, and antibodies of the invention) is used to inhibit binding of Endokine-alpha and/or APRIL to endogenous cell surface Endokine-alpha and/or APRIL receptors. Certain ligands of the TNF family (of which Endokine-alpha and APRIL are members) have been reported to bind to more than one distinct cell surface receptor protein. By binding Endokine-alpha and/or APRIL, soluble TR11, TR11SV1, and/or TR11SV2 polypeptides and antibodies of the present invention may be employed to inhibit the binding of Endokine-alpha and/or APRIL not only to cell surface TR11, TR11SV1, and/or TR11SV2, but also Endokine-alpha and/or APRIL receptor proteins that are distinct from TR1, TR11SV1, and/or TR11SV2 antagonist (including soluble TR11, TR11SV1, and/or TR11SV2 polypeptides). Thus, in another embodiment, TR11, TR11SV1, and/or TR11SV2 antagonists of the invention (including TR11, TR11SV1, and/or TR11SV2 polypeptides and antibodies of the invention) is used to inhibit a biological activity of Endokine-alpha, in in vitro or in vivo procedures. Thus, in another embodiment, TR11, TR11SV1, and/or TR11SV2 antagonists of the invention (including TR11, TR11SV1, and/or TR11SV2 polypeptides and antibodies of the invention) is used to inhibit a biological activity of APRIL, in in vitro or in vivo procedures. Thus, in another embodiment, TR11, TR11SV1, and/or TR11SV2 antagonists of the invention (including TR11, TR11SV1, and/or TR11SV2 polypeptides and antibodies of the invention) is used to inhibit a biological activity of Endokine-alpha and APRIL, in in vitro or in vivo procedures. By inhibiting binding of Endokine-alpha and/or APRIL to cell surface receptors, antagonists of the invention also inhibit biological effects that result from the binding of Endokine-alpha and/or APRIL to endogenous receptors. Various forms of TR11, TR11SV1, and/or TR11SV2 antagonists may be employed, including, for example, the above-described TR11, TR11SV1, and/or TR11SV2 fragments, derivatives, and variants, and antibodies, that are capable of binding Endokine-alpha and/or APRIL. In one preferred embodiment, a soluble TR11, TR11SV1, and/or TR11SV2 polypeptide of the invention is employed to inhibit a biological activity of Endokine-alpha. In another preferred embodiment, a soluble TR11, TR11SV1, or TR11SV2 polypeptide or antibody of the invention is employed to inhibit a biological activity of APRIL. In another preferred embodiment, a soluble TR11, TR11SV1, and/or TR11SV2 polypeptide or antibody of the invention is employed to inhibit a biological activity of Endokine-alpha and APRIL.

In another embodiment, the polypeptides and antibodies of the present invention are used as a research tool for studying the biological effects that result from inhibiting Endokine-alpha/and/or APRIL/TR11, TR11SV1, and/or TR11SV2 interactions on different cell types. TR11, TR11SV1, and TR11SV2 polypeptides and antibodies also may be employed in in vitro assays for detecting Endokine-alpha, APRIL and/or TR11, TR11SV1, and/or TR11SV2 or the interactions thereof.

In one embodiment, the invention provides a method of delivering compositions containing the polypeptides of the invention (e.g., compositions containing TR11, TR11SV1, and/or TR11SV2 polypeptides or polynucleotides, or anti-TR11, anti-TR11SV1, and/or anti-TR11SV2 antibodies associated with heterologous polypeptides, heterologous nucleic acids, toxins, or prodrugs) to targeted cells, such as, for example, T cells expressing TR11, TR11SV1, and/or TR11SV2 receptor. TR11, TR11SV1, and/or TR11SV2 polypeptides or anti-TR11, anti-TR11SV1, and/or anti-TR11SV2 antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., TR11, TR11SV1, and/or TR11SV2 polypeptides or polynucleotides, or anti-TR11, anti-TR11SV1, and/or anti-TR11SV2 antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., monocytes, activated T-cells and tumor cells) by administering polypeptides of the invention (e.g., TR11, TR11SV1, and/or TR11SV2 polypeptides or polynucleotides, or anti-TR11, anti-TR11SV1, and/or anti-TR11SV2 antibodies) in association with toxins or cytotoxic prodrugs.

In a specific embodiment, the invention provides a method for the specific destruction of cells of T cell lineage (e.g., activated T cells and T cell related leukemias or lymphomas) by administering anti-TR11, anti-TR11SV1 and/or anti-TR11SV2 antibodies in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, 35S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label polypeptides (including antibodies) of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

In accordance with the invention, it has been determined human monocytes express TR11, and that TR11 expression is upregulated in those cells when treated with endokine-alpha(also known as TL-6 and AITR-L, see International Publication No. WO98107880 which is incorporated by reference in ts entirty) a TR11 ligand. Additional treatments that result in TR11 mRNA upregulation in monocytes include, LPS, IL-4, IL-10 and IFN-gamma treatment.

Furthermore, it has been determined, in accordance with the invention, that treatment of human T cells with endokine-alpha results in the upregulation of mRNA transcripts including FAS, inducible CAMP early repressor (ICER), IFN-gamma, TNF-alpha, and thrombospondin-1 (TSP-1). Additionally, treatment of human T cells with endokine-alpha results in the downregulation of LTβR mRNA expression. Endokine-alpha treatment of T cells also results in endothelin expression, a cytokine, whose activity includes recruitment of inflammatory cells.

Additionally, endokine-alpha treatment of human monocytes can inhibit inducible IL-12 release. Human monocytes, when primed with IFN-gamma treatment and then activated with LPS, secrete IL-12. Inclusion of endokine-alpha in the priming phase with the IFN-gamma treatment, however, inhibits the production of IL-12 from human monocytes.

Murine splenocytes and a murine fetal skin dendritic cell line (FSDC) respond to endokine-alpha treatment by producing nitric oxide and by releasing cytokines such as TNF-alpha. WFN-gamma treatment concomitant with endokine-alpha treatment of murine splenocytes and FSDC results in even greater nitric oxide production and TNF-alpha secretion.

Further, endokine alpha treatment increases the proliferation of human T cells that are co-stimulated with anti-CD3 and anti-CD28.

Thus, antagonists of endokine alpha, such as TR11-, TR11SV1- and/or TR11SV2-Fc fusion proteins, TR11-, TR11SV1- and/or TR11SV2-albumin fusion proteins, or anti-TR11, TR11SV1 and/or TR11SV2 antibodies may be used in accordance with the invention to block the activities (e.g., T cell proliferation, nitric oxide production by monocytes and dendritic cells, and cytokine release by monocytes and dendritic cells, especially TNF-alpha and/or IL-10 release) mediated by endokine alpha.

In a further embodiment, a TR11, TR11SV1, and/or TR11SV2 agonist or antagonist of the invention (including TR11, TR11SV1, and/or TR11SV2 polynucleotides, polypeptides, and antibodies), is administered to a mammal (e.g., a human) to treat, detect, and/or prevent an Endokine-alpha mediated disorder. Such Endokine-alpha mediated disorders include conditions caused (directly or indirectly) or exacerbated by Endokine-alpha.

The fact that endokine-alpha treatment of immune cells in vitro results in the production of many cytokines important in regulating immune responses and cells of the immune system, and because TR11 is a ligand for endokine-alpha, indicates that TR11, TR11SV1 and/or TR11SV2 compositions of the invention (including TR11, TR11SV1 and/or TR11SV2 polynucleotides, polypeptides, agonists antagonists, anti-TR11, TR11SV1 and/or TR11SV2 antibodies, and fragments and variants of the foregoing) are useful for preventing, diagnosing and/or treating diseases and disorders of the immune system, including but not limited to inflammation and inflammatory diseases, immunodeficiencies, and autoimmune diseases described herein.

In specific embodiments, TR11, TR11SV1 and/or TR11SV2 compositions of the invention are useful for preventing, diagnosing and/or treating asthma.

In other specific embodiments, TR11, TR11SV1 and/or TR11SV2 compositions of the invention are useful for preventing, diagnosing and/or treating allergies.

In other specific embodiments, TR11, TR11SV1 and/or TR11SV2 compositions of the invention are useful for preventing, diagnosing and/or treating inflammation.

In other specific embodiments, TR11, TR11SV1 and/or TR11SV2 compositions of the invention are useful for preventing, diagnosing and/or treating autoimmune diseases.

In other specific embodiments, TR11, TR11SV1 and/or TR11SV2 compositions of the invention are useful for preventing, diagnosing and/or treating rheumatoid arthritis.

In other specific embodiments, TR11, TR11SV1 and/or TR11SV2 compositions of the invention are useful for preventing, diagnosing and/or treating systemic lupus erythematosus.

In a further embodiment, a TR11, TR11SV1, and/or TR11SV2 agonist or antagonist of the invention (including TR11, TR11SV1, and/or TR11SV2 polynucleotides, polypeptides, and antibodies), is administered to a mammal (e.g., a human) to treat, detect, and/or prevent an APRIL mediated disorder. Such APRIL mediated disorders include conditions caused (directly or indirectly) or exacerbated by APRIL.

The TR11, TR11SV1, and TR11SV2 receptor agonists (including polynucleotides, polypeptides, and antibodies of the invention) may be employed to stimulate ligand activities, such as inhibition of tumor growth and necrosis of certain transplantable tumors. The agonists may also be employed to stimulate cellular differentiation or activation, for example, T-cells, B-cells, fibroblasts and/or hematopoietic cell proliferation, differentiation and/or activation. Agonists to the TR11, TR11SV1, and TR11SV2 receptors may also augment the role of TR11, TR11SV1, and TR1SV2 in the host's defense against microorganisms and prevent related diseases (infections such as that from *Listeria monocytogenes*) and Chlamidiae. Agonists may also be employed to treat, detect, and/or prevent autoimmune diseases, for example, graft versus host rejection and allograft rejection, and B-cell mediated autoimmune diseases and T-cell mediated autoimmune diseases such as AIDS. Agonizing the receptor may prevent the proliferation of B-cells and/or T-cells and treat, detect, and/or prevent B-cell mediated or T-cell mediated autoimmune diseases.

The agonists may also be employed to protect against the deleterious effects of ionizing radiation produced during a course of radiotherapy, such as denaturation of enzymes, lipid peroxidation, and DNA damage.

Agonists to the receptor polypeptides of the present invention may be used to augment TNF's role in host defenses against microorganisms and prevent related diseases. The agonists may also be employed to protect against the deleterious effects of ionizing radiation produced during a course of radiotherapy, such as denaturation of enzymes, lipid peroxidation, and DNA damage.

The agonists may also be employed to mediate an antiviral response, to regulate growth, to mediate the immune response and to treat, detect, and/or prevent immunodeficiencies related to diseases such as HIV by increasing the rate of lymphocyte activation, proliferation, and/or differentiation.

The antagonists to the polypeptides of the present invention may be employed to inhibit ligand activities, such as stimulation of tumor growth and necrosis of certain transplantable tumors. The antagonists may also be employed to inhibit cellular proliferation, differentiation and/or activation, for example, T-cells, B-cells, fibroblasts and/or hematopoietic cell differentiation and/or activation. Antagonists may also be employed to treat, detect, and/or prevent autoimmune diseases, for example, graft versus host rejection and allograft rejection, and B-cell mediated autoimmune diseases and T-cell mediated autoimmune diseases such as AIDS. It has been shown that T-cell proliferation is stimulated via a type 2 TNF receptor. Accordingly, antagonizing the receptor may prevent the proliferation of T-cells and treat, detect, and/or prevent T-cell mediated and/or B cell mediated autoimmune diseases.

In addition, TNF-alpha has been shown to prevent diabetes in strains of animals which are prone to this affliction resulting from autoimmunity. See Porter, A., *Tibtech* 9:158–162 (1991). Thus, agonists and antagonists of the present invention may be useful in the treatment, detection, and/or prevention of autoimmune diseases such as type 1 diabetes.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Antagonists of the present invention are able to suppress the immune response to both allografts and xenografts by decreasing the rate of TR11-, TR11SV1-, and TR11SV2-mediated lymphocyte proliferation and differentiation. Such antagonists include the TR11-, TR11SV1-, and/or TR11SV2-Fc fusion proteins described in Example 5, TR11-, TR11SV1-, and/or TR11SV2-albumin fusion proteins, or anti-TR11, TR11SV1, and/or TR11SV2 antibodies. Thus, the present invention further provides a method for suppression of immune responses.

The agonists and antagonists of the invention may also be employed to mediate an anti-viral response, to regulate growth, to mediate the immune response and to treat, detect, and/or prevent immunodeficiencies related to diseases such as HIV by increasing the rate of lymphocyte activation, proliferation and/or differentiation.

In preferred embodiments, TR11, TR11SV1, and/or TR11SV2 agonists or antagonists of the invention (including TR11, TR11SV1, and/or TR11SV2 polynucleotides, polypeptides and antibodies) are used to treat or prevent AIDS and pathologies associated with AIDS. The state of immunodeficiency that defines AIDS is secondary to a decrease in the number and function of $CD4^+T$-lymphocytes. Recent reports estimate the daily loss of $CD4^+T$ cells to be between $3.5 \times 10^7$ and $2 \times 10^9$ cells (Wei X., et al., Nature 373:117–122 (1995)). One cause of $CD4^+T$ cell depletion in the setting of HIV infection is believed to be HIV-induced apoptosis. Indeed, HIV-induced apoptotic cell death has been demonstrated not only in vitro but also, more importantly, in infected individuals (Ameisen, J. C., AIDS 8:1197–1213 (1994); Finkel, T. H., and Banda, N. K., Curr. Opin. Immunol. 6:605–615(1995); Muro-Cacho, C. A. et al., J. Immunol. 154:5555–5566 (1995)). Furthermore, apoptosis and $CD4^+T$-lymphocyte depletion is tightly correlated in different animal models of AIDS (Brunner, T., et al., Nature 373:441–444 (1995); Gougeon, M. L., et al., AIDS Res. Hum. Retroviruses 9:553–563 (1993)) and, apoptosis is not observed in those animal models in which viral replication does not result in AIDS (Gougeon, M. L. et al., AIDS Res. Hum. Retroviruses 9:553–563 (1993)). Further data indicates that uninfected but primed or activated T lymphocytes from HEV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., J. Virol. 70:199–206 (1996)). Further the TNF--family ligand was detectable in uninfected macrophages and its expression was upregulated following HIV infection resulting in selective killing of uninfected CD4+T-lymphocytes (Badley, A. D. et al., J. Virol. 70:199–206 (1996)).

In addition, the role played by the TR11, TR11SV1, and TR11SV2 receptors in lymphocyte cell activation, proliferation and differentiation indicates that agonist or antagonist of the present invention may be used to treat, detect, and/or prevent disease states involving aberrant cellular expression of these receptors. TR11, TR11SV1, and TR11SV2 receptors may in some circumstances induce an inflammatory response, and antagonists may be useful reagents for blocking this response. Thus, TR11, TR11SV1, and TR11SV2 receptor antagonists (e.g., soluble forms of the TR11, TR11SV1, and TR11SV2 receptors; neutralizing antibodies) may be useful for treating, detecting, and/or preventing inflammatory diseases, such as rheumatoid arthritis, osteoarthritis, psoriasis, septicemia, and inflammatory bowel disease.

Agonists or antagonists of the TR11, TR11SV1, and TR11SV2 polypeptides of the invention may also be employed to treat, detect, and/or prevent and/or prevent septic shock, which remains a critical clinical condition. Septic shock results from an exaggerated host response, mediated by protein factors such as TNF and IL-1, rather than from a pathogen directly. For example, lipopolysaccharides have been shown to elicit the release of TNF leading to a strong and transient increase of its serum concentration. TNF causes shock and tissue injury when administered in excessive amounts. Accordingly, it is believed that agonists or antagonists to the TR11, TR11SV1, and TR11SV2 receptors will block the actions of TNF and treat, detect, and/or prevent septic shock. These antagonists may also be employed to treat, detect, and/or prevent meningococcemia in children which correlates with high serum levels of TNF.

Among other disorders which may be treated, detected, and/or prevented by the agonists or antagonists of the TR11, TR11SV1, and TR11SV2 polypeptides of the invention include, inflammation which is mediated by TNF receptor ligands, and the bacterial infections cachexia and cerebral malaria. Agonists and antagonists of the TR11, TR11SV1, and TR11SV2 polypeptides of the invention may also be employed to treat, detect, and/or prevent inflammation mediated by ligands to the receptor such as Endokine-alpha, and APRIL. While not intending to be bound by theory, TR11, TR11SV1 or TR11SV2 polypeptides, antibodies, polynucleotides and/or agonists or antagonists may be useful in treating, detecting, and/or preventing deficiencies or disorders of the immune system, by for example, activating or alternatively inhibiting the activation, proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, TR11, TR11SV1 or TR11SV2 polypeptides, antibodies, polynucleotides and/or agonists or antagonists can be used as a marker or detector of a particular immune system disease or disorder.

Similarly, TR11, TR11SV1, and TR11SV2 polynucleotides or polypeptides of the invention and/or agonists and/or antagonists thereof, may also be used to modulate inflammation. For example TR11, TR11SV1, and TR11SV2 polynucleotides or polypeptides of the invention and/or agonists or antagonists thereof, may inhibit the proliferation, activation and/or differentiation of cells involved in an inflammatory response (e.g., T cells). These molecules can be used to treat, prevent, and/or diagnose inflammatory conditions, both chronic and acute conditions, including, but not limited to, chronic prostatiis, glaucomatous prostatitis and malacoplakia, and inflammation associated with infection (e.g., septic shock, sepsis, or systemic inflammatory responsesyndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

In a specific embodiment, antibodies of the invention are used to treat, prevent, modulate, detect, and/or diagnose inflammation. In other specific embodiments, antibodies of the invention are used to treat, prevent, modulate, detect, and/or diagnose inflammatory disorders. In other specific embodiments, antibodies of the invention are used to treat, prevent, modulate, detect, and/or diagnose allergy and/or hypersensitivity.

TR11, TR11SV1 or TR11SV2 polynucleotides, polypeptides, antibodies, and/or agonists or antagonists may be useful in treating, detecting, and/or preventing deficiencies or disorders of hematopoietic cells. TR11, TR11SV1 or TR11SV2 polypeptides, antibodies, polynucleotides and/or agonists or antagonists could be used to increase differentiation and proliferation of hematopoietic cells, including the pluripotent stem cells, in an effort to treat, detect, and/or prevent those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, DiGeorge Syndrome, chronic mucocutaneous candidiasis, natural killer cell deficiency, idiopathic CD4+T-lymphocytopenia, immunodeficiency with predominant T cell defect, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria. In specific embodiments, the compositions of the invention are used to treat or prevent a T cell deficiency. T cell deficiencies that may be treated or prevented by administering the TR11, TR11SV1, TR11SV2 polypeptides (e.g., TR11-Fc fusion proteins containing the extracellular domain of TR11, and agonistic or antagonistic anti-TR11 antibodies) or polynucleotides of the invention, or antagonists or agonists thereof, include but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are treated or prevented by administering the TR11, TR11SV1, TR11SV2 polypeptides (e.g., TR11-Fc fusion proteins containing the extracellular domain of TR11, and agonistic or antagonistic anti-TR11 antibodies) or polynucleotides of the invention, and/or antagonists or agonists thereof.

As discussed above, TR11, TR11SV1 or TR11SV2 polypeptides, antibodies, polynucleotides and/or agonists or antagonists may also be useful in treatment, prevention, diagnosis and/or prognosis, of autoimmune disorders. Many autoimmune disorders result from inappropriate recognition of self as foreign material by immune cells. This inappropriate recognition results in an immune response leading to the destruction of the host tissue. Therefore, the administration of TR11, TR11SV1 or TR11SV2 polypeptides, antibodies, polynucleotides and/or agonists or antagonists that can inhibit an immune response, particularly the activation, proliferation, differentiation, or chemotaxis of T-cells, and/or B-cells may be an effective therapy in preventing autoimmune disorders.

Examples of autoimmune disorders that can be treated, prevented, diagnosed and/or prognosed using TR11, TR11SV1 or TR11SV2 polypeptides, antibodies, polynucleotides and/or agonists or antagonists include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, diagnosed and/or prognosed using TR11, TR11SV1 or TR11SV2 polypeptides, antibodies, polynucleotides and/or agonists or antagonists of the invention. Moreover, TR11, TR11SV1 or TR11SV2 polypeptides, antibodies, polynucleotides and/or agonists or antagonists can be used to treat, prevent, diagnose and/or prognose anaphylaxis, hypersensitivity to an antigenic molecule, or blood group incompatibility.

TR11, TR11SV1 or TR11SV2 polypeptides, antibodies, polynucleotides and/or agonists or antagonists may also be used to treat, prevent, diagnose and/or prognose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of TR11, TR11SV1 or TR11SV2 polypeptides, antibodies, polynucleotides and/or agonists or antagonists that inhibit an immune response, particularly the proliferation, differentiation, or chemotaxis of T-cells, may be an effective therapy in preventing organ rejection or GVHD.

Similarly, TR11, TR11SV1 or TR11SV2 polypeptides, antibodies, polynucleotides and/or agonists or antagonists may also be used to modulate inflammation. For example, TR11, TR11SV1 or TR11SV2 polypeptides, antibodies, polynucleotides and/or agonists or antagonists of the invention may inhibit the proliferation and differentiation of cells involved in an inflammatory response. These molecules can be used to treat, prevent, diagnose and/or prognose inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Moreover, TR11, TR11SV1 or TR11SV2 polypeptides, antibodies, polynucleotides and/or agonists or antagonists can also be used to modulate hemostatic (the stopping of bleeding) or thrombolytic activity (clot formation). For example, by increasing hemostatic or thrombolytic activity, TR11, TR11SV1 or TR11SV2 polypeptides, antibodies, polynucleotides and/or agonists or antagonists could be used to treat, prevent, diagnose and/or prognose blood coagulation disorders (e.g., afibrinogenemia, factor deficiencies), blood platelet disorders (e.g. thrombocytopenia), or wounds resulting from trauma, surgery, or other causes. Alternatively, TR11, TR11SV1 or TR11SV2 polypeptides, antibodies, polynucleotides and/or agonists or antagonists that can decrease hemostatic or thrombolytic activity could be used to inhibit or dissolve clotting, important in the treatment, prevention, diagnosis and/or prognosis of heart attacks (infarction), strokes, or scarring.

TR11, TR11SV1 or TR11SV2 polypeptides, antibodies, polynucleotides, and/or agonists or antagonists can be used to treat, prevent, diagnose and/or prognose hyperproliferative disorders, including neoplasms. In specific embodiments, TR11, TR11SV1 or TR11SV2 polypeptides, antibodies, polynucleotides and/or agonists or antagonists are used to treat or prevent leukemias and/or lymphomas of T cell lineage. In other specific embodiments, TR11, TR11SV1 or TR11SV2 polypeptides, antibodies, polynucleotides and/or agonists or antagonists are used to treat or prevent leukemias and/or lymphomas of B cell lineage. The molecules of the invention may treat, prevent, diagnose and/or prognose hyperproliferative disorders through direct or indirect interactions. Alternatively, TR11, TR11SV1 or TR11SV2 polypeptides, antibodies, polynucleotides and/or agonists or antagonists may proliferate other cells which can inhibit the hyperproliferative disorder. For example, by increasing an immune response, particularly increasing antigenic qualities of the hyperproliferative disorder or by proliferating, activating, inactivating, differentiating, or mobilizing T-cells or B-cells, hyperproliferative disorders can be treated, prevented, diagnosed and/or prognosed. This immune response may be increased by either enhancing an existing immune response, or by initiating a new immune response. Alternatively, decreasing an immune response may also be a method of treating, preventing, diagnosing and/or prognosing hyperproliferative disorders, such as a chemotherapeutic agent. Examples of hyperproliferative disorders that can be treated, prevented, diagnosed and/or prognosed by TR11, TR11SV1 or TR11SV2 polynucleotides, polypeptides, antibodies, and/or agonists or antagonists include, but are not limited to, neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated, prevented, diagnosed and/or prognosed by TR11, TR11SV1 or TR11SV2 polynucleotides, antibodies, polypeptides and/or agonists or antagonists. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

TR11, TR11SV1 or TR11SV2 polypeptides, antibodies, polynucleotides and/or agonists or antagonists can be used to treat, prevent, diagnose and/or prognose infectious agents. For example, by increasing the immune response, particularly increasing the proliferation activation and/or differentiation of B and/or T cells, infectious diseases may be treated, prevented, diagnosed and/or prognosed. The immune response may be increased by either enhancing an existing immune response, or by initiating a new immune response. Alternatively, TR11, TR11SV1 or TR11SV2 polypeptides, antibodies, polypeptides and/or agonists or antagonists may also directly inhibit the infectious agent, without necessarily eliciting an immune response.

Viruses are one example of an infectious agent that can cause disease or symptoms that can be treated, prevented, diagnosed and/or prognosed by TR11, TR11SV1, TR11SV2 polynucleotides or polypeptides, or agonists of TR11, TR11SV1, TR11SV2. Examples of viruses, include, but are not limited to the following DNA and RNA viruses and viral families: Arbovirus, Adenoviridae, Arenaviridae, Arterivirus, Biruaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. TR11, TR11SV1, TR11SV2 polynucleotides or polypeptides, or agonists or antagonists of TR11, TR11SV1, TR11SV2, can be used to treat, prevent, diagnose and/or prognose any of these symptoms or diseases. In specific embodiments, TR11, TR11SV1, TR11SV2 polypeptides, antibodies, polynucleotides and/or agonists or antagonists, are used to treat, prevent, diagnose and/or prognose: meningitis, Dengue, EBV, and/or hepatitis (e.g., hepatitis B). In an additional specific embodiment TR11, TR11SV1, TR11SV2 polypeptides, antibodies, polynucleotides and/or agonists or antagonists are used to treat patients nonresponsive to one or more other commercially available hepatitis vaccines. In a further specific embodiment, TR11, TR11SV1, TR11SV2 polynucleotides, polypeptides, or agonists are used to treat, prevent, diagnose and/or prognose AIDS.

Similarly, bacterial or fungal agents that can cause disease or symptoms and that can be treated, prevented, diagnosed and/or prognosed using TR11, TR11SV1, TR11SV2 polypeptides, antibodies, polynucleotides and/or agonists or antagonists of the invention, include, but are not limited to, the following Gram-Negative and Gram-positive bacteria and bacterial families and fungi: Actinomycetales (e.g., Corynebacterium, Mycobacterium, Norcardia), Cryptococcus neoformans, Aspergillosis, Bacillaceae (e.g., Anthrax, Clostridium), Bacteroidaceae, Blastomycosis, Bordetella, Borrelia (e.g., Borrelia burgdorferi, Brucellosis, Candidiasis, Campylobacter, Coccidioidomycosis, Cryptococcosis, Dermatocycoses, E. coli (e.g., Enterotoxigenic E. coli and Enterohemorrhagic E. coli), Enterobacteriaceae (Klebsiella, Salmonella (e.g., Salmonella typhi, and Salmonella paratyphi), Serratia, Yersinia), Erysipelothrix, Helicobacter, Legionellosis, Leptospirosis, listeria, Mycoplasmatales, Mycobacterium leprae, Vibrio cholerae, Neisseriaceae (e.g., Acinetobacter, Gonorrhea, Menigococcal), Neisseria meningitidis, Pasteurellacea Infections (e.g., Actinobacillus, Heamophilus (e.g., Heamophilus influenza type B), Pasteurella), Pseudomonas, Rickettsiaceae, Chlamydiaceae, Syphilis, Shigella spp., Staphylococcal, Meningiococcal, Pneumococcal and Streptococcal (e.g., Streptococcus pneumoniae and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., meningitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TR11, TR11SV1, TR11SV2 polynucleotides, antibodies, polypeptides and/or agonists or antagonists of TR11, TR11SV1, TR11SV2, can be used to treat, prevent, diagnose and/or prognose any of these symptoms or diseases. In specific embodiments, TR11, TR11SV1, TR11SV2 polypeptides, antibodies, polynucleotides and/or agonists or antagonists, thereof are used to treat, prevent, diagnose and/or prognose: tetanus, Diptheria, botulism, and/or meningitis type B.

Moreover, parasitic agents causing disease or symptoms that can be treated by TR11, TR11SV1, TR11SV2 polypeptides, antibodies, polynucleotides and/or agonists or antagonists, include, but are not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., Plasmodium virax, Plasmodium falciparium, Plasmodium malariae and Plasmodium ovale). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR11, TR11SV1, TR11SV2 polynucleotides, polypeptides, antibodies, and/or agonists or antagonists of TR11, TR11SV1, TR11SV2, can be used to treat or detect any of these symptoms or diseases. In specific embodiments, TR11, TR11SV1, TR11SV2 polypeptides, antibodies, polynucleotides and/or agonists or antagonists thereof are used to treat malaria.

An additional condition, disease or symptom that can be treated by TR11, TR11SV1, TR11SV2 polynucleotides, polypeptides, antibodies, and/or agonists or antagonists of TR11, TR11SV1, TR11SV2, is osteomyelitis.

Preferably, treatment using TR11, TR11SV1, TR11SV2 polypeptides, antibodies, polynucleotides and/or agonists or antagonists, could either be by administering an effective amount of TR11, TR11SV1, TR11SV2 polypeptide, antibody, polynucleotide, and/or agonist or antagonist, to the patient, or by removing cells from the patient, supplying the cells with TR11, TR11SV1, TR11SV2 polynucleotide, and returning the engineered cells to the patient (ex vivo therapy). Moreover, as further discussed herein, the TR11, TR11SV1, TR11SV2 polypeptide or polynucleotide can be used as an adjuvant in a vaccine to raise an immune response against infectious disease.

TR11, TR11SV1 or TR11SV2 polypeptides, antibodies, polynucleotides and/or agonists or antagonists can be used to activate, deactivate, differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, TR11, TR11SV1 or TR11SV2 polypeptides, antibodies, polynucleotides and/or agonists or antagonists may increase regeneration of tissues difficult to heal. For example, increased tendon/ligament regeneration would quicken recovery time after damage. TR11, TR11SV1 or TR11SV2 polypeptides, antibodies, polynucleotides and/or agonists or antagonists of the present invention could also be used prophylactically in an effort to avoid damage. Specific diseases that could be treated include tendonitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using TR11, TR11SV1 or TR11SV2 polypeptides, antibodies, polynucleotides and/or agonists or antagonists of the invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the TR11, TR11SV1 or TR11SV2 polypeptides, antibodies, polynucleotides and/or agonists or antagonists of the invention.

TR11, TR11SV1 or TR11SV2 polypeptides, antibodies, polynucleotides and/or agonists or antagonists may have chemotaxis activity. A chemotatic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

TR11, TR11SV1,or TR11SV2 polypeptides, antibodies, polynucleotides and/or agonists or antagonists may increase chemotatic activity of particular cells. These chemotactic molecules can then be used to treat inflammation, infection, hyperproliferative disorders, or any immune system disorder by increasing the number of cells targeted to a particular location in the body. For example, chemotactic molecules can be used to treat wounds and other trauma to tissues by attracting immune cells to the injured location. As a chemotactic molecule, TR11, TR11SV1 or TR11SV2 polypeptides, antibodies, polynucleotides and/or agonists or antagonists could also attract fibroblasts, which can be used to treat wounds.

It is also contemplated that TR11, TR11SV1 or TR11SV2 polypeptides, antibodies, polynucleotides and/or agonists or antagonists may inhibit chemotactic activity. These molecules could also be used to treat disorders. Thus, TR11, TR11SV1 or TR11SV2 polypeptides, antibodies, polynucleotides and/or agonists or antagonists could be used as an inhibitor of chemotaxis.

Additional preferred embodiments of the invention include, but are not limited to, the use of TR11, TR11SV1, TR11SV2 polypeptides, antibodies, polynucleotides and/or agonists or antagonists of the invention in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741).

A vaccine adjuvant that enhances immune responsiveness to specific antigen.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: Vibrio cholerae, Mycobacterium leprae, Salmonella typhi, Salmonella paratyphi, Neisseria meningitidis, Streptococcus pneumoniae, Group B streptococcus, Shigella spp., Entcrotoxigenic *Escherichia coli,* Enterohemorrhagic *E. coli,* Borrelia burgdorferi, and Plasmodium (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria).

As a stimulator of B cell responsiveness to pathogens.

As an activator of T cells.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell and/or T cell immunodeficient individuals. T cell deficiencies that may be ameliorated or treated by administering the TR11, TR11SV1, TR11SV2 polypeptides (e.g., TR11-Fc fusion proteins containing the extracellular domain of TR11, and agonistic or antagonistic anti-TR11 antibodies) or polynucleotides of the invention, or antagonists or agonists thereof include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are ameliorated or treated by administering the TR11, TR11SV1, TR11SV2 polypeptides (e.g., TR11-Fc fusion proteins containing the extracellular domain of TR11, and agonistic or antagonistic anti-TR11 antibodies) or polynucleotides of the invention, or antagonists or agonists thereof. Other immunodeficiencies that may be ameliorated or treated by administering the TR11, TR11SV1, TR11SV2 polypeptides ((e.g., TR11-Fc fusion proteins containing the extracellular domain of TR11, and agonistic or antagonistic anti-TR11 antibodies) or polynucleotides of the invention, and/or agonists or antagonists thereof, include, but are not limited to, severe combined immunodeficiency (SCID; e.g., X-linked SCID, autosomal SCID, and adenosine deaminase deficiency), ataxia-telangiectasia, Wiskott-Aldrich syndrome, short-limber dwarfism, X-linked lymphoproliferative syndrome (XLP), Nezelof syndrome (e.g., purine nucleoside phosphorylase deficiency), MHC Class II deficiency. In specific embodiments, ataxia-telangiectasia or conditions associated with ataxia-telangiectasia are ameliorated or treated by administering the TR11, TR11SV1, TR11SV2 polypeptides (e.g., TR11-Fc fusion proteins containing the extracellular domain of TR11, and agonistic or antagonistic anti-TR11 antibodies) or polynucleotides of the invention, and/or antagonists or agonists thereof. Other immunodeficiencies that may be ameliorated or treated by administering the TR11, TR11SV1, TR11SV2 polypeptides, antibodies, polynucleotides, and/or agonists or antagonists of the invention, include, but are not limited to, X-linked agammaglobulinemia, Ig deficiency with hyper IgM, selective IgA deficiency, IgG subclass deficiency, antibody deficiency with normal or elevated levels of Igs, immunodeficiency with thymoma, common variable immunodeficiency (CVI), hypogammaglobulinemia, B cell lymphoproliferative disorder, kappa chain deficiency, Ig heavy chain deficiency, myeloperoxidase deficiency, C2 deficiency, chronic glaucomatous disease (CGD), X-linked immunodeficiency with hyper IgM.

As an agent to boost immunoresponsiveness among individuals having an acquired loss of B cell function. Conditions resulting in an acquired loss of B cell function that may be ameliorated or treated by administering the TR11, TR11SV1, TR11SV2 polypeptides, antibodies, polynucleotides and/or agonists or antagonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the TR11, TR11SV1, TR11SV2 polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, TR11, TR11SV1, TR11SV2 polypeptides (in soluble, membrane-bound or transmembrane forms) or antibodies enhance antigen presentation or antagonizes antigen presentation in vitro or in vivo. Moreover, in related embodiments, this enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a stimulator of B cell production in pathologies such as AIDS, chronic lymphocyte disorder and/or Common Variable Immunodeficiency.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance TR11, TR11SV1, TR11SV2 mediated responses.

As a means of activating T cells.

As a means of activating monocytes/macrophages to defend against parasitic diseases that effect monocytes such as Leishmania.

As pretreatment of bone marrow samples prior to transplant. Such treatment would increase B cell representation and thus accelerate recover.

As a means of regulating secreted cytokines that are elicited by TR11, TR11SV1, TR11SV2.

As a means of modulating IgE concentrations in vitro or in vivo. Additionally, TR11, TR11SV1, TR11SV2 polypeptides or polynucleotides of the invention, or agonists thereof, may be used to treat or prevent IgE-mediated allergic reactions. Such allergic reactions include, but are not limited to, asthma, rhinitis, and eczema.

All of the above described applications as they may apply to veterinary medicine.

Alternatively, the TR11, TR11SV1, TR11SV2 polynucleotides, polypeptides, antibodies, and/or agonists or antagonists of the invention having activities opposite to those described above would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens. Although our current data speaks directly to the potential role of TR11, TR11SV1, TR11SV2 in B cell and T cell related pathologies, it remains possible that other cell types may gain expression or responsiveness to TR11. Thus, TR11, TR11SV1, TR11SV2 may, like CD40 and its ligand, be regulated by the status of the immune system and the microenvironment in which the cell is located.

A therapy for preventing the B cell proliferation and Ig secretion associated with autoimmune diseases such as idiopathic thrombocytopenic purpura, systemic lupus erythematosus and MS.

An inhibitor of B and/or T cell migration in endothelial cells. This activity disrupts tissue architecture or cognate responses and is useful, for example in disrupting immune responses, and blocking sepsis.

An inhibitor of graft versus host disease or transplant rejection.

A therapy for B cell and/or T cell malignancies such as ALL, Hodgkin's disease, non-Hodgkin's lymphoma, Chronic lymphocyte leukemia, plasmacytomas, multiple myeloma, Burkitt's lymphoma, and EBV-transformed diseases.

A therapy for chronic hypergammaglobulinemia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

TR11, TR11SV1, TR11SV2 polypeptides, antibodies, polynucleotides and/or agonists or antagonists of the invention may be used to modulate IgE concentrations in vitro or in vivo. Additionally, administration of TR11, TR11SV1, TR11SV2 polypeptides, antibodies, polynucleotides and/or agonists or antagonists of the invention, may be used to treat or prevent IgE-mediated allergic reactions including, but not limited to, asthma, rhinitis, and eczema.

An inhibitor of signaling pathways involving ERK1, COX2 and Cyclin D2 which have been associated with TR11, TR11SV1 and/or TR11SV2 induced B cell activation.

The agonists and antagonists of the invention may be employed in a composition with a pharmaceutically acceptable carrier, e.g., as described above.

The agonists and antagonists may be employed for instance to inhibit TR11, TR11SV1 and/or TR11SV2 chemotaxis and activation of macrophages and their precursors, and of neutrophils, basophils, B lymphocytes and some T-cell subsets, e.g., activated and CD8 cytotoxic T cells and natural killer cells, in certain auto-immnune and chronic inflammatory and infective diseases. Examples of auto-immune diseases include multiple sclerosis, and insulin-dependent diabetes. The antagonists and antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the TR11, TR11SV1 and/or TR11SV2 polypeptides of the present invention. The agonists and antagonists may also be employed for treating atherosclerosis, by preventing monocyte infiltration in the artery wall. The agonists and antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The agonists and antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists and antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The agonists and antagonists may be employed to interfere with the deleterious cascades attributed primarily to IL-1 and TNF, which prevents the biosynthesis of other inflammatory cytokines. In this way, the agonists and antagonists may be employed to prevent inflammation. The agonists and antagonists may also be employed to inhibit prostaglandin-independent fever induced by TR11, TR11SV1 and/or TR11SV2. The agonists and antagonists may also be employed to treat cases of bone marrow failure, for example, aplastic anemia and myelodysplastic syndrome. The agonists and antagonists may also be employed to treat asthma and allergy by preventing eosinophil accumulation in the lung. The agonists and antagonists may also be employed to treat subepithelial basement membrane fibrosis which is a prominent feature of the asthmatic lung.

Antibodies against TR11, TR11SV1 and/or TR11SV2 may be employed to bind to and inhibit TR11, TR11SV1 and/or TR11SV2 activity to treat ARDS, by preventing infiltration of neutrophils into the lung after injury. The antagonists and antagonists of the instant may be employed in a composition with a pharmaceutically acceptable carrier, e.g., as described hereinafter.

Agonists and antagonist of the invention also have uses in stimulating wound and tissue repair, stimulating angiogenesis, stimulating the repair of vascular or lymphatic diseases or disorders. Additionally, agonists and antagonists of the invention may be used to stimulate the regeneration of mucosal surfaces.

Polynucleotides, polypeptides, and antibodies, and/or agonists or antagonists of the invention are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephriltis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides, polypeptides, antibodies, and/or agonists or antagonists of the invention are useful in promoting angiogenesis, regulating hematopoiesis, and wound healing (e.g., wounds, bums, and bone fractures).

Polynucleotides, polypeptides, antibodies and/or agonists and/or antagonists of the invention are also useful as an adjuvant to enhance immune responsiveness to specific antigen and/or anti-viral immune responses.

More generally, polynucleotides, polypeptides, antibodies, and/or agonists or antagonists of the invention are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides, polypeptides, antibodies, and/or agonists or antagonists of the invention are useful as immunosuppressive agents, for example in the treatment or prevention of autoimmune disorders. In specific embodiments, polynucleotides, polypeptides, antibodies, and/or agonists or antagonists of the invention are used to treat or prevent chronic inflammatory, allergic or autoimmune conditions, such as those described herein or are otherwise known in the art.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments the host is a human.

Modes of administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit TR11, TR11SV1, and TR11SV2 receptor mediated activity. Of course, where cell proliferation and/or differentiation is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or pro-drug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgement. The specific therapeutically effective dose level for any particular patient will depend upon factors well known in the medical arts.

As a general proposition, the total pharmaceutically effective amount of a TR11, TR11SV1 or TR11SV2 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR11, TR11SV1, and TR11SV2 polypeptides are typically administered at a dose rate of about 1 μg/kg/hour to about 50 μg/kg/hour, either by 1–4 injections per day or by continuous subcutaneous infusions, for example, using a mini-pump. An intravenous bag solution may also be employed.

Pharmaceutical compositions containing the TR11, TR11SV1, and TR11SV2 receptor polypeptides of the invention may be administered orally, rectally, parenterally, intracistemally, intravaginally, intraperitoneally, topically (as by powders, ointments, drops or transdermnal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

The compositions of the invention may be administered alone or in combination with other adjuvants. Adjuvants that may be administered with the compositions of the invention include, but are not limited to, alum, alum plus deoxycholate (IrnmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The compositions of the invention may be administered alone or in combination with other therapeutic agents. Therapeutic agents that may be administered in combination with the compositions of the invention, include but not limited to, other members of the TNF family, chemotherapeutic agents, antibiotics, antivirals, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, (CD40L, 4-1BBL, DcR3, OX40L, TNF-gamma (International Publication No. WO 96/14328), AIM-I (International Publication No. WO 97/33899), AIM-II (International Publication No. WO 97/34911), endokine-alpha (International Publication No. WO 98/07880), TR6 (International Publication No. WO 98/30694), OPG, and neutrokine-alpha (International Publication No. WO 98/18921, OX40, and nerve growth factor (NGF), ancl soluble forms of Fas, CD30, CD27, CD40 and 4-1BB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), and TR12, and soluble forms CDE154, CD70, and CD153.

In a preferred embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g, agonistic or antagonistic antibodies), and/or anti-CD40 antibodies (e.g, agonistic or antagonistic antibodies).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumon-ia infection. In another specific embodiment, compositions of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat or prevent an opportunistic fungal infection. In another specific embodiment, compositions of the invention are used in any combination with ACYCLOVIR™ and/or FAMCICOLVIR™ to prophylactically treat or prevent an opportunistic herpes simplex virus type I and/or type II infection. In another specific embodiment, compositions of the invention are used in any combination with PYRIMETHAMINE™ and/or LEUCOVORIN™ to prophylactically treat or prevent an opportunistic *Toxoplasma gondii* infection. In another specific embodiment, compositions of the invention are used in any combination with LEUCOVORIN™ and/or NEUPOGEN™ to prophylactically treat or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azatlhioprine, FK-506, 15-deoxyspergualin, and other immunosuppressive agents that act by suppressing the function of responding T cells.

Additionally, immunosuppressants preparations that may be administered with the composition of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BI[F-1 149 (Boehringer Ingelheim), LeukoVax (Inflarmmatics), MK-663 (Merck), ST-1482 (Sigma-Tau), and butixocort propionate (WainerLambert).

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone.

In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FI, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate. In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituximab and CHOP, or Rituximab and any combination of the components of CHOP.

In an additional embodiment, the compositions of the invention are administered in combination with cytokines. Cytokines that may be administered with the compositions of the invention include, but are not limited to, GM-CSF, G-CSF, IL-1 alpha, IL-1 beta, [IL-2, IL,3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, anti-CD40, CD40L, IFN-alpha, IFN-beta, IFN-gamma, TNF-alpha, and TNF-beta.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-6821 10; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In alternative embodiments, In an additional embodiment, the compositions of the invention are administered alone or in combination with an anti-angiogenic agent. Anti-angiogenic agents that may be administered with the compositions of the invention include, but are not limited to, Angiostatin (Entremed, Rockville, Md.), Troponin-1 (Boston Life Sciences, Boston, Mas.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312–316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. ]3 rem and J. Folkmnan J Pediatr. Surg. 28:445–51 (1993)); an integrin alpha v beta 3 antagonist (C. Storgard et al., J Clin. Invest. 103:47–54 (1999)); carboxynaminolmidazole; Carboxyamidotriazole (CAI) (National Cancer Institute, Bethesda, Md.); Conbretastatin A-4 (CA4P) (OXiGENE, Boston, MA); Squalamine (Magainin Pharmaceuticals, Plymouth Meeting, PA); TNP-470, (Tap Pharmaceuticals, Deerfield, IL); ZD-0101 AstraZeneca (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Sorrmatostatin); Panretin; Penacillamine; Photopoint; PI-88; Prinomastat (AG-3340) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the compositions of the invention include, but are not limited to, AG-3340 (Agouron, La Jolla, Calif.), BAY-12-9566 (Bayer, West Haven, Conn.), BMS-275291 (Bristol Myers Squibb, Princeton, N.J.), C,GS-27032A (Novartis, East Hanover, N.J.), Marimastat (British Biotech, Oxford, UK), and Metastat (Aeterna, St-Foy, Quebec). Examples of anti-angiogenic inhibitors that act by blocking the function of endothelial cell-extracellular matrix adhesion molecules and which may be administered in combination with the compositions of the invention include, but are not limited to, EMD-121974 (Merck KcgaA Darmstadt, Germany) and Vitaxin (ixsys, La Jolla, Calif./Medimmune, Gaithersburg, Md.). Examples of anti-angiogenic agents that act by directly antagonizing or inhibiting angiogenesis inducers and which may be administered in combination with the compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of compositions of the invention in combination with anti-angiogenic agents is contemplated for the treatment, prevention, and/or amelioration of an autoimmune disease, such as for example, an autoimmune disease described herein.

In a particular embodiment, the use of compositions of the invention in combination with anti-angiogenic agents is contemplated for the treatment, prevention, and/or amelioration of arthritis. In a more particular embodiment, the use of compositions of the invention in combination with anti-angiogenic agents is contemplated for the treatment, prevention, and/or amelioration of rheumatoid arthritis.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In an additional embodiment, the compositions of the invention are administered in combination with hematopoietic growth factors. Hematopoietic growth factors that may be administered with the compositions of the invention included, but are not limited to, LEUKINE™ (SARGRAMOSTIM™) and NEUPOGEN™ (FILGRASTIM™).

In additional embodiments, the compositions of the invention are administered in combination with other therapeutic or prophylactic regimens, such as, for example, radiation therapy.

EXAMPLES

Having generally described the invention, the same will be more readily understood by reference to the following examples, which are provided by way of illustration and are not intended as limiting.

Example 1: Expression and Purification of TR11 in *E. coli*.

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp'") and contains a bacterial origin of replication ("ori"), an IPTG inducible promoter, a ribosome binding site ("RBS"), six codons encoding histidine residues that allow affinity purification using nickel-ntrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

Alternatively, the novel pHE4 series of bacterial expression vectors, in particular, the pHE4–5 vector may be used for bacterial expression in this example. The pHE4–5/MPIFD23 vector plasmid DNA containing an insert which encodes another ORF (using the Nde I and Asp 718 flanking restriction sites, one of ordinary skill in the art could easily use current molecular biological techniques to replace the irrelevant ORF in the pHE4–5 vector with the ORF of the present invention) was deposited on Sep. 30, 1997 at the American Type Culture Collection, 10801 University Boulevard, Manassas, Va. 20110–2209, and given ATCC Deposit No. 209311. The bacterial expression vector pBE4–5 includes a neomycin phosphotranferase gene for selection, an *E. coli* origin of replication, a T5 phage promoter sequence, two lac operator sequences, a Shine-Delgamno sequence, and the lactose operon repressor gene (laclq). The promoter and operator sequences of the pHE4–5 vector were made synthetically. Synthetic production of nucleic acid sequences is well known in the art (CLONTECH 95/96 Catalog, pages 215–216, CLONTECH, 1020 East Meadow Circle, Palo Alto, Calif. 94303).

The DNA sequence encoding the desired portion of the TR11 protein lacking the hydrophobic leader sequence is amplified from the deposited cDNA clone using PCR oligonucleotide primers which anneal to the amino terminal sequences of the desired portion of the TR11 protein and to sequences in the deposited construct 3' to the cDNA coding sequence. Additional nucleotides containing restriction sites to facilitate cloning in the pQE60 vector are added to the 5' and 3' sequences, respectively.

For cloning the soluble extracellular domain of the TR11 protein, the 5' primer has the sequence: 5'-CGC <u>CCA TGG</u> CAG CGC CCC ACC G-3' (SEQ ID NO: 10) containing the underlined Nco I restriction site followed by 13 nucleotides complementary to the amino terminal coding sequence of the extracellular domain of the TR11 sequence in FIGS. 1A and 1B (nucleotides 184–195 of SEQ ID NO:1). One of ordinary skill in the art would appreciate, of course, that the point in the protein coding sequence where the 5' primer begins may be varied to amplify a desired portion of the complete protein shorter or longer than the mature form. The 3' primer for the soluble extracellular domain has the sequence: 5'CGC <u>AAG CTT</u> GGC TCT GCC GGC G 3' (SEQ ID NO:11) containing the underlined Hind III restriction site followed by 13 nucleotides complementary to the 3' end of the extracellilar domain portion of the nucleotide sequence shown in FIGS. 1A and 1B (nucleotides 590–602 in SEQ ID NO: 1) encoding the extracellular domain of the TR11 receptor.

The amplified TR11 DNA fragments and the vector pQE60 are digested with Nco I and Hind III and the digested DNAs are then ligated together. Insertion of the TR11 DNA into the restricted pQE60 vector places the TR11 protein coding region downstream from the IPTG-inducible promoter and in-frame with an initiating AUG.

The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain Ml5/rep4, containing multiple copies of the plasmid pREP4, which expresses the lac repressor and confers kanamycin resistance ("Kan'"), is used in carrying out the illustrative example described herein. This strain, which is only one of many that are suitable for expressing TR11 protein, is available commercially from QIAGEN, Inc., supra. Transfornmants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacd repressor. Cells subsequently are incubated further for 3 to 4 hours. Cells then are harvested by centrifugation.

The cells are then stirred for 3–4 hours at 4° C. in 6 M guanidine-HCl, pH 8. The cell debris is removed by centrifugation, and the supernatant containing the TR11 extracellular domain polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure TR11 extracellular domain polypeptide. The purified protein is stored at 4° C. or frozen at -80° C.

The skilled artisan appreciates that a similar approach could easily be designed and utilized to generate pQE60-based bacterial expression constructs for the expression of TR11SV1 and TR11SV2 in *E. coli*. This would be done by designing PCR primers containing similar restriction endonuclease recognition sequences combined with gene-specific sequences for TR11SV1 and TR11SV2 and proceeding as described above.

Example 2(a): Cloning and Expression of a Soluble Fragment of TR11 Protein in a Baculovirus Expression System.

In this example, the plasmid shuttle vector pA2GP was used to insert the cloned DNA encoding the mature extracellular domain of the TR11 receptor protein shown in FIGS. 1A and 1B, lacking its naturally associated secretory signal (leader) sequence, into a baculovirus. This protein was expressed using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the Autographa californica nuclear polyhedrosis virus (AcMNPV) followed by the secretory signal peptide (leader) of the baculovirus gp67 protein and convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIMi1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding essentially the extracellular domain with leader (amino acids 1 to 162 shown in FIGS. 1A and 1B) of the TR11 receptor protein in the deposited clone (ATCC Deposit Number 209341) is amplified using PCR oligonucleotide primers corresponding to the relevant 5' and 3' sequences of the gene. The 5' primer for the above has the sequence: 5-CUC GGA TCC CAG CGC CCC ACC G-3' (SEQ ID NO:12) containing the underlined Bam HI restriction enzyme site, an efficient signal for initiation of translation in eukaryotic cells, as described by Kozak, M., *J. Mol. Biol.* 196:947–950 (1987), followed by 13 bases of the coding sequence of the TR11 protein shown in FIGS. 1A and 1B (nucleotides 193–205 in SEQ ID NO:1). The 3' primer has the sequence: 5' CGC GGT ACC GGC TCT GCC GGC G-3' (SEQ ID NO:13) containing the underlined Asp 718 restriction sites followed by 13 nucleotides complementary to the coding sequence in FIGS. 1A and 1B (nucleotides 590–602 in SEQ ID NO:1).

The amplified fragment is isolated from a 1% agarose gel using a commercially available kit ("Geneclean," BIO 101 Inc., La Jolla, Calif.). The fragment was then digested with Bam HI and Asp 718 and purified on a 1% agarose gel. This fragment is designated herein "F1".

The plasmid is digested with the restriction enzymes Bam HI and Asp 718 dephosphorylated using calf intestinal phosphatase. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 cells are transformed with the ligation mixture and spread on culture plates. Other suitable *E. coli* hosts such as XL-1 Blue (Stratagene Cloning Systems, La Jolla, Calif.) may also be used. Bacteria are identified that contain the plasmid with the human TR11 sequences using the PCR method, in which one of the above primers is used to amplify the gene and the second primer is from well within the vector so that only those bacterial colonies containing TR11 gene fragments show amplification of the DNA. The sequence of the cloned fragment is confirmed by DNA sequencing. The plasmid is designated herein pBacTR11-T.

Five micrograms of pBacTR11-T is co-transfected with 1.0 μg of a commercially available linearized baculovirus DNA ("BaculoGold baculovirus DNA", Pharmingen, San Diego, Calif.), using the lipofection method described by Felgner et al., *Proc. Natl. Acad. Sci. USA* 84:7413–7417 (1987). 1 μg of BaculoGold virus DNA and 5 μg of plasmid pBacTR11-T are mixed in a sterile well of a microtiter plate containing 50 μl of serum-free Grace's medium (Life Technologies Inc., Gaithersburg, Md.). Afterwards, 10 μl lipofectin plus 90 μl Grace's medium are added, mixed and incubated for 15 minutes at room temperature. Then the transfection mixture is added dropwise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After ]Four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-TR1 -T.

To verify the expression of the gene used, Sf9 cells are grown in Grace's medium supplemented with 10% heat inactivated FBS. The cells are infected with the recombinant baculovirus V-TR11-T at a multiplicity of infection ("MOI") of about 2. Six hours later the medium is removed and replaced with SF900 II medium minus methionine and cysteine (available from Life Technologies Inc., Rockville, Md.). Forty-two hours later, 5 µCi of $^{35}$S-methionine and 5 µCi $^{35}$S-cysteine (available from Amersham) are added to radiolabel proteins. The cells are further incubated for 16 hours and then they are harvested by centrifugation. The proteins in the supernatant as well as the intracellular proteins are analyzed by SDS-PAGE followed by autoradiography. Microsequencing of the amino acid sequence of the amino terminus of purified protein is used to determine the amino terminal sequence of the mature protein and thus the cleavage point and length of the secretory signal peptide.

Example 2(b): (Cloning and Expression of the Full-Length Gene for TR11 Protein in a Baculovirus Expression System Similarly to the cloning and expression of the truncated version of the TR11 receptor described in Example 2(a), recombinant baculoviruses were generated which express the full length TR11 receptor protein shown in FIGS. 1A and 1B (SEQ ID NO:2).

In this example, the plasmid shuttle vector pA2 is used to insert the cloned DNA encoding the complete protein, including its naturally associated secretary signal (leader) sequence, into a baculovirus to express the mature TR11 protein. Other attributes of the pA2 vector are as described for the pA2GP vector used in Example 2(a).

The cDNA sequence encoding the full length TR11 protein in the deposited clone, including the AUG initiation codon and the naturally associated leader sequence shown in FIGS. 1A and 1B (SEQ ID NO:2), is amplified using PCR oligonucleotide primers corresponding to the 5' and 3' sequences of the gene. The 5' primer for the above has the sequence: 5-CGC GGA TCC CCG CCA TCA TGG CAC AGC ACG GGG CG-3' (SEQ ID NO: 14) containing the underlined Bam fu restriction enzyme site, an efficient signal for initiation of translation in eukaryotic cells (in italics), as described by Kozak, M., *J. Mol. Biol.* 196:947–950 (1987), followed by 16 bases of the coding sequence of the TR11 protein shown in FIGS. 1A and 1B (nucleotides 118–135 in SEQ ID NO:1). A suitable 3' primer for this purpose has the sequence: 5'CGC GGT ACC CAC CCA CAG GTC TCC C-3' (SEQ ID NO:15) containing the underlined Asp 718 restriction sites followed by 16 nucleotides complementary to the coding sequence in FIGS. 1A and 1B (nucleotides 804–819 in SEQ ID NO: 1).

The amplified fragment is isolated and digested with restriction enzymes as described in Example 2(a) to produce plasmid pBacTR11

5 µg of pBacTR11 is co-transfected with 1 µg of BaculoGold (Pharmingen) viral DNA and 10 µl of Lipofectin (Life Technologies, Inc.) in a total volume of 200 µl serum free media. The primary viruses are harvested at 4–5 days post-infection (pi), and used in plaque assays. Plaque purified viruses are subsequently amplified and frozen, as described in Example 2(a).

For radiolabeling of expressed proteins, Sf9 cells are seeded in 12 well dishes with 2.0 ml of a cell suspension containing 0.5×10$^6$ cells/ml and allowed to attach for 4 hours. Recombinant baculoviruses are used to infect the cells at an MOI of 1–2. After 4 hours, the media is replaced with 1.0 ml of serum free media depleted for methionine and cysteine (-Met/-Cys). At 3 days pi, the culture media is replaced with 0.5 ml -Met/-Cys containing 2 µCi each [$^{35}$S]-Met and [$^{35}$S]-Cys. Cells are labeled for 16 hours after which the culture media is removed and clarified by centrifugation (Supernatant). The cells are lysed in the dish by addition of 0.2 ml lysis buffer (20 mM HEPES, pH 7.9; 130 mM NaCl; 0.2 mM EDTA; 0.5 mM DTT and 0.5% vol/vol NP-40) and then diluted up to 1.0 ml with dH$_2$O (Cell Extract). 30 µl of each supernatant and cell extract are resolved by 15% SDS-PAGE. Protein gels are stained, destained, amplified, dried and autoradiographed. Labeled bands corresponding to the recombinant proteins are visible after 16–72 hours exposure.

The skilled artisan appreciates that a similar approach could easily be designed and utilized to generate pA2GP- and pA2-based baculovirus expression constructs for the expression of TR11SV1 and TR11SV2 in insect cells. This would be done by designing PCR primers containing similar restriction endonuclease recognition sequences combined with gene-specific sequences for TR11SV1 and TR11SV2 and proceeding as described above.

Example 3: Cloning and Expression of TR11 in Mammalian Cells.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (TRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human HeLa 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS; Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438447 (March, 1985)) plus a fragment of the CMV-enhancer (Boshart et al., *Cell* 41:521–530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

Example 3(a): Cloning and Expression in COS Cells.

The expression plasmid, pTR11HA, is made by cloning a cDNA encoding the soluble extracellular portion of the TR11 protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding a TR11 protein is cloned into the polylinker region of the vector so that recombinant protein expression is directed by the CMV promoter. The plasmid construction strategy is as follows. The TR11 cDNA of the deposited clone is amplified using primers that contain convenient restriction sites, much as described above for construction of vectors for expression of TR11 in *E. coli*. Suitable primers include the following, which are used in this example. The 5' primer, containing the underlined Bam HI site, a Kozak sequence (in italics), an AUG start codon and 13 additional codons, of the 5' coding region of the complete TR11 has the following sequence: 5'-CGC GGA TCC GCC ATC ATG CAG CGC CCC ACC G-3' (SEQ ID NO: 16). The 3' primer has the sequence: 5'CGC TCT AGA TCA AGC GTA GTC TGG GAC GTC GTA TGG GTA TTA GGC TCT GCC GGC G-3' (SEQ ID NO: 17) containing the underlined Xba I restriction site followed by a stop codon, a sequence encoding a 6×his tag, and 15 nucleotides complementary to the coding sequence in FIGS. 1A and 1B (nucleotides 590–602 in SEQ ID NO: 1).

The PCR amplified DNA fragment and the vector, pcDNAI/Amp, are digested with Bam HI and Xba I and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the TR11-encoding fragment.

For expression of recombinant TR11, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TR11 by the vector.

Expression of the TR11-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing [$^{35}$S]-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b): Cloning and Expression in CHO Cells.

The vector pC4 is used for the expression of TR11 protein. Plasmid pC4 is a derivative of the plasmid pSV2-dhfr (ATCC Accession No. 37146). The plasmid contains the mouse DHFR gene under control of the SV40 early promoter. Chinese hamster ovary-or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are Bam HI, Xba I, and Asp 718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. Clontech's Tet-Off and Tet-On gene expression systems and similar systems can be used to express the TR11 protein in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphatase by procedures known in the art. The vector is then isolated from a 1% agarose gel.

The DNA sequence encoding the complete TR11 protein including its leader sequence is amplified using PCR oligonucleotide primers corresponding to the 5' and 3' sequences of the gene having, for instance, the same sequences as the 5' and 3' primers used for cloning in baculovirus pA vectors as shown in Example 2, above.

The amplified fragment is digested with the endonucleases Bam HI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5, μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

The skilled artisan appreciates that a similar approach could easily be designed and utilized to generate pcDNAIII- and pC4-based bacterial expression constructs for the expression of TR11SV1 and TR11SV2 in mammalian cells. This would be done by designing PCR primers containing similar restriction endonuclease recognition sequences combined with gene-specific sequences for TR11SV1 and TR11SV2 and proceeding as described above.

Example 4: Tissue Distribution of TR11, TR11SV1, and TR11SV2 mRNA Expression.

Northern blot analysis is carried out to examine TR11, TR11SV1, and TR11SV2 gene expression in human tissues, using methods described by, among others, Sambrook et al., cited above. cDNA probes containing the entire nucleotide sequences of the TR11, TR11SV1, and TR11SV2 proteins (SEQ ID NO: 1, SEQ ID NO:3, and SEQ ID NO:5, respectively) are labeled with $^{35}P$ using the rediprime DNA labeling system (Amersham Life Science), according to manufacturer's instructions. After labeling, the probe is purified using a CHROMA SPIN-100 column (Clontech Laboratories, Inc.), according to manufacturer's protocol number PT1200-1. The purified labeled probe is then used to examine various human tissues for TR11, TR11SV1, and TR11SV2 mRNA.

Multiple Tissue Northern (MTN) blots containing various human tissues (H) or human immune system tissues (IM) are obtained from Clontech and are examined with the labeled probe using ExpressHyb hybridization solution (Clontech) according to manufacturer's protocol number PT1190-1. Following hybridization and washing, the blots are mounted and exposed to film at −70° C. overnight, and films developed according to standard procedures.

Example 5(a): Expression and Purification of TR11-Fc (TR11-Ig Fusion Protein) and Cleaved TR11.

The putative transmembrane domain of translated TR11 receptor is determined by hydrophobicity using the method of Goldman et al. (*Ann. Rev. of Biophys. Biophys. Chem.* 15:321–353 (1986)) for identifying nonpolar transbilayer helices. The region upstream of this transmembrane domain, encoding the putative leader peptide and extracellular domain, is selected for the production of an Fc fusion protein. Primers are designed to amplify the corresponding coding region from the deposited clone by PCR with the addition of a Bgl II site, a Factor Xa protease site, and an Asp 718 site at the 3' end. This is cloned into COSFclink to give the TR11-Fclink plasmid. The PCR product is digested with Eco RI and Asp 718 and ligated into the COSFclink plasmid (Johansen, et al., *J. Biol. Chem.* 270:9459–9471 (1995)) to produce TR11-Fclink.

COS cells are transiently transfected with TR11 -Fclink and the resulting supernatant is immunoprecipitated with protein A agarose. Western blot analysis of the immunoprecipitate using goat anti-human Fc antibodies reveals a strong band consistent with the expected size for glycosylated TR11-Fc (greater than 65,940 kD). A 15L transient COS transfection is performed and the resulting supernatant is purified. The purified protein is used to immunize mice following DNA injection for the production of mAbs.

CHO cells are transfected with TR11-Fclink to produce stable cell lines. Five lines are chosen by dot blot analysis for expansion and are adapted to shaker flasks. The line with the highest level of TR11-Fc protein expression is identified by Western blot analysis. TR11-Fc protein purified from the supernatant of this line is used for cell binding studies by flow cytometry, either as intact protein or after factor Xa cleavage and biotinylation.

The skilled artisan appreciates that a similar approach could easily be designed and utilized to generate expression constructs for the expression of TR11SV1 and TR11SV2 as Fc fusion proteins. This would be done by designing PCR primers containing similar restriction endonuclease recognition sequences combined with gene-specific sequences for TR11SV1 and TR11SV2 and proceeding as described above.

Example 5(b): Punitfication of TR11-Fc from CHO EIA Conditioned Media Followed by Cleavage and Biotinylation of TR11.

Assays

Product purity through the purification is monitored on 15% Laemmli SDS-PAGE gels run under reducing and non-reducing conditions. Protein concentration is monitored by $A_{280}$ assuming extinction coefficients for the receptor and the chimera calculated from the sequences.

Protein G Chromatography of the TR11-Fc Fusion Protein

All steps described below are carried out at 4° C. 15L of CHO conditioned media (CM; $0.2\mu$ filtered following harvest in cell culture) is applied to a 5×10 cm column of Proteiri G at a linear flow rate of 199 cm/h. The column is previously washed with 100 mM glycine, pH 2.5 and equilibrated in 20 mM sodium phosphate, 150 mM sodium chloride, pH 7 prior to sample application. After the CM is loaded the column is washed with 5 column volumes of 20 mM sodium phosphate, 150 mM sodium chloride, pH 7 and eluted with 100 mM glycine, pH 2.5. The eluate is immediately neutralized with 3 M Tris, pH 8.5 and $0.2\mu$ filtered.

Concentration/Dialysis

Protein G eluate is concentrated about 10 fold in an Amicon stirred cell fitted with a 30K membrane. The concentrate is dialyzed against buffer.

Factor Xa Cleavage and Purification to Generate Free Receptor

TR11-Fc is added to 50 $\mu$g of Factor Xa resulting in a 1:200 e:s ratio. The mixture is incubated overnight at 4° C.

Protein G Chromatography of the Free TR11 receptor

A 1 ml column of Protein G is equilibrated in 20 mM sodium phosphate, 150 mM sodium chloride, pH 6.5 in a disposable column using gravity flow. The cleaved receptor is passed over the column 3 times after which the column is washed with 20 mM sodium phosphate, 150 mM sodium chloride, pH 6.5 until no $A_{280}$ absorbance is seen. The column is eluted with 2.5 ml of 100 mM glycine, pH 2.5 neutralized with 83 $\mu$l of 3 M Tris, pH 8.5. TR11 elutes in the nonbound fraction.

Concentration

The nonbound fraction from the Protein G column is concentrated in a Centricon 1OK cell (Amicon) to about a final concentration of 3.5 mg/ml estimated by $A_{280}$ extinction coefficient 0.7.

Mono S Chromatography

The concentrated sample is diluted to 5 ml with 20 mM sodium phosphate, pH 6 and applied to a 0.5×5 cm Mono S column equilibrated in 20 mM sodium phosphate, pH 6 at a linear flow rate of 300 cm/h. The column is washed with 20 mM sodium phosphate, pH 6 and eluted with a 20 column volume linear gradient of 20 mM sodium phosphate, pH 6 to 20 mM sodium phosphate, 1 M sodium chloride, pH 6. TR11 protein elutes in the nonbound fraction.

Concentration/Dialysis

The nonbound fraction from the Mono S column is concentrated to 1 ml as above using a Centricon 1OK cell and is dialyzed against 20 mM sodium phosphate, 150 mM sodium chloride, pH 7.

Biotinylation 0.5 mg of TR11 at about 1–2 mg/ml is dialyzed against 100 mM borate, pH 8.5. A 20-fold molar excess of NHS-LC Biotin is added and the mixture is left on a rotator overnight at 4° C. The biotinylated TR11 is dialyzed against 20 mM sodium phosphate, 150 mM sodium chloride, pH 7, sterile filtered and stored at −70° C. Biotinylation is demonstrated on a Western blot probed with streptavidin HRP and subsequently developed with ECL reagent.

Example 6: Chromosomal Mapping of TR11, TR11SV1, or TR11SV2.

An oligonucleotide primer set is designed according to the sequence at the 5' end of SEQ ID NO:1, SEQ ID NO:3, or SEQ ID NO:5. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 7: Construction of N-Terminal and/or C-Terminal Deletion Mutants.

The following general approach may be used to clone an N-terminal or C-terminal deletion TR11, TR11SV1 or TR11SV2 deletion mutant. Generally, two oligonucleotide primers of about 15–25 nucleotides are derived from the desired 5' and 3' positions of a polynucleotide of SEQ ID NO: 1 (or from SEQ ID NOs:3 and 5, if constructing an N- or C-terminal deletion of TR11SV1 or TR11SV2, respectively). One of skill in the art will recognize that the procedures outlined in this example may also easily be used to generate TR11SV1 and TR11SV2 N- and C-terminal deletions in place of TR11 deletions. The 5' and 3' positions of the primers are determined based on the desired TR11 polynucleotide fragment. An initiation and stop codon are added to the 5' and 3' primers respectively, if necessary, to express the TRI 1 polypeptide fragment encoded by the polynucleotide fragment. Preferred TR11 polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the TR11 polynucleotide fragment in a desired vector may also be added to the 5' and 3' primer sequences. The TR11 polynucleotide fragment is amplified from genomic DNA or from the deposited cDNA clone using the appropriate PCR oligonucleotide primers and conditions discussed herein or known in the art. The TR11 polypeptide fragments encoded by the TR11 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the TR11 polypeptide fragment R-59 to P-162 is amplified and cloned as follows: A 5' primer is generated comprising a restriction enzyme site followed by an initiation codon in frame with the polynucleotide sequence encoding the N-terminal portion of the polypeptide fragment beginning with R-59. A complementary 3' primer is generated comprising a restriction enzyme site followed by a stop codon in frame with the polynucleotide sequence encoding C-terminal portion of the TR11 polypeptide fragment ending with P-162.

The amplified polynucleotide fragment and the expression vector are digested with restriction enzymes which recognize the sites in the primers. The digested polynucleotides are then ligated together. The TR11 polynucleotide fragment is inserted into the restricted expression vector, preferably in a manner which places the TR11 polypeptide fragment coding region downstream from the promoter. The ligation mixture is transformed into competent E. coli cells using standard procedures and as described in the Examples herein. Plasmid DNA is isolated from resistant colonies and the identity of the cloned DNA confirmed by restriction analysis, PCR and DNA sequencing.

Example 8: Protein Fusions of TR11, TR11SV1 or TR11SV2.

TR11, TR11SV1 or TR11SV2 polypeptides are preferably fused to other proteins. These fusion proteins can be used for a variety of applications. For example, fusion of TR11, TR11SV1 or TR11SV2 polypeptides to His-tag, HA-tag, protein A, IgG domains, and maltose binding protein facilitates purification. (See Example 1; see also EP A 394,827; Traunecker, et al., Nature 331:84–86 (1988).) Similarly, fusion to IgG-1, IgG-3, and albumin increases the half-life time in vivo. Nuclear localization signals fused to TR11, TR11SV1 or TR11SV2 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 1.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the Bam HI cloning site. Note that the 3' Bam HI site should be destroyed. Next, the vector containing the human Fc portion is re-restricted with Bam HI, linearizing the vector, and TR11, TR11SV1 or TR11SV2 polynucleotide is ligated into this Bam HI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

Example 9: Production of an Antibody.

(a) Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with polypeptide(s) of the invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line

```
GGGATCCGGAGCCCAAATCTTCTGACAAAACTCACACATGCCCACC            (SEQ ID NO:18)

GTGCCCAGCACCTGAATTCGAGGGTGCACCGTCAGTCTTCCTCTTCCCCCCAA

AACCCAAGGACACCCTCATGATCTCCCGGACTCCTGAGGTCACATGCGTGGTG

GTGGACGTAAGCCACGAAGACCCTGAGGTCAAGTTCAACTGGTACGTGGACG

GCGTGGAGGTGCATAATGCCAAGACAAAGCCGCGGGAGGAGCAGTACAACAG

CACGTACCGTGTGGTCAGCGTCCTCACCGTCCTGCACCAGGACTGGCTGAATG

GCAAGGAGTACAAGTGCAAGGTCTCCAACAAAGCCCTCCCAACCCCCATCGA

GAAAACCATCTCCAAAGCCAAAGGGCAGCCCCGAGAACCACAGGTGTACACC

CTGCCCCCATCCCGGGATGAGCTGACCAAGAACCAGGTCAGCCTGACCTGCCT

GGTCAAAGGCTTCTATCCAAGCGACATCGCCGTGGAGTGGGAGAGCAATGGG

CAGCCGGAGAACAACTACAAGACCACGCCTCCCGTGCTGGACTCCGACGGCT

CCTTCTTCCTCTACAGCAAGCTCACCGTGGACAAGAGCAGGTGGCAGCAGGGG

AACGTCTTCTCATGCTCCGTGATGCATGAGGCTCTGCACAACCACTACACGCA

GAAGAGCCTCTCCCTGTCTCCGGGTAAATGAGTGCGACGGCCGCGACTCTAGA

GGAT.
``` may be employed in accordance wine present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the polypeptide(s) of the invention.

Alternatively, additional antibodies capable of binding to polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by polypeptide(s) of the invention. Such antibodies comprise anti-idiotypic antibodies to the protein-specific antibody and are used to immunize an animal to induce formation of further protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

(b) Isolation Of Antibody Fragments Directed Against Polypeptide(s) From A Library Of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library.

A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library.

Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders.

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 10: Production of TR11, TR11SV1 or TR11SV2 Protein For High-Throughput Screening Assays.

The following protocol produces a supernatant containing the soluble or extracellular portion of TR11, TR11SV1 or TR11SV2 polypeptides, constructed in Examples 1 and 7, to be tested. This supernatant can then be used in the Screening Assays described in the following Examples.

First, dilute Poly-D-Lysine (644 587 Boehringer-Mannheim) stock solution (1 mg/ml in PBS)I 1:20 in PBS (w/o calcium or magnesium 17–516F Biowhittaker) for a working solution of 50 ug/ml. Add 200 ul of this solution to each well (24 well plates) and incubate at RT for 20 minutes. Be sure to distribute the solution over each well (note: a 12-channel pipettor may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at 2×10$^5$ cells/well in 0.5 ml DMEM (Dulbecco's Modified Eagle Medium)(with 4.5 G/L glucose and L-glutamine (12–604F Biowhittaker))/10% heat inactivated FBS(14–503F Biowhittaker)/1× Penstrep(17–602E Biowhittaker). Let the cells grow overnight.

The next day, mix together in a sterile solution basin: 300 ul Lipofectamine (18324-012 Gibco/BRL) and 5 ml Opti-mem I (31985070 Gibco/BRL)/96-well plate. With a small volume multi-channel pipettor, aliquot approximately 2 ug of an expression vector containing a polynucleotide insert, produced by the methods described in Examples 8–10, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a12-channel pipettor with tips on every other channel, adds the 200 ul of DNA/Lipofectamine/Optimem I complex to the odd wells first, then to the even wells, to each row on the 24-well plates. Incubate at 37 degree C. for 6 hours.

While cells are incubating, prepare appropriate media, either 1%BSA in DMEM with 1× pen/strep, or HGS CHO-5 media (116.6 mg/L of CaCl2 (anhyd); 0.00130 mg/L CuSO$_{4-5}$E[$_2$O; 0.050 mg/L of Fe(NO$_3$)$_{3-9}$H$_2$O; 0.417 mg/L of FeSO$_{4-7}$H$_2$O; 311.80 mg/L of KCl; 28.64 mg/L of MgCl$_2$; 48.84 mg/L of MgSO$_4$; 6995.50 mg/L of NaCl; 2400.0 mg/L of NaHCO$_3$; 62.50 mg/L of NaH$_2$PO$_4$-H$_2$O; 71.02 mg/L of Na$_2$HPO4; 0.4320 mg/L of ZnSO$_{4-7}$H$_2$O; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Llnolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Sitearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-H$_2$O; 6.65 mg/ml of L-Aspartic Acid; 29.56 mg/ml of L-Cystine-2HCL-H$_2$0; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Hlistidine-HCL-H$_2$0; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalanine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2H$_2$O; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin B$_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1× pen/strep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1% BSA for 45 hours or CHO-5 for 72 hours.

On day four, using a 300 ul multichannel pipettor, aliquot 600 ul in one 1 ml deep well plate and the remaining supernatant into a 2 ml deep well. The supernatants from each well can then be used in the assays described in the following Examples.

It is specifically understood that when activity is obtained in any of the assays described below using a supernatant, the activity originates from either the TR11, TR11SV1 or TR11SV2 polypeptide directly (e.g., as a soluble protein) or by TR11, TR11SV1 or TR11SV2 inducing expression of other proteins, which are then secreted into the supernatant. Thus, the invention further provides a method of identifying the protein in the supernatant characterized by an activity in a particular assay.

Example 11: Construction of GAS Reporter Construct.

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ I) NO:5)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation ancl differentiation of cells. For example, growth factors and cytokines are known to activate the Jaks-STATs pathway. (See Table below.) Thus, by using GAS elements linked to reporter molecules, activators of the Jaks-STATs pathway can be identified.

|  | JAKs | | | | | |
| --- | --- | --- | --- | --- | --- | --- |
| Ligand | tyk2 | Jak1 | Jak2 | Jak3 | STATS | GAS (elements) or ISRE |
| IFN family | | | | | | |
| IFN-a/B | + | + | − | − | 1, 2, 3 | ISRE |
| IFN-g |  | + | + | − | 1 | GAS (IRF1 > Lys6 > IFP) |
| Il-10 | + | ? | ? | − | 1, 3 | |
| gp130 family | | | | | | |
| IL-6 (Pleiotropic) | + | + | + | ? | 1, 3 | GAS (IRF1 > Lys6 > IFP) |
| Il-11 (Pleiotropic) | ? | + | ? | ? | 1, 3 | |
| OnM (Pleiotropic) | ? | + | + | ? | 1, 3 | |
| LIF (Pleiotropic) | ? | + | + | ? | 1, 3 | |
| CNTF (Pleiotropic) | −/+ | + | + | ? | 1, 3 | |
| G-CSF (Pleiotropic) | ? | + | ? | ? | 1, 3 | |
| IL-12 (Pleiotropic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6) (IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS (B − CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is: 5'-GCG CCT CGA GAT TTC CCC GAA ATC TAG ATT TCC CCG AAA TGA TTT CCC CGA AAT GAT TTC CCC GAA ATA TCT GCC ATC TCA ATT AG-3' (SEQ ID NO:19). The downstream primer is complementary to the SV40 promoter and is flanked with a Hind III site: 5'-GCG GCA AGC TTT TTG CAA AGC CTA GGC-3' (SEQ ID NO:20).

PCR amplification is performed using the SV40 promoter template present in the B-gal:promoter plasmid obtained from Clontech. The resulting PCR fragment is digested with Xhol/Hind III and subcloned into BLSK2-. (Stratagene.) Sequencing with forward and reverse primers confirms that the insert contains the following sequence:

5':<u>CTCGAG</u>ATTTCCCCGAAATCTAGATTTCCCCGAAATGATTTCCCC (SEQ ID NO:21)

GAAATGATTTCCCCGAAATATCTGCCATCTCAATTAGTCAGCAACCATAGTCC

CGCCCCTAACTCCGCCCATCCCGCCCCTAACTCCGCCCAGTTCCGCCCATTCTC

CGCCCCATGGCTGACTAATTTTTTTTATTTATGCAGAGGCCGAGGCCGCCTCGG

CCTCTGAGCTATTCCAGAAGTAGTGAGGAGGCTTTTTTGGAGGCCTAGGCTTT

TGCAAA<u>AAGCTT</u>:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in the following Examples.

Other constructs can be made using the above description and replacing GAS with a different promoter sequence. For example, construction of reporter molecules containing NFK-B and EGR promoter sequences are described in the following Examples. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, II-2/NFAT, or NF-KB/GAS). Similarly, other cell lines can be used to test reporter construct activity, such as HELA (epithelial), HUNEC (endothelial), Reh (B-cell), Saos-2 (osteoblast), HUVAC (aortic), or Cardiomyocyte.

Example 12: High-Throughput Screening Assay for T-cell Activity.

The following protocol is used to assess T-cell activity of TR11, TR11SV1 or TR11SV2 by determining whether TR11, TR11SV1 or TR11SV2 supernatant proliferates and/or differentiates T-cells. T-cell activity is assessed using the GAS/SEAP/Neo construct produced in previous Examples. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml geneticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37 degree C. for 6 hrs. After the incubation, add 10 ml of RPMI+15% serum.

The Jurkat:GAS-SEAP stable reporter lines are maintained in RPMI+10% serum, 1 mg/ml Geneticin, and 1% Pen-Strep. These cells are treated with supernatants containing TR11, TR11SV1 or TR11SV2 polypeptides or TR11, TR11SV1 or TR11SV2 induced polypeptides as produced by the protocol described in the previous Examples.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100, 000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells:H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using cellophane covers) and stored at -20 degree C until SEAP assays are performed according to the following Examples. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 13: High-Throughput Screening Assay Identifying Myeloid Activity.

The following protocol is used to assess myeloid activity of TR11, TR11SV1 or TR11SV2 by determining whether TR11, TR11SV1 or TR11SV2 proliferates and/or differentiates myeloid cells. Myeloid cell activity is assessed using the GAS/SEAP/Neo construct produced in the Examples. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 13, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4 \cdot 7H_2O$, 1 mM $MgCl_2$, and 675 uM $CaCl_2$. Incubate at 37 degree C. for 45 min.

Wash the cells with RPMI 1640 medium containing 10% FBS and then resuspend in 10 ml complete medium and incubate at 37 degree C. for 36 hr.

The GAS-SEAP[U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 12. Incubate at 37 degrees C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in the Examples.

Example 14: High-Throughput Screening Assay Identifying Neuronal Activity.

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by TR11, TR11SV1 or TR11SV2.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by TR11, TR11SV1 or TR11SV2 can be assessed.

The EGR/SEAP reporter construct can be assembled by the following protocol. The EGR-1 promoter sequence (–633 to +1)(Sakamoto K et al., Oncogene 6:867–871 (1991)) can be PCR amplified from human genomic DNA using the following primers:

(SEQ ID NO:22)
5'-GCG CTC GAG GGA TGA CAG CGA TAG AAC CCC GG-3'
and
(SEQ ID NO:23)
5'-GCG AAG CTT CGC GAC TCC CCG GAT CCG CCT C-3'.

Using the GAS:SEAP/Neo vector produced in Example 13, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08–115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 12. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 10, 37 degree C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to the Examples.

Example 15: High-Throughput Screening Assay for T-cell Activity.

NF-kappaB (Nuclear Factor-kappaB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-kappaB regulates the expression of genes involved in immune cell activation, control of apoptosis (NF-kappaB appears to shield cells from apoptosis), B and T-cell development, anti-viral and antimicrobial responses, and multiple stress responses.

In non-stimulated conditions, NF-kappaB is retained in the cytoplasm with I-kappaB (Inhibitor kappaB). However, upon stimulation, I-kappaB is phosphorylated and degraded, causing NF-kappaB to shuttle to the nucleus, thereby activating transcription of target genes. Target genes activated by NF-kappaB include IL-2, IL-6, GM-CSF, ICAM-1 and class 1 MHC.

Due to its central role and ability to respond to a range of stimuli, reporter constructs utilizing the NF-kappaB promoter element are used to screen the supernatants produced in Example 12. Activators or inhibitors of NF-kappaB would be useful in treating diseases. For example, inhibitors of NF-kappaB could be used to treat those diseases related to the acute or chronic activation of NF-kappaB, such as rheumatoid arthritis.

To construct a vector containing the NF-kappaB promoter element, a PCR based strategy is employed. The upstream primer contains four tandem copies of the NF-kappaB binding site (GGGGACTTTCCC) (SEQ ID NO:24), 18 bp of sequence complementary to the 5' end of the SV40 early promoter sequence, and is flanked with an XhoI site: 5'-GCG GCC TCG AGG GGA CTT TCC CGG GGA CTT TCC GGG GAC TTT CCG GGA CTT TCC ATC CTG CCA TCT CAA TTA G-3' (SEQ ID NO:25). The downstream primer is complementary to the 3' end of the SV40 promoter and is flanked with a Hind III site: 5'-GCG GCA AGC TTT TTG CAA AGC CTA GGC-3' (SEQ ID NO:26).

PCR amplification is performed using the SV40 promoter template present in the pbeta-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5':CTCGAGGGGACTTCCCGGGGACTTTCCGGGGACTTTCCGGGACTTTCCATC (SEQ ID NO:27)

TGCCATCTCAATTAGTCAGCAACCATAGTCCCGCCCCTAACTCCGCCCATCCC

GCCCCTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGAAGT

AGTGAGGAGGCTTTTTTGGAGGCCTAGGCTTTTGCAAAAAGCTT:3'.

Next, replace the SV40 minimal promoter element present in the pSEAP2-promoter plasmid (Clontech) with this NF-kappaB/SV40 fragment using XhoI and HindIII. However, this vector does not contain a neomycin resistance gene, and therefore, is not preferred for mammalian expression systems.

In order to generate stable mammalian cell lines, the NF-kappaB/SV40/SEAP cassette is removed from the above NF-kappaB/SEAP vector using restriction enzymes SalI and NotI, and inserted into a vector containing neomycin resistance. Particularly, the NF-kappaB/SV40/SEAP cassette was inserted into pGFP-1 (Clontech), replacing the GFP gene, after restricting pGFP-1 with SalI and NotI.

Once NF-kappaB/SV40/SEAP/Neo vector is created, stable Jurkat T-cells are created and maintained according to the protocol described in the Examples. Similarly, the method for assaying supernatants with these stable Jurkat T-cells is also described in the Examples. As a positive control, exogenous TNF alpha (0.1,1, 10 ng) is added to wells H9, H10, and H11, with a 5–10 fold activation typically observed.

Example 16: Assay for SEAP Activity.

As a reporter molecule for the assays described in the Examples, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| # of plates | Reaction Buffer Formulation: Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |

-continued

| # of plates | Reaction Buffer Formulation: Rxn buffer diluent (ml) | CSPD (ml) |
|---|---|---|
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |

-continued

Reaction Buffer Formulation:

| # of plates | Rxn buffer diluent (ml) | CSPD (ml) |
|---|---|---|
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 17: High-Throughput Screening Assay Identifying Changes in Small Molecule Concentration and Membrane Permeability.

Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000 -20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37 degree C in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with BBSS in a 50-ml conical tube. 4 ul of 1 mg/ml fluo-3 solution in 10% pluronic acid DMSO is added to each ml of cell suspension. The tube is then placed in a 37 degree C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either TR11, TR11SV1, or TR11SV2 or a molecule induced by TR11, TR11SV1, or TR11SV2, which has resulted in an increase in the intracellular $Ca^{++}$ concentration.

Example 18: High-Throughput Screening Assay Identifying Tyrosine Kinase Activity.

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, ick, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether TR11, TR11SV1 or TR11SV2 or a molecule induced by TR11, TR11SV1 or TR11SV2 is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford,Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 10, the medium was removed and 100 ml of extraction buffer ((20 mM HEPES pH 7.5, 0.15 M NaCl, 1% Triton X-100, 0.1% SDS, 2 mM Na3VO4, 2 mM Na4P207 and a cocktail of protease inhibitors (# 1836170) obtained from Boehringer Mannheim (Indianapolis, Ind.) is added to each well and the plate is shaken on a rotating shaker for 5 minutes at 4° C. The plate is then placed in a vacuum transfer manifold and the extract filtered through the 0.45 mrn membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 nM ATP/50 mM $MgC_2$), then 10 ul of 5× Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30 degree C. for 2 min. Initial the reaction by adding lOul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degree C. for 20 min. This allows the streptavidin coated 96 well plate to associate with the biotinylated peptide. Wash the MIP module with 300 ul/well of PBS four times. Next add 75 ul of anti-phospotyrosine antibody conjugated to horse radish peroxidase(anti-P-Tyr-POD(0.5 u/ml)) to each well and incubate at 37 degree C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 19: High-Throughput Screening Assay Identifying Phosphorylation Activity.

As a potential alternative and/or compliment to the assay of protein tyrosine kinase activity described in the Examples, an assay which detects activation (phosphorylation) of major intracellular signal transduction intermediates can also be used. For example, as described below one particular assay can detect tyrosine phosphorylation of the Erk-1 and Frk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSAIPBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 12 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by TR11, TR11SV1, or TR11SV2 or a molecule induced by TR11, TR11SV1, or TR11SV2.

Example 20: Method of Determining Alterations in the TR11, TR11SV1, or TR11SV2 Gene.

RNA isolated from entire families or individual patients presenting with a phenotype of interest (such as a disease) is be isolated. cDNA is then generated from these RNA samples using protocols known in the art. (See, Sambrook.) The cDNA is then used as a template for ]PCR, employing primers surrounding regions of interest in SEQ ID NO: 1, SEQ ID NO:3, or SEQ ID NO:5. Suggested PCR conditions consist of 35 cycles at 95 degree C. for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of TR11, TR11SV1 or TR11SV2 is also determined and genomic PCR products analyzed to confirm the results. PCR products harboring suspected mutations in TR11, TR11SV1 or TR11SV2 is then cloned and sequenced to validate the results of the direct sequencing.

PCR products of TR11, TR11SV1 or TR11SV2 are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in TR11, TR11SV1, or TR11SV2 not present in unaffected individuals.

Genomic rearrangements are also observed as a method of determining alterations in the TR11 gene. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the TR11 genomic locus.

Chromosomes are counterstained with 4,6-diarnino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of TR11, TR11SV1 or TR11SV2 (hybridized by the probe) are identified as insertions, deletions, and translocations. These TR11, TR11SV1, or TR11SV2 alterations are used as a diagnostic marker for an associated disease.

Example 21: Method of Detecting Abnormal Levels of TR11, TR11SV1, or TR11SV2 in a Biological Sample.

TR11, TR11SV1 or TR11SV2 polypeptides can be detected in a biological sample, and if an increased or decreased level of TR11, TR11SV1 or TR11SV2 is detected, this polypeptide is a marker for a particular phenotype. Methods of detection are numerous, and thus, it is understood that one skilled in the art can modify the following assay to fit their particular needs.

For example, antibody-sandwich ELISAs are used to detect TR11, TR11SV1 or TR11SV2 in a sample, preferably a biological sample. Wells of a microtiter plate are coated with specific antibodies to TR11, TR11SV1 or TR11SV2, at a final concentration of 0.2 to 10 ug/ml. The antibodies are either monoclonal or polyclonal and are produced by the method described in the Examples. The wells are blocked so that non-specific binding of TR11, TR11SV1 or TR11SV2 to the well is reduced.

The coated wells are then incubated for >2 hours at RT with a sample containing TR11, T11SV1 or TR11SV2. Preferably, serial dilutions of the sample should be used to validate results. The plates are then washed three times with deionized or distilled water to remove unbounded TR11, TR11SV1 or TR11SV2.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot TR11, TR11SV1 or TR11SV2 polypeptide concentration on the X-axis (log scale) and fluorescence or absorbance of the Y-axis (linear scale). Interpolate the concentration of the TR11, TR11SV1 or TR11SV2 in the sample using the standard curve.

Example 22: Fornulating a Polypeptide.

The TR11, TR11SV1 or TR11SV2 composition will be formulated and dosed in a fashion consistent with good medical practice, taking into account the clinical condition of the individual patient (especially the side effects of treatment with the TR11, TR11SV1 or TR11SV2 polypeptide alone), the site of delivery, the method of administration, the scheduling of administration, and other factors known to practitioners. The "effective amount" for purposes herein is thus determined by such considerations.

As a general proposition, the total pharmaceutically effective amount of TR11, TR11SV1 or TR11SV2 administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, TR11, TR11SV1 or TR11SV2 is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing TR11, TR11SV1 or TR11SV2 are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

TR11, TR11SV1, TR11SV2 compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988).

Sustained-release compositions also include liposomally entrapped compositions of the invention (see generally, Langer, *Science* 249 1527–1533 (1990); Treat et al., in *Liposomes in the Therapy of Infectious Disease and Cancer,* Lopez-Berestein and Fidler (eds.), Liss, N.Y., pp. 317–327 and 353–365 (1989)). Liposomes containing TR11, TR11SV1, TR11SV2 polypeptide my be prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TR11, TR11SV1, TR11SV2 polypeptide therapy.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, TR11, TR11SV1 or TR11SV2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting TR11, TR11SV1 or TR11SV2 unifonnly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactanLs such as polysorbates, poloxamers, or PEG.

TR11, TR11SV1 or TR11SV2 is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

TR11, TR11SV1 or TR11SV2 used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

TR11, TR11SV1 or TR11SV2 polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TR11, TR11SV 1 or TR11SV2 polypeptide solution, and the resulting mixture is lyophilized. The infusion solution is prepared by reconstituting the lyophilized TR11, TR11SV1 or TR11SV2 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, TR11, TR11SV1 or TR11SV2 may be employed in conjunction with other therapeutic compounds.

Example 23: Method of Treating Decreased Levels of TR11, TR11SV1 or TR11SV2.

The present invention relates to a method for treating an individual in need of a decreased level of TR11, TR11SV1 or TR11SV2 activity in the body comprising, administering to such an individual a composition comprising a therapeutically effective amount of TR11, TR11SV1 or TR11SV2 antagonist. Preferred antagonists for use in the present invention are TR11, TR11SV1 or TR11SV2-specific antibodies.

Moreover, it will be appreciated that conditions caused by a decrease in the standard or normal expression level of TR11, TR11SV1 or TR11SV2 in an individual can be treated by administering TR11, TR11SV1 or TR11SV2, preferably in the secreted form. Thus, the invention also provides a method of treatment of an individual in need of an increased level of TR11, TR11SV1 or TR11SV2 polypeptide comprising administering to such an individual a pharmaceutical composition comprising an amount of TR11, TR11SV1 or TR11SV2 to increase the activity level of TR11, TR11SV1 or TR11SV2 in such an individual.

For example, a patient with decreased levels of TR11, TR11SV1 or TR11SV2 polypeptide receives a daily dose 0.1–100 ug/kg of the polypeptide for six consecutive days. Preferably, the polypeptide is in the secreted form. The exact details of the dosing scheme, based on administration and formulation, are provided in Example 22.

Example 24: Method of Treating Increased Levels of TR11, TR11SV1 or TR11SV2.

The present invention also relates to a method for treating an individual in need of an increased level of TR11, TR11SV1 or TR11SV2 activity in the body comprising administering to such an individual a composition comprising a therapeutically effective amount of TR11, TR11SV1 or TR11SV2 or an agonist thereof.

Antisense technology is used to inhibit production of TR11, TR11SV1 or TR11SV2. This technology is one example of a method of decreasing levels of TR11, TR11SV1 or TR11SV2 polypeptide, preferably a secreted form, due to a variety of etiologies, such as cancer.

For example, a patient diagnosed with abnormally increased levels of TR11, TR11SV1 or TR11SV2 is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 22.

Example 25: Method of Treatment Using Gene Therapy-Ex Vivo.

One method of gene therapy transplants fibroblasts, which are capable of expressing TR11, TR11SV1 or TR11SV2 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and Hindus and subsequently treated with calf intestinal phosphatase. The linear vector is fractionated on agarose gel and purified, using glass beads.

The cDNA encoding TR11, TR11SV1 or TR11SV2 can be amplified using PCR primers which correspond to the 5' and 3' end sequences respectively as set forth in the Examples. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted TR11, TR11SV1 or TR11SV2.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TR11, TR11SV1 or TR11SV2 gene is then added to the media and the packaging cells transduced with the vector. The packaging cells now produce infectious viral particles containing the TR11, TR11SV1 or TR11SV2 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TR11, TR11SV1 or TR11SV2 protein is produced.

The engineered fibroblasts are then transplanted onto the host, either alone or after having been grown to confluence on cytodex 3 microcarrier beads.

Example 26: Method of Treatment Using Gene Therapy-In Vivo.

Another aspect of the present invention is using in vivo gene therapy methods to treat disorders, diseases and conditions. The gene therapy method relates to the introduction of naked nucleic acid (DNA, RNA, and antisense DNA or RNA) TR11, TR11SV1 or TR11SV2 sequences into an animal to increase or decrease the expression of the TR11, TR11SV1 or TR11SV2 polypeptide. The TR11, TR11SV1 or TR11SV2 polynucleotide may be operatively linked to a promoter or any other genetic elements necessary for the expression of the TR11, TR11SV1 or TR11SV2 polypeptide by the target tissue. Such gene therapy and delivery techniques and methods are known in the art, see, for example, WO90/11092, WO98/11779; U.S. Pat. NO. 5693622, 5705151, 5580859; Tabata H. et al. (1997) Cardiovasc. Res. 35(3):470–479, Chao J et al. (1997) Pharmacol. Res. 35(6): 517–522, Wolff J. A. (1997) Neuromuscul. Disord. 7(5): 314–318, Schwartz B. et al. (1996) Gene Ther. 3(5): 405–411, Tsurumi Y. et al. (1996) Circulation 94(12): 3281–3290 (incorporated herein by reference).

The TR11, TR11SV1 or TR11SV2 polynucleotide constructs may be delivered by any method that delivers injectable materials to the cells of an animal, such as, injection into the interstitial space of tissues (heart, muscle, skin, lung, liver, intestine and the like). The TR11, TR11SV1 or TR11SV2 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TR11, TR11SV1 or TR11SV2 polynucleotides may also be delivered in liposome formulations (such as those taught in Felgner P. L. et al. (1995) Ann. NY Acad. Sci. 772:126–139 and Abdallah B. et al. (1995) Biol. Cell 85(1): 1–7) which can be prepared by methods well known to those skilled in the art.

The TR11, TR11SV1 or TR11SV2 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TR11, TR11SV1 or TR11SV2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, miucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TR11, TR11SV1 or TR11SV2 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TR11, TR11SV1 or TR11SV2 polynucleotide constructs can be delivered to arteries during angioplasty by the catheter used in the procedure.

The dose response effects of injected TR11, TR11SV1 or TR11SV2 polynucleotide in muscle in vivo is determined as follows. Suitable TR11, TR11SV1 or TR11SV2 template DNA for production of mRNA coding for TR11, TR11SV1 or TR11SV2 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TR11, TR11SV1 or TR11SV2 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 urn cross-section of the individual quadriceps muscles is histochemically stained for TR11, TR11SV1 or TR11SV2 protein expression. A time course for TR11, TR11SV1 or TR11SV2 protein expression may be done in a similar fashion except that quadriceps from different mice are harvested at different times. Persistence of TR11, TR11SV1 or TR11SV2 DNA in muscle following injection may be determined by Southern blot analysis after preparing total cellular DNA and H[RT supernatants from injected and control mice. The results of the above experimentation in mice can be use to extrapolate proper dosages and other treatment parameters in humans and other animals using TR11, TR11SV1 or TR11SV2 naked DNA.

Example 27: Identification of A Novel Activation-Inducible Protein of the TNF Receptor Superfamily and Its Ligand.

Background:

Members of the TNFR superfamily share similar multiple cysteine-rich pseudorepeats of the extracellular domain, each containing 30–45 amino acids with six cysteines (Smith, C. A., et al, Cell 76:959–962 (1994)). Except for the death domain-containing family which includes TNFR1 (Schall, T. J., et al, Cell 61:361–370 (1990)), Fas (Trauth, B. C., et al, Science 245:301–305 (1989), Yonehara, S., et al, J. Exp. Med. 169:1747–1756 (1989), and Oehm, A., et al, J. Biol. Chem. 267:10709–10715 (1992)), DR3 (Chinnaiyan, A. M., et al, Science 274:990–992 (1996), Kitson, J., et al, Nature 384:372–375 (1996), Bodmer, J.-L., et al, Immunity 6:79–88 (1997), and Screaton, G. R., et al, Proc. Natl. Acad. Sci. USA 94:4615–4619 (1997)), DR4 (Wiley, S. R., et al, Immunity 3:673–682 (1995), Pitti, R. M., et al, J. Biol. Chem. 271:12687–2690 (1996), and Pan, G., et al, Science 276:111–113 (1997)), DR5 (Walczak, H., et al, EMBO J. 16:5386–5397 (1997), MacFarlane, M., et al, J. Biol. Chem. 272:25417–25420 (1997), Schneider, P., et al, Immunity 7:831–836 (1997), Chaudhary, P. M., et al, Immunity 7:821–830 (1997), and Sheridan, J. P., et al, Science 277:818–821(1997)), and decoy TRAIL receptors (Marsters, S. A., et al, Cur. Biol. 7:1003–1006 (1997), Pan, G., et al, Science 277:815–815 (1997), Degli-Esposti, M. A., et al, J. Exp. Med. 186:1165–1170 (1997), and Degli-Esposti, M. A., et al, Immunity 7:813–820 (1997)), no remarkable similarity is found within the intracellular domain of these molecules. However, there is a striking homology in the cytoplasmic domains of murine and human 4-1BB, CD27, and murine GITR within TNFR superfamily members (Kwon, B. S., et al, Proc. Natl. Acad. Sci. USA 86:1963–1967 (1989), Camerimi, D., et al, J. Immunol. 147:3165–3169 (1991), and Nocentini, G., et al, Proc. Natl. Acad. Sci. USA 94:6216–6221 (1997)). Acidic amino acids are especially highly conserved in the cytoplasmic domain of this subfamily. Like other TNFR superfamily members (Smith, C. A., et al, Cell 76:959–962 (1994)), this subfamily is implicated in diverse biological functions. First of all, 4–1BB and CD27 molecules provide strong costimulatory signals for T cell proliferation when ligated with their respective ligands or with agonistic antibodies (Smith, C. A., et al, Cell 76:959–962 (1994), and Pollok, K. E., et a], J. Immunol.150:771–781 (1993)). In addition to functioning as an accessory molecule, CD27 induces apoptosis, which is mediated by a death domain-containing molecule called Siva (Prasad, K. V. S., et al, Proc. Natl. Acad. Sci. USA 94:6346–6351 (1997)). Recently identified murine GITR is shown to inhibit TCR-induced apoptosis (Nocentini, G., et al, *Proc. Natl. Acad. Sci. USA* 94:6216–6221 (1997)).

Although the immunological functions of subfamily members have been relatively well defined, insights into their signal transduction pathway have only recently been revealed (Arch, R. H., et al, Mol. Cell. Biol. 18:558–565 (1998), Jang, I. K., et al, Biochem. Biophys. Res. Corn. 242:613–620 (1998), Saoulli, K., et al, J. Exp. Med. 187:1849–1862 (1998), and Akiba, H., et al, J. Biol. Chem. 273:13353–13358 (1998)). Two groups (Arch, R. H., et al, Mol. Cell. Biol. 18:558–565 (1998), and Jang, I. K., et al, Biochem. Biophys. Res. Com. 242:613–620 (1998)) have provided data indicating that association of 4-1 BB with TRAF2 molecules initiates a signal cascade leading to activation of NF-kappaB. In the CD27 signaling pathway, both TRAF2 and TRAF5 mediate NF-kappaB and SAPK/JNK (stress-activated protein kinase/c-Jun N-terminal kinase) activation and NIK (NF-kappaB-inducing kinase) is a common downstream kinase of TRAF2 and TRAF5 (Akiba, H., et al, J. Biol. Chem. 273:13353–13358 (1998)).

Because the number of TNFR members is rapidly expanding, we expected that even more numbers of the superfamily would exist. By a PCR-based strategy with murine GITR sequence and searching an EST (expressed sequence tag) database, we identified a new member of the TNFR and its ligand. Here we give an initial characterization of the receptor and its ligand.

Experimental Procedures:

cDNA cloning-A database containing more than two million ESTs obtained from over 750 different cDNA libraries was generated by Human Genome Sciences, Inc., using high throughput automated DNA sequence analysis of randomly selected human cDNA clones. A specific homology and motif search using the known amino acid sequence and motif of TNFR members against this database revealed several ESTs with a translated sequence 35–55 % homologous to that of the TNFR family. Several clones were identified from cDNA libraries of PHA-activated T cells, T helper cells, leukocytes, a healing abdomen wound, primary dendritic cells and adipose tissue. A full-length TR-11 cDNA clone encoding an intact N-terminal signal peptide was obtained from a human activated T-cell library and selected for further investigation. The complete cDNA sequence of both strands of this clone was determined, and its homology to TNFR members was confirmed. The same gene was also identified by a PCR-based strategy with murine GITR sequence. Similarly, endokine-alpha (TNF ligand 6) (See, e.g., Int. Application Publication Number WO 98/07880, published Feb. 26, 1998) was identified through a systematic comparison of sequence homology with TNF ligand family members. Partial endokine-alpha sequences which were 25% homologous to that of TNF ligand family members were identified from endothelial, HUVEC (human umbilical vein endothelial cell), brain, and fetal liver cDNA libraries. A full-length cDNA clone was obtained from a human brain cDNA library.

Expression vectors-Full-length and HA (hemagglutinin A epitope)-tagged TR-11 encoding the putative entire TR-11 enprotein (amino acids 26–234) were amplified by PCR using sense ((5'-CTA GCT AGC TAG VVV AGC GCC CCA CCG GGG GTC CC-3', and 5'-CTA GCT AGC TAG CTA TCC ATA TGA TGT TCC AGA TTA TGC TCA GCG CCC CAC CGG GGG TCC C-3', respectively) and anti-sense (5'-AAG GAA AAA AGC GGG CCG CTC ACA CCC ACA GGT CTC CCA G-3') primers, cut with Nhe I/Not I, and fused in frame downstream of a CD5 leader sequence (Jang, I. K., et al, Biochem. Biophys. Res. Corn. 242:613–620 (1998)) into the pcDNA3.1 (pcDNA3.1/CD5L-TR-11) and pcDNA3 (pcDNA3/CD5L-TR-11), respectively. Full-length endokine-alpha was amplified by PCR (sense, 5'-AGA CCC AAG CTT TTG AAA ATG ATA TGA GAC GC-3'; anti-sense, 5'-AGA CGG GAT CCT CCT CCT ATA GTA AGA AGG C-3'), cut with Hind III/BamH I, and inserted into pcDNA3.1 (pcDNA3.1/ endokine-a) and pCEP4 (Invitrogen, Carlsbad, CA; pCEP4/ endokine-a). pRK5-based expression vectors encoding Flag-tagged full-length TRAF1, TRAF2, TRAF3, TRAF5, TRAF6, NIK, dominant negative TRAF2 (dnTRAF2), or dnNIK have been described (Jang, I. K., et al, Biochem. Biophys. Res. Corn. 242:613–620 (1998), Rothe, M., et al, Science 269:1421–1427 (1995), Hu, H. M., et al, J. Biol. Chem. 269:30069–30072 (1994), Nakano, H., et al, J. Biol. Chem. 271:14661–14664 (1996), Takeuchi, M., et al, J. Biol. Chem. 271:19935-.19942 (1996), Cao, Z., et al, Nature 383:443–446 (1996), and Song, H. Y., et al, Proc. Natl. Acad. Sci. USA 94:9792–9796 (1997)). The NF-kappaB-dependent E-selectin-luciferase reporter gene (pELAM-Luc) and pRSV-beta-galactosidase (pRSV-beta-gal) plasmids were also described elsewhere (Rothe, M., et al, Science 269:1421–1427 (1995), and Schindler, U., et al, Mol. Cell. Biol. 14:5820–9796 (1994)).

Northern blot and RT (reverse transcriptase)-PCR analysis-For Northern blot analysis, cDNA probes were labeled with $^{32}$P using the Rediprime DNA labeling system (Amersham Life Science, Arlington Height, Ill.), according to the manufacturer's instructions. Unincorporated nucleotide was removed from the labeled probe using CHROMA SPIN-100 (Clontech, Palo Alto, Calif.). Two human multiple tissue poly (A) RNA blots containing approximately 2 micrograms of poly (A) RNA per lane from various human tissues were purchased from Clontech. In addition, two cell line blots containing 20 mg total RNA from different cell lines were used. Northern blotting was performed with the Expressed Hybridization Solution (Clontech) according to the manufacturer's manual. For RT-PCR analysis, total RNA was isolated from human PBMC after stimulation with dexamethasone, PMA/ionomycin, or anti-CD3/CD28 mAbs, and from unstimulated or LPS-stimulated HUVEC cells. RT-PCR was performed under standard conditions.

Interaction of TR-11 with TRAFs-pcDNA3/CD5L-TR-11-HA plasmid (5 micrograms/10 cm-plate) was co-transfected into HEK293 EBNA cells ($2 \times 10^6$ cells/plate) by the standard calcium phosphate precipitation method with pRK/TRAF1, 2, 3, 5, or 6-Flag vector (5 micrograms/plate). Twenty four-hours after transfection, cells were lysed with 1 ml of lysis buffer (50 mM BEPES [pH7.4], 250 mM NaCl, 0.1 % Nonidet P-40, 5 mM EDTA, 10% glycerol, and protease inhibitors). For immunoprecipitation, lysates were incubated with anti-Flag M2 (Eastman Kodak, Rochester, N.Y.) or control murine IgGI mAb at 4° C for 1 h, followed by incubation with 20 microliters of a 1:1 slurry of protein G-Sepharose (PharMingen, San Diego, Calif.) for another hour. Precipitates were thoroughly washed with lysis buffer, then fractionated on a 10% SDS-polyaciylamide gel before transfer to PVDF membrane (Millipore, Bedfore, Mass.). Western blot analysis was performed with anti-HA mAb coupled with horseradish peroxidase (Boehringer Mannheim, Indianapolis, Ind.) and visualized using the enhanced chemiluminescenc e Western blotting detection system (Amersham).

Analysis of NF-kappaB by reporter assay-Approximately $0.5 \times 10^6$ HEK293 EBNA cells/well were seeded on 6-well plates. After 24 h, cells were transfected by the standard calcium phosphate precipitation method using various combinations of pcDNA3.1/CD5L-TR-11 plus pRK5 plasmids encoding TRAFs, dnTRAF2, NIK, or dnNIK. The total amount of plasmid was adjusted to 2.0 micrograms by adding empty vector. Twenty-four hours after transfection, cells were lysed in 200 microliters reporter lysis buffer (Promega, Madison, Wis.). Luciferase activity was measured using 20 microliters cell extract. 5 microliters cell extract was used to assay beta-galactosidase activity as an internal control, and luminescence values were normalized by individual beta-galactosidase activity.

Recombinant protein production and punfication-TR-11-Fc fusion protein was used for ligand screening and cell-binding experiments. A fragment encoding the predicted extracellular domain of TR-11 (amino acids 26–139) was amplified using a sense primer flanked by an Nhe I site (5'-AGA CCC AAG CTT GTG GGC TCT TGA AAC CCG GCA TG-3') and an antisense primer flanked by a Bgl II site (5'-GAA AGA TCT GGG CTC TGC CGG CGG GGA CCC TGG GAC-3'). The amplified fragment was cut with Nhe I/Bgl II and cloned into mammalian vector pCEP4, in frame with CD5L at the 5' end and with the Fc portion of human IgG1 at the 3' end (pCEP4/CD5L-TR-11-Fc). pCEP4/CD5L-TR-11-Fc was transfected into HEK293 EBNA cells. TR-11-Fc fusion protein was purified from pCEP4/CD5L-TR-11-Fc-transfected HEK293 EBNA cell supernatants using protein G column. To generate a Flag-tagged soluble form of endokine-alpha protein (amino acids 39–169), the flag-tagged endokine-alpha expression vector (pCEP4/CD5L-endokine-a-Flag) was constructed by PCR amplification of endokine-alpha coding sequences using sense (5'-CTA GCT AGC CCA GCG CCC CGA CTA CAA GGA CGA CGA TGA CAA GGA GAC TGC TAA GGA GCC C-3') and antisense (5'-CCG CTC GAG CTA TAG TAA GAA GGC TCC-3') primers, digesting the product with Nhe IXho I and cloning into pCEP4, in frame with the CD5L sequence. The construct was expressed in HEK293 EBNA cells. Transfected cell supernatants containing secreted endokine-alpha -Flag were harvested and used for binding assays. For some experiments, endokine-alpha-Flag protein was purified from harvested supernatants, using anti-Flag gel (Sigma, St. Louis. Mo.) according to the manufacturer's instructions.

Binding assay-Protein binding assays were done essentially as described (Pan, G., et al, Science 276:111–113 (1997)). For cell-binding assays, HEK293 EBNA cells were transfected using pcDNA3.1/CD5L-TR-11 or pcDNA3.1, as described above. Forty-eight hours after transfection, cells were harvested and incubated consecutively with endokine-alpha-Flag-containing supernatant, anti-Flag antibody, and FITC-conjugated anti-mouse IgG antibody (Southern Biotechnology, Birmingham, Ala.). Flow cytometry analysis was performed using the Becton Dickinson FACScan (San Jose, Calif.). Jurkat T cells were stably transfected by electroporation using linearized pcDNA3.1/CD5L-TR-11, and selected in the presence of Zeocin (Invitrogen). A binding assay for this cell line was performed as described above. To test the ability of TR-11-Fc fusion protein to bind membrane-bound endokine-a, pCEP4/ endokine-alpha was stably transfected into HEK293 EBNA cells. After selection in the presence of hygromycin, endokine-a-expressing cells were harvested and incubated with TR-11-Fc protein, followed by FITC-conjugated anti-human IgGI antibody (Southern Biotechnology). The Becton Dickinson FACScan was used for flow cytometry analysis.

Results and Discussion

TR-11 was identified by searching an EST database and by a PCR-based strategy with murine GITR sequence. A full-length cDNA of a clone from a human activated T-cell cDNA library, which is tentatively named TR-11 (for activation-inducible TNFR family member), encodes a 234 amino acid type I transmembrane protein with a calculated MW of 25 kDa. The receptor has a signal peptide (the first 25 amino acids) and a single transmembrane region (amino acids 140–158). When compared with the extracellular domain of other TNFR family members, TR-11 displays three cysteine-rich pseudorepeats corresponding to the second, third, and fourth TNFR motif, respectively. The first cysteine pseudorepeat contains eight cysteine residues and lacks C4. Therefore, it is unlikely that the canonical pattern of C1-C2, C3-C5, and C4-C6 disulfide bridges exist in this motif. The second pseudorepeat shows some features of the third TNFR motif, but it is atypical in that C5 is not present even though it contains 7 cysteine residues. The third pseudorepeat shows extensive homologies with the fourth pseudorepeat of 4-1BB. The cytoplasmic domain contains acidic amino acids which are highly conserved in the cytoplasmic domains of 4-1BB, CD27, and GITR. Overall, TR-11 exhibits a high homology (55 % identity) to murine GITR, but there is a mismatch in the first cysteine-rich pseudorepeat between GITR and TR-11, because the first pseudorepeat of GITR corresponds to the first TNFR cysteine-rich motif (Nocentini, G., et al, Proc. Natl. Acad. Sci. USA 94:6216–6221 (1997)).

We investigated expression of TR-11 mRNA in multiple human tissues by Northern blot hybridization. 1.25-kb mRNA was detected in lymph node, PBL, and, weakly, in spleen. We also tested a variety of tumor cell lines for expression of TR-11 mRNA. 1.25-kb message was detected only in the colorectal adenocarcinoma cell line, SW480, among the cell lines tested. The expression of virtually all members of the TNFR superfamily is enhanced by antigen stimulation/lymphocyte activation (Smith, C. A., et al, Cell 76:959–962 (1994)). Consistent with this idea, TR-11 expression was upregulated in PBMC after stimulation. No TR-11 message was detectable in unstimulated PBMC when we used a sensitive RT-PCR method. TR-11 expression was clearly induced within 24 h by typical PBMC stimulation such as treatment with PMA plus ionomycin or soluble anti-CD3 plus anti-CD28 mAbs. FACS analysis for TR-11 expression, however, showed that a small population of activated PBMC expressed TR-11 on the cell surface at 48 h after stimulation, suggesting that a prolonged period of stimulation is required for maximum expression of TR-11 (BK, unpublished data). Expression of TR-11 was not induced by treatment with dexamethasone. This property was different from that of GITR (Nocentini, G., et al, Proc. Natl. Acad. Sci. USA 94:6216–6221 (1997)).

Recently it has been shown that 4-1BB molecules associate with TRAF1, TRAF2, and TRAF3 (Arch, R. H., et al, Mol. Cell. Biol. 18:558–565 (1998), Jang, I. K., et al, Biochem. Biophys. Res. Com. 242:613–620 (1998), and Saoulli, K., et al, J. Exp. Med. 187:1849–1862 (1998)). Because TR-11's cytoplasmic domain is similar to that of 4–1BB, we tested its ability to co-precipitate five of the six known TRAFs that were overexpressed in HEK293 EBNA cells. We observed an interaction of TR-11 with TRAF1, TRAF2, and TRAF3 but not with TRAF5 and TRAF6. The association of TR-11 with TRAF2 suggested that, like other members of the TNFR superfamily (Arch, R. H., et al, Mol. Cell. Biol. 18:558–565 (1998), Jang, I. K., et al, Biochem. Biophys. Res. Com. 242:613–620 (1998), Akiba, H., et al, J. Biol. Chem. 273:13353–13358 (1998), Rothe, M., et al, Science 269:1421–1427 (1995), Cheng, G., et al, Science 267:1494–1498 (1995), Duckett, C. S., et al, Mol Cell. Biol. 17:1535–1542 (1997), and VanArsdale, T. L., et al, Proc. Nati. Acad. Sci. USA 94:2460–2465 (1996)), TR-11 might mediate NF-kappaB activation through TRAF2. To test this possibility, we used an NF-kappaB reporter system in HEK293 EBNA cells (Rothe, M., et al, Science 269:1421–1427 (1995)). Co-transfection with the TR-11 expression vector typically induced greater than 3-fold higher luciferase activity when compared with the vector transfection control. When co-expressed with TRAF2, TR-11 induced greater luciferase activity than did TRAF2 alone. More importantly, overexpression of dominant-negative TRAF2, which lacked the RING and zinc finger motifs (Rothe, M., et al, Science 269:1421–1427 (1995)), abrogated the luciferase activity induced by TR-11. This indicates that TRAF2 is an important mediator of NF-kappaB activation for TR-11. A similar observation was made when we blocked the activity of NIK, which was thought to lie downstream of TRAF2 in the NF-kappaB signaling pathway, by overexpression of the dominant-negative NIK (Song, H. Y., et al, Proc. Natl. Acad. Sci. USA 94:9792–9796 (1997)), which lacked the two lysine residues of catalytic domain. Taken together, these data indicate that TR-11 mediates NF-kappaB activation through the TRA21/NIK pathway. Since TRAF1 and TRAF3 were found to associate with TR-11 in HEK293 EBNA cells, we examined the effects of TRAF1 and TRAF3 on NF-kappaB activation induced by TR-11. The introduction of TRAF3 nearly abolished the luciferase activity induced by TR-11 overexpression. To a lesser extent, TRAF1 overexpression diminished TR-11-induced NF-kappaB activation. These data suggest that TRAF1 and especially TRAF3 downregulate TR-11-induced NF-kappaB activation.

To identify TR-11L, we screened a panel of Flag-tagged candidate TNF ligand proteins for binding to TR-11-Fc fusion protein by immunoprecipitation. TR-11-Fc selectively bound endokine-a-Flag among Flag-tagged TNF ligand proteins tested. In our experimental conditions, 4-1BB and TR2 (HVEM) bound their cognate ligands, 4-1BBL and LIGHT (Mauri, D. N., et al, *Immunity* 8:21–30 (1998)), respectively. Furthermore, our data clearly showed that endokine-a-Flag protein bound TR-11 transiently expressed on the cell surface of HEK293 EBNA cells and TR-11 constitutively expressed on the cell surface of Jurkat cell. Since endokine-alpha is a transmembrane protein (see below), we used flow cytometry to determine whether TR-11-Fc fusion protein was able to bind HEK293 EBNA cells that were stably transfected with full length endokine-a. We found that TR-11-Fc protein was capable of binding endokine-alpha expressed on HEK293 EBNA cells. Next, we tested whether interactions between TR-11 and endokine-alpha would result in NF-KB activation. In an NF-kappaB reporter assay, ligand-dependent NF-kappaB activation was demonstrated by cotransfecting transmembrane endokine-alpha with TR-11 or transfecting endokine-a-expressing HEK293 EBNA cells. In addition, when TR-11 was transiently transfected into HEK293 EBNA cells which constitutively secreted soluble endokine-alpha protein, NF-kappaB activation markedly increased as compared to empty vector-transfected HEK293 EBNA cells. Similarly, higher NF-kappaB activation was induced by treating with soluble endokine-alpha protein HEK293 cells which were transiently transfected with TR-11. This indicates that endokine-alpha is able to trigger TR-11-specific activation of NF-kappaB. It appears that higher induction of NF-kappaB by endokine-alpha is correlated with a stronger association of TR-11 with TRAF2 in HEK293 EBNA cells, since stronger association of TR-11 with TRAF2 was observed in cells which were cotransfected with endokine-alpha than in cells which were transfected with TR-11 alone.

Endokine-alpha was one of the TNF ligand proteins initially identified by an EST database search. Hydrophilicity analysis of a full-length endokine-alpha clone from a brain cDNA library predicts a single hydrophobic transmembrane domain and the absence of a signal sequence. Endokine-alpha contains two potential glycosylation sites in the C-terminal region. These features suggest that endokine-alpha is a type II membrane protein with the C-terminal region extracellular. Northern blot analysis of human tissue RNAs revealed expression of a single 2.4-kb endokine-alpha mRNA in pancreas. Various human cell lines and PBMC were also examined for endokine-alpha expression. No message was detectable in either unstimulated or stimulated T-cell lines (CEM-6 and Jurkat), B-cell lines (Priess and Fiev), promyelocytic cell line (HL-60), monocytic cell line (TBP-1), and PBMC by RT-PCR. In contrast, HUVEC cells constitutively expressed endokine-alpha and its expression was upregulated after stimulation with LPS. Therefore, it is speculated that TR-11 and its ligand are important for interactions between activated T lymphocytes and blood vessels.

TR-11 has 55% identity with murine GITR at the amino acid level. The high sequence conservation between human and mouse provides evidence that TR-11 is the human homologue of murine GITR. At this point, however, the possibility remains that these two receptors may serve distinct functions from one another, based on the following facts: 1) There is a mismatch in the first cysteine-rich pseudorepeat between GITR and TR-11; 2) in contrast to GITR, TR-11 is not inducible by dexamethasone.

In summary, we have identified a novel protein of the TNFR superfamily, TR-11, which activates NF-kappaB through a TRAF2-mediated mechanism. Expression of TR-11 is activation-inducible. The ligand for TR-11 is a member of the TNF ligand family and is constitutively expressed in an endothelial cell line. This indicates that TR-11 and its ligand may be involved in activated T-cell trafficking.

Example 28: Assays to detect stimulation or inhibition of B cell proliferation and differentiation.

Background:

Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL5, IL6, IL-7, IL10, IL-13, IL14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

The relative in vitro activity of TR11, TR11SV1, and/or TR11SV2 polypeptides of the invention may be assayed as follows. Purified TR11, TR11SV1, and/or TR11SV2 protein, or truncated forms thereof, is assessed for its ability to induce activation, proliferation, differentiation or inhibition and/or death in B-cell populations and their precursors. The activity of TR11, TR11SV1, and/or TR11SV2 protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220). Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (luCi/well) with 3H-thymidine (6.7 Ci/mM) beginning 72 h post factor addition. The positive and negative controls are IL2 and medium respectively.

Alternatively, the relative in vivo activity of TR11, TR11SV1, and/or TR11SV2 polypeptides of the invention may be assayed as follows. BALB/c mice are injected (i.p.) twice per day with buffer only, or 2 mg/Kg of TR11, TR11SV1, and/or TR11SV2 protein, or truncated forms thereof. Mice receive this treatment for 4 consecutive days, at which time they are sacrificed and various tissues and serum collected for analyses. Comparison of H&E sections from normal and TR11, TR11SV1, and/or TR11SV2 protein-treated spleens identify the results of the activity of TR11, TR11SV1, and/or TR11SV2 protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from TR11, TR11SV1, and/or TR11SV2 protein--treated mice is used to indicate whether TR11, TR11SV1, and/or TR11SV2 protein specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and TR11, TR11SV1, and/or TR11SV2 protein-treated mice.

The studies described in this example test the activity in TR11, TR11SV1, and/or TR11SV2 protein. However, one skilled in the art could easily modify the exemplified studies to test the activity of TR11, TR11SV1, and/or TR11SV2 polynucleotides (e.g., gene therapy), agonists, and/or antagonists of TR11, TR11SV1, and/or TR11SV2.

Example 29: Isolation of antibody fragments directed against polypeptides of the present invention from a library of scFvs.

Naturally occurring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the library

A library of scFvs is constructed from the RNA of human PBLs as described in WO92/01047. To rescue phage displaying antibody fragments, approximately $10^9$ E. coli harboring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2×10^8$ TU of delta gene 3 helper phage (M13 delta gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (EEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately 1013 TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with ]?BS for rounds 3 and 4.

Characterization of binders

Eluted phage from the 3rd and 4th rounds of selection are used to infect E. coli HB 2151 and soluble scFv is produced (Marks, et aL, 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 30: Gene Therapy Using Endogenous TR11 Gene

Another method of gene therapy according to the present invention involves operably associating the endogenous TR11 sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TR11, flanking the promoter. The targeting sequence will be sufficiently near the 5' end of TR11 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TR11 sequence. This results in the expression of TR11 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the TR11 locus, plasmid pUC18 (MBI Fermentas, Amherst, N.Y.) is digested with HindIII. The CMV promoter is amplified by PCR with an XbaI site on the 5' end and a BamHI site on the 3'end. Two TR11 non-coding sequences are amplified via PCR: one TR11 non-coding sequence (TR11 fragment 1) is amplified with a Hindel site at the 5' end and an Xba site at the 3'end; the other TR11 non-coding sequence (TR11 fragment 2) is amplified with a BamHI site at the 5'end and a HindIII site at the 3'end. The CMV promoter and TR11 fragments are digested with the appropriate enzymes (CMV promoter-XbaI and BamHI; TR11 fragment 1-XbaI; TR11 fragment 2-BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately 1.5.×106 cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 31: TR11Z-Fc inhibits B cell proliferation in vitro in a co-stimulatory assay A TR11-Fc polypeptide was prepared that consists of a soluble form of TR11 (corresponding to amino acids −25 to 139 of SEQ ID NO:2) linked to the Fc portion of a human IgG1 immunoglobulin molecule. The ability of this protein to alter the proliferative response of human B cells was assessed in a standard co-stimulatory assay. Briefly, human tonsillar B cells were purified by magnetic bead (MACS) depletion of CD3-positive cells. The resulting cell population was routinely greater than 95% B cells as assessed by expression of CD19 and CD20 staining. Various dilutions of rHu Neutrokine-alpha (International Application Publication No. WO 98/18921) or the control protein rHuIL2 were placed into individual wells of a 96-well plate to which was added $10^5$ B cells suspended in culture medium (RPMI 1640 containing 10% FBS, $5×10^{-5}$M 2ME, 100U/ml penicillin, 10 ug/ml streptomycin, and $10^{-5}$ dilution of formalin-fixed *Staphylococcus aureus* Cowan I (SAC) also known as Pansorbin (Pan)) in a total volume of 150 ul. TR II-Fc was then added at various concentrations. Plates were then placed in the incubator (37° C., 5% $CO_2$, 95% humidity) for three days. Proliferation was quantitated by a 20h pulse (1 mnicrocurie/well) of $^3$H-thymidine (6.7 Ci/mM) beginning 72 h post factor addition. The positive and negative controls are IL2 and medium respectively.

The results of this experiment confirmed that TR11-Fc inhibited B cell proliferation in the co-stimulatory assay using *Staphylococcus Aureus* Cowan 1 (SAC) as priming agent and Neutrokine-alpha as a second signal (data not shown). It is important to note that other Tumor Necrosis Factor Receptors (TNFR) fusion proteins (e.g., DR4-Fc (International Application Publication No. WO 98/32856), TR6-Fc (International Application Publication No. WO 98/31799), and TR9-Fc (International Application Publication No. WO 98/56892)) did not inhibit proliferation.

Example 32: T Cell Proliferation Assay

Proliferation assay for Resting PBLs.

A CD3-induced proliferation assay is performed on PBMCs and is measured by the uptake of $^3$H-thymidine. The assay is performed as follows. Ninety-six well plates are coated with 100 microliters per well of mAb to CD3 (HIT3a, Pharmingen) or isotype-matched control mAb (B33.1) overnight at 4° C. (1 microgram/ml in 0.05M bicarbonate buffer, pH 9.5), then washed three times with PBS. PBMC are isolated by F/H gradient centrifugation from human peripheral blood and added to quadruplicate wells ($5×10^4$/well) of mAb coated plates in RPMI containing 10% FCS and P/S in the presence of varying concentrations of TNF Delta and/or TNF Epsilon protein (total volume 200 microliters). Relevant protein buffer and medium alone are controls. After 48 hr. culture at 37° C., plates are spun for 2 min. at 1000 rpm and 100 microliters of supernatant is removed and stored −20° C. for measurement of IL-2 (or other cytokines) if effect on proliferation is observed. Wells are supplemented with 100 microliters of medium containing 0.5 microcuries of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of TNF Delta and/or TNF Epsilon proteins.

Alternatively, a proliferation assay on resting PBL (peripheral blood lymphocytes) is measured by the up-take of $^3$H-thymidine. The assay is performed as follows. PBMC are isolated by Ficoll (LSM, ICN Biotechnologies, Aurora, Ohio) gradient centrifugation from human peripheral blood, and are cultured overnight in 10% (Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non-adherent cells are collected, washed and used in the proliferation assay. The assay is performed in a 96 well plate using $2\times10^4$ cells/well in a final volume of 200 microliters. The supernatants (e.g., CHO or 293T supernatants) expressing the protein of interest are tested at a 30% final dilution, therefore 60 ul are added to 140 ul of 10% FCS/RPMI containing the cells. Control supernatants are used at the same final dilution and express the following proteins: vector (negative control), IL-2 (*), IFNγ, TNFα, IL-10 and TR2. In addition to the control supernatants, recombinant human IL-2 (R & D Systems, Minneapolis, Minn.) at a final concentration of 100 ng/ml is also used. After 24 hours of culture, each well is pulsed with 1uCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error.

(*) The amount of the control cytokines IL-2, IFNγ, TNFα and IL-10 produced in each transfection varies between 300 pg to 5 ng/ml.

Costimulation assay.

A costimiulation assay on resting PBL (peripheral blood lymphocytes) is performed in the presence of immobilized antibodies to CD3 and CD28. The use of antibodies specific for the invariant regions of CD3 mimic the induction of T cell activation that would occur through stimulation of the T cell receptor by an antigen. Cross-linking of the TCR (first signal) in the absence of a costimulatory signal (second signal) causes very low induction of proliferation and will eventually result in a state of "anergy", which is characterized by the absence of growth and inability to produce cytokines. The addition of a costimulatory signal such as an antibody to CD28, which mimics the action of the costimulatory molecule. B7-1 expressed on activated APCs, results in enhancement of T cell responses including cell survival and production of IL-2. Therefore this type of assay allows to detect both positive and negative effects caused by addition of supernatants expressing the proteins of interest on T cell proliferation.

The assay is performed as follows. Ninety-six well plates are coated with 100 ng/ml anti-CD3 and 5 ug/ml anti-CD28 (Pharmingen, San Diego, Calif.) in a final volume of 100 ul and incubated overnight at 4C. Plates are washed twice with PBS before use. PBMC are isolated by Ficoll (LSM, ICN Biotechnologies, Aurora, Ohio) gradient centrifugation from human peripheral blood, and are cultured overnight in 10% FCS(Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non adherent cells are collected, washed and used in the proliferation assay. The assay is performed in a 96 well plate using $2\times10^4$ cells/well in a final volume of 200 ul. The supernatants (e.g., CHO or 293T supernatants) expressing the protein of interest are tested at a 30% final dilution, therefore 60 ul are added to 140 ul of 10% FCS/RPMI containing the cells. Control supernatants are used at the same final dilution and express the following proteins: vector only (negative control), IL-2, IFNγ, TNFα, IL-10 and TR2. In addition to the control supernatants recombinant human IL-2 (R & D Systems, Minneapolis, Minn.) at a final concentration of 10 ng/ml is also used. After 24 hours of culture, each well is pulsed with 1 uCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error.

Proliferation assay for preactivated-resting T cells.

A proliferation assay on preactivated-resting T cells is performed on cells that are previously activated with the lectin phytohemagglutinin (PHA). Lectins are polymeric plant proteins that can bind to residues on T cell surface glycoproteins including the TCR and act as polyclonal activators. PBLs treated with PHA and then cultured in the presence of low doses of IL-2 resemble effector T cells. These cells are generally more sensitive to further activation induced by growth factors such as IL-2. This is due to the expression of high affinity IL-2 receptors that allows this population to respond to amounts of IL-2 that are 100 fold lower than what would have an effect on a naïve T cell. Therefore the use of this type of cells might enable to detect the effect of very low doses of an unknown growth factor, that would not be sufficient to induce proliferation on resting (naïve) T cells.

The assay is performed as follows. PBMC are isolated by F/H gradient centrifugation from human peripheral blood, and are cultured in 10% FCS(Fetal Calf Serum, Biofluids, Rockville, Md.)/RPMI (Gibco BRL, Gaithersburg, Md.) in the presence of 2 ug/ml PHA (Sigma, Saint Louis, Mo.) for three days. The cells are then washed in PBS and cultured in10% FCS/RPMI in the presence of 5 ng/ml of human recombinant IL-2 (R & D Systems, Minneapolis, Minn.) for 3 days. The cells are washed and rested in starvation medium (1% FCSIRPMI) for 16 hours prior to the beginning of the proliferation assay. An aliquot of the cells is analyzed by FACS to determine the percentage of T cells (CD3 positive cells) present; this usually ranges between 93–97% depending on the donor. The assay is performed in a 96 well plate using $2\times10^4$ cells/well in a final volume of 200 ul. The supernatants (e.g., CHO or 293T supernatants) expressing the protein of interest are tested at a 30% final dilution, therefore 60 ul are added to 140 ul of in10% FCS/RPMI containing the cells. Control supernatants are used at the same final dilution and express the following proteins: vector (negative control), IL-2, IFNγ, TNFα, IL-10 and TR2. In addition to the control supernatants recombinant human IL-2 at a final concentration of 10 ng/ml is also used. After 24 hours of culture, each well is pulsed with 1 uCi of $^3$H-thymidine(Nen, Boston, Mass.). Cells are then harvested 20 hours following pulsing and incorporation of $^3$H-thymidine is used as a measure of proliferation. Results are expressed as an average of triplicate samples plus or minus standard error.

The studies described in this example test activity of polypeptides of the invention. However, one skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, and the Sequence Listing and FIG. 4A submitted with U.S. Provisional Application Ser. No. 60/121,648, filed on Feb. 24, 1999; U.S. Provisional Application Ser. No. 60/134,172, filed on May 13, 1999; U.S. Provisional Application Ser. No. 60/144,076, filed on Jul. 16, 1999, U.S. Provisional Application Ser. No. 60/221,577, filed on Jul. 16, 1999, U.S. Application Ser. No. 09/512,363, filed Feb. 23, 2000; U.S. Application Ser. No. 09/176,200, filed Oct. 21, 1998; and U.S. Provisional Application Ser. No. 60/063,212, filed on Oct. 21, 1997, in both computer and paper forms, are each hereby incorporated by reference in its entirety.

Additionally, the disclosures of U.S. Provisional Application Ser. No. 60/121,648, filed on Feb. 24, 1999; U.S. Provisional Application Ser. No. 60/134,172, filed on May 13, 1999; U.S. Provisional Application Ser. No. 60/144,076, filed on Jul. 16, 1999, U.S. Provisional Application Ser. No. 60/221,577, filed on Jul. 16, 1999, U.S. Application Ser. No. 09/512,363, filed Feb. 23, 2000; U.S. Application Ser. No. 09/176,200, filed Oct. 21, 1998; and U.S. Provisional Application Ser. No. 60/063,212, filed on Oct. 21, 1997, are hereby incorporated by reference in their entireties.

What is claimed is:

1. An isolated antibody or portion thereof that specifically binds to a protein selected from the group consisting of:
   (a) a protein whose sequence consists of amino acid residues 2 to 10 of SEQ ID NO:4;
   (b) a protein whose sequence consists of amino acid residues 11 to 19 of SEQ ID NO:4;
   (c) a protein whose sequence consists of amino acid residues 27 to 35 of SEQ ID NO:4;
   (d) a protein whose sequence consists of the-amino acid residues 31 to 46 of SEQ ID NO:4;
   (e) a protein whose sequence consists of amino acid residues 38 to 46 of SEQ ID NO:4;
   (f) a protein whose sequence consists of amino acid residues 42 to 50 of SEQ ID NO:4; and
   (g) a protein whose sequence consists of the amino acid residues of the extracellular domain of the polypeptide encoded by the cDNA in ATCC Deposit No. 209343 which are distinct from the amino acid amino acid residues of the extracellular domain of the polypeptide encoded by the cDNA in ATCC Deposit No. 209341.

2. The antibody or portion thereof of claim 1 that specifically binds protein (a).

3. The antibody or portion thereof of claim 1 that specifically binds protein (b).

4. The antibody or portion thereof of claim 1 that specifically binds protein (c).

5. The antibody or portion thereof of claim 1 that specifically binds protein (d).

6. The antibody or portion thereof of claim 1 that specifically binds protein (e).

7. The antibody or portion thereof of claim 1 that specifically binds protein (f).

8. The antibody or portion thereof of claim 1 that specifically binds protein (g).

9. The antibody or portion thereof of claim 1 which is a monoclonal antibody.

10. A hybridoma that produces the antibody or portion thereof of claim 9.

11. The antibody or portion thereof of claim 1 which is a chimeric antibody.

12. The antibody or portion thereof of claim 1 which is a human antibody.

13. The antibody or portion thereof of claim 1 which is labeled.

14. The antibody of claim 13 wherein the label is selected from the group consisting of:
  (a) an enzyme label;
  (b) a radioisotope;
  (c) a fluorescent label;
  (d) a luminescent label;
  (e) a bioluminescent label; and
  (f) biotin.

15. A composition comprising the antibody or portion thereof of claim 1 and a carrier.

16. An isolated cell that produces the antibody of claim 1.

17. The antibody or portion thereof of claim 1 wherein said protein bound by said antibody or fragment thereof is glycosylated.

18. The antibody or portion thereof of claim 1 which is a polyclonal antibody.

19. The antibody or portion thereof of claim 1 which is selected from the group consisting of:
  (a) a humanized antibody;
  (b) a single chain antibody; and
  (c) a Fab fragment.

20. The antibody or portion thereof of claim 1 wherein said antibody or portion thereof specifically binds to said protein in a Western blot.

21. The antibody or portion thereof of claim 1 wherein said antibody or portibn thereof specifically binds to said protein in an ELISA.

22. An isolated antibody or portion thereof obtained from an animal that has been immunized with a protein selected from the group consisting of:
  (a) a protein whose amino acid sequence consists of amino acid residues 2 to 10 of SEQ ID NO:4;
  (b) a protein whose amino acid sequence consists of amino acid residues 11 to 19 of SEQ ID NO:4;
  (c) a protein whose amino acid sequence consists of amino acid residues 27 to 35 of SEQ ID NO:4
  (d) a protein whose amino acid sequence consists of amino acid residues 31 to 46 of SEQ ID NO:4;
  (e) a protein whose amino acid sequence consists of amino acid residues 38 to 46 of SEQ ID NO:4
  (f) a protein whose amino acid sequence consists of amino acid residues 42 to 50 of SEQ ID NO:4
  (g) a protein comprising the amino acid sequence of the extracellular domain of the polypeptide encoded by the cDNA in ATCC Deposit No. 209343 which are distinct from the amino acid amino acid residues of the extracellular domain of the polypeptide encoded by the cDNA in ATCC Deposit No. 209341;
  wherein said antibody or portion thereof specifically binds to said amino acid sequence.

23. The antibody or portion thereof of claim 22 obtained from an animal immunized with protein (a).

24. The antibody or portion thereof of claim 22 obtained from an animal immunized with protein (b).

25. The antibody or portion thereof of claim 22 obtained from an animal immunized with protein (c).

26. The antibody or portion thereof of claim 22 obtained from an animal immunized with protein (d).

27. The antibody or portion thereof of claim 22 obtained from an animal immunized with protein (e).

28. The antibody or portion thereof of claim 22 obtained from an animal immunized with protein (f).

29. The antibody or portion thereof of claim 22 obtained from an animal immunized with protein (g).

30. The antibody or portion thereof of claim 22 which is a monoclonal antibody.

31. A hybridoma that produces the antibody or portion thereof of claim 30.

32. The antibody or portion thereof of claim 22 which is a chimeric antibody.

33. The antibody or portion thereof of claim 22 which is a human antibody.

34. The antibody or portiont hereofof claim 22 which is labeled.

35. The antibody of claim 34 wherein the label is selected from the group consisting of:
  (a) an enzyme label;
  (b) a radioisotope;
  (c) a fluorescent label;
  (d) a luminescent label;
  (e) a bioluminescent label; and
  (f) biotin.

36. A composition comprising the antibody or portion thereof of claim 22.

37. An isolated cell that produces the antibody of claim 22.

38. The antibody or portion thereof of claim 22 wherein said protein bound by said antibody or fragment thereof is glycosylated.

39. The antibody or portion thereof of claim 22 which is a polyclonal antibody.

40. The antibody or portion thereof of claim 2 which is selected from the group consisting of:
  (a) a humanized antibody;
  (b) a single chain antibody; and
  (c) a Fab fragment.

41. The antibody or portion thereof of claim 22 wherein said antibody or portion thereof specifically binds to said protein in a Western blot.

42. The antibody or portion thereof of claim 22 wherein said antibody or portion thereof specifically binds to said protein in an ELISA.

43. An isolated antibody or portion thereof that specifically binds a TR11 protein expressed on the surface of a cell comprising a polynucleotide encoding amino acids 2 to 10, 11 to 19, 27 to 35, 31 to 46, 38 to 46 or 42 to 50 of SEQ ID NO:4 operably associated with a regulatory sequence that controls the expression of said polynucleotide.

44. The antibody or portion thereof of claim 43 which is a monoclonal antibody.

45. A hybridoma that produces the antibody or portion thereof of claim 44.

46. The antibody or portion thereof of claim 43 which is a human antibody.

47. The antibody or portion thereof of claim 43 which is a chimeric antibody.

48. The antibody or portion thereof of claim 43 which is labeled.

49. The antibody of claim 48 wherein the label is selected from the group consisting of:

(a) an enzyme label;

(b) a radioisotope;

(c) a fluorescent label;

(d) a luminescent label;

(e) a bioluminescent label; and (f) biotin.

50. A composition comprising the antibody or portion thereof of claim 43 and a carrier.

51. An isolated cell that produces the antibody of claim 43.

52. The antibody or portion thereof of claim 43 wherein said protein bound by said antibody or fragment thereof is glycosylated.

53. The antibody or portion thereof of claim 43 which is a polyclonal antibody.

54. The antibody or portion thereof of claim 43 which is selected from the group consisting of:

(a) a humanized antibody;

(b) a single chain antibody; and (c) a Fab fragment.

55. The antibody or portion thereof of claim 43 wherein said antibody or portion thereof specifically binds to said protein in a Western blot.

56. The antibody or portion thereof of claim 43 wherein said antibody or portion thereof specifically binds to said protein in an ELISA.

57. An antibody that specifically binds to TR11SV1 but does not specifically bind to TR11 or TR11SV2.

58. An antibody that specifically binds to TR11SV1 or TR11SV2 but does not specifically bind to TR11.

59. An antibody that specifically binds to TR11 but does not specifically bind to TR11SV1 or TR11SV2.

60. An antibody that specifically binds to TR11SV2 but does not specifically bind to TR11 or TR11SV2.

\* \* \* \* \*

SEQUENCE LISTING

```
<160> NUMBER OF SEQ ID NOS: 28

<210> SEQ ID NO 1
<211> LENGTH: 983
<212> TYPE: DNA
<213> ORGANISM: Homo sapiens
<220> FEATURE:
<221> NAME/KEY: CDS
<222> LOCATION: (118)..(819)
<221> NAME/KEY: mat_peptide
<222> LOCATION: (193)..(819)
<221> NAME/KEY: scRNA
<222> LOCATION: (118)..(192)

<400> SEQUENCE: 1
gcacttcacc tgggtcggga ttctcaggtc atgaacggtc ccagccacct ccgggcaggg      60
cgggtgagga cggggacggg gcgtgtccaa ctggctgtgg gctcttgaaa cccgagc       117 atg gca cag cac ggg gcg atg ggc gcg ttt cgg gcc ctg tgc ggc ctg     165
Met Ala Gln His Gly Ala Met Gly Ala Phe Arg Ala Leu Cys Gly Leu
-25             -20                 -15                 -10 gcg ctg ctg tgc gcg ctc agc ctg ggt cag cgc ccc acc ggg ggt ccc     213
Ala Leu Leu Cys Ala Leu Ser Leu Gly Gln Arg Pro Thr Gly Gly Pro
            -5                  -1  1                   5 ggg tgc ggc cct ggg cgc ctc ctg ctt ggg acg gga acg gac gcg cgc     261
Gly Cys Gly Pro Gly Arg Leu Leu Leu Gly Thr Gly Thr Asp Ala Arg
        10                  15                  20 tgc tgc cgg gtt cac acg acg cgc tgc tgc cgc gat tac ccg ggc gag     309
Cys Cys Arg Val His Thr Thr Arg Cys Cys Arg Asp Tyr Pro Gly Glu
    25                  30                  35 gag tgc tgt tcc gag tgg gac tgc atg tgt gtc cag cct gaa ttc cac     357
Glu Cys Cys Ser Glu Trp Asp Cys Met Cys Val Gln Pro Glu Phe His
40                  45                  50                  55 tgc gga gac cct tgc tgc acg acc tgc cgg cac cac cct tgt ccc cca     405
Cys Gly Asp Pro Cys Cys Thr Thr Cys Arg His His Pro Cys Pro Pro
                60                  65                  70 ggc cag ggg gta cag tcc cag ggg aaa ttc agt ttt ggc ttc cag tgt     453
Gly Gln Gly Val Gln Ser Gln Gly Lys Phe Ser Phe Gly Phe Gln Cys
            75                  80                  85 atc gac tgt gcc tcg ggg acc ttc tcc ggg ggc cac gaa ggc cac tgc     501
Ile Asp Cys Ala Ser Gly Thr Phe Ser Gly Gly His Glu Gly His Cys
        90                  95                  100
```

```
aaa cct tgg aca gac tgc acc cag ttc ggg ttt ctc act gtg ttc cct    549
Lys Pro Trp Thr Asp Cys Thr Gln Phe Gly Phe Leu Thr Val Phe Pro
    105                 110                 115 ggg aac aag acc cac aac gct gtg tgc gtc cca ggg tcc ccg ccg gca    597
Gly Asn Lys Thr His Asn Ala Val Cys Val Pro Gly Ser Pro Pro Ala
120                 125                 130                 135 gag ccg ctt ggg tgg ctg acc gtc gtc ctc ctg gcc gtg gcc gcc tgc    645
Glu Pro Leu Gly Trp Leu Thr Val Val Leu Leu Ala Val Ala Ala Cys
                140                 145                 150 gtc ctc ctc ctg acc tcg gcc cag ctt gga ctg cac atc tgg cag ctg    693
Val Leu Leu Leu Thr Ser Ala Gln Leu Gly Leu His Ile Trp Gln Leu
            155                 160                 165 agg aag acc cag ctg ctg ctg gag gtg ccg ccg tcg acc gaa gac gcc    741
Arg Lys Thr Gln Leu Leu Leu Glu Val Pro Pro Ser Thr Glu Asp Ala
        170                 175                 180 aga agc tgc cag ttc ccc gag gaa gag cgg ggc gag cga tcg gca gag    789
Arg Ser Cys Gln Phe Pro Glu Glu Glu Arg Gly Glu Arg Ser Ala Glu
    185                 190                 195 gag aag ggg cgg ctg gga gac ctg tgg gtg tgagcctggc cgtcctccgg     839
Glu Lys Gly Arg Leu Gly Asp Leu Trp Val
200                 205 ggccaccgac cgcagccagc ccctccccag gagctcccca ggccgcaggg gctctgcgtt   899
ctgctctggg ccgggccctg ctcccctggc agcagaagtg ggtgcaggaa ggtggcagtg   959
accagcgccc tggaccatgc agtt                                         983

<210> SEQ ID NO 2
<211> LENGTH: 234
<212> TYPE: PRT
<213> ORGANISM: Homo sapiens

<400> SEQUENCE: 2

Met Ala Gln His Gly Ala Met Gly Ala Phe Arg Ala Leu Cys Gly Leu
-25                 -20                 -15                 -10

Ala Leu Leu Cys Ala Leu Ser Leu Gly Gln Arg Pro Thr Gly Gly Pro
            -5                  -1   1                   5

Gly Cys Gly Pro Gly Arg Leu Leu Leu Gly Thr Gly Thr Asp Ala Arg
        10                  15                  20

Cys Cys Arg Val His Thr Thr Arg Cys Cys Arg Asp Tyr Pro Gly Glu
    25                  30                  35

Glu Cys Cys Ser Glu Trp Asp Cys Met Cys Val Gln Pro Glu Phe His
40                  45                  50                  55

Cys Gly Asp Pro Cys Cys Thr Thr Cys Arg His His Pro Cys Pro Pro
                60                  65                  70

Gly Gln Gly Val Gln Ser Gln Gly Lys Phe Ser Phe Gly Phe Gln Cys
            75                  80                  85

Ile Asp Cys Ala Ser Gly Thr Phe Ser Gly Gly His Glu Gly His Cys
        90                  95                  100

Lys Pro Trp Thr Asp Cys Thr Gln Phe Gly Phe Leu Thr Val Phe Pro
    105                 110                 115

Gly Asn Lys Thr His Asn Ala Val Cys Val Pro Gly Ser Pro Pro Ala
120                 125                 130                 135

Glu Pro Leu Gly Trp Leu Thr Val Val Leu Leu Ala Val Ala Ala Cys
                140                 145                 150

Val Leu Leu Leu Thr Ser Ala Gln Leu Gly Leu His Ile Trp Gln Leu
            155                 160                 165
```

```
                                            -continued

Arg Lys Thr Gln Leu Leu Glu Val Pro Pro Ser Thr Glu Asp Ala
        170                 175                 180

Arg Ser Cys Gln Phe Pro Glu Glu Arg Gly Glu Arg Ser Ala Glu
    185                 190                 195

Glu Lys Gly Arg Leu Gly Asp Leu Trp Val
200                 205

<210> SEQ ID NO 3
<211> LENGTH: 1007
<212> TYPE: DNA
<213> ORGANISM: Homo sapiens
<220> FEATURE:
<221> NAME/KEY: CDS
<222> LOCATION: (121)..(843)

<400> SEQUENCE: 3
gtcgacccac gcgtccgggg ggccacccct gggtcctgca ggggcagctc ctggttgcat     60
atggagttag cacctgggca ggggcagctg tggggcgcaa aggggagta gccaggccac    120 atg gcc cca gga gaa aga gac agc tgg ata aac cca ggt cca gac tcc    168
Met Ala Pro Gly Glu Arg Asp Ser Trp Ile Asn Pro Gly Pro Asp Ser
  1               5                  10                  15 cag cca gga gcc ctc tgc tcc ctg gag cca act gtg ggt gga gaa cgg    216
Gln Pro Gly Ala Leu Cys Ser Leu Glu Pro Thr Val Gly Gly Glu Arg
             20                  25                  30 aca acc tca ctc ccc tgg agg gcc gag ggg agg cct ggg gag gag ggg    264
Thr Thr Ser Leu Pro Trp Arg Ala Glu Gly Arg Pro Gly Glu Glu Gly
         35                  40                  45 gcc tca gcc cag ctg ctg ggg ggc tgg cct gtc tcc tgc cca ggc gag    312
Ala Ser Ala Gln Leu Leu Gly Gly Trp Pro Val Ser Cys Pro Gly Glu
     50                  55                  60 gag tgc tgt tcc gag tgg gac tgc atg tgt gtc cag cct gaa ttc cac    360
Glu Cys Cys Ser Glu Trp Asp Cys Met Cys Val Gln Pro Glu Phe His
 65                  70                  75                  80 tgc gga gac cct tgc tgc acg acc tgc cgg cac cac cct tgt ccc cca    408
Cys Gly Asp Pro Cys Cys Thr Thr Cys Arg His His Pro Cys Pro Pro
                 85                  90                  95 ggc cag ggg gta cag tcc cag ggg aaa ttc agt ttt ggc ttc cag tgt    456
Gly Gln Gly Val Gln Ser Gln Gly Lys Phe Ser Phe Gly Phe Gln Cys
            100                 105                 110 atc gac tgt gcc tcg ggg acc ttc tcc ggg ggc cac gaa ggc cac tgc    504
Ile Asp Cys Ala Ser Gly Thr Phe Ser Gly Gly His Glu Gly His Cys
        115                 120                 125 aaa cct tgg aca gac tgc acc cag ttc ggg ttt ctc act gtg ttc cct    552
Lys Pro Trp Thr Asp Cys Thr Gln Phe Gly Phe Leu Thr Val Phe Pro
    130                 135                 140 ggg aac aag acc cac aac gct gtg tgc gtc cca ggg tcc ccg ccg gca    600
Gly Asn Lys Thr His Asn Ala Val Cys Val Pro Gly Ser Pro Pro Ala
145                 150                 155                 160 gag ccg ctt ggg tgg ctg acc gtc gtc ctc ctg gcc gtg gcc gcc tgc    648
Glu Pro Leu Gly Trp Leu Thr Val Val Leu Leu Ala Val Ala Ala Cys
                165                 170                 175 gtc ctc ctc ctg acc tcg gcc cag ctt gga ctg cac atc tgg cag ctg    696
Val Leu Leu Leu Thr Ser Ala Gln Leu Gly Leu His Ile Trp Gln Leu
            180                 185                 190 agg agt cag tgc atg tgg ccc cga gag acc cag ctg ctg ctg gag gtg    744
Arg Ser Gln Cys Met Trp Pro Arg Glu Thr Gln Leu Leu Leu Glu Val
        195                 200                 205 ccg ccg tcg acc gaa gac gcc aga agc tgc cag ttc ccc gag gaa gag    792
Pro Pro Ser Thr Glu Asp Ala Arg Ser Cys Gln Phe Pro Glu Glu Glu
    210                 215                 220
```

-continued

```
cgg ggc gag cga tcg gca gag gag aag ggg cgg ctg gga gac ctg tgg      840
Arg Gly Glu Arg Ser Ala Glu Glu Lys Gly Arg Leu Gly Asp Leu Trp
225                 230                 235                 240 gtg tgagcctggc cgtcctccgg ggccaccgac cgcagccagc ccctccccag           893
Val gagctcccca ggccgcaggg gctctgcgtt ctgctctggg ccgggccctg ctcccctggc    953
agcagaagtg ggtgcaggaa ggtggcagtg accagcgccc tggaccatgc agtt         1007

<210> SEQ ID NO 4
<211> LENGTH: 241
<212> TYPE: PRT
<213> ORGANISM: Homo sapiens

<400> SEQUENCE: 4

Met Ala Pro Gly Glu Arg Asp Ser Trp Ile Asn Pro Gly Pro Asp Ser
 1               5                  10                  15

Gln Pro Gly Ala Leu Cys Ser Leu Glu Pro Thr Val Gly Gly Glu Arg
             20                  25                  30

Thr Thr Ser Leu Pro Trp Arg Ala Glu Gly Arg Pro Gly Glu Glu Gly
         35                  40                  45

Ala Ser Ala Gln Leu Leu Gly Gly Trp Pro Val Ser Cys Pro Gly Glu
     50                  55                  60

Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
                 85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 5
<211> LENGTH: 1074
<212> TYPE: DNA
<213> ORGANISM: Homo sapiens
<220> FEATURE:
<221> NAME/KEY: CDS
<222> LOCATION: (1)..(720)
<221> NAME/KEY: sig_peptide
<222> LOCATION: (1)..(57)
<221> NAME/KEY: mat_peptide
<222> LOCATION: (58)..(720)
```

```
<400> SEQUENCE: 5 atg ggc gcg ttt cgg gcc ctg tgc ggc ctg gcg ctg ctg tgc gcg ctc        48
Met Gly Ala Phe Arg Ala Leu Cys Gly Leu Ala Leu Leu Cys Ala Leu
            -15                 -10                  -5 agc ctg ggt cag cgc ccc acc ggg ggt ccc ggg tgc ggc cct ggg cgc        96
Ser Leu Gly Gln Arg Pro Thr Gly Gly Pro Gly Cys Gly Pro Gly Arg
    -1   1                  5                 10 ctc ctg ctt ggg acg gga acg gac gcg cgc tgc tgc cgg gtt cac acg       144
Leu Leu Leu Gly Thr Gly Thr Asp Ala Arg Cys Cys Arg Val His Thr
        15                  20                  25 acg cgc tgc tgc cgc gat tac ccg gcc cag ctg ctg ggg ggc tgg cct       192
Thr Arg Cys Cys Arg Asp Tyr Pro Ala Gln Leu Leu Gly Gly Trp Pro
 30              35                  40                  45 gtc tcc tgc cca ggc gag gag tgc tgt tcc gag tgg gac tgc atg tgt       240
Val Ser Cys Pro Gly Glu Glu Cys Cys Ser Glu Trp Asp Cys Met Cys
             50                  55                  60 gtc cag cct gaa ttc cac tgc gga gac cct tgc tgc acg acc tgc cgg       288
Val Gln Pro Glu Phe His Cys Gly Asp Pro Cys Cys Thr Thr Cys Arg
                 65                  70                  75 cac cac cct tgt ccc cca ggc cag ggg gta cag tcc cag ggg aaa ttc       336
His His Pro Cys Pro Pro Gly Gln Gly Val Gln Ser Gln Gly Lys Phe
             80                  85                  90 agt ttt ggc ttc cag tgt atc gac tgt gcc tcg ggg acc ttc tcc ggg       384
Ser Phe Gly Phe Gln Cys Ile Asp Cys Ala Ser Gly Thr Phe Ser Gly
         95                 100                 105 ggc cac gaa ggc cac tgc aaa cct tgg aca gac tgc acc cag ttc ggg       432
Gly His Glu Gly His Cys Lys Pro Trp Thr Asp Cys Thr Gln Phe Gly
110                 115                 120                 125 ttt ctc act gtg ttc cct ggg aac aag acc cac aac gct gtg tgc gtc       480
Phe Leu Thr Val Phe Pro Gly Asn Lys Thr His Asn Ala Val Cys Val
                130                 135                 140 cca ggg tcc ccg ccg gca gag ccg ctt ggg tgg ctg acc gtc gtc ctc       528
Pro Gly Ser Pro Pro Ala Glu Pro Leu Gly Trp Leu Thr Val Val Leu
            145                 150                 155 ctg gcc gtg gcc gcc tgc gtc ctc ctc ctg acc tcg gcc cag ctt gga       576
Leu Ala Val Ala Ala Cys Val Leu Leu Leu Thr Ser Ala Gln Leu Gly
        160                 165                 170 ctg cac atc tgg cag ctg agg aag acc cag ctg ctg ctg gag gtg ccg       624
Leu His Ile Trp Gln Leu Arg Lys Thr Gln Leu Leu Leu Glu Val Pro
175                 180                 185 ccg tcg acc gaa gac gcc aga agc tgc cag ttc ccc gag gaa gag cgg       672
Pro Ser Thr Glu Asp Ala Arg Ser Cys Gln Phe Pro Glu Glu Glu Arg
190                 195                 200                 205 ggc gag cga tcg gca gag gag aag ggg cgg ctg gga gac ctg tgg gtg       720
Gly Glu Arg Ser Ala Glu Glu Lys Gly Arg Leu Gly Asp Leu Trp Val
                210                 215                 220 tgagcctggc cgtcctccgg ggccaccgac cgcagccagc ccctccccag gagctcccca    780
ggccgcaggg gctctgcgtt ctgctctggg ccgggccctg ctcccctggc agcagaagtg    840
ggtgcaggaa ggtggcagtg accagcgccc tggaccatga agttcggcgg ccgcggctgg    900
gccctgcagg agggagagag agacacagtc atggcccect tcctcccttg ctggccctga    960
tggggtgggg tcttaggacg ggaggctgtg tccgtgggtg tgcagtgccc agcacgggac   1020
ccggctgcag gggaccttca ataaacactt gtccagtaaa aaaaaaaaaa aaaa         1074

<210> SEQ ID NO 6
<211> LENGTH: 240
<212> TYPE: PRT
```

```
<213> ORGANISM: Homo sapiens

<400> SEQUENCE: 6

Met Gly Ala Phe Arg Ala Leu Cys Gly Leu Ala Leu Leu Cys Ala Leu
             -15                 -10                  -5
Ser Leu Gly Gln Arg Pro Thr Gly Gly Pro Gly Cys Gly Pro Gly Arg
         -1   1               5                  10
Leu Leu Leu Gly Thr Gly Thr Asp Ala Arg Cys Cys Arg Val His Thr
             15                  20                  25
Thr Arg Cys Cys Arg Asp Tyr Pro Ala Gln Leu Leu Gly Gly Trp Pro
 30                  35                  40                  45
Val Ser Cys Pro Gly Glu Glu Cys Cys Ser Glu Trp Asp Cys Met Cys
                 50                  55                  60
Val Gln Pro Glu Phe His Cys Gly Asp Pro Cys Cys Thr Thr Cys Arg
                 65                  70                  75
His His Pro Cys Pro Pro Gly Gln Gly Val Gln Ser Gln Gly Lys Phe
                 80                  85                  90
Ser Phe Gly Phe Gln Cys Ile Asp Cys Ala Ser Gly Thr Phe Ser Gly
             95                 100                 105
Gly His Glu Gly His Cys Lys Pro Trp Thr Asp Cys Thr Gln Phe Gly
110                 115                 120                 125
Phe Leu Thr Val Phe Pro Gly Asn Lys Thr His Asn Ala Val Cys Val
                130                 135                 140
Pro Gly Ser Pro Pro Ala Glu Pro Leu Gly Trp Leu Thr Val Val Leu
                145                 150                 155
Leu Ala Val Ala Ala Cys Val Leu Leu Leu Thr Ser Ala Gln Leu Gly
                160                 165                 170
Leu His Ile Trp Gln Leu Arg Lys Thr Gln Leu Leu Leu Glu Val Pro
                175                 180                 185
Pro Ser Thr Glu Asp Ala Arg Ser Cys Gln Phe Pro Glu Glu Glu Arg
190                 195                 200                 205
Gly Glu Arg Ser Ala Glu Glu Lys Gly Arg Leu Gly Asp Leu Trp Val
                210                 215                 220

<210> SEQ ID NO 7
<211> LENGTH: 228
<212> TYPE: PRT
<213> ORGANISM: Mus musculus

<400> SEQUENCE: 7

Met Gly Ala Trp Ala Met Leu Tyr Gly Val Ser Met Leu Cys Val Leu
 1               5                  10                  15
Asp Leu Gly Gln Pro Ser Val Val Glu Glu Pro Gly Cys Gly Pro Gly
                 20                  25                  30
Lys Val Gln Asn Gly Ser Gly Asn Asn Thr Arg Cys Cys Ser Leu Tyr
             35                  40                  45
Ala Pro Gly Lys Glu Asp Cys Pro Lys Glu Arg Cys Ile Cys Val Thr
 50                  55                  60
Pro Glu Tyr His Cys Gly Asp Pro Gln Cys Lys Ile Cys Lys His Tyr
 65                  70                  75                  80
Pro Cys Gln Pro Gly Gln Arg Val Glu Ser Gln Gly Asp Ile Val Phe
                 85                  90                  95
Gly Phe Arg Cys Val Ala Cys Ala Met Gly Thr Phe Ser Ala Gly Arg
                100                 105                 110
Asp Gly His Cys Arg Leu Trp Thr Asn Cys Ser Gln Phe Gly Phe Leu
```

```
                115                 120                      125

Thr Met Phe Pro Gly Asn Lys Thr His Asn Ala Val Cys Ile Pro Glu
             130                 135                 140

Pro Leu Pro Thr Glu Gln Tyr Gly His Leu Thr Val Ile Phe Leu Val
        145                 150                 155                 160

Met Ala Ala Cys Ile Phe Phe Leu Thr Thr Val Gln Leu Gly Leu His
                        165                 170                 175

Ile Trp Gln Leu Arg Arg Gln His Met Cys Pro Arg Glu Thr Gln Pro
                    180                 185                 190

Phe Ala Glu Val Gln Leu Ser Ala Glu Asp Ala Cys Ser Phe Gln Phe
                195                 200                 205

Pro Glu Glu Arg Gly Glu Gln Thr Glu Lys Cys His Leu Gly
            210                 215                 220

Gly Arg Trp Pro
        225

<210> SEQ ID NO 8
<211> LENGTH: 466
<212> TYPE: DNA
<213> ORGANISM: Homo sapiens
<220> FEATURE:
<221> NAME/KEY: misc_feature
<222> LOCATION: (323)
<223> OTHER INFORMATION: n equals a, t, g or c
<221> NAME/KEY: misc_feature
<222> LOCATION: (337)
<223> OTHER INFORMATION: n equals a, t, g or c
<221> NAME/KEY: misc_feature
<222> LOCATION: (392)
<223> OTHER INFORMATION: n equals a, t, g or c
<221> NAME/KEY: misc_feature
<222> LOCATION: (406)
<223> OTHER INFORMATION: n equals a, t, g or c
<221> NAME/KEY: misc_feature
<222> LOCATION: (441)
<223> OTHER INFORMATION: n equals a, t, g or c
<221> NAME/KEY: misc_feature
<222> LOCATION: (452)
<223> OTHER INFORMATION: n equals a, t, g or c

<400> SEQUENCE: 8
gcgcacttca cctgggtcgg gattctcagg tcatgaacgg tcccagccac ctccgggcag      60
ggcgggtgag gacgggacgg gggcgtgtcc aactggctgt gggctcttga aacccgagca    120
tggcacagca cggggcgatg ggcgcgtttc gggccctgtg cggcctggcg ctgctgtgcg    180
cgctcagcct gggtcagcgc cccaccgggg gtcccgggtg cggccctggg cgcctcctgc    240
ttgggacggg aaaggacgcg cgctgcttgc cggggtttca acacgaacgc gctgctgccg    300
cgattaaccc ggggcgaaga atngtggttt ccgagtnggg aactgcaatg tgttgttcaa    360
gccttgaaat tccaattgcg gaagaaccct tngcttgcaa cgaacntgcc cgggaaacaa    420
acctttgttc ccccaaagcc naaggggggta anaattccca ggggga                  466

<210> SEQ ID NO 9
<211> LENGTH: 581
<212> TYPE: DNA
<213> ORGANISM: Homo sapiens
<220> FEATURE:
<221> NAME/KEY: misc_feature
<222> LOCATION: (291)
<223> OTHER INFORMATION: n equals a, t, g or c
<221> NAME/KEY: misc_feature
<222> LOCATION: (293)
<223> OTHER INFORMATION: n equals a, t, g or c
<221> NAME/KEY: misc_feature
```

<222> LOCATION: (295)
<223> OTHER INFORMATION: n equals a, t, g or c
<221> NAME/KEY: misc_feature
<222> LOCATION: (319)
<223> OTHER INFORMATION: n equals a, t, g or c
<221> NAME/KEY: misc_feature
<222> LOCATION: (402)
<223> OTHER INFORMATION: n equals a, t, g or c
<221> NAME/KEY: misc_feature
<222> LOCATION: (424)
<223> OTHER INFORMATION: n equals a, t, g or c
<221> NAME/KEY: misc_feature
<222> LOCATION: (452)
<223> OTHER INFORMATION: n equals a, t, g or c
<221> NAME/KEY: misc_feature
<222> LOCATION: (440)
<223> OTHER INFORMATION: n equals a, t, g or c
<221> NAME/KEY: misc_feature
<222> LOCATION: (471)
<223> OTHER INFORMATION: n equals a, t, g or c
<221> NAME/KEY: misc_feature
<222> LOCATION: (483)
<223> OTHER INFORMATION: n equals a, t, g or c
<221> NAME/KEY: misc_feature
<222> LOCATION: (495)
<223> OTHER INFORMATION: n equals a, t, g or c
<221> NAME/KEY: misc_feature
<222> LOCATION: (516)
<223> OTHER INFORMATION: n equals a, t, g or c
<221> NAME/KEY: misc_feature
<222> LOCATION: (545)
<223> OTHER INFORMATION: n equals a, t, g or c
<221> NAME/KEY: misc_feature
<222> LOCATION: (559)
<223> OTHER INFORMATION: n equals a, t, g or c

<400> SEQUENCE: 9

```
gggtcgaccc acgcgtccgg ggggccaccc tgggtcctgc aggggcagct cctggttgca    60
tatggagtta gcacctgggc aggggcagct gtggggcgca aagggggagt agccaggcca   120
catggcccca ggagaaagag acagctggat aaacccaggg tccagactcc agccaggga    180 gccctctgct ccctggagcc aactgtgggt ggagaacgga caacctcact cccctggtag   240
ggccgagggg aggcctgggg aggaggggc ctcagcccag ctgctggggg nanannctgt    300
ctcctgccca ggcgaggant gctgttccga gtgggaatgc atgtgtgtcc agcctgaatt   360
ccattgcgga gaaccttgct gcacgaattg ccggcaacaa cntgttcccc caagccaggg   420
ggtnacattc caggggaan ttcattttg gnttccatgt ttcgatgtgc ntcggggaat    480
ttntccgggg gccanaaggc aatgcaaaac ttganaaag gaccatttcg gttttcacgg   540
ttccngggaa aagaccanaa gtttttggtc caggtccccc g                      581
```

<210> SEQ ID NO 10
<211> LENGTH: 22
<212> TYPE: DNA
<213> ORGANISM: Artificial sequence
<220> FEATURE:
<223> OTHER INFORMATION: TR11 forward primer containing NcoI restriction
      site

<400> SEQUENCE: 10

```
cgcccatggc agcgccccac cg                                            22
```

<210> SEQ ID NO 11
<211> LENGTH: 22
<212> TYPE: DNA
<213> ORGANISM: Artificial sequence
<220> FEATURE:
<223> OTHER INFORMATION: TR11 reverse primer containing HindIII
      restriction site

<400> SEQUENCE: 11
cgcaagcttg gctctgccgg cg                22

<210> SEQ ID NO 12
<211> LENGTH: 22
<212> TYPE: DNA
<213> ORGANISM: Artificial sequence
<220> FEATURE:
<223> OTHER INFORMATION: TR11 forward pimer containing BamHI restriction
      site

<400> SEQUENCE: 12
cgcggatccc agcgccccac cg                22

<210> SEQ ID NO 13
<211> LENGTH: 22
<212> TYPE: DNA
<213> ORGANISM: Artificial sequence
<220> FEATURE:
<223> OTHER INFORMATION: TR11 reverse primer containing Asp718
      restriction site

<400> SEQUENCE: 13
cgcggtaccg gctctgccgg cg                22

<210> SEQ ID NO 14
<211> LENGTH: 35
<212> TYPE: DNA
<213> ORGANISM: Artificial sequence
<220> FEATURE:
<223> OTHER INFORMATION: TR11 forward pimer containing BamHI restriction
      site

<400> SEQUENCE: 14
cgcggatccc cgccatcatg gcacagcacg gggcg                35

<210> SEQ ID NO 15
<211> LENGTH: 25
<212> TYPE: DNA
<213> ORGANISM: Artificial sequence
<220> FEATURE:
<223> OTHER INFORMATION: TR11 reverse primer containing Asp718
      restriction site

<400> SEQUENCE: 15
cgcggtaccc acccacaggt ctccc                25

<210> SEQ ID NO 16
<211> LENGTH: 31
<212> TYPE: DNA
<213> ORGANISM: Artificial sequence
<220> FEATURE:
<223> OTHER INFORMATION: TR11 forward primer containing BamHI
      restriction site and Kozak sequence

<400> SEQUENCE: 16
cgcggatccg ccatcatgca gcgccccacc g                31

<210> SEQ ID NO 17
<211> LENGTH: 55
<212> TYPE: DNA
<213> ORGANISM: Artificial sequence
<220> FEATURE:
<223> OTHER INFORMATION: TR11 reverse primer containing XbaI restriction
      site

<400> SEQUENCE: 17
cgctctagat caagcgtagt ctgggacgtc gtatgggtat taggctctgc cggcg     55

<210> SEQ ID NO 18
<211> LENGTH: 733
<212> TYPE: DNA
<213> ORGANISM: Homo sapiens

<400> SEQUENCE: 18
gggatccgga gcccaaatct tctgacaaaa ctcacacatg cccaccgtgc ccagcacctg     60
aattcgaggg tgcaccgtca gtcttcctct tcccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agccctccca acccccatcg    360
agaaaaccat ctccaaagcc aaagggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                        733

<210> SEQ ID NO 19
<211> LENGTH: 86
<212> TYPE: DNA
<213> ORGANISM: Artificial sequence
<220> FEATURE:
<223> OTHER INFORMATION: forward primer for constructing GAS containing
      promoter element

<400> SEQUENCE: 19
gcgcctcgag atttccccga aatctagatt tccccgaaat gatttccccg aaatgatttc     60
cccgaaatat ctgccatctc aattag                                          86

<210> SEQ ID NO 20
<211> LENGTH: 27
<212> TYPE: DNA
<213> ORGANISM: Artificial sequence
<220> FEATURE:
<223> OTHER INFORMATION: reverse primer for constructing GAS containing
      promoter element

<400> SEQUENCE: 20
gcggcaagct ttttgcaaag cctaggc                                         27

<210> SEQ ID NO 21
<211> LENGTH: 271
<212> TYPE: DNA
<213> ORGANISM: Homo sapiens

<400> SEQUENCE: 21
ctcgagattt ccccgaaatc tagatttccc cgaaatgatt tccccgaaat gatttccccg     60
aaatatctgc catctcaatt agtcagcaac catagtcccg cccctaactc cgcccatccc    120
gcccctaact ccgcccagtt ccgcccattc tccgccccat ggctgactaa ttttttttat    180

```
ttatgcagag gccgaggccg cctcggcctc tgagctattc cagaagtagt gaggaggctt      240
ttttggaggc ctaggctttt gcaaaaagct t                                    271
```

<210> SEQ ID NO 22
<211> LENGTH: 32
<212> TYPE: DNA
<213> ORGANISM: Artificial sequence
<220> FEATURE:
<223> OTHER INFORMATION: primer for amplifying EGR-1 promoter sequence

<400> SEQUENCE: 22

```
gcgctcgagg gatgacagcg atagaacccc gg                                    32
```

<210> SEQ ID NO 23
<211> LENGTH: 31
<212> TYPE: DNA
<213> ORGANISM: Artificial sequence
<220> FEATURE:
<223> OTHER INFORMATION: primer for amplifying EGR-1 promoter sequence

<400> SEQUENCE: 23

```
gcgaagcttc gcgactcccc ggatccgcct c                                     31
```

<210> SEQ ID NO 24
<211> LENGTH: 12
<212> TYPE: DNA
<213> ORGANISM: Homo sapiens

<400> SEQUENCE: 24

```
ggggactttc cc                                                          12
```

<210> SEQ ID NO 25
<211> LENGTH: 73
<212> TYPE: DNA
<213> ORGANISM: Artificial sequence
<220> FEATURE:
<223> OTHER INFORMATION: primer for constructing NF-kappaB promoter
      element

<400> SEQUENCE: 25

```
gcggcctcga ggggactttc ccggggactt tccggggact tccgggact ttccatcctg       60 ccatctcaat tag                                                         73
```

<210> SEQ ID NO 26
<211> LENGTH: 27
<212> TYPE: DNA
<213> ORGANISM: Artificial sequence
<220> FEATURE:
<223> OTHER INFORMATION: primer for constructing NF-kappaB promoter
      element

<400> SEQUENCE: 26

```
gcggcaagct ttttgcaaag cctaggc                                          27
```

<210> SEQ ID NO 27
<211> LENGTH: 256
<212> TYPE: DNA
<213> ORGANISM: Homo sapiens

<400> SEQUENCE: 27

```
ctcgaggga ctttcccggg gactttccgg ggactttccg ggactttcca tctgccatct       60
caattagtca gcaaccatag tcccgcccct aactccgccc atcccgcccc taactccgcc     120
```

-continued

```
cagttccgcc cattctccgc cccatggctg actaattttt tttatttatg cagaggccga    180
ggccgcctcg gcctctgagc tattccagaa gtagtgagga ggcttttttg gaggcctagg    240
cttttgcaaa aagctt                                                   256
```

<210> SEQ ID NO 28
<211> LENGTH: 241
<212> TYPE: PRT
<213> ORGANISM: Homo sapiens

<400> SEQUENCE: 28

```
Met Ala Gln His Gly Ala Met Gly Ala Phe Arg Ala Leu Cys Gly Leu
 1               5                  10                  15

Ala Leu Leu Cys Ala Leu Ser Leu Gly Gln Arg Pro Thr Gly Gly Pro
             20                  25                  30

Gly Cys Gly Pro Gly Arg Leu Leu Leu Gly Thr Gly Thr Asp Ala Arg
         35                  40                  45

Cys Cys Arg Val His Thr Thr Arg Cys Cys Arg Asp Tyr Pro Gly Glu
     50                  55                  60

Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
             85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
        130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```